(12) United States Patent
Donnell et al.

(10) Patent No.: US 9,394,263 B2
(45) Date of Patent: Jul. 19, 2016

(54) SUBSTITUTED HETERO-AZEPINONES

(71) Applicant: Hoffman-La Roche Inc., Little Falls, NJ (US)

(72) Inventors: Andrew F. Donnell, West Windsor, NJ (US); Xiaochun Han, Cedar Grove, NJ (US); Robert Francis Kester, West Orange, NJ (US); Norman Kong, Beijing (CN); Kang Le, Green Brook, NJ (US); Yan Lou, Fremont, CA (US); Christophe Michoud, New York, NY (US); John Anthony Moliterni, Bloomfield, NJ (US); Stacy Remiszewski, Washington Township, NJ (US); Kenneth Carey Rupert, Bedminster, NJ (US); Weiya Yun, Warren, NJ (US)

(73) Assignee: F. HOFFMANN-LA ROCHE AG, Basel (CH)

( * ) Notice: Subject to any disclaimer, the term of this patent is extended or adjusted under 35 U.S.C. 154(b) by 0 days.

(21) Appl. No.: 14/418,383

(22) PCT Filed: Aug. 6, 2013

(86) PCT No.: PCT/EP2013/066431
§ 371 (c)(1),
(2) Date: Jan. 29, 2015

(87) PCT Pub. No.: WO2014/023708
PCT Pub. Date: Feb. 13, 2014

(65) Prior Publication Data
US 2015/0361059 A1    Dec. 17, 2015

Related U.S. Application Data

(60) Provisional application No. 61/681,337, filed on Aug. 9, 2012.

(51) Int. Cl.
| C07D 267/14 | (2006.01) |
| C07D 498/10 | (2006.01) |
| C07D 281/10 | (2006.01) |
| C07D 267/12 | (2006.01) |
| C07D 413/06 | (2006.01) |
| C07D 413/12 | (2006.01) |
| C07D 413/14 | (2006.01) |
| C07D 417/06 | (2006.01) |
| C07D 417/12 | (2006.01) |

(52) U.S. Cl.
CPC ............ C07D 267/14 (2013.01); C07D 267/12 (2013.01); C07D 281/10 (2013.01); C07D 413/06 (2013.01); C07D 413/12 (2013.01); C07D 413/14 (2013.01); C07D 417/06 (2013.01); C07D 417/12 (2013.01); C07D 498/10 (2013.01)

(58) Field of Classification Search
CPC ... C07D 267/14; C07D 498/10; C07D 281/10
See application file for complete search history.

(56) References Cited

U.S. PATENT DOCUMENTS

| 2009/0054398 | A1* | 2/2009 | Hudson | ................ | C07D 223/16 |
| | | | | | 514/211.03 |
| 2010/0144715 | A1* | 6/2010 | Hoyt | ................... | C07D 245/06 |
| | | | | | 514/221 |

FOREIGN PATENT DOCUMENTS

| WO | 2006/133147 A2 | 12/2006 |
| WO | 2007/101347 A1 | 9/2007 |

OTHER PUBLICATIONS

ISR for PCT/EP2013/066431, (2013).

* cited by examiner

*Primary Examiner* — Bruck Kifle
(74) *Attorney, Agent, or Firm* — Alex Andrus

(57) ABSTRACT

There are provided compounds of the formula

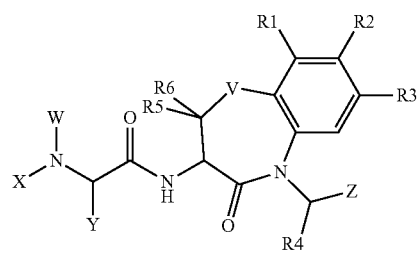

wherein:
V, W, X, Y, Z, R1, R2, R3, R4, R5 and R6 are described herein. The compounds are useful for the treatment of proliferative diseases, including cancer.

19 Claims, No Drawings

SEQUENCE LISTING

```
<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: TR-FRET peptide

<400> SEQUENCE: 1

Ala Val Pro Ile Ala Gln Lys Ser Glu Lys
1               5                   10

<210> SEQ ID NO 2
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 2

Met Arg His His His His His His Arg Asp His Phe Ala Leu Asp Arg
1               5                   10                  15

Pro Ser Glu Thr His Ala Asp Tyr Leu Leu Arg Thr Gly Gln Val Val
                20                  25                  30

Asp Ile Ser Asp Thr Ile Tyr Pro Arg Asn Pro Ala Met Tyr Ser Glu
            35                  40                  45

Glu Ala Arg Leu Lys Ser Phe Gln Asn Trp Pro Asp Tyr Ala His Leu
        50                  55                  60

Thr Pro Arg Glu Leu Ala Ser Ala Gly Leu Tyr Tyr Thr Gly Ile Gly
65                  70                  75                  80

Asp Gln Val Gln Cys Phe Ala Cys Gly Gly Lys Leu Lys Asn Trp Glu
                85                  90                  95

Pro Gly Asp Arg Ala Trp Ser Glu His Arg Arg His Phe Pro Asn Cys
            100                 105                 110

Phe Phe Val Leu Gly Arg Asn Leu Asn Ile Arg Ser Glu
        115                 120                 125

<210> SEQ ID NO 3
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 3

Met Arg His His His His His His Arg Ser Asp Ala Val Ser Ser Asp
1               5                   10                  15

Arg Asn Phe Pro Asn Ser Thr Asn Leu Pro Arg Asn Pro Ser Met Ala
                20                  25                  30
```

```
Asp Tyr Glu Ala Arg Ile Phe Thr Phe Gly Thr Trp Ile Tyr Ser Val
        35              40              45
Asn Lys Glu Gln Leu Ala Arg Ala Gly Phe Tyr Ala Leu Gly Glu Gly
    50              55              60
Asp Lys Val Lys Cys Phe His Cys Gly Gly Gly Leu Thr Asp Trp Lys
65              70              75              80
Pro Ser Glu Asp Pro Trp Glu Gln His Ala Lys Trp Tyr Pro Gly Cys
            85              90              95
Lys Tyr Leu Leu Glu Gln Lys Gly Gln Glu Tyr Ile Asn Asn Ile His
        100             105             110
Leu Thr His Ser Leu Glu Glu Cys Leu Val Arg Thr Thr
        115             120             125
```

SUBSTITUTED HETERO-AZEPINONES

This application is a National Stage Application under 35 USC §371 and claims the benefit of priority to International Application No PCT/EP2013/066431 having an International Filing Date of 6 Aug. 2013, which claims the benefit of priority to U.S. Ser. No. 61/681,337, filed 9 Aug. 2012, which are herein incorporated by reference in their entireties.

SEQUENCE LISTING

The instant application contains a Sequence Listing which has been submitted electronically in ASCII format and is hereby incorporated by reference in its entirety. Said ASCII copy, created on Jan. 29, 2015, is named P31000-US-1_SequenceListing.txt and is 2.66 kilobytes in size.

FIELD OF THE INVENTION

The present invention relates to substituted hetero-azepinones and their use to inhibit SMAC protein binding to Inhibitor of Apoptosis Proteins (IAPs) and/or inhibit activated caspase proteins binding to IAPs for the treatment of human diseases such as cancer.

BACKGROUND OF THE INVENTION

Cancer is a disease of uncontrolled cell growth causing local expansion of a tumor and, potentially, distant metastases. One mechanism by which cancer cells grow is by avoidance of apoptosis, or programmed cell death. Alterations in apoptotic pathways have been linked to cancer cells being resistant to standard treatments, e.g., chemotherapeutics or radiation, and to the incidence and progression of cancer.

The two basic pathways for apoptotic cell death are the intrinsic pathway and the extrinsic pathway. The intrinsic apoptotic pathway can be initiated by various mechanisms including cellular stress, drug-induced damage or DNA damage. The extrinsic pathway can be initiated by activation of the death receptors by a chemokine Initiation of either pathway results in the activation of a family of proteases called caspases. Once activated, the caspases can act to cleave a variety of substrates creating a cascade of events that lead to the activation of the effector caspases 3 and 7 and eventual cell death. The IAP family of proteins can bind to and inhibit the activity of caspases thus inhibiting apoptosis.

The IAPs can contain up to three copies of homologous structural domains called baculoviral IAP repeat (BIR) domains, BIR1, BIR2 and BIR3. The BIR3 domain of the prototypical IAPs, cIAP and XIAP, can bind to and inhibit activated caspase 9. The BIR2 domain, in contrast, binds to and inhibits caspases 3 and 7. The proapoptotic protein Smac (also known as DIABLO) can bind to the BIR2 and BIR3 domains of IAPs competing with activated caspases resulting in release of the activated caspases from the IAPs and completion of the apoptotic program. Peptides and small molecules have been reported to bind to the Bir3 region of XIAP and cIAP, mimicking the action of Smac protein, releasing activated caspased inhibited by IAPs. Targeting the Bir2 region of IAPs, including XIAP, with small molecules has been less explored.

SUMMARY OF THE INVENTION

The present invention relates to compounds of general Formula 1 or pharmaceutically acceptable salts thereof:

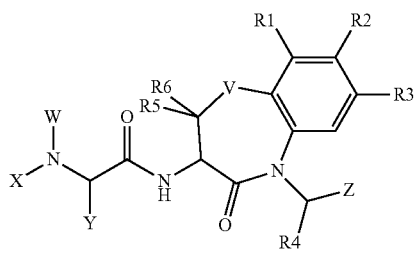

wherein:
W, X, Y, Z, R1, R2, R3, R4, R5 and R6 are described in this application. These compounds bind to the BIR2 and/or BIR3 regions of IAP proteins including XIAP and cIAP resulting in activation or reactivation of the caspase cascade and, as such, are useful for the treatment of proliferative diseases, including cancer.

DETAILED DESCRIPTION OF THE INVENTION

The present invention is directed to compounds of the formula

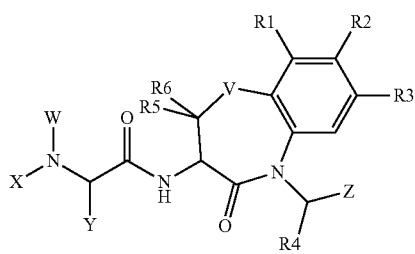

wherein:
W and X are the same or different and are independently selected from H, alkyl, arylalkyl, cycloalkylalkyl, alkenylalkyl or alkynylalkyl, or X and W together with the nitrogen to which they are bound can form a $C_{2-9}$-heterocycle, or W together with the nitrogen to which it is bound and Y together with the carbon to which it is bound can form a $C_{3-9}$-heterocycle; Y is $C_{1-6}$-alkyl or $C_{3-7}$-cycloalkyl-$C_{1-6}$-alkyl; R1 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano or $SO_2R10$; R2 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano or $SO_2R10$; R3 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano or $SO_2R10$; R4 is H or $C_{1-6}$-alkyl; R5 and R6 are the same or different and are independently selected from H, $C_{1-6}$-alkyl, aryl or $C_{3-7}$-cycloalkyl, or R5 and R6 together with the carbon to which they are bound can form a $C_{4-7}$-carbocycle or heterocycle and with the proviso that R5 and R6 are not both hydrogen; V is S or O; Z is selected from aryl, heteroaryl, polycyclic aromatics, polycyclic heteroaromatics, mixed aryl and non-aryl polycycles or mixed aryl and non-aryl polyheterocycles; R7 is $C_{1-6}$-alkyl, aryl, heteroaryl or sulfonyl; R8 and R9 are the same or different and independently selected from H, $C_{1-6}$-alkyl, aryl, aryl-$C_{1-6}$-alkyl or heteroaryl-$C_{1-6}$-alkyl; and R10 is $C_{1-6}$-alkyl, aryl, heterocyclyl or aryl-$C_{1-6}$-alkyl;
or a pharmaceutically acceptable salt thereof.

One aspect of the invention is directed to compounds of formula 1 where

W and X are the same or different and are independently selected from H, $C_{1-6}$-alkyl, hydoxy-$C_{1-6}$-alkyl, aryl-$C_{1-6}$-alkyl, $C_{3-7}$-cycloalkyl-$C_{1-6}$-alkyl, $C_{2-6}$-alkenyl-$C_{1-6}$-alkyl, $C_{2-6}$-alkynyl-$C_{1-6}$-alkyl and heterocycle or X and W together with the nitrogen to which they are bound can form a $C_{2-9}$-heterocycle, or W together with the nitrogen to which it is bound and Y together with the carbon to which it is bound can form a $C_{3-9}$-heterocycle;

Y is $C_{1-6}$-alkyl, hydoxy-$C_{1-6}$-alkyl or $C_{3-7}$-cycloalkyl-$C_{1-6}$-alkyl;

R1 is selected from H, halo, $C_{1-6}$-alkyl halo-$C_{1-6}$-alkyl, aryl-$C_{1-6}$-alkyl, $C_{3-7}$-cycloalkyl-$C_{1-6}$-alkyl, COOH, C(O)NR8'R9', acyl, OR7, SR7, NR8R9, N-acyl, N-sulfonyl, cyano and $SO_2R10$;

R2 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano and $SO_2R10$;

R3 is selected from H, halo, $C_{1-6}$-alkyl, halo-$C_{1-6}$-alkyl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano and $SO_2R10$;

R4 is H or $C_{1-6}$-alkyl;

R5 and R6 are the same or different and are independently selected from H, $C_{1-6}$-alkyl, $C_{1-6}$-alkyl-S—$C_{1-6}$-alkyl, $C_{1-6}$-alkyl-O—$C_{1-6}$-alkyl, aryl and $C_{3-7}$-cycloalkyl, or R5 and R6 together with the carbon to which they are bound can form a $C_{4-7}$-carbocycle or heterocycle, which is optionally substituted by $C_{1-6}$-alkyl-$SO_2$;

V is S, O or SO2

Z is selected from $C_{1-6}$-alkyl, aryl, optionally substituted by $C_{3-7}$-cycloalkyl, $C_{1-6}$-alkyl, $C_{1-6}$-alkoxy, halo, halo-$C_1$-6-alkoxy, C(O)N($C_{1-6}$-alkyl,$C_{1-6}$-alkyl), C(O)NHSO$_2$—$C_{1-6}$-alkyl, C(O)N($C_{1-6}$-alkyl,hydroxy-$C_{1-6}$-alkyl), C(O)N($C_{1-6}$-alkyl,COOH—$C_{1-6}$-alkyl), phenyl optionally substituted by cyano, COO—$C_{1-6}$-alkyl or COOH; aryl-$C_{1-6}$-alkyl, heteroaryl optionally substituted by cyano, $C_{1-6}$-alkoxy or phenyl optionally substituted by C(O)N(H,$C_{1-6}$-alkyl), cyano or COOH, polycyclic aromatics, polycyclic heteroaromatics, optionally substituted by halo, $SO_2$-phenyl, $C_{1-6}$-alkyl-phenyl or phenyl optionally substituted by cyano;

mixed aryl and non-aryl polycycles and mixed aryl and non-aryl polyheterocycles; optionally substituted by $SO_2$—$C_{1-6}$-alkyl, oxo, halo or $C_{1-6}$-alkyl;

R7 is $C_{1-6}$-alkyl, aryl, heteroaryl or sulfonyl;

R8 and R9 are the same or different and independently selected from H, $C_{1-6}$-alkyl, aryl, aryl-$C_{1-6}$-alkyl, whereby the alkyl portion is optionally substituted by oxo; and heteroaryl-$C_{1-6}$-alkyl, R8' is selected from H and $C_{1-6}$-alkyl R9' is selected from HOOC—$C_{1-6}$-alkyl, hydroxy-$C_{1-6}$-alkyl and aryl-$C_{1-6}$-alkyl, wherein the aryl portion is substituted by COOH, or R8' and R9' form together with the nitrogen to which they are attached a heterocyclyl, substituted by hydroxy-$C_{1-6}$-alkyl; and R10 is $C_{1-6}$-alkyl, aryl, heterocyclyl or aryl-$C_{1-6}$-alkyl or a pharmaceutically acceptable salt thereof.

One aspect of the invention is directed to compounds of formula 1 where

W and X are the same or different and are independently selected from H, $C_{1-6}$-alkyl, hydoxy-$C_{1-6}$-alkyl, and heterocycle or Y is $C_{1-6}$-alkyl or hydoxy-$C_{1-6}$-alkyl; R1 is H, halo, $C_{1-6}$-alkyl, halo-$C_{1-6}$-alkyl, COOH, C(O)NR8'R9', NR8R9, N-acyl or N-sulfonyl;

R2 is H, halo, $C_{1-6}$-alkyl or cyano;

R3 is H, or halo-$C_{1-6}$-alkyl;

R4 is H or $C_{1-6}$-alkyl;

R5 and R6 are the same or different and are H, $C_{1-6}$-alkyl, $C_{1-6}$-alkyl-S—$C_{1-6}$-alkyl, $C_{1-6}$-alkyl-O—$C_{1-6}$-alkyl or $C_{3-7}$-cycloalkyl, or R5 and R6 together with the carbon to which they are bound can form a $C_{4-7}$-carbocycle or heterocycle, which is optionally substituted by $C_{1-6}$-alkyl-$SO_2$, V is S or O; SO2

Z is selected from $C_{1-6}$-alkyl, aryl, optionally substituted by $C_{3-7}$-cycloalkyl, $C_{1-6}$-alkyl, $C_{1-6}$-alkoxy, halo, halo-$C_{1-6}$-alkoxy, C(O)N($C_{1-6}$-alkyl,$C_{1-6}$-alkyl), C(O)NHSO$_2$—$C_{1-6}$-alkyl, C(O)N($C_{1-6}$-alkyl,hydroxy-$C_{1-6}$-alkyl), C(O)N($C_{1-6}$-alkyl,COOH—$C_{1-6}$-alkyl), phenyl optionally substituted by cyano, COO—$C_{1-6}$-alkyl or COOH; aryl-$C_{1-6}$-alkyl, heteroaryl optionally substituted by cyano, $C_{1-6}$-alkoxy or phenyl optionally substituted by C(O)N(H,$C_{1-6}$-alkyl), cyano or COOH, polycyclic heteroaromatics, optionally substituted by halo, $SO_2$-phenyl, $C_{1-6}$-alkyl-phenyl or phenyl optionally substituted by cyano; and mixed aryl and non-aryl polyheterocycles; optionally substituted by $SO_2$—$C_{1-6}$-alkyl, oxo, halo or $C_{1-6}$-alkyl;

R8 and R9 are the same or different and independently selected from H, $C_{1-6}$-alkyl, aryl, aryl-$C_{1-6}$-alkyl, whereby the alkyl portion is optionally substituted by oxo; and heteroaryl-$C_{1-6}$-alkyl, R8' is selected from H and $C_{1-6}$-alkyl;

R9' is selected from HOOC—$C_{1-6}$-alkyl, hydroxy-$C_{1-6}$-alkyl and aryl-$C_{1-6}$-alkyl, wherein the aryl portion is substituted by COOH, or R8' and R9' form together with the nitrogen to which they are attached a heterocyclyl, substituted by hydroxy-$C_{1-6}$-alkyl; and R10 is $C_{1-6}$-alkyl, aryl, heterocyclyl or aryl-$C_{1-6}$-alkyl or a pharmaceutically acceptable salt thereof.

One aspect of the invention is directed to compounds of formula 1 wherein W is H.

One aspect of the invention is directed to compounds of formula 1 wherein X is $C_{1-6}$alkyl, in particular methyl One aspect of the invention is directed to compounds of formula 1 wherein Y is $C_{1-6}$-alkyl, in particular methyl.

One aspect of the invention is directed to compounds of formula 1 wherein R1, R2, R3 and R4 are H.

One aspect of the invention is directed to compounds of formula 1 wherein R5 and R6 are individually selected from H and $C_{1-6}$-alkyl or form together a $C_{4-7}$-carbocycle.

One aspect of the invention is directed to compounds of formula 1 wherein R5 and R6 are individually selected from H, $C_{1-6}$-alkyl, in particular methyl.

One aspect of the invention is directed to compounds of formula 1 wherein Z is naphthyl, optionally substituted 0-2 substituents selected from halo, $C_{1-6}$-alkyl and $C_{1-6}$-alkoxy.

One aspect of the invention is directed to compounds of formula 1 wherein W is H, X and Y are methyl, R1, R2, R3 and R4 are H, V is O, R5 and R6 are individually selected from H, $C_{1-6}$-alkyl, in particular methyl, and Z is naphthyl, optionally substituted 0-2 substituents selected from halo, $C_{1-6}$-alkyl and $C_{1-6}$-alkoxy.

One aspect of the invention is directed to compounds of formula 1 wherein W is H, X and Y are methyl, R1, R2, R3 and R4 are H, V is S, R5 and R6 are individually selected from H, $C_{1-6}$-alkyl, in particular methyl, and Z is naphthyl, optionally substituted 0-2 substituents selected from halo, $C_{1-6}$-alkyl and $C_{1-6}$-alkoxy.

One aspect of the invention is directed to compounds of formula 1 wherein W is H, X and Y are methyl, R1, R2, R3 and R4 are H, V is O, R5 and R6 form together $C_{4-7}$-carbocycle, and Z is naphthyl, optionally substituted 0-2 substituents selected from halo, $C_{1-6}$-alkyl and $C_{1-6}$-alkoxy.

One aspect of the invention is directed to compounds of formula 1 wherein W is H, X and Y are methyl, R1, R2, R3 and R4 are H, V is S, R5 and R6 form together $C_{4-7}$-carbocycle, and Z is naphthyl, optionally substituted 0-2 substituents selected from halo, $C_{1-6}$-alkyl and $C_{1-6}$-alkoxy.

One aspect of the invention is directed to compounds of formula 1 wherein

W and X are the same or different and are independently selected from H, $C_{1-6}$-alkyl, aryl-$C_{1-6}$-alkyl, $C_{3-7}$-cycloalkyl-$C_{1-6}$-alkyl, $C_{2-6}$-alkenyl-$C_{1-6}$-alkyl or $C_{2-6}$-alkynyl-$C_{1-6}$-alkyl, or X and W together with the nitrogen to which they are bound can form a $C_{2-9}$-heterocycle, or W together with the nitrogen to which it is bound and Y together with the carbon to which it is bound can form a $C_{3-9}$-heterocycle;

Y is $C_{1-6}$-alkyl, or $C_{3-7}$-cycloalkyl-$C_{1-6}$-alkyl;

R1 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano or $SO_2R10$;

R2 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano or $SO_2R10$;

R3 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano or $SO_2R10$;

R4 is H or $C_{1-6}$-alkyl;

R5 and R6 are the same or different and are independently selected from H, $C_{1-6}$-alkyl, aryl or $C_{3-7}$-cycloalkyl, or R5 and R6 together with the carbon to which they are bound can form a $C_{4-7}$-carbocycle or heterocycle, with the proviso that R5 and R6 are not both hydrogen;

V is S or O;

Z is selected from aryl, heteroaryl polycyclic aromatics, polycyclic heteroaromatics, mixed aryl and non-aryl polycycles or mixed aryl and non-aryl polyheterocycles;

R7 is $C_{1-6}$-alkyl, aryl, heteroaryl or sulfonyl;

R8 and R9 are the same or different and independently selected from H, $C_{1-6}$-alkyl, aryl, aryl-$C_{1-6}$-alkyl, or heteroaryl-$C_{1-6}$-alkyl, R10 is $C_{1-6}$-alkyl, aryl, heterocyclyl or aryl-$C_{1-6}$-alkyl or a pharmaceutically acceptable salt thereof.

One aspect of the invention is directed to compounds of formula 1 wherein

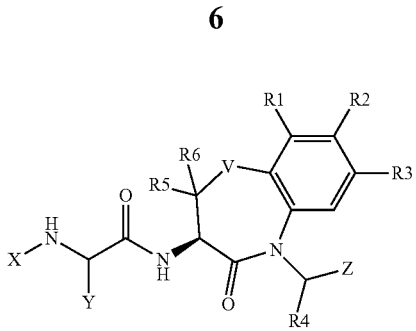

II wherein:

X is selected from $C_{1-6}$-alkyl, aryl-$C_{1-6}$-alkyl, $C_{3-7}$-cycloalkyl-$C_{1-6}$-alkyl, $C_{2-6}$-alkenyl-$C_{1-6}$-alkyl or $C_{2-6}$-alkynyl-$C_{1-6}$-alkyl;

Y is selected from $C_{1-6}$-alkyl or $C_{3-7}$-cycloalkyl-$C_{1-6}$-alkyl;

R1 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano or $SO_2R10$;

R2 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano or $SO_2R10$;

R3 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano or $SO_2R10$;

R4 is selected from H or $C_{1-6}$-alkyl;

R5 and R6 are the same or different and independently selected from H, $C_{1-6}$-alkyl, aryl or $C_{3-7}$-cycloalkyl-$C_{1-6}$-alkyl, or R5 and R6 together with the carbon to which they are bound can form a $C_{3-7}$-carbocycle or heterocycle with the proviso that R5 and R6 are not both hydrogen;

V is selected from S or O;

Z is selected from aryl, heteroaryl, polycyclic aromatics, polycyclic heteroaromatics, mixed aryl and non-aryl polycycles or mixed aryl and non-aryl polyheterocycles;

R7 is selected from $C_{1-6}$-alkyl, aryl, heteroaryl or sulfonyl;

R8 and R9 are the same or different and independently selected from H, $C_{1-6}$-alkyl, aryl, aryl-$C_{1-6}$-alkyl or heteroaryl-$C_{1-6}$-alkyl;

R10 is selected from $C_{1-6}$-alkyl, aryl, heterocyclyl or aryl-$C_{1-6}$-alkyl;

or a pharmaceutically acceptable salt thereof.

One aspect of the invention is directed to compounds of formula 1 wherein

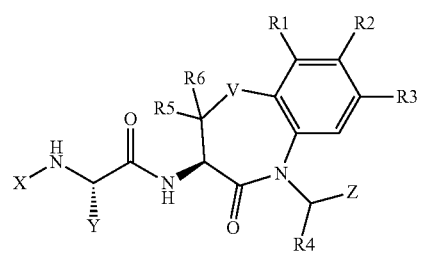

III wherein:

X is selected from $C_{1-6}$-alkyl, aryl-$C_{1-6}$-alkyl or $C_{3-7}$-cycloalkyl-$C_{1-6}$-alkyl;

Y is selected from $C_{1-6}$-alkyl or $C_{3-7}$-cycloalkyl-$C_{1-6}$-alkyl;

R1 is selected from H, halo, $C_{1-6}$-alkyl, acyl, OR7, N-acyl, N-sulfonyl, cyano or $SO_2R10$;

R2 is selected from H, halo, $C_{1-6}$-alkyl, acyl, OR7, N-acyl, N-sulfonyl, cyano or $SO_2R10$;

R3 is selected from H, halo, $C_{1-6}$-alkyl, acyl, OR7, N-acyl, N-sulfonyl, cyano or $SO_2R10$;

R4 is selected from H or $C_{1-6}$-alkyl;

R5 and R6 are the same or different and independently selected from H or $C_{1-6}$-alkyl but are not both hydrogen, or R5 and R6 together with the carbon to which they are bound can form a $C_{3-6}$-carbocycle or heterocycle;

V is selected from S or O;

Z is selected from aryl, heteroaryl, polycyclic aromatics or polycyclic heteroaromatics;

R7 is selected from $C_{1-6}$-alkyl, aryl, heteroaryl or sulfonyl;

R10 is selected from $C_{1-6}$-alkyl, aryl, heterocyclyl or aryl-$C_{1-6}$-alkyl;

or a pharmaceutically acceptable salt thereof.

One aspect of the invention is directed to compounds of formula 1 wherein

X is selected from methyl, ethyl, methyl-d3, ethyl-d5, n-propyl; i-propyl, 2-hydroxyethyl, 3-hydroxypropyl, cyclopropyl, cyclobutyl, cyclopentyl or oxetan-3-yl;

Y is selected from methyl, ethyl, cyclopropyl, methylcyclocproplyl, hydroxymethyl, (S)-1-hydroxyethyl or (R)-1-hydroxyethyl;

R1 is selected from H, halo, $C_{1-6}$-alkyl, acyl, OR7, N-acyl, N-sulfonyl or cyano;

R2 is selected from H, halo, $C_{1-6}$-alkyl, acyl, OR7, N-acyl, N-sulfonyl or cyano;

R3 is selected from H, halo, $C_{1-6}$-alkyl, acyl, OR7, N-acyl, N-sulfonyl or cyano;

R4 is selected from H or $C_{1-6}$-alkyl;

R5 and R6 are the same or different and independently selected from H or $C_{1-6}$-alkyl but are not both hydrogen, or R5 and R6 together with the carbon to which they are bound can form a $C_{3-6}$-carbocycle or heterocycle;

V is selected from S or O;

Z is selected from aryl, heteroaryl, polycyclic aromatics or polycyclic heteroaromatics;

R7 is selected from $C_{1-6}$-alkyl, aryl, heteroaryl or sulfonyl;

or a pharmaceutically acceptable salt thereof.

One aspect of the invention is directed to compounds of formula 1 wherein

X is selected from methyl, ethyl, methyl-d3, ethyl-d5 or 2-hydroxyethyl;

Y is selected from methyl, ethyl, cyclopropyl, hydroxymethyl or (S)-1-hydroxyethyl;

R1 is selected from H, halo, $C_{1-6}$-alkyl, acyl, N-acyl or N-sulfonyl, cyano;

R2 is selected from H, halo, $C_{1-6}$-alkyl, acyl, N-acyl or N-sulfonyl, cyano;

R3 is selected from H, halo, $C_{1-6}$-alkyl, acyl, N-acyl, N-sulfonyl or cyano;

R4 is selected from H, methyl or ethyl;

R5 and R6 are the same or different and independently selected from H or $C_{1-6}$-alkyl but are not both hydrogen, or R5 and R6 together with the carbon to which they are bound can form a $C_{3-6}$-carbocycle or heterocycle;

V is selected from S or O;

Z is selected from aryl, heteroaryl, polycyclic aromatics or polycyclic heteroaromatics;

or a pharmaceutically acceptable salt thereof.

One aspect of the invention is directed to compounds of formula 1 wherein

X is selected from methyl, ethyl, methyl-d3, ethyl-d5 or 2-hydroxyethyl;

Y is selected from methyl, ethyl, hydroxymethyl or (S)-1-hydroxyethyl;

R1 is selected from H, F, Cl, Br, carboxyamide, N-acyl, N-sulfonyl or cyano;

R2 is selected from H, F, Cl, Br, carboxyamide, N-acyl, N-sulfonyl or cyano;

R3 is selected from H, F, Cl, Br, carboxyamide, N-acyl, N-sulfonyl or cyano;

R4 is H;

R5 and R6 are the same or different and independently selected from H or $C_{1-6}$-alkyl but are not both hydrogen, or R5 and R6 together with the carbon to which they are bound can form a $C_{3-6}$-carbocycle or heterocycle;

V is selected from S or O;

Z is selected from aryl, heteroaryl, polycyclic aromatics or polycyclic heteroaromatics;

or a pharmaceutically acceptable salt thereof.

One aspect of the invention is directed to compounds of formula 1 wherein

X is selected from methyl, ethyl, methyl-d3 or ethyl-d5;

Y is selected from methyl, ethyl, hydroxymethyl or (S)-1-hydroxyethyl;

R1 is selected from H, F, Cl, Br, carboxyamide, N-acyl, N-sulfonyl or cyano;

R2 is selected from H, F, Cl, Br, carboxyamide, N-acyl, N-sulfonyl or cyano;

R3 is selected from H, F, Cl, Br or cyano;

R4 is H;

R5 and R6 are the same or different and independently selected from H or $C_{1-6}$-alkyl but are not both hydrogen, or R5 and R6 together with the carbon to which they are bound can form a $C_{3-6}$-carbocycle or heterocycle;

V is O;

Z is selected from 2,5-disubstituted phenyl, 2-substituted-naphthalen-1-yl, 2,5-disubstituted-naphthalen-1-yl, 2,6-disubstituted-naphthalen-1-yl, 2,7-disubstituted-naphthalen-1-yl, 5-substituted-naphthalen-1-yl, 1-substituted-1H-indazol-3-yl, benzo[d]isoxazole-3-yl, 4-quinolinyl, 5-quinolinyl, 3-substituted-quinolin-4-yl, 1,2-disubstituted-indol-3-yl, 1,6-disubstituted-1H-indazol-3-yl, 1-substituted-1,3-dihydro-indol-2-one-4-yl, 1,6-1H-quinolin-2-one-4-yl, 2-substituted-2,3-dihydro-1H-isoindol-4-yl, 2-(4-methyl-indol-1-yl)-benzonitrile or 1-substituted-indol-4-yl;

or a pharmaceutically acceptable salt thereof.

One aspect of the invention is directed to compounds of formula 1 wherein

X is selected from methyl, ethyl, methyl-d3 or ethyl-d5;

Y is selected from methyl, ethyl, hydroxymethyl or (S)-1-hydroxyethyl;

R1 is selected from H, F, Cl, Br, carboxyamide, N-acyl, N-sulfonyl or cyano;

R2 is selected from H, F, Cl, Br, carboxyamide, N-acyl, N-sulfonyl or cyano;

R3 is selected from H, F, Cl, Br or cyano;

R4 is H;

R5 and R6 are methyl or H but are not both hydrogen;

V is O;

Z is selected from 5-bromo-2-methoxynaphthalen-1-yl, 6-bromo-2-(d3-methoxy)-naphthalen-1-yl, 6-bromo-2-methoxy-naphthalen-1-yl, 3-methoxyquinolin-4-yl, quinolin-4-yl, 2-(2,2,2-trifluoroethoxyl)naphthalen-1-yl, 2-difluoromethoxy-naphthalen-1-yl,

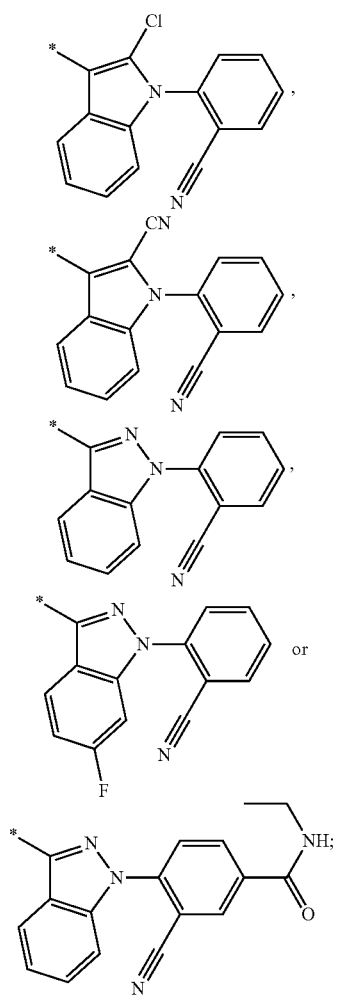

or a pharmaceutically acceptable salt thereof.

One aspect of the invention is directed to compounds of formula 1 wherein

X is selected from methyl, ethyl, methyl-d3 or ethyl-d5;

Y is selected from methyl, ethyl, hydroxymethyl or (S)-1-hydroxyethyl;

R1 is selected from H, F, Cl, Br, carboxyamide, N-acyl, N-sulfonyl or cyano;

R2 is selected from H, F, Cl, Br, carboxyamide, N-acyl, N-sulfonyl or cyano;

R3 is selected from H, F, Cl, Br or cyano;

R4 is H;

R5 and R6 together form a ring selected from

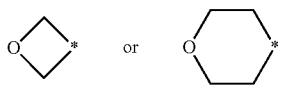

V is O;

Z is selected from 5-bromo-2-methoxynaphthalen-1-yl, 6-bromo-2-(d3-methoxy)-naphthalen-1-yl, 6-bromo-2-methoxy-naphthalen-1-yl, 3-methoxyquinolin-4-yl, quinolin-4-yl, 2-(2,2,2-trifluoroethoxyl)naphthalen-1-yl, 2-difluoromethoxy-naphthalen-1-yl,

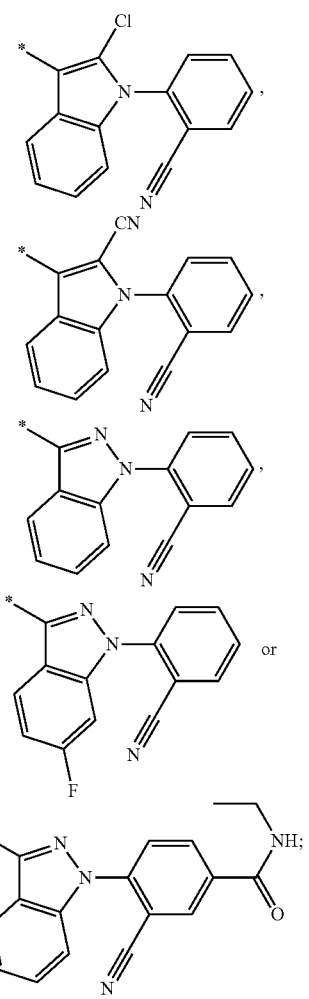

or a pharmaceutically acceptable salt thereof.

One aspect of the invention is directed to compounds of formula 1 wherein

X is selected from methyl, ethyl, methyl-d3 or ethyl-d5;

Y is selected from methyl, ethyl, hydroxymethyl or (S)-1-hydroxyethyl;

R1 is selected from H, F, Cl, Br, carboxyamide, N-acyl, N-sulfonyl or cyano;

R2 is selected from H, F, Cl, Br, carboxyamide, N-acyl, N-sulfonyl or cyano;

R3 is selected from H, F, Cl, Br or cyano;

R4 is H;

R5 is

R6 is

V is O;

Z is selected from 5-bromo-2-methoxynaphthalen-1-yl, 6-bromo-2-(d3-methoxy)-naphthalen-1-yl, 6-bromo-2- methoxy-naphthalen-1-yl, 3-methoxyquinolin-4-yl, quinolin-4-yl, 2-(2,2,2-trifluoroethoxyl)naphthalen-1-yl, 2-difluoromethoxy-naphthalen-1-yl,

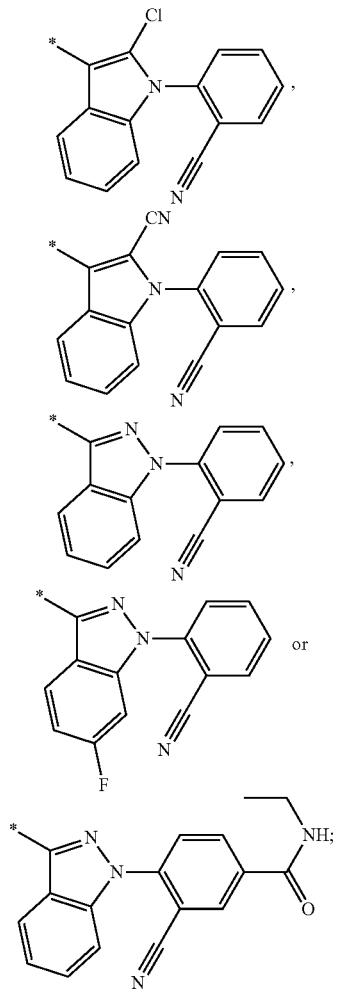

or a pharmaceutically acceptable salt thereof.

One aspect of the invention is directed to compounds of formula 1 wherein

X is selected from methyl, ethyl, methyl-d3 or ethyl-d5;
Y is selected from methyl, ethyl, hydroxymethyl or (S)-1-hydroxyethyl;
R1 is selected from H, F, Cl, Br, carboxyamide, N-acyl, N-sulfonyl or cyano;
R2 is selected from H, F, Cl, Br, carboxyamide, N-acyl, N-sulfonyl or cyano;
R3 is selected from H, F, Cl, Br or cyano;
R4 is H;
R5 is

R6 is

V is O;
Z is selected from 5-bromo-2-methoxynaphthalen-1-yl, 6-bromo-2-(d3-methoxy)-naphthalen-1-yl, 6-bromo-2-methoxy-naphthalen-1-yl, 3-methoxyquinolin-4-yl, quinolin-4-yl, 2-(2,2,2-trifluoroethoxyl)naphthalen-1-yl, 2-difluoromethoxy-naphthalen-1-yl,

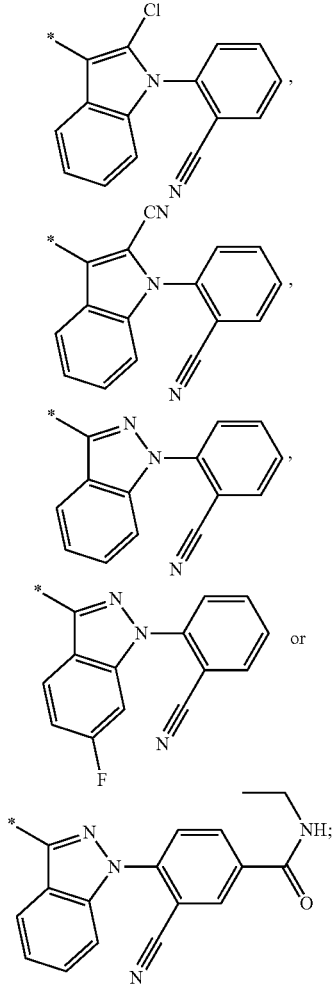

or a pharmaceutically acceptable salt thereof.

One aspect of the invention is directed to compounds of formula 1 wherein the compound is selected from
(2S)-N-(5-(6-Bromo-2-methoxynaphthalen-1-yl)methyl)-(3S)-4-oxo-4,5-dihydro-3H-spiro[benzo[b][1,4]oxazepine-2,1'-cyclohexane]-3-yl)-2-(methylamino)propanamide hydrochloride;
6-Methoxy-5-(((S)-3-((S)-2-(methylamino)propanamido)-4-oxo-2',3',5',6'-tetrahydro-3H-spiro[benzo[b][1,4]oxazepine-2,4'-pyran]-5(4H)-yl)methyl)-2-naphthoic acid trifluoroacetate;
6-Methoxy-5-(((S)-3-((S)-2-(methylamino)propanamido)-4-oxo-2',3',5',6'-tetrahydro-3H-spiro[benzo[b][1,4]oxazepine-2,4'-pyran]-5(4H)-yl)methyl)-N-(methylsulfonyl)-2-naphthamide trifluoroacetate;
(R)-N-[(S)-5-((6-Bromo-2-methoxy-naphthalen-1-ylmethyl)-2,2-dimethyl-4-oxo-2,3,4,5-tetrahydro-benzo[b][1,4]thiazepin-3-yl]-2-methylamino-propionamide hydrochloride
(S)-N-(5-Benzyl-4-oxo-2,3,4,5-tetrahydrobenzo[b][1,4]thiazepin-3-yl)-2-methylaminopropanamide hydrochloride;
N-(5-Benzyl-1,1,4-trioxo-2,3,4,5-tetrahydrobenzo[b][1,4]thiazepin-3-yl)-2-(S)-(methylamino)propanamide hydrochloride;

N-(5-(4-Phenyl-butyl)-1,1,4-trioxo-2,3,4,5-tetrahydrobenzo[b][1,4]thiazepin-3-yl)-2-(S)-(methylamino)propanamide hydrochloride;

N-(5-Biphenyl-3-ylmethyl-4-oxo-2,3,4,5-tetrahydro-benzo[b][1,4]thiazepin-3-yl)-2-(S)-methylamino-propionamide hydrochloride;

(2S)-N-(5-((6-Bromo-2-methoxynaphthalen-1-yl)methyl)-(3R)-8,9-difluoro-4-oxo-2',3',5',6'-tetrahydro-3H-spiro[benzo[b][1,4]oxazepine-2,4'-pyran]-3-yl)-2-(methylamino)propanamide hydrochloride;

(2S)-N-(5-((6-Bromo-2-methoxynaphthalen-1-yl)methyl)-(3S)-8,9-difluoro-4-oxo-2',3',5',6'-tetrahydro-3H-spiro[benzo[b][1,4]oxazepine-2,4'-pyran]-3-yl)-2-(methylamino)propanamide hydrochloride;

(2S)-N-(5-((6-Bromo-2-methoxynaphthalen-1-yl)methyl)-(3R)-9-fluoro-4-oxo-2',3',5',6'-tetrahydro-3H-spiro[benzo[b][1,4]oxazepine-2,4'-pyran]-3-yl)-2-(methylamino)propanamide hydrochloride;

(2S)-N-(5-((6-Bromo-2-methoxynaphthalen-1-yl)methyl)-(3S)-9-fluoro-4-oxo-2',3',5',6'-tetrahydro-3H-spiro[benzo[b][1,4]oxazepine-2,4'-pyran]-3-yl)-2-(methylamino)propanamide hydrochloride and (2S)-N-(5-((6-Bromo-2-methoxynaphthalen-1-yl)methyl)-(3R)-9-fluoro-4-oxo-2',3',5',6'-tetrahydro-3H-spiro[benzo[b][1,4]oxazepine-2,4'-pyran]-3-yl)-2-(methylamino)butanamide hydrochloride.

(2S)-N-(5-((6-Bromo-2-methoxynaphthalen-1-yl)methyl)-(3S)-9-fluoro-4-oxo-2',3',5',6'-tetrahydro-3H-spiro[benzo[b][1,4]oxazepine-2,4'-pyran]-3-yl)-2-(methylamino)butanamide hydrochloride;

(2S)-N-(5-((6-Bromo-2-methoxynaphthalen-1-yl)methyl)-(3S)-8-fluoro-4-oxo-2',3',5',6'-tetrahydro-3H-spiro[benzo[b][1,4]oxazepine-2,4'-pyran]-3-yl)-2-(methylamino)propanamide hydrochloride;

(2S)-N-(5-((6-Bromo-2-methoxynaphthalen-1-yl)methyl)-(3S)-8-fluoro-4-oxo-2',3',5',6'-tetrahydro-3H-spiro[benzo[b][1,4]oxazepine-2,4'-pyran]-3-yl)-2-(methylamino)butanamide hydrochloride;

(S)-N-((S)-5-((6-Bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-(2-hydroxyethylamino)propanamide;

(2S)-N-(5-((3-Methoxyquinolin-N-oxide-4-yl)methyl)-(3S)-4-oxo-2',3',5',6'-tetrahydro-3H-spiro[benzo[b][1,4]oxazepine-2,4'-pyran]-3-yl)-2-(methylamino)propanamide;

(2S)-N-(5-((6-Bromo-2-methoxynaphthalen-1-yl)methyl)-(3S)-4-oxo-2',3',5',6'-tetrahydro-3H-spiro[benzo[b][1,4]oxazepine-2,4'-pyran]-3-yl)-2-(methyl-d3-amino)propanamide hydrochloride;

(2S)-N-(5-((6-Bromo-2-(methoxy-d3)-naphthalen-1-yl)methyl)-(3S)-4-oxo-2',3',5',6'-tetrahydro-3H-spiro[benzo[b][1,4]oxazepine-2,4'-pyran]-3-yl)-2-(methyl-d3-amino)propanamide hydrochloride;

(R)-N-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-aminopropanamide;

(S)-N-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-aminopropanamide;

(S)-N-{(R)-9-[2-(2-Methoxy-ethoxy)-acetylamino]-5-naphthalen-1-ylmethyl-4-oxo-2,3,4,5-tetrahydro-benzo[b][1,4]thiazepin-3-yl}-2-methylamino-propionamide hydrochloride;

1-Acetyl-piperidine-4-carboxylic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide and 5-Oxo-hexanoic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide hydrochloride.

3,4,5-Trimethoxy-N-[(R)-3-((S)-2-methylamino-propionylamino)-5-naphthalen-1-ylmethyl-4-oxo-2,3,4,5-tetrahydro-benzo[b][1,4]thiazepin-9-yl]-benzamide hydrochloride;

6-Oxo-heptanoic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide hydrochloride;

(S)-N-((R)-9-Amino-5-naphthalen-1-ylmethyl-4-oxo-2,3,4,5-tetrahydro-benzo[b][1,4]thiazepin-3-yl)-2-methylamino-propionamide hydrochloride;

N-[(R)-3-((S)-2-Methylamino-propionylamino)-5-naphthalen-1-ylmethyl-4-oxo-2,3,4,5-tetrahydro-benzo[b][1,4]thiazepin-9-yl]-benzamide hydrochloride;

(S)-N-[(S)-9-(6-Bromo-2-methoxy-naphthalen-1-ylmethyl)-8-oxo-6,7,8,9-tetrahydro-5-oxa-9-aza-benzocyclohepten-7-yl]-2-methylamino-propionamide trifluoroacetate;

(S)-N-[(S)-9-(6-Cyclopropyl-2-methoxy-naphthalen-1-ylmethyl)-8-oxo-6,7,8,9-tetrahydro-5-oxa-9-aza-benzocyclohepten-7-yl]-2-methylamino-propionamide trifluoroacetate;

Methyl 6-methoxy-5-(((S)-3-((S)-2-(methylamino)propanamido)-4-oxo-3,4-dihydrobenzo[b][1,4]oxazepin-5(2H)-yl)methyl)-2-naphthoate trifluoroacetate;

6-Methoxy-5-(((S)-3-((S)-2-(methylamino)propanamido)-4-oxo-3,4-dihydrobenzo[b][1,4]oxazepin-5(2H)-yl)methyl)-2-naphthoic acid trifluoroacetate;

6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carboxylic acid (2-hydroxyethyl)-methyl-amide;

4-({6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carbonyl}-amino)-butyric acid trifluoroacetate;

6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carboxylic acid dimethylamide trifluoroacetate and (S)-N-[(S)-9-(7-Bromo-3-methoxy-naphthalen-2-ylmethyl)-3-methyl-8-oxo-6,7,8,9-tetrahydro-5-oxa-9-aza-benzocyclohepten-7-yl]-2-methylamino-propionamide trifluoroacetate.

(2S,3R)-2-Amino-N-[(S)-9-(7-bromo-3-methoxy-naphthalen-2-ylmethyl)-3-methyl-8-oxo-6,7,8,9-tetrahydro-5-oxa-9-aza-benzocyclohepten-7-yl]-3-hydroxy-butyramide trifluoracetate;

(2S,3S)-2-Amino-N-[(S)-9-(7-bromo-3-methoxy-naphthalen-2-ylmethyl)-3-methyl-8-oxo-6,7,8,9-tetrahydro-5-oxa-9-azabenzocyclohepten-7-yl]-3-hydroxy-butyramide trifluoroacetate;

(S)-N-((2S,3S)-5-((6-Bromo-2-methoxynaphthalen-1-yl)methyl)-2,8-dimethyl-4-oxo-2,3,4,5-tetrahydrobenzo[b][1,4]oxazepin-3-yl)-2-(methylamino)propanamide trifluoracetate;

Methyl 5-(((2S,3S)-2,8-dimethyl-3-((S)-2-(methylamino)propanamido)-4-oxo-3,4-dihydrobenzo[b][1,4]oxazepin-5(2H)-yl)methyl)-6-methoxy-2-naphthoate trifluoroacetate;

(2S,3S)-2-Amino-N-[(6S,7S)-9-(6-bromo-2-methoxy-naphthalen-1-ylmethyl)-3,6-dimethyl-8-oxo-6,7,8,9-tetrahydro-5-oxa-9-aza-benzocyclohepten-7-yl]-3-hydroxy-butyramide trifluoroacetate;

(S)-N-((S)-5-((6-Bromo-2-methoxynaphthalen-1-yl)methyl)-4-oxo-7-(trifluoromethyl)-2,3,4,5-tetrahydrobenzo[b][1,4]oxazepin-3-yl)-2-(methylamino)propanamide trifluoroacetate;

(S)-N-[(6S,7S)-9-(6-Bromo-2-methoxy-naphthalen-1-ylmethyl)-6-methyl-8-oxo-2-trifluoromethyl-6,7,8,9-tetrahydro-5-oxa-9-aza-benzocyclohepten-7-yl]-2-methylamino-propionamide trifluoroacetate;

(S)-2-Methylamino-N-[(S)-9-((2-methyl-naphthalen-1-ylmethyl)-8-oxo-6,7,8,9-tetrahydro-5-oxa-9-aza-benzocyclohepten-7-yl]-propionamide;

(S)-N-((S)-5-((2-Chlorobenzyl)-4-oxo-2,3,4,5-tetrahydrobenzo[b][1,4]oxazepin-3-yl)-2-(methylamino)propanamide;

(S)-N-((S)-5-(3-Chlorobenzyl)-4-oxo-2,3,4,5-tetrahydrobenzo[b][1,4]oxazepin-3-yl)-2-(methylamino)propanamide;

(S)-N-((S)-5-(4-Chlorobenzyl)-4-oxo-2,3,4,5-tetrahydrobenzo[b][1,4]oxazepin-3-yl)-2-(methylamino)propanamide;

(S)-5-((6-bromo-2-methoxynaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate and 3-{[(S)-9-(6-Bromo-2-methoxy-naphthalen-1-ylmethyl)-7-((S)-2-methylamino-propionylamino)-8-oxo-6,7,8,9-tetrahydro-5-oxa-9-aza-benzocycloheptene-4-carbonyl]-amino}-propionic acid trifluoroacetate.

4-({[(S)-9-(6-Bromo-2-methoxy-naphthalen-1-ylmethyl)-7-((S)-2-methylamino-propionylamino)-8-oxo-6,7,8,9-tetrahydro-5-oxa-9-aza-benzocycloheptene-4-carbonyl]-amino}-methyl)-benzoic acid methyl ester;

(S)-5-((6-Carboxy-2-methoxynaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate;

5-(((S)-9-((2-Hydroxyethyl)(methyl)carbamoyl)-3-((S)-2-(methylamino)propanamido)-4-oxo-3,4-dihydrobenzo[b][1,4]oxazepin-5(2H)-yl)methyl)-6-methoxy-2-naphthoic acid trifluoroacetate;

S)-5-((4-Bromonaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate;

(S)-N-((S)-5-((4-Bromonaphthalen-1-yl)methyl)-9-(4-(2-hydroxyethyl)piperazine-1-carbonyl)-4-oxo-2,3,4,5-tetrahydrobenzo[b][1,4]oxazepin-3-yl)-2-(methylamino)propanamide;

(S)-N-((S)-5-((4-Bromonaphthalen-1-yl)methyl)-9-(4-(3-hydroxypropyl)piperazine-1-carbonyl)-4-oxo-2,3,4,5-tetrahydrobenzo[b][1,4]oxazepin-3-yl)-2-(methylamino)propanamide;

(S)-N-((S)-5-((2-Chloro-1-(2-cyanophenyl)-1H-indol-3-yl)methyl)-4-oxo-2,3,4,5-tetrahydrobenzo[b][1,4]oxazepin-3-yl)-2-(methylamino)propanamide;

(S)-N-((S)-5-((1-(2-Cyanophenyl)-1H-indol-4-yl)methyl)-4-oxo-2,3,4,5-tetrahydrobenzo[b][1,4]oxazepin-3-yl)-2-(methylamino)propanamide;

(S)-N-((S)-5-((2-Chloro-1-(phenylsulfonyl)-1H-indol-3-yl)methyl)-4-oxo-2,3,4,5-tetrahydrobenzo[b][1,4]oxazepin-3-yl)-2-(methylamino)propanamide;

(S)-N-[(S)-9-(1-Benzenesulfonyl-2-chloro-1H-indol-3-ylmethyl)-8-oxo-6,7,8,9-tetrahydro-5-oxa-9-aza-benzocyclohepten-7-yl]-2-methylamino-propionamide hydrochloride;

(S)-N-((S)-5-((6-Fluoro-1-methyl-2-oxo-1,2-dihydroquinolin-4-yl)methyl)-4-oxo-2,3,4,5-tetrahydrobenzo[b][1,4]oxazepin-3-yl)-2-(methylamino)propanamide;

(S)-N-[(S)-9-(1-Benzyl-2-chloro-1H-indol-3-ylmethyl)-8-oxo-6,7,8,9-tetrahydro-5-oxa-9-aza-benzocyclohepten-7-yl]-2-methylamino-propionamide and (S)-N-((S)-5-((1-Ethyl-2-oxoindolin-4-yl)methyl)-4-oxo-2,3,4,5-tetrahydrobenzo[b][1,4]oxazepin-3-yl)-2-(methylamino)propanamide.

(S)-2-Amino-N-((S)-5-((1-(2-cyanophenyl)-1H-indazol-3-yl)methyl)-4-oxo-2,3,4,5-tetrahydrobenzo[b][1,4]oxazepin-3-yl)propanamide;

(S)-N-((S)-5-((2-Cyano-1-(2-cyanophenyl)-1H-indol-3-yl)methyl)-4-oxo-2,3,4,5-tetrahydrobenzo[b][1,4]oxazepin-3-yl)-2-(methylamino)propanamide trifluoroacetate;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(oxetan-3-ylamino)propanamide;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(2-hydroxy-2-methylpropylamino)propanamide;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(2-hydroxyethylamino)propanamide;

(S)-N-((S)-5-((1-(2-Cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(ethyl-d5-amino)propanamide;

(S)-N-((S)-5-((1-(2-Cyanophenyl)-6-fluoro-1H-indazol-3-yl)methyl)-4-oxo-2,3,4,5-tetrahydrobenzo[b][1,4]oxazepin-3-yl)-2-(ethylamino)propanamide;

S)-N-((S)-5-((6-Bromo-1-(2-cyanophenyl)-1H-indazol-3-yl)methyl)-4-oxo-2,3,4,5-tetrahydrobenzo[b][1,4]oxazepin-3-yl)-2-(methylamino)propanamide trifluoroacetate;

(S)-N-((S)-5-((2-Cyano-1-(2-cyanophenyl)-1H-indol-3-yl)methyl)-4-oxo-2',3',4,5,5',6'-hexahydro-3H-spiro[benzo[b][1,4]oxazepine-2,4'-pyran]-3-yl)-2-(methylamino)propanamide;

(2S)-N-((2S,3S)-5-((1-(2-Cyanophenyl)-1H-indazol-3-yl)methyl)-2-methyl-4-oxo-2,3,4,5-tetrahydrobenzo[b][1,4]oxazepin-3-yl)-2-(ethylamino)propanamide trifluoroacetate;

(S)-N-((R)-5-((2-Cyano-1-(2-cyanophenyl)-1H-indol-3-yl)methyl)-2,2-dimethyl-4-oxo-2,3,4,5-tetrahydrobenzo[b][1,4]thiazepin-3-yl)-2-(ethylamino)propanamide and (S)-N-((2S,3S)-5-((2-Cyano-1-(2-cyanophenyl)-1H-indol-3-yl)methyl)-2-methyl-4-oxo-2,3,4,5-tetrahydrobenzo[b][1,4]oxazepin-3-yl)-2-(methylamino)propanamide.

(S)-N-((2S,3S)-5-((2-Cyano-1-(2-cyanophenyl)-1H-indol-3-yl)methyl)-2-methyl-4-oxo-2,3,4,5-tetrahydrobenzo[b][1,4]oxazepin-3-yl)-2-(ethylamino)propanamide;

(S)-N-((S)-8-Bromo-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide trifluoroacetate;

(S)-N-((S)-8-Cyano-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide 2,2,2-trifluoroacetate;

3-Cyano-4-(3-(((2S,3S)-2-methyl-3-((S)-2-(methylamino)propanamido)-4-oxo-3,4-dihydrobenzo[b][1,4]oxazepin-5(2H)-yl)methyl)-1H-indazol-1-yl)benzoic acid trifluoroacetate;

3-Cyano-N-ethyl-4-(3-(((2S,3S)-2-methyl-3-((S)-2-(methylamino)propanamido)-4-oxo-3,4-dihydrobenzo[b][1,4]oxazepin-5(2H)-yl)methyl)-1H-indazol-1-yl)benzamide trifluoroacetate;

(S)-N-((S)-5-((6-Bromo-2-methoxynaphthalen-1-yl)methyl)-4-oxo-2,3,4,5-tetrahydrobenzo[b][1,4]oxazepin-3-yl)-2-(methylamino)butanamide hydrochloride;

(S)-N-((S)-5-((6-Bromo-2-methoxynaphthalen-1-yl)methyl)-4-oxo-2,3,4,5-tetrahydrobenzo[b][1,4]oxazepin-3-yl)-2-(2-hydroxyethylamino)butanamide trifluoroacetate;

(S)-N-((S)-5-(Benzo[d]isoxazol-3-ylmethyl)-4-oxo-2',3',4,5,5',6'-hexahydro-3H-spiro[benzo[b][1,4]oxazepine-2,4'-pyran]-3-yl)-2-(methylamino)propanamide hydrochloride;

(S)-N-((S)-5-((2-(Difluoromethoxy)naphthalen-1-yl)methyl)-4-oxo-2',3',4,5,5',6'-hexahydro-3H-spiro[benzo[b][1,4]oxazepine-2,4'-pyran]-3-yl)-2-(methylamino)propanamide hydrochloride;

(S)-N-((R)-5-((2-(Difluoromethoxy)naphthalen-1-yl)methyl)-4-oxo-2',3',4,5,5',6'-hexahydro-3H-spiro[benzo[b][1,4]oxazepine-2,4'-pyran]-3-yl)-2-(methylamino)propanamide hydrochloride;

(S)-N-((S)-5-((6-Bromo-2-methoxynaphthalen-1-yl)methyl)-9-fluoro-4-oxo-2,3,4,5-tetrahydrobenzo[b][1,4]oxazepin-3-yl)-2-(methylamino)propanamide hydrochloride and (S)-N-((S)-5-((6-Bromo-2-methoxynaphthalen-1-yl)methyl)-4-oxo-9-(trifluoromethyl)-2,3,4,5-tetrahydrobenzo[b][1,4]oxazepin-3-yl)-2-(methylamino)propanamide hydrochloride.

(S)-2-(Methylamino)-N-((S)-5-((2-methylnaphthalen-1-yl)methyl)-4-oxo-9-(trifluoromethyl)-2,3,4,5-tetrahydrobenzo[b][1,4]oxazepin-3-yl)propanamide hydrochloride;

(S)-N-((S)-5-(Benzo[d]isoxazol-3-ylmethyl)-4-oxo-9-(trifluoromethyl)-2,3,4,5-tetrahydrobenzo[b][1,4]oxazepin-3-yl)-2-(methylamino)propanamide hydrochloride;

(S)-N-((S)-9-Bromo-5-((2-methylnaphthalen-1-yl)methyl)-4-oxo-2,3,4,5-tetrahydrobenzo[b][1,4]oxazepin-3-yl)-2-(methylamino)propanamide hydrochloride;

(S)-5-((2-Methoxynaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate and (S)-N-((S)-5-((6-Bromo-2-methoxynaphthalen-1-yl)methyl)-9-methyl-4-oxo-2,3,4,5-tetrahydrobenzo[b][1,4]oxazepin-3-yl)-2-(methylamino)propanamide hydrochloride.

One aspect of the invention is directed to compounds of formula 1 where W is H and X is methyl, methyl-d3, ethyl, ethyl-d5, n-propyl, 2-hydroxyethyl, cyclobutyl or oxetan-3-yl.

In another aspect, the invention is directed to compounds of formula 1 where Y is methyl, ethyl, hydroxymethyl, or 1-hydroxyethyl.

In another aspect, the invention is directed to compounds of formula 1 where R1 is H, $C_{1-6}$-alkyl, cyano, or halo.

In another aspect, the invention is directed to compounds of formula 1 where R2 is H, $C_{1-6}$-alkyl, halo, cyano, or alkoxy In another aspect, the invention is directed to compounds of formula 1 where R3 is H, $C_{1-6}$-alkyl, halo, cyano, or $C_{1-6}$-alkoxy In another aspect, the invention is directed to compounds of formula 1 where R4 is H or $C_{1-6}$-alkyl.

In another aspect, the invention is directed to compounds of formula 1 where Z is aryl or aryl-$C_{1-6}$-alkyl-bicyclic.

Another aspect of the invention is directed to compounds of the formula II

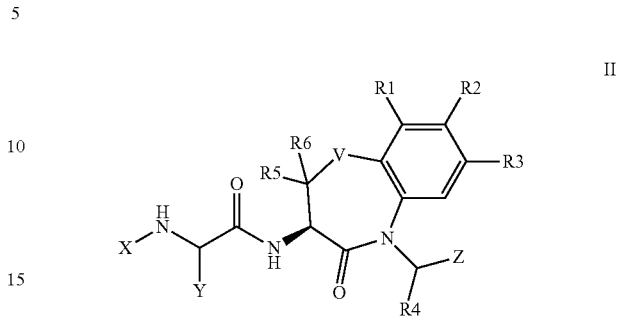

wherein:

X is selected from $C_{1-6}$-alkyl, aryl-$C_{1-6}$-alkyl, $C_{3-7}$-cycloalkyl-$C_{1-6}$-alkyl, $C_{2-6}$-alkenyl$C_{1-6}$-alkyl or $C_{2-6}$-alkynyl$C_{1-6}$-alkyl; Y is selected from $C_{1-6}$-alkyl or $C_{3-7}$-cycloalkyl-$C_{1-6}$-alkyl; R1 is selected from H, halo, $C_{1-6}$-alkyl, aryl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano or $SO_2R10$; R2 is selected from H, halo, $C_{1-6}$-alkyl, aryl, aryl-$C_{1-6}$-alkyl, $C_{3-7}$-cycloalkyl-$C_{1-6}$-alkyl, acyl, OR7, SR7, NR8R9, N-acyl, N-sulfonyl, cyano or $SO_2R10$; R3 is selected from H, halo, $C_{1-6}$-alkyl, aryl, aryl-$C_{1-6}$alkyl, $C_{3-7}$-cycloalkyl-$C_{1-6}$-alkyl, acyl, OR7, SR7, NR8R9, N-acyl, N-sulfonyl, cyano or $SO_2R10$; R4 is selected from H or $C_{1-6}$-alkyl; R5 and R6 are the same or different and independently selected from H, $C_{1-6}$-alkyl, aryl or $C_{3-7}$-cycloalkyl, or R5 and R6 together with the carbon to which they are bound can form a $C_{3-7}$-carbocycle or heterocycle and with the proviso that R5 and R6 are not both hydrogen; V is selected from S or O; Z is selected from aryl, heteroaryl, polycyclic aromatics, polycyclic heteroaromatics, mixed aryl and non-aryl polycycles or mixed aryl and non-aryl polyheterocycles; R7 is selected from $C_{1-6}$-alkyl, aryl, heteroaryl or sulfonyl; R8 and R9 are the same or different and independently selected from H, $C_{1-6}$-alkyl, aryl, aryl-$C_{1-6}$-alkyl or heteroaryl-$C_{1-6}$-alkyl; R10 is selected from $C_{1-6}$alkyl, aryl, heterocyclyl or aryl-$C_{1-6}$-alkyl;

or a pharmaceutically acceptable salt thereof.

Another aspect of the present invention is compounds of formula III:

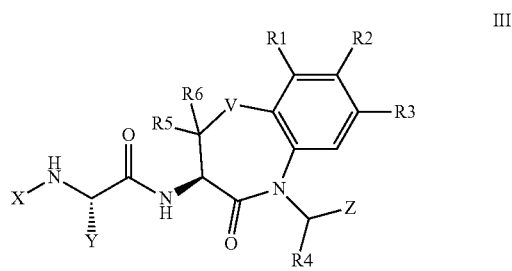

wherein:

X is selected from $C_{1-6}$-alkyl, aryl-$C_{1-6}$-alkyl or $C_{3-7}$-cycloalkyl-$C_{1-6}$-alkyl; Y is selected from $C_{1-6}$-alkyl or $C_{3-7}$-cycloalkyl-$C_{1-6}$-alkyl; R1 is selected from H, halo, $C_{1-6}$-alkyl, acyl, OR7, N-acyl, N-sulfonyl, cyano or $SO_2R10$; R2 is selected from H, halo, $C_{1-6}$alkyl, acyl, OR7, N-acyl, N-sulfonyl, cyano or $SO_2R10$; R3 is selected from H, halo, $C_{1-6}$-alkyl, acyl, OR7, N-acyl, N-sulfonyl, cyano or $SO_2R10$; R4 is selected from H or C$_{1-6}$-alkyl; R5 and R6 are the same or different and independently selected from H or C$_{1-6}$-alkyl but are not both hydrogen, or R5 and R6 together with the carbon to which they are bound can form a C$_{3-6}$-carbocycle or heterocycle V is selected from S or O; Z is selected from aryl, heteroaryl, polycyclic aromatics or polycyclic heteroaromatics; R7 is selected from C$_{1-6}$-alkyl, aryl, heteroaryl or sulfonyl; R10 is selected from C$_{1-6}$-alkyl, aryl, heterocyclyl or aryl-C$_{1-6}$-alkyl;

or a pharmaceutically acceptable salt thereof.

Another aspect of the present invention is the compound of formula III wherein:

X is selected from methyl, ethyl, methyl-d3, ethyl-d5, n-propyl; i-propyl, 2-hydroxyethyl, 3-hydroxypropyl, cyclopropyl, methylcyclopropyl, cyclobutyl, cyclopentyl or oxetan-3-yl;

Y is selected from methyl, ethyl, cyclopropyl, hydroxymethyl, (S)-1-hydroxyethyl or (R)-1-hydroxyethyl; R1 is selected from H, halo, C$_{1-6}$-alkyl, acyl, OR7, N-acyl, N-sulfonyl or cyano; R2 is selected from H, halo, C$_{1-6}$-alkyl, acyl, OR7, N-acyl, N-sulfonyl or cyano; R3 is selected from H, halo, C$_{1-6}$-alkyl, acyl, OR7, N-acyl, N-sulfonyl or cyano; R4 is selected from H or C$_{1-6}$-alkyl; R5 and R6 are the same or different and independently selected from H or C$_{1-6}$-alkyl but are both not hydrogen, or R5 and R6 together with the carbon to which they are bound can form a C$_{3-6}$-carbocycle or heterocycle; V is selected from S or O; Z is selected from aryl, heteroaryl, polycyclic aromatics or polycyclic heteroaromatics; R7 is selected from C$_{1-6}$-alkyl, aryl, heteroaryl or sulfonyl;

or a pharmaceutically acceptable salt thereof.

Another aspect of the present invention are compounds of formula III wherein:

X is selected from methyl, ethyl, methyl-d3, ethyl-d5 or 2-hydroxyethyl; Y is selected from methyl, ethyl, cyclopropyl, hydroxymethyl or (S)-1-hydroxyethyl; R1 is selected from H, halo, C$_{1-6}$-alkyl, acyl, N-acyl, N-sulfonyl or cyano; R2 is selected from H, halo, C$_{1-6}$-alkyl, acyl, N-acyl, N-sulfonyl or cyano; R3 is selected from H, halo, C$_{1-6}$-alkyl, acyl, N-acyl, N-sulfonyl or cyano; R4 is selected from H, methyl or ethyl; R5 and R6 are the same or different and independently selected from H or C$_{1-6}$-alkyl but are both not hydrogen, or R5 and R6 together with the carbon to which they are bound can form a C$_{3-6}$-carbocycle or heterocycle; V is selected from S or O; Z is selected from aryl, heteroaryl, polycyclic aromatics or polycyclic heteroaromatics;

or a pharmaceutically acceptable salt thereof.

Another aspect of the present invention relates to compounds of formula III wherein:

X is selected from methyl, ethyl, methyl-d3, ethyl-d5 or 2-hydroxyethyl; Y is selected from methyl, ethyl, hydroxymethyl or (S)-1-hydroxyethyl; R1 is selected from H, F, Cl, Br, carboxyamide, N-acyl, N-sulfonyl or cyano; R2 is selected from H, F, Cl, Br, carboxyamide, N-acyl, N-sulfonyl or cyano; R3 is selected from H, F, Cl, Br, carboxyamide, N-acyl, N-sulfonyl or cyano; R4 is H; R5 and R6 are the same or different and independently selected from H or C$_{1-6}$-alkyl but are both not hydrogen, or R5 and R6 together with the carbon to which they are bound can form a C$_3$-C$_6$ carbocycle or heterocycle; V is selected from S or O; Z is selected from aryl, heteroaryl, polycyclic aromatics or polycyclic heteroaromatics;

or a pharmaceutically acceptable salt thereof.

Yet another aspect of the present invention relates to compounds of formula III wherein:

X is selected from methyl, ethyl, methyl-d3 or ethyl-d5; Y is selected from methyl, ethyl, hydroxymethyl or (S)-1-hydroxyethyl; R1 is selected from H, F, Cl, Br, carboxyamide, N-acyl, N-sulfonyl or cyano; R2 is selected from H, F, Cl, Br, carboxyamide, N-acyl, N-sulfonyl or cyano; R3 is selected from H, F, Cl, Br or cyano; R4 is H; R5 and R6 are the same or different and independently selected from H or C$_{1-6}$-alkyl but are both not hydrogen, or R5 and R6 together with the carbon to which they are bound can form a C$_{3-6}$-carbocycle or heterocycle; V is O; Z is selected from 2,5-disubstituted phenyl, 2-substituted-naphthalen-1-yl, 2,5-disubstituted-naphthalen-1-yl, 2,6-disubstituted-naphthalen-1-yl, 2,7-disubstituted-naphthalen-1-yl, 5-substituted-naphthalen-1-yl, 1-substituted-1H-indazol-3-yl, benzo[d]isoxazole-3-yl, 4-quinolinyl, 5-quinolinyl, 3-substituted-quinolin-4-yl, 1,2-disubstituted-indol-3-yl, 1,6-disubstituted-1H-indazol-3-yl, 1-substituted-1,3-dihydro-indol-2-one-4-yl, 1,6-1H-quinolin-2-one-4-yl, 2-substituted-2,3-dihydro-1H-isoindol-4-yl, 2-(4-Methyl-indol-1-yl)-benzonitrile or 1-substituted-indol-4-yl;

or a pharmaceutically acceptable salt thereof.

Another aspect of the present invention relates to compounds of formula III wherein:

X is selected from methyl, ethyl, methyl-d3 or ethyl-d5; Y is selected from methyl, ethyl, hydroxymethyl or (S)-1-hydroxyethyl; R1 is selected from H, F, Cl, Br, carboxyamide, N-acyl, N-sulfonyl or cyano; R2 is selected from H, F, Cl, Br, carboxyamide, N-acyl, N-sulfonyl or cyano; R3 is selected from H, F, Cl, Br or cyano; R4 is H; R5 and R6 are methyl or H but are not both hydrogen; V is O; Z is selected from 5-bromo-2-methoxynaphthalen-1-yl, 6-bromo-2-(d3-methoxy)-naphthalen-1-yl, 6-bromo-2-methoxy-naphthalen-1-yl, 3-methoxyquinolin-4-yl, quinolin-4-yl, 2-(2,2,2-trifluoroethoxyl)naphthalen-1-yl, 2-difluoromethoxy-naphthalen-1-yl,

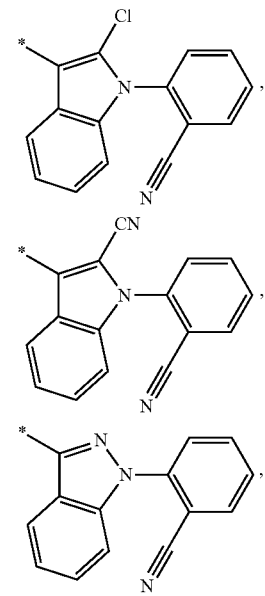

-continued

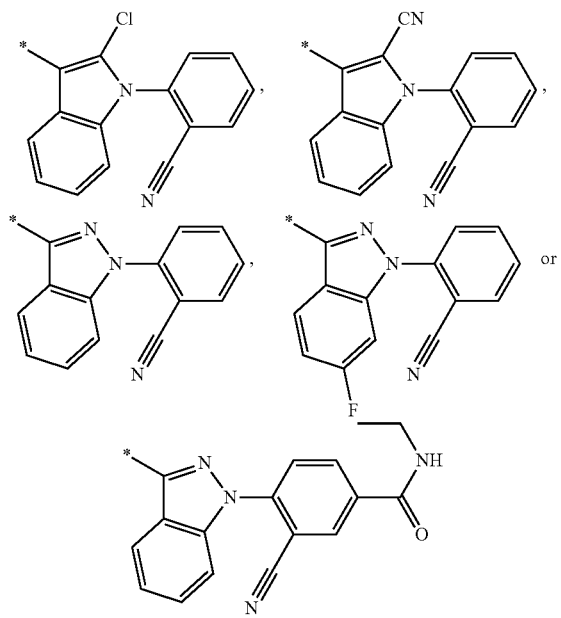

or a pharmaceutically acceptable salt thereof.

Yet another aspect of the present invention relates to compounds of formula III
wherein:

X is selected from methyl, ethyl, methyl-d3 or ethyl-d5; Y is selected from methyl, ethyl, hydroxymethyl or (S)-1-hydroxyethyl; R1 is selected from H, F, Cl, Br, carboxyamide, N-acyl, N-sulfonyl or cyano; R2 is selected from H, F, Cl, Br, carboxyamide, N-acyl, N-sulfonyl or cyano; R3 is selected from H, F, Cl, Br or cyano; R4 is H; R5 and R6 together form a ring selected from

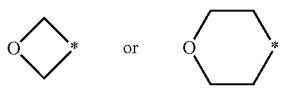

V is O; Z is selected from 5-bromo-2-methoxynaphthalen-1-yl, 6-bromo-2-(d3-methoxy)-naphthalen-1-yl, 6-bromo-2-methoxy-naphthalen-1-yl, 3-methoxyquinolin-4-yl, quinolin-4-yl, 2-(2,2,2-trifluoroethoxyl)naphthalen-1-yl, 2-difluoromethoxy-naphthalen-1-yl,

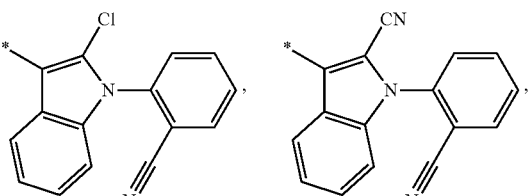

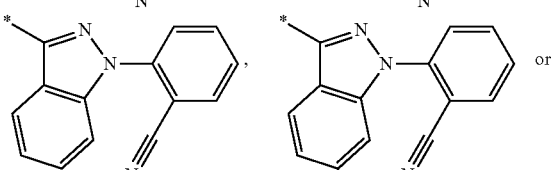

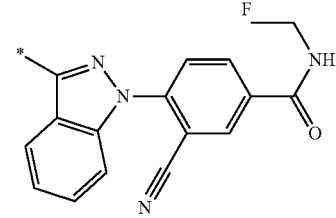

or a pharmaceutically acceptable salt thereof.

Another aspect of the present invention relates to compounds of formula III
wherein:

X is selected from methyl, ethyl, methyl-d3 or ethyl-d5; Y is selected from methyl, ethyl, hydroxymethyl or (S)-1-hydroxyethyl; R1 is selected from H, F, Cl, Br, carboxyamide, N-acyl, N-sulfonyl or cyano; R2 is selected from H, F, Cl, Br, carboxyamide, N-acyl, N-sulfonyl or cyano; R3 is selected from H, F, Cl, Br or cyano; R4 is H; R5 is

R6 is

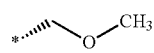

V is O; Z is selected from 5-bromo-2-methoxynaphthalen-1-yl, 6-bromo-2-(d3-methoxy)-naphthalen-1-yl, 6-bromo-2-methoxy-naphthalen-1-yl, 3-methoxyquinolin-4-yl, quinolin-4-yl, 2-(2,2,2-trifluoroethoxy)naphthalen-1-yl, 2-difluoromethoxy-naphthalen-1-yl, or a pharmaceutically acceptable salt thereof.

Another aspect of the present invention relates to compounds of formula III
wherein:

X is selected from methyl, ethyl, methyl-d3 or ethyl-d5; Y is selected from methyl, ethyl, hydroxymethyl or (S)-1-hydroxyethyl; R1 is selected from H, F, Cl, Br, carboxyamide, N-acyl, N-sulfonyl or cyano; R2 is selected from H, F, Cl, Br, carboxyamide, N-acyl, N-sulfonyl or cyano; R3 is selected from H, F, Cl, Br or cyano; R4 is H; R5 is

R6 is

V is O; Z is selected from 5-bromo-2-methoxynaphthalen-1-yl, 6-bromo-2-(d3-methoxy)-naphthalen-1-yl, 6-bromo-2-methoxy-naphthalen-1-yl, 3-methoxyquinolin-4-yl, quinolin-4-yl, 2-(2,2,2-trifluoroethoxyl)naphthalen-1-yl, 2-difluoromethoxy-naphthalen-1-yl,

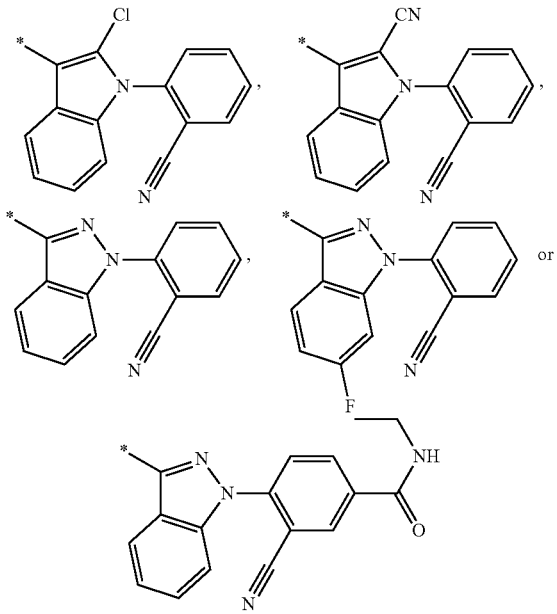

or a pharmaceutically acceptable salt thereof.

Another aspect of the invention relates to compounds of the formula (2S)-N-(5-(((6-Bromo-2-methoxynaphthalen-1-yl)methyl)-(3S)-4-oxo-4,5-dihydro-3H-spiro[benzo[b][1,4]oxazepine-2,1'-cyclohexane]-3-yl)-2-(methylamino)propanamide hydrochloride;

6-Methoxy-5-(((S)-3-((S)-2-(methylamino)propanamido)-4-oxo-2',3',5',6'-tetrahydro-3H-spiro[benzo[b][1,4]oxazepine-2,4'-pyran]-5(4H)-yl)methyl)-2-naphthoic acid trifluoroacetate;

6-Methoxy-5-(((S)-3-((S)-2-(methylamino)propanamido)-4-oxo-2',3',5',6'-tetrahydro-3H-spiro[benzo[b][1,4]oxazepine-2,4'-pyran]-5(4H)-yl)methyl)-N-(methylsulfonyl)-2-naphthamide trifluoroacetate;

(R)-N-[(S)-5-(((6-Bromo-2-methoxy-naphthalen-1-ylmethyl)-2,2-dimethyl-4-oxo-2,3,4,5-tetrahydro-benzo[b][1,4]thiazepin-3-yl]-2-methylamino-propionamide hydrochloride (S)-N-(5-Benzyl-4-oxo-2,3,4,5-tetrahydrobenzo[b][1,4]thiazepin-3-yl)-2-methylaminopropanamide hydrochloride;

N-(5-Benzyl-1,1,4-trioxo-2,3,4,5-tetrahydrobenzo[b][1,4]thiazepin-3-yl)-2-(S)-(methylamino)propanamide hydrochloride;

N-(5-(4-Phenyl-butyl)-1,1,4-trioxo-2,3,4,5-tetrahydrobenzo[b][1,4]thiazepin-3-yl)-2-(S)-(methylamino)propanamide hydrochloride;

N-(5-Biphenyl-3-ylmethyl-4-oxo-2,3,4,5-tetrahydro-benzo[b][1,4]thiazepin-3-yl)-2-(S)-methylamino-propionamide hydrochloride;

(2S)-N-(5-(((6-Bromo-2-methoxynaphthalen-1-yl)methyl)-(3R)-8,9-difluoro-4-oxo-2',3',5',6'-tetrahydro-3H-spiro[benzo[b][1,4]oxazepine-2,4'-pyran]-3-yl)-2-(methylamino)propanamide hydrochloride;

(2S)-N-(5-(((6-Bromo-2-methoxynaphthalen-1-yl)methyl)-(3S)-8,9-difluoro-4-oxo-2',3',5',6'-tetrahydro-3H-spiro[benzo[b][1,4]oxazepine-2,4'-pyran]-3-yl)-2-(methylamino)propanamide hydrochloride;

(2S)-N-(5-(((6-Bromo-2-methoxynaphthalen-1-yl)methyl)-(3R)-9-fluoro-4-oxo-2',3',5',6'-tetrahydro-3H-spiro[benzo[b][1,4]oxazepine-2,4'-pyran]-3-yl)-2-(methylamino)propanamide hydrochloride;

(2S)-N-(5-(((6-Bromo-2-methoxynaphthalen-1-yl)methyl)-(3S)-9-fluoro-4-oxo-2',3',5',6'-tetrahydro-3H-spiro[benzo[b][1,4]oxazepine-2,4'-pyran]-3-yl)-2-(methylamino)propanamide hydrochloride;

(2S)-N-(5-(((6-Bromo-2-methoxynaphthalen-1-yl)methyl)-(3R)-9-fluoro-4-oxo-2',3',5',6'-tetrahydro-3H-spiro[benzo[b][1,4]oxazepine-2,4'-pyran]-3-yl)-2-(methylamino)butanamide hydrochloride;

(2S)-N-(5-(((6-Bromo-2-methoxynaphthalen-1-yl)methyl)-(3S)-9-fluoro-4-oxo-2',3',5',6'-tetrahydro-3H-spiro[benzo[b][1,4]oxazepine-2,4'-pyran]-3-yl)-2-(methylamino)butanamide hydrochloride;

(2S)-N-(5-(((6-Bromo-2-methoxynaphthalen-1-yl)methyl)-(3S)-8-fluoro-4-oxo-2',3',5',6'-tetrahydro-3H-spiro[benzo[b][1,4]oxazepine-2,4'-pyran]-3-yl)-2-(methylamino)propanamide hydrochloride;

(2S)-N-(5-(((6-Bromo-2-methoxynaphthalen-1-yl)methyl)-(3S)-8-fluoro-4-oxo-2',3',5',6'-tetrahydro-3H-spiro[benzo[b][1,4]oxazepine-2,4'-pyran]-3-yl)-2-(methylamino)butanamide hydrochloride;

(S)-N-((S)-5-((6-Bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-(2-hydroxyethylamino)propanamide;

(2S)-N-(5-(((3-Methoxyquinolin-N-oxide-4-yl)methyl)-(3S)-4-oxo-2',3',5',6'-tetrahydro-3H-spiro[benzo[b][1,4]oxazepine-2,4'-pyran]-3-yl)-2-(methylamino)propanamide;

(2S)-N-(5-(((6-Bromo-2-methoxynaphthalen-1-yl)methyl)-(3S)-4-oxo-2',3',5',6'-tetrahydro-3H-spiro[benzo[b][1,4]oxazepine-2,4'-pyran]-3-yl)-2-(methyl-d3-amino)propanamide hydrochloride;

(2S)-N-(5-(((6-Bromo-2-(methoxy-d3)-naphthalen-1-yl)methyl)-(3S)-4-oxo-2',3',5',6'-tetrahydro-3H-spiro[benzo[b][1,4]oxazepine-2,4'-pyran]-3-yl)-2-(methyl-d3-amino)propanamide hydrochloride;

(R)-N-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-aminopropanamide;

(S)-N-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-aminopropanamide;

(S)-N-{(R)-9-[2-(2-Methoxy-ethoxy)-acetylamino]-5-naphthalen-1-ylmethyl-4-oxo-2,3,4,5-tetrahydro-benzo[b][1,4]thiazepin-3-yl}-2-methylamino-propionamide hydrochloride;

1-Acetyl-piperidine-4-carboxylic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide;

5-Oxo-hexanoic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide hydrochloride;

3,4,5-Trimethoxy-N-[(R)-3-((S)-2-methylamino-propionylamino)-5-naphthalen-1-ylmethyl-4-oxo-2,3,4,5-tetrahydro-benzo[b][1,4]thiazepin-9-yl]-benzamide hydrochloride;

6-Oxo-heptanoic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide hydrochloride;

(S)-N-((R)-9-Amino-5-naphthalen-1-ylmethyl-4-oxo-2,3,4,5-tetrahydro-benzo[b][1,4]thiazepin-3-yl)-2-methylamino-propionamide hydrochloride;

N-[(R)-3-((S)-2-Methylamino-propionylamino)-5-naphthalen-1-ylmethyl-4-oxo-2,3,4,5-tetrahydro-benzo[b][1,4]thiazepin-9-yl]-benzamide hydrochloride;

(S)-N-[(S)-9-(6-Bromo-2-methoxy-naphthalen-1-ylmethyl)-8-oxo-6,7,8,9-tetrahydro-5-oxa-9-aza-benzocyclohepten-7-yl]-2-methylamino-propionamide trifluoroacetate;

(S)-N-[(S)-9-(6-Cyclopropyl-2-methoxy-naphthalen-1-ylmethyl)-8-oxo-6,7,8,9-tetrahydro-5-oxa-9-aza-benzocyclohepten-7-yl]-2-methylamino-propionamide trifluoroacetate;

Methyl 6-methoxy-5-(((S)-3-((S)-2-(methylamino)propanamido)-4-oxo-3,4-dihydrobenzo[b][1,4]oxazepin-5(2H)-yl)methyl)-2-naphthoate trifluoroacetate;

6-Methoxy-5-(((S)-3-((S)-2-(methylamino)propanamido)-4-oxo-3,4-dihydrobenzo[b][1,4]oxazepin-5(2H)-yl)methyl)-2-naphthoic acid trifluoroacetate;

6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carboxylic acid (2-hydroxy-ethyl)-methyl-amide;

4-({6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carbonyl}-amino)-butyric acid trifluoroacetate;

6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carboxylic acid dimethylamide trifluoroacetate;

(S)-N-[(S)-9-(7-Bromo-3-methoxy-naphthalen-2-ylmethyl)-3-methyl-8-oxo-6,7,8,9-tetrahydro-5-oxa-9-aza-benzocyclohepten-7-yl]-2-methylamino-propionamide trifluoroacetate;

(2S,3R)-2-Amino-N-[(S)-9-(7-bromo-3-methoxy-naphthalen-2-ylmethyl)-3-methyl-8-oxo-6,7,8,9-tetrahydro-5-oxa-9-aza-benzocyclohepten-7-yl]-3-hydroxy-butyramide trifluoroacetate;

(2S,3S)-2-Amino-N-[(S)-9-(7-bromo-3-methoxy-naphthalen-2-ylmethyl)-3-methyl-8-oxo-6,7,8,9-tetrahydro-5-oxa-9-azabenzocyclohepten-7-yl]-3-hydroxy-butyramide trifluoroacetate;

(S)-N-((2S,3S)-5-((6-Bromo-2-methoxynaphthalen-1-yl)methyl)-2,8-dimethyl-4-oxo-2,3,4,5-tetrahydrobenzo[b][1,4]oxazepin-3-yl)-2-(methylamino)propanamide trifluoroacetate;

Methyl 5-(((2S,3S)-2,8-dimethyl-3-((S)-2-(methylamino)propanamido)-4-oxo-3,4-dihydrobenzo[b][1,4]oxazepin-5(2H)-yl)methyl)-6-methoxy-2-naphthoate trifluoroacetate;

(2S,3S)-2-Amino-N-[(6S,7S)-9-(6-bromo-2-methoxy-naphthalen-1-ylmethyl)-3,6-dimethyl-8-oxo-6,7,8,9-tetrahydro-5-oxa-9-aza-benzocyclohepten-7-yl]-3-hydroxy-butyramide trifluoroacetate;

(S)-N-((S)-5-((6-Bromo-2-methoxynaphthalen-1-yl)methyl)-4-oxo-7-(trifluoromethyl)-2,3,4,5-tetrahydrobenzo[b][1,4]oxazepin-3-yl)-2-(methylamino)propanamide trifluoroacetate;

(S)-N-[(6S,7S)-9-(6-Bromo-2-methoxy-naphthalen-1-ylmethyl)-6-methyl-8-oxo-2-trifluoromethyl-6,7,8,9-tetrahydro-5-oxa-9-aza-benzocyclohepten-7-yl]-2-methylamino-propionamide trifluoroacetate;

(S)-2-Methylamino-N-[(S)-9-((2-methyl-naphthalen-1-ylmethyl)-8-oxo-6,7,8,9-tetrahydro-5-oxa-9-aza-benzocyclohepten-7-yl]-propionamide;

(S)-N-((S)-5-((2-Chlorobenzyl)-4-oxo-2,3,4,5-tetrahydrobenzo[b][1,4]oxazepin-3-yl)-2-(methylamino)propanamide;

(S)-N-((S)-5-(3-Chlorobenzyl)-4-oxo-2,3,4,5-tetrahydrobenzo[b][1,4]oxazepin-3-yl)-2-(methylamino)propanamide;

(S)-N-((S)-5-(4-Chlorobenzyl)-4-oxo-2,3,4,5-tetrahydrobenzo[b][1,4]oxazepin-3-yl)-2-(methylamino)propanamide;

(S)-5-((6-bromo-2-methoxynaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate;

3-{[(S)-9-(6-Bromo-2-methoxy-naphthalen-1-ylmethyl)-7-((S)-2-methylamino-propionylamino)-8-oxo-6,7,8,9-tetrahydro-5-oxa-9-aza-benzocycloheptene-4-carbonyl]-amino}-propionic acid trifluoroacetate;

4-({[(S)-9-(6-Bromo-2-methoxy-naphthalen-1-ylmethyl)-7-((S)-2-methylamino-propionylamino)-8-oxo-6,7,8,9-tetrahydro-5-oxa-9-aza-benzocycloheptene-4-carbonyl]-amino}-methyl)-benzoic acid methyl ester;

(S)-5-((6-Carboxy-2-methoxynaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate;

5-(((S)-9-((2-Hydroxyethyl)(methyl)carbamoyl)-3-((S)-2-(methylamino)propanamido)-4-oxo-3,4-dihydrobenzo[b][1,4]oxazepin-5(2H)-yl)methyl)-6-methoxy-2-naphthoic acid trifluoroacetate;

S)-5-((4-Bromonaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate;

(S)-N-((S)-5-((4-Bromonaphthalen-1-yl)methyl)-9-(4-(2-hydroxyethyl)piperazine-1-carbonyl)-4-oxo-2,3,4,5-tetrahydrobenzo[b][1,4]oxazepin-3-yl)-2-(methylamino)propanamide;

(S)-N-((S)-5-((4-Bromonaphthalen-1-yl)methyl)-9-(4-(3-hydroxypropyl)piperazine-1-carbonyl)-4-oxo-2,3,4,5-tetrahydrobenzo[b][1,4]oxazepin-3-yl)-2-(methylamino)propanamide;

(S)-N-((S)-5-((2-Chloro-1-(2-cyanophenyl)-1H-indol-3-yl)methyl)-4-oxo-2,3,4,5-tetrahydrobenzo[b][1,4]oxazepin-3-yl)-2-(methylamino)propanamide;

(S)-N-((S)-5-((1-(2-Cyanophenyl)-1H-indol-4-yl)methyl)-4-oxo-2,3,4,5-tetrahydrobenzo[b][1,4]oxazepin-3-yl)-2-(methylamino)propanamide;

(S)-N-((S)-5-((2-Chloro-1-(phenylsulfonyl)-1H-indol-3-yl)methyl)-4-oxo-2,3,4,5-tetrahydrobenzo[b][1,4]oxazepin-3-yl)-2-(methylamino)propanamide;

(S)-N-[(S)-9-(1-Benzenesulfonyl-2-chloro-1H-indol-3-ylmethyl)-8-oxo-6,7,8,9-tetrahydro-5-oxa-9-aza-benzocyclohepten-7-yl]-2-methylamino-propionamide hydrochloride;

(S)-N-((S)-5-((6-Fluoro-1-methyl-2-oxo-1,2-dihydroquinolin-4-yl)methyl)-4-oxo-2,3,4,5-tetrahydrobenzo[b][1,4]oxazepin-3-yl)-2-(methylamino)propanamide;

(S)-N-[(S)-9-(1-Benzyl-2-chloro-1H-indol-3-ylmethyl)-8-oxo-6,7,8,9-tetrahydro-5-oxa-9-aza-benzocyclohepten-7-yl]-2-methylamino-propionamide;

(S)-N-((S)-5-((l-Ethyl-2-oxoindolin-4-yl)methyl)-4-oxo-2,3,4,5-tetrahydrobenzo[b][1,4]oxazepin-3-yl)-2-(methylamino)propanamide;

(S)-2-Amino-N-((S)-5-((1-(2-cyanophenyl)-1H-indazol-3-yl)methyl)-4-oxo-2,3,4,5-tetrahydrobenzo[b][1,4]oxazepin-3-yl)propanamide;

(S)-N-((S)-5-((2-Cyano-1-(2-cyanophenyl)-1H-indol-3-yl)methyl)-4-oxo-2,3,4,5-tetrahydrobenzo[b][1,4]oxazepin-3-yl)-2-(methylamino)propanamide trifluoroacetate;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(oxetan-3-ylamino)propanamide;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(2-hydroxy-2-methylpropylamino)propanamide;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(2-hydroxyethylamino)propanamide;

(S)-N-((S)-5-((1-(2-Cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(ethyl-d5-amino)propanamide;

(S)-N-((S)-5-((1-(2-Cyanophenyl)-6-fluoro-1H-indazol-3-yl)methyl)-4-oxo-2,3,4,5-tetrahydrobenzo[b][1,4]oxazepin-3-yl)-2-(ethylamino)propanamide;

S)-N-((S)-5-((6-Bromo-1-(2-cyanophenyl)-1H-indazol-3-yl)methyl)-4-oxo-2,3,4,5-tetrahydrobenzo[b][1,4]oxazepin-3-yl)-2-(methylamino)propanamide trifluoroacetate;

(S)-N-((S)-5-((2-Cyano-1-(2-cyanophenyl)-1H-indol-3-yl)methyl)-4-oxo-2',3',4,5,5',6'-hexahydro-3H-spiro[benzo[b][1,4]oxazepine-2,4'-pyran]-3-yl)-2-(methylamino)propanamide;

(2S)-N-((2S,3S)-5-((1-(2-Cyanophenyl)-1H-indazol-3-yl)methyl)-2-methyl-4-oxo-2,3,4,5-tetrahydrobenzo[b][1,4]oxazepin-3-yl)-2-(ethylamino)propanamide trifluoroacetate;

(S)-N-((R)-5-((2-Cyano-1-(2-cyanophenyl)-1H-indol-3-yl)methyl)-2,2-dimethyl-4-oxo-2,3,4,5-tetrahydrobenzo[b][1,4]thiazepin-3-yl)-2-(ethylamino)propanamide;

(S)-N-((2S,3S)-5-((2-Cyano-1-(2-cyanophenyl)-1H-indol-3-yl)methyl)-2-methyl-4-oxo-2,3,4,5-tetrahydrobenzo[b][1,4]oxazepin-3-yl)-2-(methylamino)propanamide;

(S)-N-((2S,3S)-5-((2-Cyano-1-(2-cyanophenyl)-1H-indol-3-yl)methyl)-2-methyl-4-oxo-2,3,4,5-tetrahydrobenzo[b][1,4]oxazepin-3-yl)-2-(ethylamino)propanamide;

(S)-N-((S)-8-Bromo-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide trifluoroacetate;

(S)-N-((S)-8-Cyano-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide 2,2,2-trifluoroacetate;

3-Cyano-4-(3-(((2S,3S)-2-methyl-3-((S)-2-(methylamino)propanamido)-4-oxo-3,4-dihydrobenzo[b][1,4]oxazepin-5(2H)-yl)methyl)-1H-indazol-1-yl)benzoic acid trifluoroacetate;

3-Cyano-N-ethyl-4-(3-(((2S,3S)-2-methyl-3-((S)-2-(methylamino)propanamido)-4-oxo-3,4-dihydrobenzo[b][1,4]oxazepin-5(2H)-yl)methyl)-1H-indazol-1-yl)benzamide trifluoroacetate;

(S)-N-((S)-5-((6-Bromo-2-methoxynaphthalen-1-yl)methyl)-4-oxo-2,3,4,5-tetrahydrobenzo[b][1,4]oxazepin-3-yl)-2-(methylamino)butanamide hydrochloride;

(S)-N-((S)-5-((6-Bromo-2-methoxynaphthalen-1-yl)methyl)-4-oxo-2,3,4,5-tetrahydrobenzo[b][1,4]oxazepin-3-yl)-2-(2-hydroxyethylamino)butanamide trifluoroacetate;

(S)-N-((S)-5-(Benzo[d]isoxazol-3-ylmethyl)-4-oxo-2',3',4,5,5',6'-hexahydro-3H-spiro[benzo[b][1,4]oxazepine-2,4'-pyran]-3-yl)-2-(methylamino)propanamide hydrochloride;

(S)-N-((S)-5-((2-(Difluoromethoxy)naphthalen-1-yl)methyl)-4-oxo-2',3',4,5,5',6'-hexahydro-3H-spiro[benzo[b][1,4]oxazepine-2,4'-pyran]-3-yl)-2-(methylamino)propanamide hydrochloride;

(S)-N-((R)-5-((2-(Difluoromethoxy)naphthalen-1-yl)methyl)-4-oxo-2',3',4,5,5',6'-hexahydro-3H-spiro[benzo[b][1,4]oxazepine-2,4'-pyran]-3-yl)-2-(methylamino)propanamide hydrochloride;

(S)-N-((S)-5-((6-Bromo-2-methoxynaphthalen-1-yl)methyl)-9-fluoro-4-oxo-2,3,4,5-tetrahydrobenzo[b][1,4]oxazepin-3-yl)-2-(methylamino)propanamide hydrochloride;

(S)-N-((S)-5-((6-Bromo-2-methoxynaphthalen-1-yl)methyl)-4-oxo-9-(trifluoromethyl)-2,3,4,5-tetrahydrobenzo[b][1,4]oxazepin-3-yl)-2-(methylamino)propanamide hydrochloride;

(S)-2-(Methylamino)-N-((S)-5-((2-methylnaphthalen-1-yl)methyl)-4-oxo-9-(trifluoromethyl)-2,3,4,5-tetrahydrobenzo[b][1,4]oxazepin-3-yl)propanamide hydrochloride;

(S)-N-((S)-5-(Benzo[d]isoxazol-3-ylmethyl)-4-oxo-9-(trifluoromethyl)-2,3,4,5-tetrahydrobenzo[b][1,4]oxazepin-3-yl)-2-(methylamino)propanamide hydrochloride;

(S)-N-((S)-9-Bromo-5-((2-methylnaphthalen-1-yl)methyl)-4-oxo-2,3,4,5-tetrahydrobenzo[b][1,4]oxazepin-3-yl)-2-(methylamino)propanamide hydrochloride;

(S)-5-((2-Methoxynaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate and (S)-N-((S)-5-((6-Bromo-2-methoxynaphthalen-1-yl)methyl)-9-methyl-4-oxo-2,3,4,5-tetrahydrobenzo[b][1,4]oxazepin-3-yl)-2-(methylamino)propanamide hydrochloride.

A preferred aspect of the invention are compounds of the formula (2S)-N-(5-((6-bromo-2-methoxynaphthalen-1-yl)methyl)-2,2-dimethyl-4-oxo-2,3,4,5-tetrahydrobenzo[b][1,4]oxazepin-3-yl)-2-(methylamino)propanamide hydrochloride;

(2S)-N-(5-((6-bromo-2-methoxynaphthalen-1-yl)methyl)-4-oxo-4,5-dihydro-3H-spiro[benzo[b][1,4]oxazepine-2,3'-oxetane]-3-yl)-2-(methylamino)propanamide 2,2,2-trifluoroacetate;

(2S)-N-(5-((6-bromo-2-methoxynaphthalen-1-yl)methyl)-2-(methoxymethyl)-2-methyl-4-oxo-2,3,4,5-tetrahydrobenzo[b][1,4]oxazepin-3-yl)-2-(methylamino)propanamide hydrochloride;

(2S,3S)-2-amino-N-(5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-3-hydroxybutanamide hydrochloride;

(S)-N-((S)-5-((3-methoxyquinolin-4-yl)methyl)-4-oxo-2',3',4,5,5',6'-hexahydro-3H-spiro[benzo[b][1,4]oxazepine-2,4'-pyran]-3-yl)-2-(methylamino)propanamide dihydrochloride;

(S)-2-(methylamino)-N-((S)-4-oxo-5-(quinolin-4-ylmethyl)-2',3',4,5,5',6'-hexahydro-3H-spiro[benzo[b][1,4]oxazepine-2,4'-pyran]-3-yl)propanamide dihydrochloride;

(S)-2-(methylamino)-N-((S)-4-oxo-5-((2-(2,2,2-trifluoroethoxyl)naphthalen-1-yl)methyl)-2',3',4,5,5',6'-hexahydro-3H-spiro[benzo[b][1,4]oxazepine-2,4'-pyran]-3-yl)propanamide hydrochloride;

(S)-N-((S)-5-((2-Chloro-1-(2-cyanophenyl)-1H-indol-3-yl)methyl)-4-oxo-2,3,4,5-tetrahydrobenzo[b][1,4]oxazepin-3-yl)-2-(methylamino)propanamide;

(S)-N-((S)-5-((2-Cyano-1-(2-cyanophenyl)-1H-indol-3-yl)methyl)-4-oxo-2,3,4,5-tetrahydrobenzo[b][1,4]oxazepin-3-yl)-2-(methylamino)propanamide trifluoroacetate;
(S)-N-((S)-5-((6-Bromo-2-methoxynaphthalen-1-yl)methyl)-4-oxo-2,3,4,5-tetrahydrobenzo[b][1,4]oxazepin-3-yl)-2-(2-hydroxyethylamino)butanamide trifluoroacetate;
(S)-N-((S)-5-((2-(Difluoromethoxy)naphthalen-1-yl)methyl)-4-oxo-2',3',4,5,5',6'-hexahydro-3H-spiro[benzo[b][1,4]oxazepine-2,4'-pyran]-3-yl)-2-(methylamino)propanamide hydrochloride;
(S)-N-((S)-5-((1-(2-Cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide;
(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(2-hydroxyethylamino)propanamide;
(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(ethyl-d5-amino)propanamide;
(S)-N-((S)-5-((1-(2-Cyanophenyl)-6-fluoro-1H-indazol-3-yl)methyl)-4-oxo-2,3,4,5-tetrahydrobenzo[b][1,4]oxazepin-3-yl)-2-(ethylamino)propanamide;
(S)-N-((S)-5-((2-Cyano-1-(2-cyanophenyl)-1H-indol-3-yl)methyl)-4-oxo-2',3',4,5,5',6'-hexahydro-3H-spiro[benzo[b][1,4]oxazepine-2,4'-pyran]-3-yl)-2-(methylamino)propanamide;
(2S)-N-((2S,3S)-5-((1-(2-Cyanophenyl)-1H-indazol-3-yl)methyl)-2-methyl-4-oxo-2,3,4,5-tetrahydrobenzo[b][1,4]oxazepin-3-yl)-2-(ethylamino)propanamide trifluoroacetate;
(S)-N-((2S,3S)-5-((2-Cyano-1-(2-cyanophenyl)-1H-indol-3-yl)methyl)-2-methyl-4-oxo-2,3,4,5-tetrahydrobenzo[b][1,4]oxazepin-3-yl)-2-(methylamino)propanamide;
(S)-N-((2S,3S)-5-((2-Cyano-1-(2-cyanophenyl)-1H-indol-3-yl)methyl)-2-methyl-4-oxo-2,3,4,5-tetrahydrobenzo[b][1,4]oxazepin-3-yl)-2-(ethylamino)propanamide;
(S)-N-((S)-8-Cyano-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide 2,2,2-trifluoroacetate and
3-Cyano-N-ethyl-4-(3-(((2S,3S)-2-methyl-3-((S)-2-(methylamino)propanamido)-4-oxo-3,4-dihydrobenzo[b][1,4]oxazepin-5(2H)-yl)methyl)-1H-indazol-1-yl)benzamide trifluoroacetate.

A certain aspect of this invention relates to a compound as defined herein for use as therapeutically active substance.

A certain aspect of this invention relates to a compound according to any one of claims 1 to 20 for use in the treatment or prophylaxis of cancer.

A certain aspect of this invention relates to a pharmaceutical composition comprising a compound as defined herein and a therapeutically inert carrier.

A certain aspect of this invention relates to an use of a compound as defined herein for the treatment or prophylaxis of cancer.

A certain aspect of this invention relates to an use of a compound as defined herein for the preparation of a medicament for the treatment or prophylaxis of cancer.

A certain aspect of this invention relates to a method for the treatment or prophylaxis of cancer, which method comprises administering an effective amount of a compound as defined herein.

Definitions

As used herein, the following terms shall have the following definitions.

The term "alkyl" refers to straight- or branched-chain saturated hydrocarbon groups having from 1 to about 12 carbon atoms, including groups having from 1 to about 7 carbon atoms and from 1 to 6 carbons. In certain embodiments, alkyl substituents may be lower alkyl substituents. The term "lower alkyl" refers to alkyl groups having from 1 to 6 carbon atoms ($C_{1-6}$-alkyl), preferably from 1 to 4 carbon atoms ($C_{1-4}$-alkyl). Examples of alkyl groups include, but are not limited to, methyl, ethyl, n-propyl, i-propyl, n-butyl, s-butyl, t-butyl, n-pentyl, and s-pentyl. The alkyl group can be optionally enriched in deuterium, e.g., $-CD_3$, $-CD_2CD_3$ and the like.

The term "alkenyl" as used herein means an unsaturated straight-chain or branched aliphatic hydrocarbon group containing at least one double bond and having 2 to 6 ($C_{2-6}$-alkenyl), preferably 2 to 4 carbon atoms ($C_{2-4}$-alkenyl). Examples of such "alkenyl group" are vinyl, ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

"$C_{2-6}$-alkenyl-$C_{1-6}$-alkyl" refers to an $C_{1-6}$-alkyl as defined herein linked to an $C_{2-6}$-alkenyl as defined herein.

"Alkoxy, alkoxyl or lower alkoxy" refers to any of the above lower alkyl groups which is attached to the remainder of the molecule by an oxygen atom (RO-). $C_{1-6}$-alkoxy refers to alkoxy groups where the alkyl moiety is having from 1 to 6 carbon atoms Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

The term "alkynyl" as used herein means an unsaturated straight-chain or branched aliphatic hydrocarbon group containing one triple bond and having 2 to 6 ($C_{2-6}$-alkynyl), preferably 2 to 4 carbon atoms ($C_{2-4}$-alkynyl). Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

"$C_{2-6}$-alkynyl-$C_{1-6}$-alkyl" refers to an $C_{1-6}$-alkyl as defined herein linked to an $C_{2-6}$-alkynyl as defined herein.

"Acyl" substituents include groups of the formula -C(O)R11 where R11 is H, alkyl, aryl, arylalkyl, heterocyclyl, for example, acetyl, propionyl, nicotinyl and the like.

"Sulfonyl" substituents include groups of the formula -SO2R11 for example, methanesulfonyl, benzenesulfonyl, tosyl and the like.

Amino means the group $-NH_2$.

"Aryl" means a monocyclic, bicyclic or polycyclic aromatic carbocyclic or heterocyclic radical, preferably a 6-14 member aromatic ring system. Preferred aryl groups include, but are not limited to, phenyl, naphthyl, tolyl, xylyl, pyridinyl, quinolinyl, pyrimidinyl, imidazole, thiazole and tetrazolyl. Aryl groups can be optionally substituted by, for example, lower alkyl, cycloalkyl, e.g., cyclopropyl, trihalo-lower alkyl, e.g., trifluoromethyl, hydroxyl, alkoxy. When two or more substituents are present on an aryl or heteroaryl ring they may also be present in the form of a fused ring. Such fused rings include, but are not limited to, 3,4-methylenedioxyphenyl and 3,4-ethylenedioxyphenyl.

"Aryl" means a monovalent, monocyclic or bicyclic, aromatic carboxylic hydrocarbon radical, preferably a 6-10 member aromatic ring system. Preferred aryl groups include, but are not limited to, phenyl, naphthyl, tolyl, and xylyl. A particular aryl is phenyl.

"aryl-$C_{1-6}$-alkyl" refers to an $C_{1-6}$-alkyl as defined herein linked to an aryl as defined herein.

"$C_{3-7}$-cycloalkyl-$C_{1-6}$-alkyl" refers to an $C_{1-6}$-alkyl as defined herein linked to an $C_{3-7}$-cycloalkyl as defined herein.

"carbocycle" or "carbocyclic ring" refers to a ring containing carbon.

"Carboxyl or carboxy" means the monovalent group —COOH. Carboxy lower alkyl means —COOR, wherein R is lower alkyl. "Carboxy lower alkoxy" means —COOROH wherein the R is lower alkyl.

Carbonyl means the group

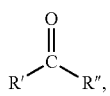

where R' and R" independently can be any of a number of chemical groups including alkyl.

The term "cycloalkyl" as used herein means any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. A specific cycloalkyl is "$C_{3-7}$-cycloalkyl", that is a cycloalkyl with 3 to 7 carbons. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "$C_{3-7}$-cycloalkyl-$C_{1-6}$-alkyl" as used herein refers to a $C_{3-7}$-cycloalkyl group linked to a $C_{1-6}$-alkyl group.

The terms "halogen" or "halo" as used herein means fluoro (F), chloro (Cl), bromo (Br), or iodo (I), preferably fluoro and chloro.

"halo-$C_{1-6}$-alkyl" refers to a $C_{1-6}$-alkyl as defined herein substituted with 1 or 2 halogen groups.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole substituted or unsubstituted triazolyl and substituted or unsubstituted tetrazolyl.

In the case of aryl or heteroaryl which are bicyclic it should be understood that one ring may be aryl while the other is heteroaryl and both being substituted or unsubstituted.

"Hetero atom" means an atom selected from N, O and S.

"Heterocycle", "heterocyclyl" or "heterocyclic ring" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like which in turn can be substituted.

Hydroxy or hydroxyl is a prefix indicating the presence of a monovalent 0-H group.

"hydroxy-$C_{1-6}$-alkyl" refers to a $C_{1-6}$-alkyl as defined herein substituted with 1 or 2 hydroxy groups.

"Lower" as in "lower alkenyl" means a group having 1 to 6 carbon atoms.

"mixed aryl and non-aryl polycycles" refers to ring systems of 2 rings, wherein one ring is an aryl as defined herein and the other ring is a cycloalkyl as defined herein.

"mixed aryl and non-aryl polyheterocycles" refers to ring systems of 2 rings, wherein one ring is an aryl as defined herein and the other ring is a heterocyclyl as defined herein.

"Nitro" means -$NO_2$.

Oxo means the group =O.

"Substituted," as in e.g.substituted alkyl, means that the substitution can occur at one or more positions and, unless otherwise indicated, that the substituents at each substitution site are independently selected from the specified options.

The term "optionally substituted" refers to the fact that one or more hydrogen atoms of a chemical group (with one or more hydrogen atoms) can be, but does not necessarily have to be, substituted with another substituent. In the specification where indicated the various groups may be substituted by preferably, 1-3 substituents independently selected from the group consisting of H, carboxyl, amido, hydroxyl, alkoxy, substituted alkoxy, sulfide, sulfone, sulfonamide, sulfoxide, halogen, nitro, amino, substituted amino, lower alkyl, substituted lower alkyl, oxyalkyl, lower cycloalkyl, substituted lower cycloalkyl, lower alkenyl, substituted lower alkenyl, lower cycloalkenyl, substituted lower cycloalkenyl, acyl, acylamino, aryl, substituted aryl, heteroaryl, substituted heteroaryl, heterocycle or substituted heterocycle.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

The term "polycyclic aromatics" refers to an aryl as defined herin containing 2 or more aromatic rings.

The term "polycyclic heteroaromatics" refers to an heteroaryl as defined herin containing 2 or more aromatic rings.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The compounds of formula 1 as well as their salts have at least one asymmetric carbon atom and therefore may be present as mixtures of different stereoisomers. The various isomers can be isolated by known separation methods, e.g., chromatography.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Another embodiment includes a pharmaceutical composition comprising a compound of Formula I for use in the treatment of a hyperproliferative disease. Another embodiment includes a pharmaceutical composition comprising a compound of Formula I for use in the treatment of cancer.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

"Therapeutically effective amount or effective amount" means an amount of at least one designated compound that significantly inhibits proliferation and/or prevents differentiation of a human tumor cell, including human tumor cell lines.

The compounds of the present invention are useful in the treatment or control of cell proliferative disorders such as, in particular, oncological disorders. These compounds and formulations containing said compounds may be useful in the treatment or control
of blood cancers, such as, for example, acute myeloid leukemia, or solid tumors, such as, for example, breast, colon, lung and prostate tumors.

The compounds of the invention preferably bind to BIR domains of an IAP preventing the IAP from binding to other proteins. Examples of Bir binding proteins include, but are not limited to, caspase 3, caspase 7, caspase 9, Smac and the like. Examples of IAPs include, but are not limited to, XIAP, cIAP1, cIAP2 or NAIP. In one aspect, the compound of the invention bind to the BIR2 and/or BIR3 domains of XIAP, cIAP 1 and/or cIAP2. In another aspect, the compounds of the invention bind to the BIR2 domain of XIAP, cIAP1 and/or cIAP2.

Compounds of the invention are useful for inducing apoptosis in cells or sensitizing cells to apoptotic signals, in particular cancer cells. Apoptotic signals can be induced in cancer cells by, e.g., radiation therapy or antineoplastic chemotherapy. Alternatively, apoptotic signals can be induced in cancer cells by activation of the death receptors by death receptor agonists. Death receptor agonists can be naturally occurring, e.g., tumor necrosis factor α, (TNF-α) or non-naturally occurring, e.g., a synthetic antibody such as a DR4 or DR5 antibody.

Reaction Schemes

The compounds in the present invention (compounds of general formula 1) can be prepared using the general reacton scheme set out in Scheme 1

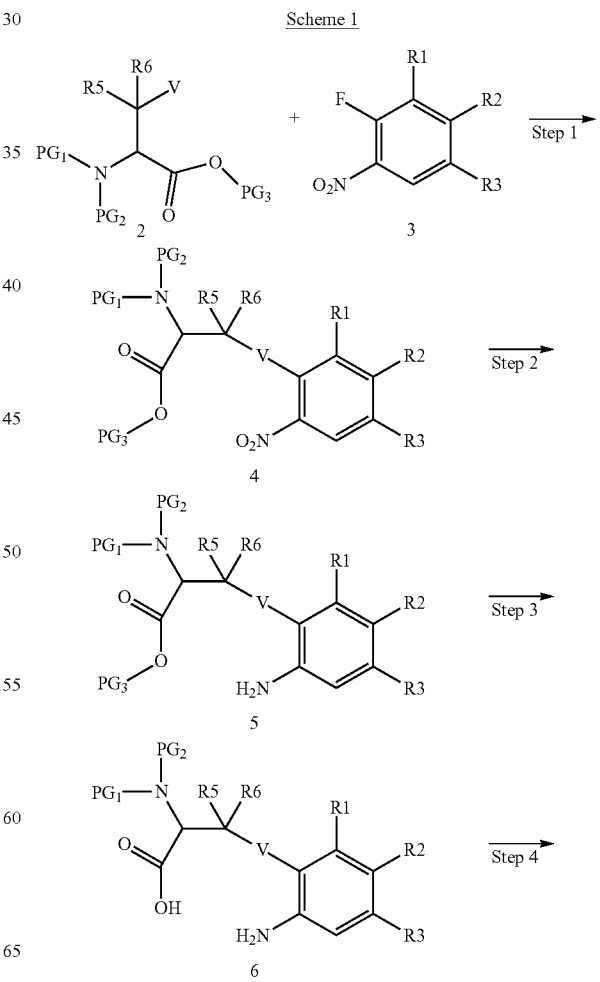

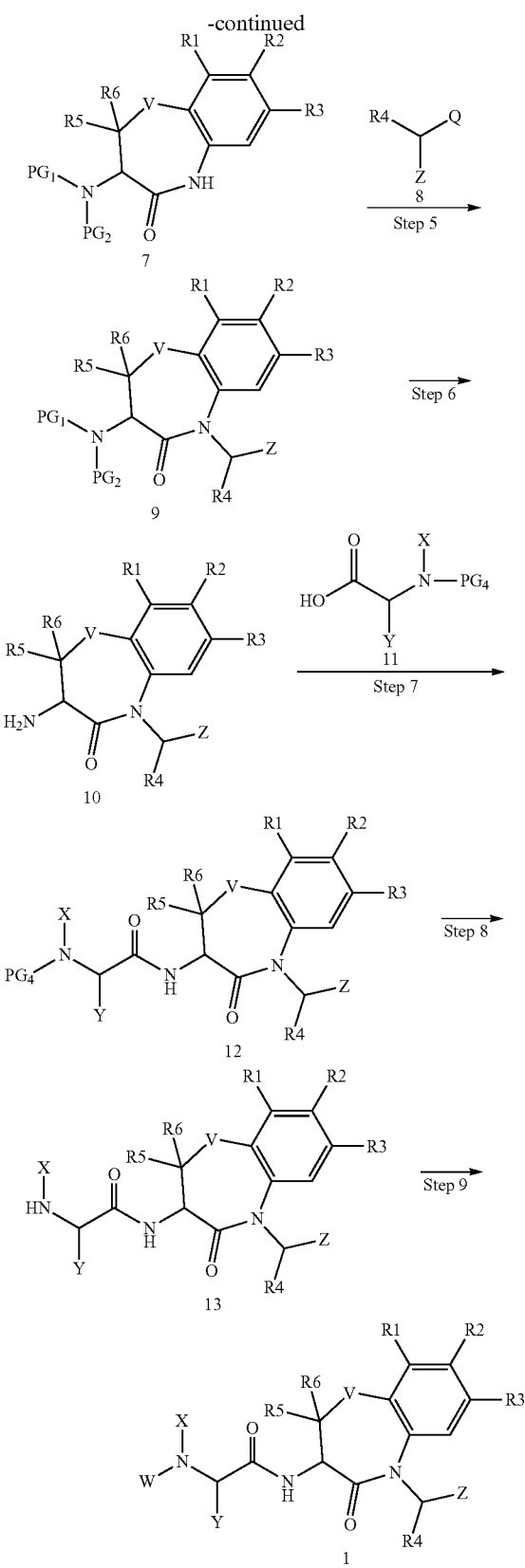

reaction conditions used in the rest of the synthetic sequence and PG2 is an optional group that renders the 2-amine N inert to reaction conditions used in the rest of synthetic sequence and PG3 is an optional group that renders the carboxylic acid inert to rection conditions used in the rest of synthetic sequence, and a substituted or unsubstituted 1-fluoro-2-nitrobenzene of general formula 3 can be reacted with a base in an appropriate solvent and at an appropriate temperature for an amount of time sufficient to provide a product of general formula 4. The base can be inorganic, e.g., NaH, $Na_2CO_3$ or $Cs_2CO_3$, or organic, e.g., sodium bis(trimethylsilyl)amide. Solvents are chosen to be compatible with the base and other reaction conditions, such as temperature, and include, but are not limited to, e.g., THF or DMF. Temperatures suitable for this reaction can range from about −40° C. to about 150° C. Preferred choices for protecting group PG1, PG2 and PG3 may be made by reference to organic chemistry text books (e.g. Protective Groups in Organic Synthesis, Theodora W. Greene et al.), the original chemistry literature, or would be generally known to one knowledgeable in the art of organic synthesis. In particular, when the 2-amine N is mono-protected by PG1, carbamate-based protecting groups, e.g. tert-butyloxycarbonyl and benzyloxycarbonyl, are preferred. When the 2-amine N is di-protected by PG1 and PG2, arylalkyl-based protecting groups, e.g. benzyl or 4-methoxybenzyl, are preferred. Other amine-protecting groups for PG1 alone or PG1 and PG2 together may also be effective. PG3 can be H or can be an alkyl group, e.g., methyl, ethyl, tert-butyl.

Step 2: This step involves the reduction of the nitro group in compounds of general formula 4 to provide compounds of general formula 5. Those skilled in the art will recognize there are several methods to accomplish this reduction including catalytic hydrogenation and chemical reduction. The choice of reduction method will be influenced by the substitution on the phenyl ring indicated by R1, R2 and R3 and by the protecting groups PG1, PG2 and PG3 so that unwanted side reactions do not occur. For example, compounds of general formula 4 can treated with an appropriate hydrogenation catalyst, e.g., 10% Pd/C in an appropriate solvent, e.g., MeOH and subjected to hydrogenation at pressures ranging from atmospheric pressure to elevated pressure, up to about 60 PSI for an amount of time sufficient to carry out this transformation. Alternatively, compounds of general formula 4 can be treated with an appropriate chemical reducing agent, e.g. Zn or $SnCl_2$, in an appropriate solvent or solvent mixture, e.g., EtOAc or a mixture of EtOAc and EtOH or a mixture of EtOH and HCl, at an appropriate temperature, ranging from about 0° C. to about 80° C. for an amount of time sufficient to carry out this transformation.

Step 3: The optional carboxylic acid protecting group PG3 in compounds of general formula 5 can be removed to afford compounds of general formula 6. As mentioned above, the choice of protecting group PG3 and conditions used during step 3 for removal of PG3 is influenced by what other potentially reactive functional groups are present in compounds of general formula 5 and the requirement of avoiding undesired reactions elsewhere in the starting material or product of the reaction, i.e., compounds of general formulae 5 and 6, respectively. For example, if PG2 is an ester, e.g., methyl or ethyl, compounds of general formula 4 can be treated with a base, e.g., NaOH or LiOH, in an appropriate solvent or solvent mixture, e.g., THF/$H_2O$ or MeOH/$H_2O$ at an appropriate temperature, ranging from 0° C. to about 80° C. for an amount of time sufficient to carry out this transformation. Those skilled in the art will recognize that there are a variety of conditions for removing protecting groups from carboxylic Step 1: A suitably protected 2-amino-3-hydroxypropionic acid or 2-amino-3-thiopropionic acid of general formula 2, where PG1 is a group that render the 2-amine N inert to acids which may be identified by reference to organic chemistry text books (e.g. Protective Groups in Organic Synthesis, Theodora W. Greene et al.) or the original chemistry literature. It will be recognized that compounds of general formula 5 where PG3=H are equivalent to compounds of general formula 6.

Step 4: This step entails the conversion of compounds of general formula 6 to lactams of general formula 7. Reagents which may be employed to achieve this transformation include diimide based reagents e.g. dicyclohexylcarbodiimide, (3-dimethylamino-propyl)-ethyl-carbodiimide hydrochloride; or uronium based reagents, e.g. O-benzotriazol-1-yl-N,N,N',N'-tetramethyluronium hexaflurorophosphate or O-benzotriazol-1-yl-N,N,N',N'-bis(tetramethylene)uronium hexaflurorophosphate. Additionally, a catalyst can be optionally added to the reaction, e.g., 1-hydroxybenzotriazole or N-hydroxysuccinimide. Alternative reagents may also effective in performing this conversion whose selection may be made by reference to the original chemistry literature or would be generally known to one knowledgeable in the art of organic synthesis.

Step 5: This step involves the reaction of compounds of general structure 7 with compounds of general structure 8 to form compounds of general structure 9, where Q is a suitable leaving group, e.g., a halogen, such as Br or I, or a sulfonate ester, such as methanesulfonate ester or Q is hydroxyl. In cases where Q is a leaving group, step 5 can be accomplished by treating compounds of general structure 7 with a base and compounds of general structure 9 in a suitable solvent for an amount of time sufficient to carry out this transformation. The base used can be inorganic, e.g., $Cs_2CO_3$ or organic, e.g., lithium bis(trimethylsilyl)amide. Solvents are chosen to be compatible with the base and other reaction conditions, such as temperature, and include, but are not limited to, e.g., THF or DMF. Temperatures suitable for this reaction can range from −78° C. to 100° C. Those skilled in the art will recognize that a catalyst can be added to the reaction mixture. Such catalysts can include, but are not limited to, e.g., NaI or tetrabutylammonium iodide.

If, in compounds of general structure 8 Q is hydroxyl, the conversion of compounds general formula 7 to compounds of general formula 9 can be accomplished by means of a Mitsunobu reaction. For example, compounds of general structure 7 and general structure 8, where Q=OH, can be treated with an azodicarboxylate, e.g., diethyl azodicarboxylate or diisopropyl azodicarboxylate, and a phosphine, e.g., triphenylphosphine or another suitable phosphine, in a suitable solvent for an amount of time sufficient to carry out this transformation. Solvents are chosen to be compatible with the reaction conditions, such as temperature, and include, but are not limited to, e.g., THF, toluene, $CH_2Cl_2$ or DMF. Temperatures suitable for this reaction can range from about 0° C. to 100° C. Additional methods to achieve this transformation would be generally known to one knowledgeable in the art of organic synthesis and an overview of the Mitsunobu reaction has been described in a recent review: Chem. Rev., 2009, 109 (6), pp 2551-2651.

Step 6: This step entails the removal of protecting group PG1 and optional protecting group PG2 from compounds of general formula 9 to form amine-containing compounds of general formula 10. As mentioned above, the choice of protecting group PG1 and optional PG2 and conditions used during step 6 for removal of PG1 and optional PG2 are influenced by what other potentially reactive functional groups are present in compounds of general formula 10 and the requirement of avoiding undesired reactions elsewhere in the starting material or product of the reaction, i.e., compounds of general formulae 9 and 10, respectively. In the case where the amine-protecting group PG1 present in compounds of general formula 5 is tert-butyloxycarbonyl, the protecting group can be removed under acidic conditions such as trifluoroacetic acid in dichloromethane or hydrochloric acid in p-dioxane or ether. Removal of the tert-butyloxycarbonyl group under acidic conditions initially liberates the corresponding salt of the compound of general formula 10, from which the free amine of general formula 10 can be optionally liberated after treatment with base. Alternatively, if the 2-amino N is di-protected by protecting group PG1 and PG2 and they are, e.g., benzyl, their removal can be accomplished by catalytic hydrogenation using a suitable catalyst, e.g., 10% Pd/C and treating the mixture with a hydrogen source, e.g., $H_2$ or ammonium formate, in an appropriate solvent, e.g., EtOH. Those skilled in the art will recognize that there are a variety of conditions for removing protecting groups from nitrogen atoms which may be identified by reference to organic chemistry text books (e.g. Protective Groups in Organic Synthesis, Theodora W. Greene et al.) or the original chemistry literature.

Step 7: This step entails the coupling of a suitably protected a-amino-acid of general structure 11 to compounds of general structure 10, where PG4 is a group that renders the a-amine N inert to reaction conditions used in the rest of the synthetic sequence and W is as described above. Preferred choices for protecting group PG4 may be made by reference to organic chemistry text books (e.g. Protective Groups in Organic Synthesis, Theodora W. Greene et al.), the original chemistry literature, or would be generally known to one knowledgeable in the art of organic synthesis. In particular, carbamate-based protecting groups, e.g. tert-butyloxycarbonyl and benzyloxycarbonyl, are preferred but other amine-protecting groups may also be effective. Those skilled in the art will recognize there are several methods using known peptide coupling reaction techniques to convert compounds of general formula 10 and compounds of general formula 11 to compounds of general formula 12. Typical peptide coupling reagents which may be employed include diimide based reagents e.g. dicyclohexylcarbodiimide, (3-dimethylamino-propyl)-ethyl-carbodiimide hydrochloride; or uronium based reagents, e.g. O-benzotriazol-1-yl-N,N,N',N'-tetramethyluronium hexaflurorophosphate or O-benzotriazol-1-yl-N,N,N',N'-bis(tetramethylene)uronium hexaflurorophosphate. Additionally, a catalyst can be optionally added to the reaction, e.g., 1-hydroxybenzotriazole or N-hydroxysuccinimide. Alternative peptide coupling reagents may also effective in performing this conversion. Selection of alternative peptide coupling reagents may be made by reference to the original chemistry literature or would be generally known to one knowledgeable in the art of organic synthesis.

Step 8: This step entails the removal of protecting group PG4 from compounds of general formula 12 to provide amine compounds of general formula 13. The conditions and methods used for this step are analogous to those described above for Step 6.

In cases where X in general formula 1 is desired to be H no further reactions are needed as compounds of general formula 13 are equivalent to compounds of general formula 1, where W=H.

Step 9 involves the introduction of an additional substitution to the nitrogen atom bearing group X in compounds of general structure 13. Those skilled in the art will recognize there are several ways to accomplish this transformation. These include, but are not limited to, reductive amination or alkylation. For example, compounds of general formula 13 can be treated with an aldehyde, e.g., acetaldehyde, benzaldehyde or 3-pyridinecarboxaldehyde and a reducing agent, e.g., NaBH$_4$ or NaBH$_3$CN in a suitable solvent, e.g., MeOH or EtOH at an appropriate temperature, ranging from about −20° C. to about 100° C. for an amount of time sufficient to carry out this transformation. Alternatively, compounds can be treated with an alkylating agent, e.g., methyl iodide, benzyl bromide or allyl bromide, and a base, e.g., pyridine or triethyelamine (TEA), in a suitable solvent, e.g., dichloromethane (DCM) or THF at an appropriate temperature, ranging from about −20° C. to about 100° C. for an amount of time sufficient to carry out this transformation. Those skilled in the art will recognize that a catalyst can be added to the reaction mixture. Such catalysts can include, but are not limited to, e.g., NaI or tetrabutylammonium iodide.

It will be apparent to one knowledgeable in the art of organic synthesis that when one or more of the substituents labeled X, W, Y or R1 through R6, or substituents included in their definitions, in the compounds shown in Scheme 1 are in and of themselves chemically reactive groups, or contains chemically reactive groups, then additional modification of the compounds of general formula 1 through 13 which contain those reactive groups may be possible. The point in the synthetic sequence at which modification of the chemically reactive groups takes place may be chosen such that the newly elaborated group is chemically inert to the reagents to be employed during the remaining steps of the synthetic sequence and does not interfere with the remaining steps in the synthetic sequence shown in Scheme 1. Alternatively, if the newly elaborated group is not chemically inert or can interfere with the remaining steps in the synthetic sequence it may be necessary to temporarily mask the reactive functional group with an appropriate protecting group or to derivatize the functional group into a moiety which is stable to the remaining transformations in the synthetic sequence and will be present in the final product of the reaction sequence. If a protecting group is introduced which is not required in the final compound of general structure 1 then it may either be removed under the conditions remaining in the synthetic sequence shown in Scheme 1 or by introduction of an additional deprotection step into the synthetic sequence depending upon the nature of the protecting group employed.

Step 10: A suitably protected 2-aminoacetic acid, e.g., N,N-dibenzylglycine ethyl ester, can be treated with a base and compounds of general structure 15, where R5 and R6 are as described above, in a suitable solvent for an amount of time sufficient to carry out this transformation to give compounds of general structure 2, where V=O. The base used can be organic, e.g., lithium diisopropylamide, or inorganic, e.g., NaH. Solvents are chosen to be compatible with the base and other reaction conditions, such as temperature, and include, but are not limited to, e.g., THF or DMF. Temperatures suitable for this reaction can range from about −78° C. to about 80° C.

In some instances, it may be desirable to remove the protecting group PG3 to afford compounds of general structure 16, which is illustrated in Step 11. As mentioned above, the choice of protecting group PG3 and conditions used during step 11 for removal of PG3 is influenced by what other potentially reactive functional groups are present in compounds of general formulae 2 and 16, respectively and the requirement of avoiding undesired reactions elsewhere in the starting material or product of the reaction. In the case where PG3 is an alkyl ester, compounds of general structure 2, where V=O, can be treated with a base, e.g., NaOH, KOH or LiOH.H$_2$O in a suitable solvent or solvent mixtue, e.g., MeOH, MeOH/H$_2$O or THF/H$_2$O at an appropriate temperature, ranging from about 0° C. to about 100° C. for an amount of time sufficient to carry out this transformation. Those skilled in the art will recognize that there are a variety of conditions for removing protecting groups from carboxylic acids which may be identified by reference to organic chemistry text books (e.g. Protective Groups in Organic Synthesis, Theodora W. Greene et al.) or the original chemistry literature. It will be recognized that compounds of general structure 16 are equivalent to compound of general structure 2 where PG3 is optionally absent and V=O.

The reaction conditions for the above reactions can vary to a certain extent. Those skilled in the art will recognize that the sequence of some reaction steps described in Scheme 1 can vary, as shown in Scheme 3.

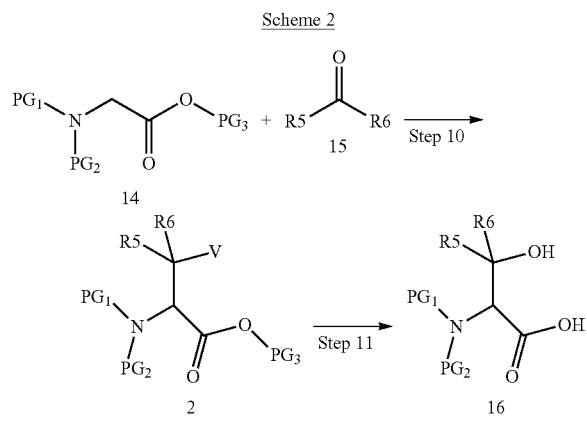

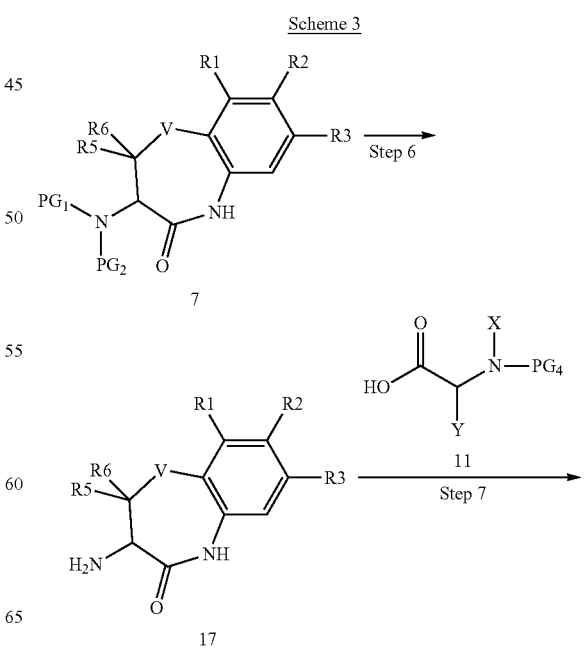

Those skilled in the art will recognize that in certain instances where a suitably protected 2-amino-3-hydroxypropionic acid is not known in the literature or commercially available it would be necessary to synthesize the compound. Scheme 2 illustrates one general synthesis of protected 2-amino-3-hydroxypropionic acids.

-continued

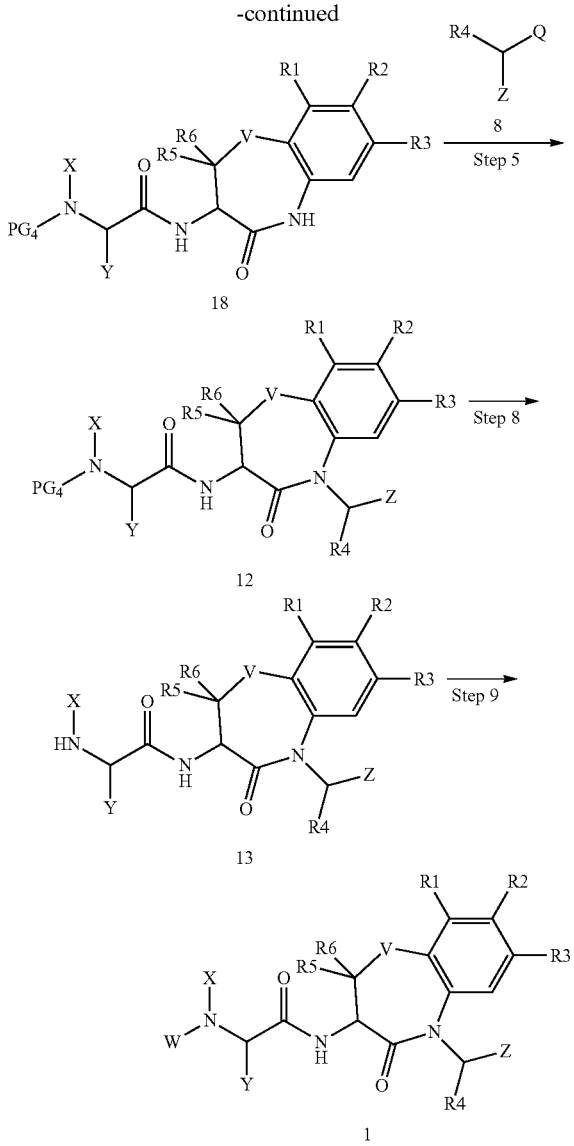

Compounds of general structure 7 can be treated above as described for step 6 to provide compounds of general structure 17.

Compounds of general structure 17 can be treated above as described for step 7 to provide compounds of general structure 18.

Compounds of general structure 18 can be treated above as described for step 5 to provide compounds of general structure 12.

Compounds of general structure 12 can be treated above as described for step 8 to provide compounds of general structure 13.

Compounds of general structure 13 can be treated above as described for step 9 to provide compounds of general structure 1.

Methods to perform the above described reactions and processes would be apparent to those of ordinary skill in the art based on the present disclosure, or can be deduced in analogy from the examples. Starting materials are commercially available or can be made by methods analogous to those described in the Examples.

The following examples shall illustrate preferred embodiments of the present invention but are not intended to limit the scope of the invention.

PREPARATION OF INTERMEDIATES (S)-tert-Butyl 4-oxo-2,3,4,5-tetrahydrobenzo[b][1,4]oxazepin-3-ylcarbamate

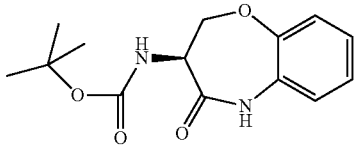 [SMILES: CC(C)(C)OC(=O)N[C@H]1COc2ccccc2NC1=O]

Step 1: To a suspension of NaH (60% in mineral oil, 2.88 g, 72 mmol) in DMF (25 mL) at 0° C. was added (S)-2-(tert-butoxycarbonylamino)-3-hydroxypropanoic acid (7 g, 34 mmol) in DMF (25 mL). After 2 h 1-fluoro-2-nitrobenzene (5.29 g, 37.5 mmol) in DMF (25 mL) was added and the resulting mixture stirred for 3 h at 0° C. The mixture was poured into ice/$H_2O$ (200 mL), acidified to pH 5.0 with 1 N HCl and extracted with EtOAc. The combined extracts were dried over $Na_2SO_4$, concentrated and purified by flash chromatography to give (S)-2-tert-butoxycarbonylamino-3-(2-nitro-phenoxy)-propionic acid (10.9 g, 97%).

Step 2: A mixture of (S)-2-tert-butoxycarbonylamino-3-(2-nitro-phenoxy)-propionic acid (7.6 g, 23.3 mmol, 1eq) and 10% Pd/C (496 mg) in MeOH (215 mL) was hydrogenated at 1 atm for 2 h. After the theoretical uptake of hydrogen, the reaction mixture was filtered through Celite and washed with MeOH. The filtrate was concentrated and the residue was triturated with hexanes to give a solid that was filtered and washed with hexanes to give (S)-3-(2-amino-phenoxy)-2-tert-butoxycarbonylamino-propionic acid (3.8 g, 55%) as a white solid which was used without purification.

Step 3: A mixture of (S)-3-(2-amino-phenoxy)-2-tert-butoxycarbonylamino-propionic acid (3.8 g, 12.8 mmol, 1 eq) and N-(3-dimethylaminopropyl)-N'-ethylcarbodiimide hydrochloride (EDCI, 2.46 g, 12.8 mmol, 1 eq) in DMF (56.4 mL) was stirred for 1 h 45 min. The reaction was poured into $H_2O$ (250 mL) and extracted with EtOAc. The combined extracts were washed with $H_2O$, dried over $Na_2SO_4$ and concentrated to give the title compound (3.1 g, 87%) as a tan solid which was used without purification.

(S)-3-Amino-2,3-dihydrobenzo[b][1,4]oxazepin-4(5H)-one trifluoroacetate

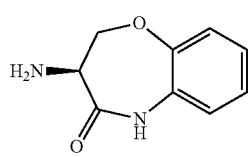 [SMILES: N[C@H]1COc2ccccc2NC1=O]

To a solution of (S)-tert-butyl 4-oxo-2,3,4,5-tetrahydrobenzo[b][1,4]oxazepin-3-ylcarbamate (2 g, 7.19 mmol, Eq: 1.00) in DCM (16.7 mL) at 0° C. was added trifluoroacetic acid (TFA, 16.4 g, 10.7 mL, 144 mmol, Eq: 20.00). After 1 h the mixture was concentrated, and the residue was triturated with 5 mL of $Et_2O$ and 35 ml of pentane to give a gum.

The solution was removed and this gummy residue material was dried to give the title compound (2.1 g) as a pink foam which was used without purification.

tert-Butyl methyl((S)-1-oxo-1-((S)-4-oxo-2,3,4,5-tetrahydrobenzo[b][1,4]oxazepin-3-ylamino)propan-2-yl)carbamate

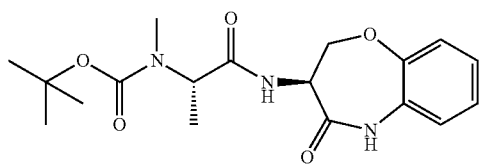 [SMILES: C[C@@H](C(=O)N[C@H]1COc2ccccc2NC1=O)N(C)C(=O)OC(C)(C)C]

To a mixture of (S)-3-amino-2,3-dihydrobenzo[b][1,4]oxazepin-4(5H)-one trifluoroacetate (500 mg, 1.71 mmol, Eq: 1.00), (S)-2-(tert-butoxycarbonyl(methyl)amino)propanoic acid (348 mg, 1.71 mmol, Eq: 1.00), O-benzotriazol-1-yl-N,N,N',N'-tetramethyluronium hexafluorophosphate (HBTU, 682 mg, 1.8 mmol, Eq: 1.05) and 1-hydroxybenzotriazole hydrate (HOBT120, 243 mg, 1.8 mmol, Eq: 1.05) in DMF (5 mL) was added N,N-diisopropylethylamine (DIEA, 553 mg, 4.28 mmol, Eq: 2.50). The mixture was stirred for 45 min., diluted with 50 mL EtOAc and washed H$_2$O, 2% KHSO$_4$, 5% NaHCO$_3$ and 5% brine. The organic solution was dried over Na$_2$SO$_4$, filtered and concentrated to give the title compound (525 mg, 84%) as a tan foam which was used without purification.

(S)-Methyl 3-(tert-butoxycarbonylamino)-4-oxo-2,3,4,5-tetrahydrobenzo[b][1,4]oxazepine-9-carboxylate

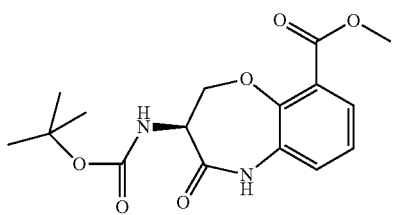 [SMILES: COC(=O)c1cccc2c1OC[C@H](NC(=O)OC(C)(C)C)C(=O)N2]

Step 1: A suspension of NaH (60% in mineral oil, 1.48 g, 36.9 mmol, Eq: 2.10) in DMF (15 mL) was cooled to 0° C. and (S)-2-(tert-butoxycarbonylamino)-3-hydroxypropanoic acid (3.61 g, 17.6 mmol, Eq: 1.00) in DMF (15 mL) was added dropwise over 15 min. The mixture was stirred at 0° C. for 30 min. and at room temp. (RT) for 30 min. The mixture was cooled to 0° C. and methyl 2-fluoro-3-nitrobenzoate (3.5 g, 17.6 mmol, Eq: 1.00) in DMF (15 mL) was added dropwise over 10 min. After 2.5 h the mixture was diluted with ice cold H$_2$O and extracted with EtOAc. The combined extracts were dried over Na$_2$SO$_4$ filtered and concentrated to give a residue that was purified by chromatography to afford 2-((S)-2-tert-butoxycarbonylamino-2-carboxy-ethoxy)-3-nitrobenzoic acid methyl ester (4.3 g, 50%) as a yellow foam.

Step 2: In a similar manner to that described for (S)-3-(2-amino-phenoxy)-2-tert-butoxycarbonylamino-propionic acid, except the material obtained after the filtrate was concentrated and not triturated, (S)-3-(2-amino-phenoxy)-2-tert-butoxycarbonylamino-propionic acid (4.3 g, 11.2 mmol) was converted to (S)-3-(2-amino-6-(methoxycarbonyl)phenoxy)-2-(tert-butoxycarbonylamino)propanoic acid (3.9 g, 50%) as an off-white foam which was used without purification.

Step 3: In a similar manner to that described for the preparation of (S)-tert-butyl 4-oxo-2,3,4,5-tetrahydrobenzo[b][1,4]oxazepin-3-ylcarbamate except the crude product was purified by silica gel chromatography, (S)-3-(2-amino-6-(methoxycarbonyl)phenoxy)-2-(tert-butoxycarbonylamino)propanoic acid (3.9 g, 6.6 mmol) was converted to the title compound (1.46 g, 65%) as a white foam.

tert-Butyl (2R,3S)-2-methyl-4-oxo-2,3,4,5-tetrahydrobenzo[b][1,4]oxazepin-3-ylcarbamate

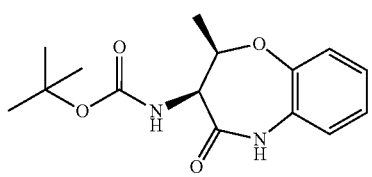 [SMILES: C[C@H]1Oc2ccccc2NC(=O)[C@H]1NC(=O)OC(C)(C)C]

Step 1: In a similar manner to that described for the preparation of (S)-2-tert-butoxycarbonylamino-3-(2-nitro-phenoxy)-propionic acid except the mixture of (2S,3R)-2-tert-butoxycarbonylamino-3-hydroxybutyric acid and NaH (60% in mineral oil) was stirred at 0° C. for 30 min., room temp. for 1 h and cooled to 0° C., (2S,3R)-2-tert-butoxycarbonylamino-3-hydroxy-butyric acid (4.99 g) and 1-fluoro-2-nitrobenzene (3.22 g) was converted to (2S,3R)-2-tert-butoxycarbonylamino-3-(2-nitro-phenoxy)-butyric acid (3.6 g, 53%) as a yellow foam.

Step 2: In a similar manner to that described for the (S)-3-(2-amino-phenoxy)-2-tert-butoxycarbonylamino-propionic acid, except the material obtained after the filtrate was concentrated but not triturated, (2S,3R)-2-tert-butoxycarbonylamino-3-(2-nitro-phenoxy)-butyric acid (3.6 g, 10.6 mmol) was converted to (2S,3R)-3-(2-amino-phenoxy)-2-tert-butoxycarbonylamino-butyric acid (3.4 g, 90%) as a violet foam which was used without purification.

Step 3: In a similar manner to that described for the preparation of (S)-tert-butyl 4-oxo-2,3,4,5-tetrahydrobenzo[b][1,4]oxazepin-3-ylcarbamate except the crude product was purified by silica gel chromatography, (S)-3-(2-amino-6-(methoxycarbonyl)phenoxy)-2-(tert-butoxycarbonylamino)propanoic acid (1.5 g, 4.83 mmol) was converted to the title compound (0.65 g, 46%) as a white solid.

(6R,7S)-7-Amino-6-methyl-6,7-dihydro-9H-5-oxa-9-aza-benzocyclohepten-8-one

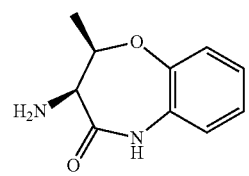

To a solution of tert-butyl (2R,3S)-2-methyl-4-oxo-2,3,4,5-tetrahydrobenzo[b][1,4]oxazepin-3-ylcarbamate (0.65 g, 2.22 mmol, Eq: 1.00) in DCM (11.2 mL) at 0° C. was added TFA (12.7 g, 8.26 mL, 111 mmol, Eq: 50.00). After 1 h the mixture was concentrated, the residue dissolved in 50 mL DCM and washed with sat. NaHCO$_3$. The NaHCO$_3$ mixture was extracted with DCM and the combined extracts dried over $Na_2SO_4$, filtered and concentrated to afford the title compound (0.42 g, 96%) as a yellow foam which was used without purification.

Methyl-[(S)-1-((6R,7S)-6-methyl-8-oxo-6,7,8,9-tetrahydro-5-oxa-9-aza-benzocyclo hepten-7-ylcarbamoyl)-ethyl]-carbamic acid tert-butyl ester

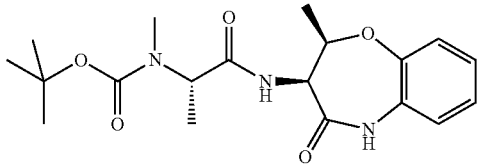 [SMILES: C[C@H]1Oc2ccccc2NC(=O)[C@H]1NC(=O)[C@H](C)N(C)C(=O)OC(C)(C)C]

In a similar manner to that described for the preparation of tert-butyl methyl((S)-1-oxo-1-((S)-4-oxo-2,3,4,5-tetrahydrobenzo[b][1,4]oxazepin-3-ylamino)propan-2-yl)carbamate except the mixture was stirred 1.5 h and the crude product purified by silica gel chromatography, (2R,3S)-3-amino-2-methyl-2,3-dihydrobenzo[b][1,4]-oxazepin-4 (5H)-one (420 mg, 2.19 mmol) was converted to the title compound (505 mg, 61%) as a white foam.

(S)-Methyl 5-(6-bromo-2-methoxynaphthalen-1-yl)methyl)-3-(tert-butoxycarbonyl amino)-4-oxo-2,3,4,5-tetrahydrobenzo[b][1,4]oxazepine-9-carboxylate

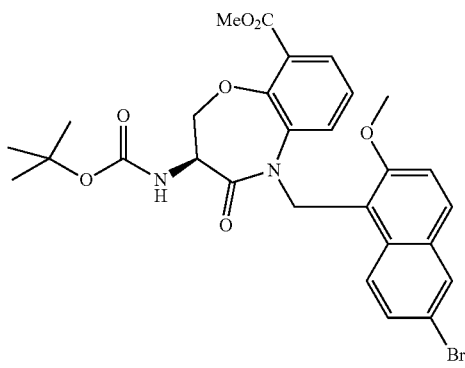 [SMILES: COC(=O)c1cccc2c1OC[C@H](NC(=O)OC(C)(C)C)C(=O)N2Cc1c(OC)ccc2cc(Br)ccc12]

$Cs_2CO_3$ (1.02 g, 3.12 mmol, Eq: 1.05) and NaI (446 mg, 2.97 mmol, Eq: 1.0) were added to a solution of (S)-methyl 3-(tert-butoxycarbonylamino)-4-oxo-2,3,4,5-tetrahydrobenzo[b][1,4]oxazepine-9-carboxylate (1 g, 2.97 mmol, Eq: 1.00) and 6-bromo-1-(chloromethyl)-2-methoxynaphthalene (866 mg, 3.03 mmol, Eq: 1.02) in DMF (20 mL). The mixture was stirred at RT for 30 min. then heated to 50° C. After 75 min., the mixture was cooled to RT and diluted with 1/1 EtOAc/$H_2O$. The aqueous layer was extracted with EtOAc and the combined organic phases were washed with $H_2O$, brine, dried over $Na_2SO_4$ and concentrated. The residue was purified by silica gel chromatography to afford (S)-methyl 5-((6-bromo-2-methoxynaphthalen-1-yl)methyl)-3-(tert-butoxycarbonyl amino)-4-oxo-2,3,4,5-tetrahydro benzo[b][1,4]oxazepine-9-carboxylate (1.35 g, 75%) as a white foam.

(S)-Methyl 5-((6-bromo-2-methoxynaphthalen-1-yl)methyl)-3-((S)-2-(tert-butoxycarbonyl(methyl)amino)propanamido)-4-oxo-2,3,4,5-tetrahydrobenzo[b][1,4]oxazepine-9-carboxylate

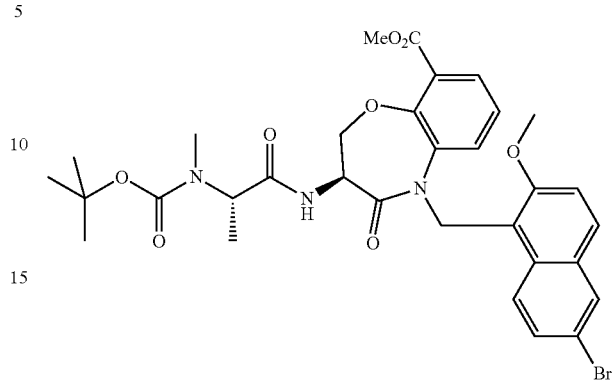

Step 1: In a similar manner to that described for the preparation of (S)-3-amino-2,3-dihydrobenzo[b][1,4]oxazepin-4 (5H)-one trifluoroacetate, (S)-methyl 5-((6-bromo-2-methoxynaphthalen-1-yl)methyl)-3-(tert-butoxycarbonylamino)-4-oxo-2,3,4,5-tetrahydrobenzo[b][1,4]oxazepine-9-carboxylate (652 mg, 1.11 mmol) was converted to (S)-methyl 3-amino-5-((6-bromo-2-methoxynaphthalen-1-yl)methyl)-4-oxo-2,3,4,5-tetrahydrobenzo[b][1,4]oxazepine-9-carboxylate trifluoroacetate (660 mg, 99%) which was used without purification.

Step 2: DIEA (712 mg, 972 μl, 5.51 mmol, Eq: 5.00) was added to a mixture of (S)-methyl 3-amino-5-((6-bromo-2-methoxynaphthalen-1-yl)methyl)-4-oxo-2,3,4,5-tetrahydrobenzo[b][1,4]oxazepine-9-carboxylate trifluoroacetate (660 mg, 1.1 mmol, Eq: 1.00), (S)-2-(tert-butoxycarbonyl(methyl)amino)propanoic acid (224 mg, 1.1 mmol, Eq: 1.0), HBTU (418 mg, 1.1 mmol, Eq: 1.0) and HOBT.$H_2O$ (149 mg, 1.1 mmol, Eq: 1.0) in DMF (12.5 mL) at 0° C. The mixture was warmed to RT, stirred for 1 h, diluted with EtOAc, washed with $H_2O$, brine and dried over $Na_2SO_4$. The mixture was filtered and concentrated to afford the title compound (725 mg, 98%) as an off-white foam which was used without purification.

(S)-5-((6-Bromo-2-methoxynaphthalen-1-yl)methyl)-3-((S)-2-(tert-butoxycarbonyl (methyl)amino)propanamido)-4-oxo-2,3,4,5-tetrahydrobenzo[b][1,4]oxazepine-9-carboxylic acid

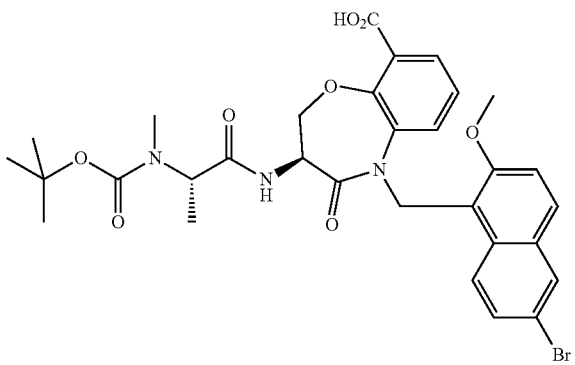 [SMILES: COc1ccc2cc(Br)ccc2c1CN1C(=O)[C@@H](NC(=O)[C@H](C)N(C)C(=O)OC(C)(C)C)COc2c(C(=O)O)cccc21]

LiOH.$H_2O$ (31.3 mg, 746 μmol, Eq: 2.5) and $H_2O$ (1.00 mL) was added to a solution of (S)-methyl 5-((6-bromo-2- methoxynaphthalen-1-yl)methyl)-3-((S)-2-(tert-butoxycarbonyl (methyl)amino)propanamido)-4-oxo-2,3,4,5-tetrahydrobenzo[b][1,4]oxazepine-9-carboxylate (200 mg, 298 µmol, Eq: 1.00) in MeOH (6.0 mL) and the mixture heated to 50° C. After 90 min. the mixture was concentrated, diluted with H₂O and extracted with Et₂O. The combined Et₂O extracts were extracted with 5% NaHCO₃. The combined aqueous mixture was acidified to pH 2.0 with 1 N HCl, extracted with EtOAc and the combined organic extracts washed with brine, dried over Na₂SO₄ and concentrated to afford the title compound (180 mg, 91%) as an off white foam which was used without purification.

(S)-5-((4-Bromonaphthalen-1-yl)methyl)-3-((S)-2-(tert-butoxycarbonyl(methyl) amino)propanamido)-4-oxo-2,3,4,5-tetrahydrobenzo[b][1,4]oxazepine-9-carboxylic acid

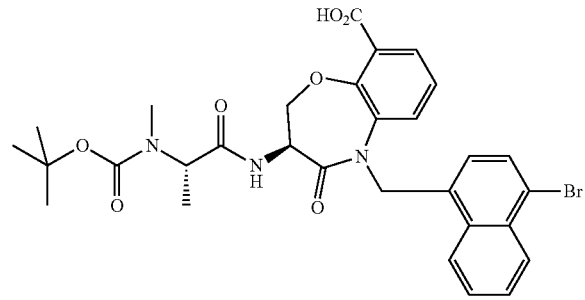 [SMILES: C[C@@H](C(=O)N[C@H]1COc2c(C(=O)O)cccc2N(Cc2ccc(Br)c3ccccc23)C1=O)N(C)C(=O)OC(C)(C)C]

Step 1: In a similar manner to that described for (S)-methyl 5-((6-bromo-2-methoxynaphthalen-1-yl)methyl)-3-(tert-butoxycarbonylamino)-4-oxo-2,3,4,5-tetrahydrobenzo[b][1,4]oxazepine-9-carboxylate except 0.01 eq. NaI was used and the mixture stirred at RT for 2 h 45 min., (S)-methyl 3-(tert-butoxycarbonylamino)-4-oxo-2,3,4,5-tetrahydrobenzo[b][1,4]oxazepine-9-carboxylate (349 mg, 1.04 mmol, Eq: 1.00) and 1-bromo-4-(bromomethyl)naphthalene (311 mg, 1.04 mmol, Eq: 1.0) were converted to (S)-methyl 5-((4-bromonaphthalen-1-yl)methyl)-3-(tert-butoxycarbonylamino)-4-oxo-2,3,4,5-tetrahydrobenzo[b][1,4]oxazepine-9-carboxylate (519 mg, 90%) as a white foam.

Step 2: In a similar manner to that described for (S)-3-amino-2,3-dihydrobenzo[b][1,4]oxazepin-4(5H)-one trifluoroacetate, (S)-methyl 5-((4-bromonaphthalen-1-yl)methyl)-3-(tert-butoxycarbonylamino)-4-oxo-2,3,4,5-tetrahydrobenzo[b][1,4]oxazepine-9-carboxylate (519 mg, 934 µmol) was converted to (S)-methyl 3-amino-5-((4-bromonaphthalen-1-yl)methyl)-4-oxo-2,3,4,5-tetrahydrobenzo[b][1,4]oxazepine-9-carboxylate trifluoroacetate (511 mg, 96%) as a white solid.

Step 3: In a similar manner to that described for the preparation of (S)-methyl 5-((6-bromo-2-methoxynaphthalen-1-yl)methyl)-3-((S)-2-(tert-butoxycarbonyl(methyl)amino)propanamido)-4-oxo-2,3,4,5-tetrahydrobenzo[b][1,4]oxazepine-9-carboxylate Step 2 except the product obtained was triturated with Et₂O/pentane, (S)-methyl 3-amino-5-((4-bromonaphthalen-1-yl)methyl)-4-oxo-2,3,4,5-tetrahydrobenzo[b][1,4]oxazepine-9-carboxylate 2,2,2-trifluoroacetate (511 mg, 898 µmol, Eq: 1.00) and (S)-2-(tert-butoxycarbonyl(methyl)amino)propanoic acid (182 mg, 898 µmol, Eq: 1.0) was converted to (S)-methyl 5-((4-bromonaphthalen-1-yl)methyl)-3-((S)-2-(tert-butoxycarbonyl (methyl) amino)propanamido)-4-oxo-2,3,4,5-tetrahydrobenzo[b][1,4]oxazepine-9-carboxylate (568 mg, 99%) obtained as a white solid.

Step 4: A 0.1 M solution of LiOH.H₂O (8.87 mL, 887 µmol, Eq: 1.00) was added to a solution of (S)-methyl 5-((4-bromonaphthalen-1-yl)methyl)-3-((S)-2-(tert-butoxycarbonyl(methyl)amino)propanamido)-4-oxo-2,3,4,5-tetrahydrobenzo[b][1,4]oxazepine-9-carboxylate (568 mg, 887 µmol, Eq: 1.00) in MeOH (10 mL) at 0° C. The mixture was stirred at RT for 20 min. then heated to 40° C. After 6.5 h the MeOH was removed in vacuo and the aqueous mixture diluted with sat. NaHCO₃ and extracted with Et₂O. The aqueous mixture was cooled 0° C., acidified to pH 3 with 3 N HCl and extracted with EtOAc. The combined extracts were washed with brine, dried over Na₂SO₄, filtered and concentrated to afford the title compound (433 mg, 78%) as a white foam which was used without purification.

(S)-3-Amino-8-methyl-2,3-dihydrobenzo[b][1,4]oxazepin-4(5H)-one trifluoroacetate

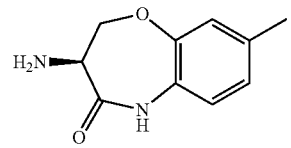

Step 1: (S)-2-(tert-butoxycarbonylamino)-3-hydroxypropanoic acid (5.5 g, 26.8 mmol, Eq: 1.00) was dissolved in DMF (90 mL) at 0° C. and NaH (60% in mineral oil, 2.57 g, 64.3 mmol, Eq: 2.4) was added in small portions The mixture was stirred for 30 min. and 2-fluoro-4-methyl-1-nitrobenzene (4.16 g, 26.8 mmol, Eq: 1.00) in DMF (10 mL) was added dropwise. The resulting mixture was stirred for 60 min., diluted with 1.0 M KHSO₄ and extracted with EtOAc. The combined organic extracts were washed with water, brine, dried over Na₂SO₄ and concentrated. The residue was purified by silica gel chromatography to afford (S)-2-(tert-butoxycarbonylamino)-3-(5-methyl-2-nitrophenoxy)propanoic acid (7.60 g, 83%) as red oil.

Step 2: (S)-2-(tert-butoxycarbonylamino)-3-(5-methyl-2-nitrophenoxy)propanoic acid (7.50 g, 22.0 mmol, Eq: 1.00) and 10% Pd/C (0.75 g, Eq: 0.03) in MeOH (300 mL) were hydrogenated at ambient pressure for 4 h at RT. The mixture was filtered through a pad of silica gel and the filtrate was concentrated to give (S)-3-(2-amino-5-methylphenoxy)-2-(tert-butoxycarbonylamino)propanoic acid (3.85, 56%) as a yellow solid which was used without purification.

Step 3: (S)-3-(2-amino-5-methylphenoxy)-2-(tert-butoxycarbonylamino)propanoic acid (3.85 g, 12.4 mmol, Eq: 1.00) and EDCI (2.38 g, 12.4 mmol, Eq: 1.00) were dissolved in DMF (50 mL) and the mixture was stirred at RT for 3 h. The mixture was diluted with EtOAc and washed with water, brine and the organic solution dried over Na₂SO₄. The mixture was filtered, concentrated and the residue was purified by silica gel chromatography to afford (S)-tert-butyl 8-methyl-4-oxo-2,3,4,5-tetrahydrobenzo[b][1,4]oxazepin-3-ylcarbamate (2.51 g, 69%) as an off white foam.

Step 4: (S)-tert-butyl 8-methyl-4-oxo-2,3,4,5-tetrahydrobenzo[b][1,4]oxazepin-3-ylcarbamate (2.50 g, 8.55 mmol, Eq: 1.00) was dissolved in dichloromethane (DCM, 10 mL) at 0° C. and TFA (10 mL) was added. The mixture was stirred at 0° C. for 1.5 h and concentrated to give the title compound (2.69 g, 103%) which was used without purification.

(2S,3S)-3-Amino-2,8-dimethyl-2,3-dihydrobenzo[b] [1,4]oxazepin-4 (5H)-one trifluoro acetate

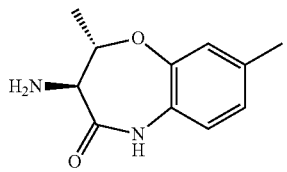

Step 1: In a similar manner to that described for the preparation of (S)-2-(tert-butoxycarbonylamino)-3-(5-methyl-2-nitrophenoxy)propanoic acid except the reaction mixture was stirred at 0° C. for 4 h, (2S,3S)-2-(tert-butoxycarbonylamino)-3-hydroxybutanoic acid DCHA (2.0 g, 5.00 mmol) and 2-fluoro-4-methyl-1-nitrobenzene (1.55 g, 9.99 mmol) were converted to (2S,3S)-2-tert-butoxycarbonylamino-3-(5-methyl-2-nitro-phenoxy)-butyric acid (0.95 g, 53.6% yield).

Step 2: (2S,3S)-2-tert-butoxycarbonylamino-3-(5-methyl-2-nitro-phenoxy)-butyri c acid (0.95 g, 2.68 mmol, Eq: 1.00) and 5% Pd/C (200 mg, 94.0 µmol, Eq: 0.0351) in EtOH (100 mL) were hydrogenated overnight at RT and ambient pressure and an additional portion of 10% Pd/C (100 mg, 47.0 µmol, Eq: 0.0176) was added. After 2 h the mixture was filtered through Celite, the filtrate was concentrated and the residue was purified by silica gel chromatography to afford (2S,3S)-3-(2-amino-5-methyl-phenoxy)-2-tert-butoxycarbonylamino-butyric acid (294 mg, 34%) as a solid.

Step 3: In a similar manner to that described for the preparation of (S)-tert-butyl 8-methyl-4-oxo-2,3,4,5-tetrahydrobenzo[b][1,4]oxazepin-3-ylcarbamate, except 1.5 eq. of EDCI was used, (2S,3S)-3-(2-amino-5-methyl-phenoxy)-2-tert-butoxycarbonylamino-butyric acid (290 mg, 894 µmol) was converted to tert-butyl (2S,3S)-2,8-dimethyl-4-oxo-2,3,4,5-tetrahydrobenzo[b][1,4]oxazepin-3-ylcarbamate (152 mg, 55.5% yield) as a solid.

Step 4: In a similar manner to that described for the preparation of (S)-3-amino-8-methyl-2,3-dihydrobenzo[b][1,4] oxazepin-4(5H)-one trifluoroacetate except the reaction mixture was stirred at 0° C. for 30 min. and at RT for 20 min., tert-butyl (2S,3S)-2,8-dimethyl-4-oxo-2,3,4,5-tetrahydrobenzo[b][1,4]oxazepin-3-ylcarbamate was converted to the title compound (175 mg, 112%) which was used without purification.

(S)-3-Amino-7-trifluormethyl-2,3-dihydrobenzo[b] [1,4]oxazepin-4 (5H)-one trifluoro acetate

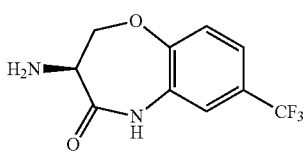 [SMILES: N[C@H]1COc2ccc(C(F)(F)F)cc2NC1=O]

In a similar manner to that described for the preparation of (S)-3-amino-8-methyl-2,3-dihydrobenzo[b][1,4]oxazepin-4 (5H)-one trifluoroacetate except in Step 3 the reaction mixture was stirred for 4 h and in the material obtained in Step 4 was triturated with hexane, (S)-2-(tert-butoxycarbonylamino)-3-hydroxypropanoic acid (4.1 g, 20.0 mmol) and 1-fluoro-2-nitro-4-(trifluoromethyl)benzene (4.18 g, 20.0 mmol) were converted to the title compound (1.06 g) which was used without purification.

(2S,3S)-3-Amino-2-methyl-7-(trifluoromethyl)-2,3-dihydrobenzo[b][1,4]oxazepin-4(5H)-one trifluoroacetate

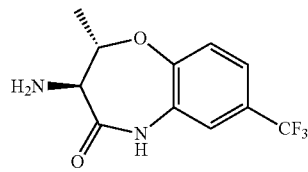 [SMILES: C[C@@H]1Oc2ccc(C(F)(F)F)cc2NC(=O)[C@H]1N]

In a similar manner to that described for the preparation of (S)-3-amino-8-methyl-2,3-dihydrobenzo[b][1,4]oxazepin-4 (5H)-one trifluoroacetate except in Step 1 the mixture was stirred overnight and in Step 2 the mixture was stirred 3 h, (2S,3S)-2-(tert-butoxycarbonylamino)-3-hydroxybutanoic acid discyclohexylamine salt (2.0 g, 5.00 mmol) and 1-fluoro-2-nitro-4-(trifluoromethyl)benzene (1.04 g, 5.00 mmol) were converted to the title compound (58 mg) which was used without purification.

(S)-3-Amino-8-trifluormethyl-2,3-dihydrobenzo[b] [1,4]oxazepin-4 (5H)-one trifluoroacetate

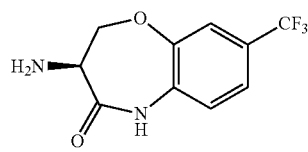 [SMILES: N[C@H]1COc2cc(C(F)(F)F)ccc2NC1=O]

In a similar manner to that described for the preparation of (S)-3-amino-8-methyl-2,3-dihydrobenzo[b][1,4]oxazepin-4 (5H)-one trifluoroacetate except in Step 3 1.2 eq. EDCI was used and the reaction mixture was stirred for 2 h and in Step 4 the mixture was stirred for 1 h and the material obtained was triturated with Et₂O/pentane, (S)-2-(tert-butoxycarbonylamino)-3-hydroxypropanoic acid (4.96 g, 24.2 mmol) and 2-fluoro-1-nitro-4-(trifluoromethyl)benzene (5.05 g, 24.2 mmol) were converted to the title compound (1.6 g) as a pale yellow solid.

((R)-9-Amino-4-oxo-2,3,4,5-tetrahydro-benzo[b][1, 4]thiazepin-3-yl)-carbamic acid tert-butyl ester

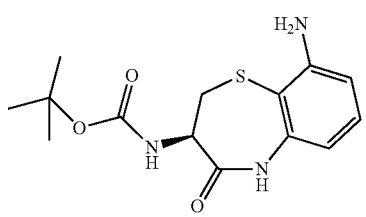 [SMILES: CC(C)(C)OC(=O)N[C@H]1CSc2c(N)cccc2NC1=O]

Step 1: To a solution of 2-chloro-1,3-dinitrobenzene (1.0 g, 4.9 mmol) in DMF (25 mL) was added Cs₂CO₃ (4.0 g, 12.3 mmol) followed by L-BOC-Cys-OH (1.1 g, 4.9 mmol) and the resulting mixture was allowed to stir at room temperature for 15 min. The reaction was cooled to 0° C., acidified with 1.0 N HCl (15 mL) and extracted with EtOAc. The organic layers were combined, washed with H₂O, brine, dried over Na₂SO₄, filtered and concentrated to give (R)-2-tert-butoxy-carbonylamino-3-(2,6-dinitro-phenylsulfanyl)-propionic acid which was used without purification (1.9 g).

Step 2: To a solution of (R)-2-tert-butoxycarbonylamino-3-(2,6-dinitro-phenylsulfanyl)-propionic acid (1.7 g, 4.4 mmol) in 3:1 v/v MeOH/H₂O (80 mL) containing NH₄Cl (7.0 g, 130 mmol) was added Zn dust (5.7 g, 87.2 mmol) and the resulting mixture was stirred for 1 h. The mixture was filtered through a pad of Celite, the filtrate volume was reduced in vacuuo and acidified to pH 4 with 1.0 M HCl. The mixture was extracted with EtOAc, the combined extracts washed with H₂O, brine, dried over Na₂SO₄, filtered and concentrated to give (R)-2-tert-butoxycarbonylamino-3-(2,6-diamino-phenylsulfanyl)-propionic acid (1.0 g) which was used without purification.

Step 3: To a solution of (R)-2-tert-butoxycarbonylamino-3-(2,6-diamino-phenylsulfanyl)-propionic acid (1.0 g, 3.1 mmol) in DMF (12 mL) was added DIEA (1.6 mL, 9.1 mmol), HOBT.H₂O (859 mg, 6.2 mmol) and HBTU (2.3 g, 6.2 mmol). The mixture was stirred under an atmosphere of N₂ at room temperature for 3 h. The reaction was poured into H₂O and extracted with EtOAc. The organic extracts were combined, washed with 0.5 M HCl, H₂O, brine, dried over Na₂SO₄, filtered and concentrated. The residue was purified by chromatography by silica gel chromatography to give the title compound (560 mg, 59%).

[(S)-1-((R)-9-Amino-5-naphthalen-1-ylmethyl-4-oxo-2,3,4,5-tetrahydro-benzo[b][1,4]thiazepin-3-ylcarbamoyl)-ethyl]-methyl-carbamic acid tert-butyl ester

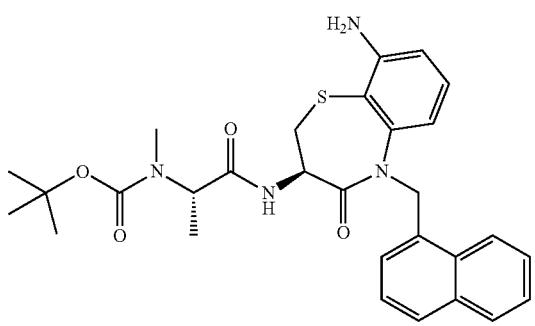 [SMILES: C[C@@H](C(=O)N[C@H]1CSc2c(N)cccc2N(Cc2cccc3ccccc23)C1=O)N(C)C(=O)OC(C)(C)C]

Step 1: Hydrogen chloride gas was bubbled for 1 min. into a solution of ((R)-9-amino-4-oxo-2,3,4,5-tetrahydro-benzo[b][1,4]thiazepin-3-yl)-carb amic acid tert-butyl ester (560 mg, 1.8 mmol) in dioxane (15 mL) at 0° C. and the reaction was warmed to RT. After 1 h the mixture was concentrated and the residue was triturated with Et₂O. The resulting solid was filtered, washed with hexanes and dried to give (R)-3,9-diamino-2,3-dihydro-5H-benzo[b][1,4]thiazepin-4-one dihydrochloride (500 mg. 99%).

Step 2: To a solution of (R)-3,9-diamino-2,3-dihydro-5H-benzo[b][1,4]thiazepin-4-one dihydrochloride (500 mg, 1.8 mmol) in DMF (10 mL) was added L-BOC-Ala-OH (396 mg, 1.9 mmol), DIEA (1.2 mL, 7.2 mmol), HOBT.H₂O (489 mg, 3.6 mmol) and HBTU (1.3 g, 3.6 mmol). After 3 h, the reaction was diluted with H₂O and extracted with EtOAc. The combined extracts were washed with 0.5 M HCl, H₂O, brine, dried over Na₂SO₄, filtered and concentrated. The residue was purified by silica gel chromatography to give (S)-1-((R)-9-amino-4-oxo-2,3,4,5-tetrahydro-benzo[b][1,4]thiazepin-3-ylcarbamoyl)-ethyl-methyl-carbamic acid tert-butyl ester (660 mg, 94%).

Step 3: To a solution of (S)-1-((R)-9-amino-4-oxo-2,3,4,5-tetrahydro-benzo[b][1,4]thiazepin-3-ylcarbamoyl)-ethyl-methyl-carbamic acid tert-butyl ester (1.5 g, 3.9 mmol) in DMF (25 mL) was added K₂CO₃ (2.6 g, 19.0 mmol) and 1-bromomethyl-naphthalene (631 mg, 2.9 mmol) in DMF (10 mL) was added dropwise. After 36 h, the mixture was diluted with sat. aq. citric acid and extracted with EtOAc. The combined extracts were washed with H₂O, brine, dried over Na₂SO₄, filtered and concentrated. The residue was purified by silica gel chromatography to give the title compound (1.3 g, 81%).

1-Benzyl-2-fluoro-3-nitro-benzene

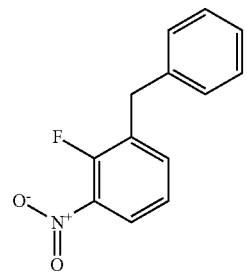 [SMILES: O=[N+]([O-])c1cccc(Cc2ccccc2)c1F]

To a mixture 1-bromo-2-fluoro-3-nitrobenzene (800 mg, 3.6 mmol), potassium benzyltrifluoroborate (2.2 g, 10.9 mmol) and Cs₂CO₃ (3.6 g, 10.9 mmol) in dioxane/H2O (10:1, 18 mL) was added [1,1'-bis(diphenylphosphino)ferrocene] palladium(II) dichloride (60 mg, 2 mol %) and the mixture was heated to 100° C. for 8 h. The mixture was cooled to RT, diluted with H₂O and extracted with EtOAc. The combined extracts were washed with H2O, brine, dried over Na₂SO₄, filtered and concentrated. The residue was purified by silica gel chromatography to give the title compound (520 mg, 62%).

2-(Dibenzylamino)-2-(1-hydroxycyclohexyl)acetic acid

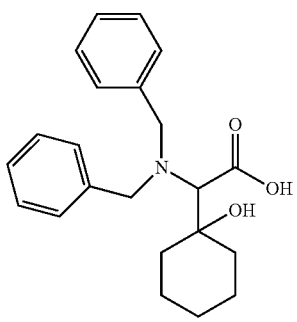 [SMILES: O=C(O)C(N(Cc1ccccc1)Cc1ccccc1)C1(O)CCCCC1]

Step 1: Ethyl 2-(dibenzylamino)acetate (4.92 g, 17.4 mmol, Eq: 1.2) in THF (40 mL) was added to a solution of LDA in THF at −40° C. After 15 min. the mixture was cooled to −78° C. and cyclohexanone (1.42 g, 1.5 mL, 14.5 mmol, Eq: 1.00) in THF (10 mL) was added. After 2 h, 10 mL of sat. NH$_4$Cl was added and the mixture warmed to RT. After 2 h, the mixture was diluted with H$_2$O and extracted with EtOAc. The combined extracts were washed with H$_2$O, dried over Na$_2$SO$_4$ and concentrated. The residue was purified by flash chromatography to give 2-(dibenzylamino)-2-(1-hydroxycyclohexyl)acetate as a colorless oil (1.63 g, 30%) MS m/z 382.1 (MH$^+$)

Step 2: KOH (1.44 g, 25.6 mmol, Eq: 6) in H$_2$O (20 mL) was added to as solution of ethyl 2-(dibenzylamino)-2-(1-hydroxycyclohexyl)acetate (1.63 g, 4.27 mmol, Eq: 1.00) in MeOH (60 mL) and the mixture was heated to 60° C. After 18 h the reaction was cooled to RT and diluted with 100 mL H$_2$O. The pH of the reaction was adjusted to about 4 using sat. KHSO$_4$, and extracted with EtOAc. The combined extracts were washed with H$_2$O, dried over Na$_2$SO$_4$ and concentrated the title compound as a white foam (1.44 g, 95%) which was used without purification. MS m/e 354.1 (MH$^+$).

3-Amino-3H-spiro[benzo[b][1,4]oxazepine-2,1'-cyclohex an]-4 (5H)-one

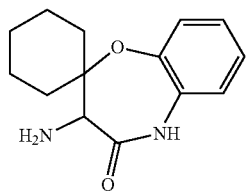 [SMILES: NC1C(=O)Nc2ccccc2OC12CCCCC2]

Step 1: 2-(dibenzylamino)-2-(1-hydroxycyclohexyl)acetic acid (0.70 g, 1.98 mmol, Eq: 1.00) and 1-fluoro-2-nitrobenzene (293 mg, 219 µl, 2.08 mmol, Eq: 1.05) were dissolved in THF (10 mL) and a solution of potassium bis(trimethylsilyl)amide 0.5 M in toluene (8.71 mL, 4.36 mmol, Eq: 2.2) was added. The mixture was heated to 60° C. After 1 h the mixture was cooled to RT and 0.2 mL 1-fluoro-2-nitrobenzene and an additional 9 mL of potassium bis(trimethylsilyl)amide (0.5 M in toluene) were added and the mixture stirred at 60° C. for 90 min. The mixture was diluted with H$_2$O, acidified with sat. KHSO$_4$, and extracted with EtOAc. The combined extracts were washed with H$_2$O, brine, dried over Na$_2$SO$_4$ and concentrated. The residue was purified by flash chromatography to afford 2-(1-(2-aminophenoxyl)cyclohexyl)-2-(dibenzylamino)acetic acid as a light brown oil (0.80 g, 85%). MS m/z 475.1 (MH$^+$)

Step 2: 2-(Dibenzylamino)-2-(1-(2-nitrophenoxyl)cyclohexyl)acetic acid (0.8 g, 1.69 mmol, Eq: 1.00), NH$_4$Cl (180 mg, 3.37 mmol, Eq: 2) and Zn (1.71 g, 26.1 mmol, Eq: 15.5) were combined with MeOH (35.0 mL) to give a grey suspension, and the mixture was heated to 65° C. for 90 min. The mixture was filtered through Celite, the filtrate was concentrated and partitioned between sat. aq. NaOAc and Et$_2$O. The phases were separated and the organic layer washed with H$_2$O, brine, dried over Na$_2$SO$_4$ and concentrated to afford 2-(1-(2-aminophenoxyl)cyclohexyl)-2-(dibenzylamino)acetic acid as light brown solid (0.6365 g, 85%). MS m/z 475.1 (MH$^+$).

Step 3: A mixture of 2-(1-(2-Aminophenoxyl)cyclohexyl)-2-(dibenzylamino)acetic acid (0.6365 g, 1.43 mmol, Eq: 1.00), HOBT.H$_2$O (307 mg, 2.00 mmol, Eq: 1.4) and EDCI (274 mg, 1.43 mmol, Eq: 1.00) in DMF (12 mL) were stirred at RT for 1 h and the mixture was diluted with EtOAc. The mixture was washed with sat. NaHCO$_3$, brine, dried over Na$_2$SO$_4$ and concentrated. The residue was purified by flash chromatography to afford 3-(dibenzylamino)-3H-spiro[benzo[b][1,4]oxazepine-2,1'-cyclohexan]-4 (5H)-one as an off-white solid (0.387 g, 64%). MS m/z 427.1 (MH$^+$)

Step 4: 3-(Dibenzylamino)-3H-spiro[benzo[b][1,4]oxazepine-2,1'-cyclohexan]-4 (5H)-one (0.3875 g, 908 µmol, Eq: 1.00) and 20% Pd(OH)$_2$/C (0.47 g, 3.35 mmol, Eq: 3.68) were combined with MeOH (100 mL) and acetic acid (0.1 mL) and the mixture was hydrogenated at 50 psi. After 18 h, the mixture was filtered through Celite, the filtrate concentrated, the residue dissolved in MeCN/H$_2$O and lyophilized to afford of the title compound as an off-white solid (0.297 g, 100%) which was used without purification. MS m/z 247.0 (MH$^+$)

The compounds in Table 1 were prepared by analogous methods.

TABLE 1

| Entry | Ketone | Product | MS (m/z) |
|---|---|---|---|
| 1 | ![ketone1] | ![product1] | 247.9 (M—Boc) |
| 2 | ![ketone2] | ![product2] | 207.0 |

TABLE 1-continued

| Entry | Ketone | Product | MS (m/z) |
|---|---|---|---|
| 3 | cyclopentanone | spiro product | 233.0 |
| 4 | 1-(methylsulfonyl)piperidin-4-one | spiro product | 326.0 |
| 5 | tetrahydro-2H-pyran-3-one | spiro product | 249.0 |
| 6 | cyclobutanone | spiro product | 220.9 |
| 7 | (methylthio)acetone | product | 253.0 |
| 8 | tetrahydro-2H-pyran-3-one | spiro product | 248.9 |
| 9 | methoxyacetone | product | 237.0 |

TABLE 1-continued

| Entry | Ketone | Product | MS (m/z) |
|---|---|---|---|
| 10 | | | 251.0 |
| 11 | | | ND |
| 12 | | | ND |

Methyl-(tert-butyl)-(2S)-1-oxo-1-((3R)-(4-oxo-2',3', 4,5,5',6'-hexahydro-3H-spiro[benzo[b][1,4]oxazepine-2,1'-cyclohexan]-3-ylamino))propan-2-yl carbamate and methyl-(tert-butyl)-(2S)-1-oxo-1-((3S)-(4-oxo-2',3',4,5,5',6'-hexahydro-3H-spiro [benzo[b][1,4]oxazepine-2,1'-cyclohexan]-3-ylamino))propan-2-yl carbamate

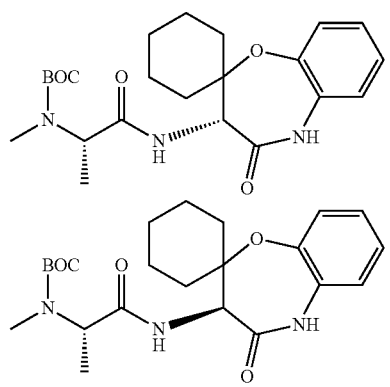

3-Amino-3H-spiro[benzo[b][1,4]oxazepine-2,1'-cyclohexan]-4 (5H)-one (0.29 g, 1.18 mmol, Eq: 1.00), BOC-N-Me-Ala-OH (287 mg, 1.41 mmol, Eq: 1.2) and TEA (357 mg, 492 μl, 3.53 mmol, Eq: 3) were combined with DMF (10 mL) and a solution of HBTU (536 mg, 1.41 mmol, Eq: 1.2) and HOBT.H2O (216 mg, 1.41 mmol, Eq: 1.2) in DMF (10 mL) was added. After 1 h, the mixture was diluted with EtOAc, washed with 1:1 sat NaHCO₃/brine, brine, dried over Na₂SO₄ and concentrated. The residue was purified by flash chromatography to afford two diastereomers, methyl-(tert-butyl)-(2S)-1-oxo-1-((3R)-(4-oxo-2',3',4,5,5',6'-hexahydro-3H-spiro[benzo[b][1,4]oxazepine-2,1'-cyclohexan]-3-yl amino))propan-2-yl carbamate, which eluted first and methyl-(tert-butyl)-(2S)-1-oxo-1-((3S)-(4-oxo-2',3',4,5,5', 6'-hexahydro-3H-spiro[benzo[b][1,4]oxazepine-2,1'-cyclohexan]-3-ylamino))propan-2-yl carbamate, which eluted second. Each diastereomer was separately dissolved in MeCN/H₂O and lyophilized to afford each diastereomer as a white solid: methyl-(tert-butyl)-(2S)-1-oxo-1-((3R)-(4-oxo-2',3',4, 5,5',6'-hexahydro-3H-spiro[benzo[b][1,4]oxazepine-2,1'-cyclohexan]-3-ylamino))propan-2-yl carbamate (98.2 mg) and methyl-(tert-butyl)-(2S)-1-oxo-1-((3S)-(4-oxo-2',3',4,5,5', 6'-hexahydro-3H-spiro[benzo[b][1,4]oxazepine-2,1'-cyclohexan]-3-ylamino))propan-2-yl carbamate (44.1 mg).

tert-butyl methyl((S)-1-oxo-1-((S)-4-oxo-2',3',4,5,5', 6'-hexahydro-3H-spiro[benzo[b][1,4]oxazepine-2,4'-pyran]-3-ylamino)propan-2-yl)carbamate

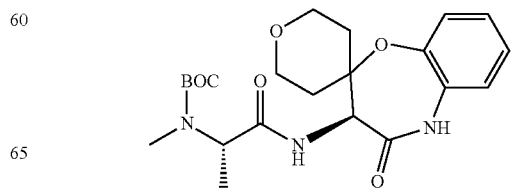

A solution of HBTU (43.2 g, 114 mmol, Eq: 1.2) and HOBT.H2O (17.4 g, 114 mmol, Eq: 1.2) in DMF (300 mL) was added to a mixture of 3-amino-2',3',5',6'-tetrahydro-3H-spiro[benzo[b][1,4]oxazepine-2,4'-pyran]-4(5H)-one hydrochloride (27 g, 94.8 mmol, Eq: 1.00), BOC-N-Me-Ala-OH (23.1 g, 114 mmol, Eq: 1.2) and TEA (38.4 g, 52.9 mL, 379 mmol, Eq: 4) in DMF (300 mL). After 18 h the mixture was poured into brine (750 mL) and the mixture extracted with EtOAc. The combined extracts were washed with 1:1 sat NaHCO3/brine, brine, dried over Na2SO4, and concentrated. The residue was purified by flash chromatography to afford a mixture of diastereomers (36.2 g) as a light yellow solid. The diastereomers were separated by supercritical fluid chromatography (SFC) using a Daicel AD column (5×25 cm) eluted with 15% MeOH/CO2 at 200 mL/min and 220 nM detection at 100 bar backpressure and 35° C. oven. The first diastereomer eluted from the column afforded the title compound (15.29 g, 37%) as an off-white foam. MS m/z 434.1 (MH+).

3-Amino-2,2-dimethyl-2,3-dihydrobenzo[b][1,4]thiazepin-4(5H)-one

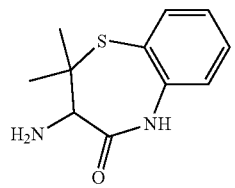

Benzyl 2,2-dimethyl-4-oxo-2,3,4,5-tetrahydrobenzo[b][1,4]thiazepin-3-ylcarbamate (0.67 g, 1.88 mmol, Eq: 1.00, WO96/11940) and 33% HBr/HOAc (9 µl, 54.7 mmol, Eq: 29) were combined to give a yellow solution. After 75 min. the mixture was diluted with 100 mL Et2O. The resulting precipitate was collected by filtration, washed with Et2O and added to 100 mL of aq. NaHCO3. The mixture was extracted with EtOAc and DCM. The combined extracts were dried over Na2SO4, filtered and the filtrate concentrated to give the title compound as a white solid (0.3370 g, 81%) which was used without purification. MS m/z 379.0 (MH+).

tert-Butyl (S)-1-((S)-2,2-dimethyl-4-oxo-2,3,4,5-tetrahydrobenzo[b][1,4]thiazepin-3-ylamino)-1-oxopropan-2-yl(methyl)carbamate and tert-butyl (S)-1-((R)-2,2-dimethyl-4-oxo-2,3,4,5-tetrahydrobenzo[b][1,4]thiazepin-3-ylamino)-1-oxopropan-2-yl(methyl)carbamate

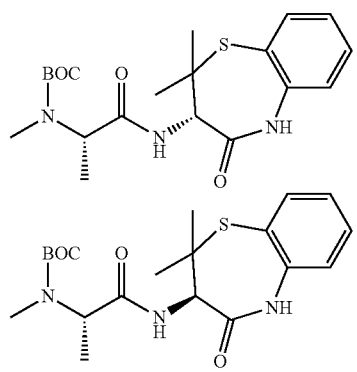

3-Amino-2,2-dimethyl-2,3-dihydrobenzo[b][1,4]thiazepin-4 (5H)-one (0.337 g, 1.52 mmol, Eq: 1.00), BOC—N-Me-Ala-OH (370 mg, 1.82 mmol, Eq: 1.2) and TEA (460 mg, 634 IA, 4.55 mmol, Eq: 3) were combined with DMF (5 mL) and a solution of HBTU (690 mg, 1.82 mmol, Eq: 1.2) and HOBTH2O (279 mg, 1.82 mmol, Eq: 1.2) in DMF (5 mL) was added. After 15 h, the mixture was diluted with EtOAc, washed with 1:1 sat NaHCO3/brine, brine, dried over Na2SO4 and concentrated. The residue was purified by flash chromatography. Two diastereomers were isolated, tert-butyl (S)-1-((S)-2,2-dimethyl-4-oxo-2,3,4,5-tetrahydrobenzo[b][1,4]thiazepin-3-ylamino)-1-oxopropan-2-yl(methyl)carbamate (eluted first, 0.241 g, white foam) and tert-butyl (S)-1-((R)-2,2-dimethyl-4-oxo-2,3,4,5-tetrahydrobenzo[b][1,4]thiazepin-3-ylamino)-1-oxopropan-2-yl(methyl)carbamate (eluted second, 0.207 g, white foam).

tert-Butyl (S)-1-(4-oxo-2,3,4,5-tetrahydrobenzo[b][1,4]thiazepin-3-ylamino)-1-oxopropan-2-yl(methyl)carbamate

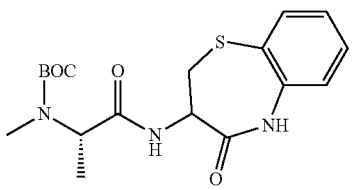 [SMILES: C[C@@H](C(=O)NC1CSc2ccccc2NC1=O)N(C)C(=O)OC(C)(C)C]

3-Amino-2,3-dihydro-1,5-benzothiazepin-4(5H)-one hydrochloride (1.0 g, 5.15 mmol, Eq: 1.00), BOC—N-Me-Ala-OH (1.26 g, 1.62 mmol, Eq: 1.2) and TEA (2.2 mL, 15.45 mmol, Eq: 3.00) were dissolved in DMF (30 mL) and HOBT.H2O (697 mg, 5.14 mmol, Eq: 1.20) and HBTU (2.34 g, 6.18 mmol, Eq: 1.20) were added. After 1 h 20 min. the mixture was diluted with 1 N HCl and extracted with EtOAc. The organic extracts were washed with 1 N NaOH, brine, dried over Na2SO4 and concentrated to afford the title compound (1.66 g, 85% yield) which was used without purification.

3-Amino-8,9-difluoro-2',3',5',6'-tetrahydro-3H-spiro[benzo[b][1,4]oxazepine-2,4'-pyran]-4(5H)-one

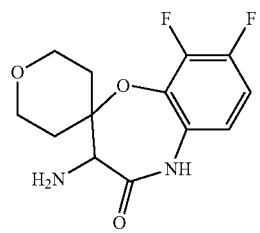 [SMILES: NC1C(=O)Nc2ccc(F)c(F)c2OC12CCOCC2]

Step 1: Potassium bis(trimethylsilyl) amide, 1 M solution in THF (4.22 mL, 4.22 mmol, Eq: 3.00), was added to a solution of 2-(dibenzylamino)-2-(4-hydroxytetrahydro-2H-pyran-4-yl)-acetic acid (0.5 g, 1.41 mmol, Eq: 1.00) in THF (10 mL) at RT and the mixture stirred for 15 min. The mixture was cooled to 0° C., 2,3,4-trifluoronitrobenzene (1.25 g, 0.83 mL, 7 mmol, Eq: 5.00) was added and the mixture stirred at 0° C. for 45 min. The mixture was diluted with H2O at 0° C. and was warmed to RT. The pH was adjusted to ~2-3 with sat KHSO4, the mixture extracted with EtOAc. The combined extracts were washed with brine, dried over Na2SO4, concentrated and the residue purified by flash chromatography to afford 2-(dibenzylamino)-2-(4-(5,6-difluoro-2-nitrophenoxy)tetrahydro-2H-pyran-4-yl)-acetic acid (0.23 g, 32% yield). MS m/z 513.0 (MH$^+$)

Step 2: NH$_4$Cl (48.0 mg, 0.90 mmol, Eq: 2) and Zn powder (440 mg, 6.73 mmol, Eq: 15) were added to a solution of 2-(dibenzylamino)-2-(4-(2,3-difluoro-6-nitrophenoxy)tetrahydro-2H-pyran-4-yl)-acetic acid (230 mg, 449 μmol, Eq: 1.00) in MeOH (10 mL) and the mixture was heated to 65° C. After 2 h the mixture was filtered through Celite. The filtrate was concentrated and partitioned between 1 N NaOAc and EtOAc. The organic layer was dried over Na$_2$SO$_4$ then concentrated under reduced pressure to afford [4-(6-amino-2,3-difluoro-phenoxy)-tetrahydro-pyran-4-yl]-dibenzylamino-acetic acid (185 mg) which was used without purification.

Step 3: HOBT.H$_2$O (70.5 mg, 460 μmol, Eq: 1.2) and EDCI (88.2 mg, 460 μmol, Eq: 1.2) were added to a solution of [4-(6-amino-2,3-difluoro-phenoxy)-tetrahydro-pyran-4-yl]-dibenzylamino-acetic acid (185 mg, 383 μmol, Eq: 1.00) in DMF (5 mL). The mixture was stirred at RT overnight, diluted with H$_2$O and extracted with EtOAc. The combined extracts were washed with brine, dried over Na$_2$SO$_4$ and concentrated under reduced pressure. The residue was purified by flash chromatography to afford 3-(dibenzylamino)-8,9-difluoro-2',3',5',6'-tetrahydro-3H-spiro[benzo[b][1,4]oxazepine-2,4'-pyran]-4(5H)-one (102 mg, 57% yield). MS m/z 465.0 (MH$^+$)

Step 4: 3-(Dibenzylamino)-8,9-difluoro-2',3',5',6'-tetrahydro-3H-spiro[benzo[b][1,4]oxazepine-2,4'-pyran]-4(5H)-one (100 mg, 215 μmol, Eq: 1.00) was added to MeOH (10 mL) and the mixture warmed 40° C. to give a light yellow suspension. 20% Pd(OH)$_2$/C (100 mg, 215 μmol, Eq: 1.00) was added, the mixture was degassed and stirred at RT under H$_2$ for 6.5 h. The mixture was filtered through Celite and concentrated under reduced pressure to afford 3-amino-8,9-difluoro-2',3',5',6'-tetrahydro-3H-spiro[benzo[b][1,4]oxazepine-2,4'-pyran]-4(5 h)-one (60 mg, 98% yield) as colorless oil which was used without purification. MS m/z 285.0 (MH$^+$)

tert-Butyl-(2S)-1-oxo-1-((3R)-(8,9-difluoro-4-oxo-2',3',4,5,5',6'-hexahydro-3H-spiro[benzo[b][1,4]oxazepine-2,4'-pyran]-3-ylamino))propan-2-yl carbamate and tert-butyl-(2S)-1-oxo-1-((3S)-(8,9-difluoro-4-oxo-2',3',4,5,5',6'-hexahydro-3H-spiro[benzo[b][1,4]oxazepine-2,4'-pyran]-3-ylamino))propan-2-yl carbamate

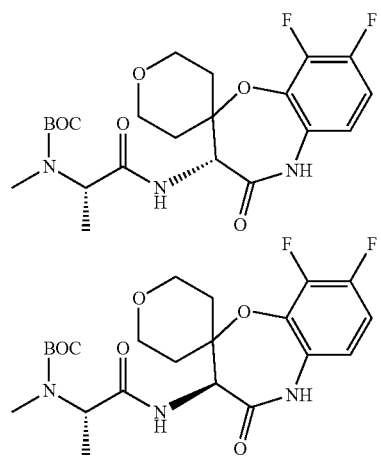

HOBT.H$_2$O (38.8 mg, 253 μmol, Eq: 1.2) and HBTU (96.1 mg, 253 μmol, Eq: 1.2) were added to a mixture of 3-amino-8,9-difluoro-2',3',5',6'-tetrahydro-3H-spiro[benzo[b][1,4]oxazepine-2,4'-pyran]-4(5 h)-one (60 mg, 211 μmol, Eq: 1.00), BOC-N-Me-Ala-OH (51.5 mg, 253 μmol, Eq: 1.2) and TEA (53.4 mg, 74.2 μl, 528 μmol, Eq: 2.5) in DMF (3 mL). After 2 h, the mixture was diluted with H$_2$O/1 N HCl and extracted with EtOAc. The combined extracts were washed with 1 N NaOH, brine, dried over Na$_2$SO$_4$ and concentrated. The residue was purified by flash chromatography to afford tert-butyl-(2S)-1-oxo-1-((3R)-(8,9-difluoro-4-oxo-2',3',4,5,5',6'-hexahydro-3H-spiro[benzo[b][1,4]oxazepine-2,4'-pyran]-3-ylamino))propan-2-yl carbamate (eluted first, 40 mg, 40%) and tert-butyl-(2S)-1-oxo-1-((3S)-(8,9-difluoro-4-oxo-2',3',4,5,5',6'-hexahydro-3H-spiro[benzo[b][1,4]oxazepine-2,4'-pyran]-3-ylamino))propan-2-yl carbamate (eluted second, 42 mg, 42% yield).

3-Amino-9-fluoro-2',3',5',6'-tetrahydro-3H-spiro[benzo[b][1,4]oxazepine-2,4'-pyran]-4(5H)-one

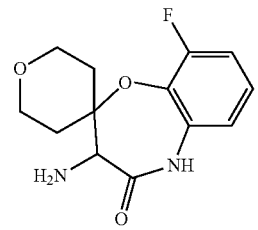 [SMILES: NC1C(=O)Nc2cccc(F)c2OC12CCOCC2]

In a similar manner to that described for the preparation of 3-amino-8,9-difluoro-2',3',5',6'-tetrahydro-3H-spiro[benzo[b][1,4]oxazepine-2,4'-pyran]-4(5H)-one except in step 4 the mixture was hydrogenated overnight, 2,3-difluoronitrobenzene (4.48 g, 2.98 mL, 28.1 mmol) was converted to the title compound as a beige solid (480 mg) which was used without purification. MS m/z 266.9 (MH$^+$)

tert-butyl-(2S)-1-oxo-1-((3R)-(9-fluoro-4-oxo-2',3',4,5,5',6'-hexahydro-3H-spiro[benzo[b][1,4]oxazepine-2,4'-pyran]-3-ylamino))propan-2-yl carbamate and tert-butyl-(2S)-1-oxo-1-43S)-(9-fluoro-4-oxo-2',3',4,5,5',6'-hexahydro-3H-spiro[benzo[b][1,4]oxazepine-2,4'-pyran]-3-ylamino))propan-2-yl carbamate

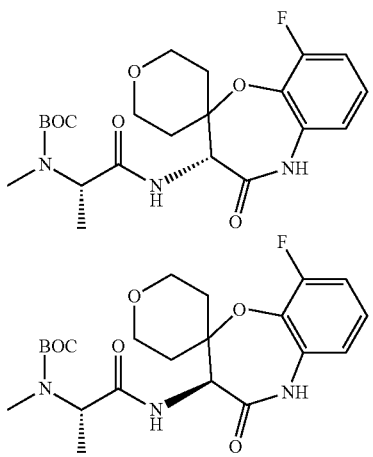

In a similar manner to that described for the preparation of tert-butyl-(25)-1-oxo-1-((3R)-(8,9-difluoro-4-oxo-2',3',4,5,5',6'-hexahydro-3H-spiro[benzo[b][1,4]oxazepine-2,4'-pyran]-3-ylamino))propan-2-yl carbamate and tert-butyl-(2S)-

1-oxo-1-((3S)-(8,9-difluoro-4-oxo-2',3',4,5,5',6'-hexahydro-3H-spiro[benzo[b][1,4]oxazepine-2,4'-pyran]-3-ylamino))propan-2-yl carbamate except the mixture was stirred for 1 h, 3-amino-9-fluoro-2',3',5',6'-tetrahydro-3H-spiro[benzo[b][1,4]oxazepine-2,4'-pyran]-4(5H)-one (80 mg, 300 μmol, Eq: 1.00) and BOC-N-Me-Ala-OH (73.3 mg, 361 μmol, Eq: 1.2) were converted to tert-butyl-(2S)-1-oxo-1-((3R)-(9-fluoro-4-oxo-2',3',4,5,5',6'-hexahydro-3H-spiro[benzo[b][1,4]oxazepine-2,4'-pyran]-3-ylamino))propan-2-yl carbamate (eluted first, 64 mg, 47%, MS m/z 492.0 (MH+)) and tert-butyl-(2S)-1-oxo-1-((3S)-(9-fluoro-4-oxo-2',3',4,5,5',6'-hexahydro-3H-spiro[benzo[b][1,4]oxazepine-2,4'-pyran]-3-ylamino))propan-2-yl carbamate (eluted second, 49 mg, 36%, MS m/z 492.0 (MH+)).

tert-Butyl-(2S)-1-oxo-1-((3R)-(9-fluoro-4-oxo-2',3',4,5,5',6'-hexahydro-3H-spiro[benzo[b][1,4]oxazepine-2,4'-pyran]-3-ylamino))butan-2-yl carbamat and tert-butyl-(2S)-1-oxo-1-((3S)-(9-fluoro-4-oxo-2',3',4,5,5',6'-hexahydro-3H-spiro[benzo[b][1,4]oxazepine-2,4'-pyran]-3-ylamino))butan-2-yl carbamate

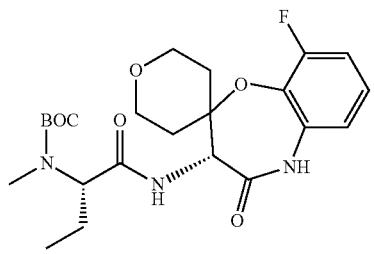

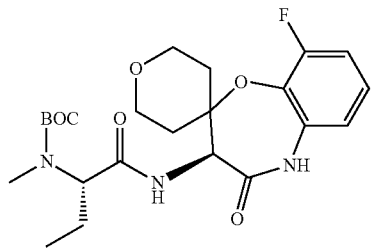

In a similar manner to that described for the preparation of tert-butyl-(2S)-1-oxo-1-((3R)-(8,9-difluoro-4-oxo-2',3',4,5,5',6'-hexahydro-3H-spiro[benzo[b][1,4]oxazepine-2,4'-pyran]-3-ylamino))propan-2-yl carbamate and tert-butyl-(2S)-1-oxo-1-((3S)-(8,9-difluoro-4-oxo-2',3',4,5,5',6'-hexahydro-3H-spiro[benzo[b][1,4]oxazepine-2,4'-pyran]-3-ylamino))propan-2-yl carbamate except the mixture was stirred for 1 h, 3-amino-9-fluoro-2',3',5',6'-tetrahydro-3H-spiro[benzo[b][1,4]oxazepine-2,4'-pyran]-4(5H)-one (80 mg, 300 μmol, Eq: 1.00) and (S)-2-(tert-butoxycarbonyl(methyl)amino)butanoic acid (78 mg, 361 μmol, Eq: 1.20) were converted to tert-butyl-(2S)-1-oxo-1-((3R)-(9-fluoro-4-oxo-2',3',4,5,5',6'-hexahydro-3H-spiro[benzo[b][1,4]oxazepine-2,4'-pyran]-3-ylamino))butan-2-yl carbamate (eluted first, 50 mg, 36%, MS m/z 488.0 (MH+)) and tert-butyl-(2S)-1-oxo-1-((3S)-(9-fluoro-4-oxo-2',3',4,5,5',6'-hexahydro-3H-spiro[benzo[b][1,4]oxazepine-2,4'-pyran]-3-ylamino))butan-2-yl carbamate (eluted second, 40 mg, 36%, MS m/z 488.0 (MH+)).

3-Amino-8-fluoro-2',3',5',6'-tetrahydro-3H-spiro[benzo[b][1,4]oxazepine-2,4'-pyran]-4(5H)-one

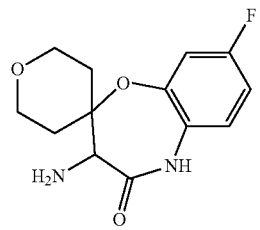 [SMILES: NC1C(=O)Nc2ccc(F)cc2OC12CCOCC2]

In a similar manner to that described for the preparation of 3-amino-8,9-difluoro-2',3',5',6'-tetrahydro-3H-spiro[benzo[b][1,4]oxazepine-2,4'-pyran]-4(5H)-one except in step 2 2.5 eq. of NH₄Cl and 12 eq. of Zn were used, in step 3 the mixture was stirred for 6 h and in step 4 the mixture was hydrogenated overnight, 2,4-difluoronitrobenzene (2.69 g, 1.79 mL, 16.9 mmol) was converted to the title compound as a beige solid (110 mg) which was used without purification.

tert-Butyl-(2S)-1-oxo-1-((3R)-(8-fluoro-4-oxo-2',3',4,5,5',6'-hexahydro-3H-spiro[benzo[b][1,4]oxazepine-2,4'-pyran]-3-ylamino))propan-2-yl carbamate and tert-butyl-(2S)-1-oxo-1-((3S)-(8-fluoro-4-oxo-2',3',4,5,5',6'-hexahydro-3H-spiro[benzo[b][1,4]oxazepine-2,4'-pyran]-3-ylamino))propan-2-yl carbamate

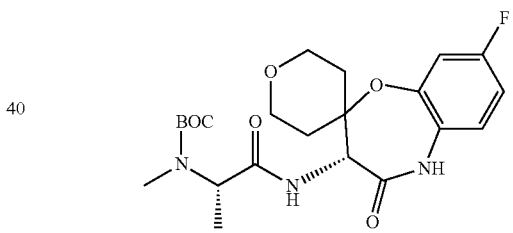

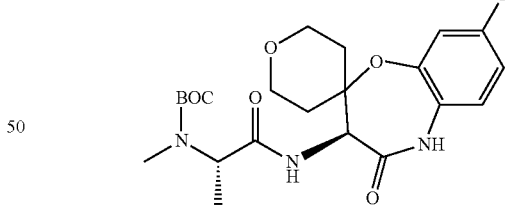

In a similar manner to that described for the preparation of tert-butyl-(2S)-1-oxo-1-((3R)-(8,9-difluoro-4-oxo-2',3',4,5,5',6'-hexahydro-3H-spiro[benzo[b][1,4]oxazepine-2,4'-pyran]-3-ylamino))propan-2-yl carbamate and tert-butyl-(2S)-1-oxo-1-((3S)-(8,9-difluoro-4-oxo-2',3',4,5,5',6'-hexahydro-3H-spiro[benzo[b][1,4]oxazepine-2,4'-pyran]-3-ylamino))propan-2-yl carbamate except the mixture was stirred for 1.5 h, 3-amino-8-fluoro-2',3',5',6'-tetrahydro-3H-spiro[benzo[b][1,4]oxazepine-2,4'-pyran]-4(5H)-one (59 mg, 222 1=01, Eq: 1.00), BOC-N-Me-Ala-OH (54.0 mg, 266 μmol, Eq: 1.2) were converted to tert-butyl-(2S)-1-oxo-1-((3R)-(8-fluoro-4-oxo-2',3',4,5,5',6'-hexahydro-3H-spiro[benzo[b][1,4]oxazepine-2,4'-pyran]-3-ylamino))propan-2-yl carbamate (eluted first, 42 mg, 42%, MS m/z 474.0 (M+Na⁺)) and tert-butyl-(2S)-1-oxo-1-((3S)-(8-fluoro-4-oxo-2',3',4,5,5',6'-hexahydro-3H-spiro[benzo[b][1,4]oxazepine-2,4'-pyran]-3-ylamino))propan-2-yl carbamate (eluted second, 42 mg, 42%, MS m/z 474.0 (M+Na⁺)).

tert-Butyl-(2S)-1-oxo-1-((3R)-(8-fluoro-4-oxo-2',3',4,5,5',6'-hexahydro-3H-spiro[benzo[b][1,4]oxazepine-2,4'-pyran]-3-ylamino))butan-2-yl carbamate and tert-butyl-(2S)-1-oxo-1-((3S)-(8-fluoro-4-oxo-2',3',4,5,5',6'-hexahydro-3H-spiro[benzo[b][1,4]oxazepine-2,4'-pyran]-3-ylamino))butan-2-yl carbamate

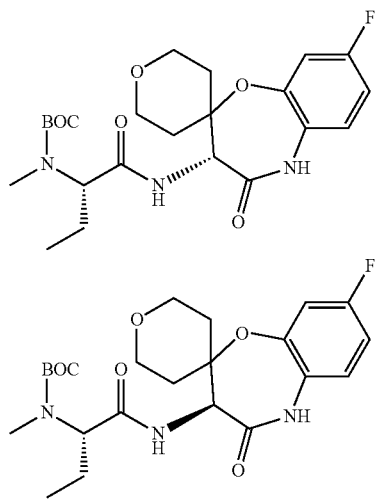

In a similar manner to that described for the preparation of tert-butyl-(2S)-1-oxo-1-((3R)-(8,9-difluoro-4-oxo-2',3',4,5,5',6'-hexahydro-3H-spiro[benzo[b][1,4]oxazepine-2,4'-pyran]-3-ylamino))propan-2-yl carbamate and tert-butyl-(2S)-1-oxo-1-((3S)-(8,9-difluoro-4-oxo-2',3',4,5,5',6'-hexahydro-3H-spiro[benzo[b][1,4]oxazepine-2,4'-pyran]-3-ylamino)) propan-2-yl carbamate except the mixture was stirred for 1.5 h, 3-amino-8-fluoro-2',3',5',6'-tetrahydro-3H-spiro[benzo[b][1,4]pyran]-4(5H)-one (54 mg, 203 μmol, Eq: 1.00), (S)-2-(tert-butoxycarbonyl(methyl)amino)butanoic acid (52.9 mg, 243 μmol, Eq: 1.2) were converted to tert-butyl-(2S)-1-oxo-1-((3R)-(8-fluoro-4-oxo-2',3',4,5,5',6'-hexahydro-3H-spiro[benzo[b][1,4]oxazepine-2,4'-pyran]-3-ylamino))butan-2-yl carbamate (eluted first, 40 mg, 42%, MS m/z 488.0 (M+Na⁺)) and tert-butyl-(2S)-1-oxo-1-((3S)-(8-fluoro-4-oxo-2',3',4,5,5',6'-hexahydro-3H-spiro[benzo[b][1,4]oxazepine-2,4'-pyran]-3-ylamino))butan-2-yl carbamate (eluted second, 42 mg, 44%, MS m/z 488.0 (M+Na⁺).

BOC-N-(methyl-d3)-Ala-OH

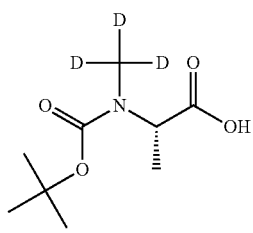 [SMILES: [2H]C([2H])([2H])N(C(=O)OC(C)(C)C)[C@@H](C)C(=O)O]

Sodium hydride (1.27 g, 31.7 mmol, Eq: 3.00) was added to a mixture of (S)-2-(tert-butoxycarbonylamino)propanoic acid (2 g, 10.6 mmol, Eq: 1.00) and iodomethane-d3 (12.3 g, 5.26 mL, 84.6 mmol, Eq: 8.00) in THF (40 mL) at 0° C. and the mixture stirred for 5 min then at RT. After 4 h the mixture was diluted with water and extracted with Et₂O. The pH of the aqueous mixture was adjusted to ~2 and extracted with Et₂O and these combined extract were washed with brine, dried over Na₂SO₄ and concentrated to afford the title compound as colorless oil which solidified upon standing (2.1 g, 96% yield) and was used without purification.

Methyl-d3-(tert-butyl)-(2S)-1-oxo-1-((3R)-(4-oxo-2',3',4,5,5',6'-hexahydro-3H-spiro[benzo[b][1,4]oxazepine-2,4'-pyran]-3-ylamino))propan-2-yl carbamate and methyl-d3-(tert-butyl)-(2S)-1-oxo-1-43 S)-(4-oxo-2',3',4,5,5',6'-hexahydro-3H-spiro[benzo[b][1,4]oxazepine-2,4'-pyran]-3-ylamino))propan-2-yl carbamate

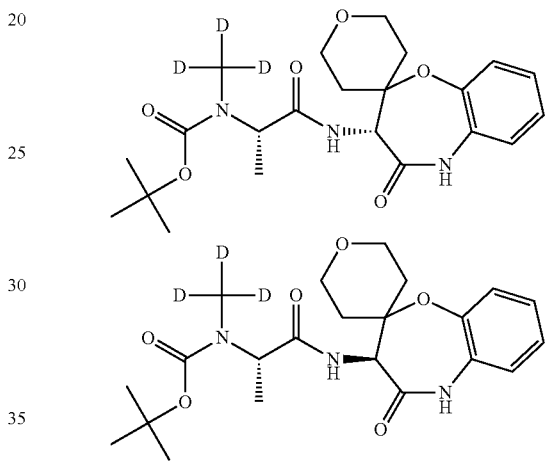

In a similar manner to that described for the preparation of tert-butyl-(2S)-1-oxo-1-((3R)-(8,9-difluoro-4-oxo-2',3',4,5,5',6'-hexahydro-3H-spiro[benzo[b][1,4]oxazepine-2,4'-pyran]-3-ylamino))propan-2-yl carbamate and tert-butyl-(2S)-1-oxo-1-((3S)-(8,9-difluoro-4-oxo-2',3',4,5,5',6'-hexahydro-3H-spiro[benzo[b][1,4]oxazepine-2,4'-pyran]-3-ylamino)) propan-2-yl carbamate except the mixture was stirred for 2.5 h, 3-amino-2',3',5',6'-tetrahydro-3H-spiro[benzo[b][1,4]oxazepine-2,4'-pyran]-4(5H)-one hydrochloride (80 mg, 281 μmol, Eq: 1.00), BOC-N-(methyl-d3)-Ala-OH (69.5 mg, 337 μmol, Eq: 1.2) were converted to methyl-d3-(tert-butyl)-(2S)-1-oxo-1-((3R)-(4-oxo-2',3',4,5,5',6'-hexahydro-3H-spiro[benzo[b][1,4]oxazepine-2,4'-pyran]-3-ylamino))propan-2-yl carbamate (eluted first, 41 mg, 33%, MS m/z 459.1 (M+Na⁺)) and methyl-d3-(tert-butyl)-(2S)-1-oxo-1-((3S)-(4-oxo-2',3',4,5,5',6'-hexahydro-3H-spiro[benzo[b][1,4]oxazepine-2,4'-pyran]-3-ylamino))propan-2-yl carbamate (eluted second, 50 mg, 41%, MS m/z 459.1 (M+Na⁺)).

6-Bromo-1-chloromethyl-2-(methoxy-d3)-naphthalene

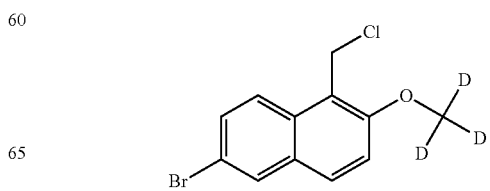

Step 1: Iodomethane-d3 (3.9 g, 1.67 mL, 26.9 mmol, Eq: 1.2) was added to a mixture of 6-bromo-2-naphthol (5 g, 22.4 mmol, Eq: 1.00) and K$_2$CO$_3$ (4.65 g, 33.6 mmol, Eq: 1.5) in DMF (100 mL) and the mixture stirred overnight. The mixture was diluted with H$_2$O, the resulting precipitate was filtered, dissolved in EtOAc and successively washed with 1 N NaOH and brine. The organic solution was dried over Na$_2$SO$_4$ and concentrated to afford 6-bromo-2-(d3-methoxy)-naphthol as a beige solid (5 g, 93%) which was used without purification.

Step 2: Titanium tetrachloride, 1.0 M in DCM (18.3 mL, 18.3 mmol, Eq: 2.2) and dichloromethyl methyl ether (1.05 g, 817 μl, 9.16 mmol, Eq: 1.1) were combined with DCM (70 mL) and the solution cooled to 0° C. 6-Bromo-2-(d3-methoxy)-naphthol (2 g, 8.33 mmol, Eq: 1.00) in DCM (10 mL) was added, the mixture warmed to RT. After 2.5 h the mixture was diluted with 1 N HCl (150 mL) and extracted with DCM. The combined extracts were washed with brine, dried over Na$_2$SO$_4$ and concentrated to afford 6-bromo-2-(d3-methoxy)-naphthalene-1-carbaldehyde (2.11 g, 95%) which was used without purification.

Step 3: Sodium borohydride (1.19 g, 31.3 mmol, Eq: 4.00) was added in 3 portions to 6-bromo-2-(d3-methoxy)-naphthalene-1-carbaldehyde (2.1 g, 7.83 mmol, Eq: 1.00) in MeOH (50 mL) at RT. After 10 min., the mixture was diluted with 1 N HCl and H$_2$O, the resulting precipitate was filtered and purified by flash chromatography to afford the (6-bromo-2-(d3-methoxy)-naphthalene-1-yl)-methanol (1.38 g, 65%). MS m/z 253.9 (M-H$_2$O+H)$^+$ Step 4: Pyridine (606 mg, 618 μl, 7.66 mmol, Eq: 1.5) and thionyl chloride (912 mg, 559 μl, 7.66 mmol, Eq: 1.5) were added to (6-bromo-2-(d3-methoxy)-naphthalene-1-yl)-methanol (1.38 g, 5.11 mmol, Eq: 1.00) in DCM (30 mL) and the mixture was stirred at RT overnight. The mixture was diluted with sat. NaHCO$_3$, extracted with DCM, the organic extracts were dried over Na$_2$SO$_4$ and concentrated to afford the desired compound as a beige solid (1.4 g, 95% yield).

2-(2-Chloro-3-(hydroxymethyl)-1H-indol-1-yl)benzonitrile

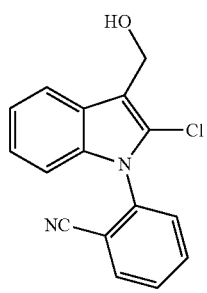 [SMILES: N#Cc1ccccc1-n1c(Cl)c(CO)c2ccccc21]

Step 1: NaH (60% in mineral oil, 223 mg, 5.57 mmol, Eq: 1.00) was added to a solution of 2-chloro-1H-indole-3-carbaldehyde (1 g, 5.57 mmol, Eq: 1.00) in 1-methyl-2-pyrrolidinone (NMP, 5 mL) in a microwave vial. After 10 min., 2-fluorobenzonitrile (3.37 g, 3.02 mL, 27.8 mmol, Eq: 5) was added. The reaction was sealed and heated at 150° C. After 16 h. the mixture was diluted with sat. NH$_4$Cl solution, extracted with EtOAc and the combined extracts concentrated to give a residue that was purified by silica gel chromatography to afford 2-(2-chloro-3-formyl-1H-indol-1-yl)benzonitrile (120 mg, 8%) as a light brown solid.

Step 2: NaBH$_4$ (6 mg, 159 μmol, Eq: 0.387) was added to a solution of 2-(2-chloro-3-formyl-1H-indol-1-yl)benzonitrile (115 mg, 410 μmol, Eq: 1.00) in DCM (3 mL) and MeOH (3.00 mL) at 0° C. and the mixture brought to RT. After 2 h 15 min. the mixture was diluted with sat. NH$_4$Cl and extracted with DCM and the extracts concentrated to afford the title compound (116 mg, 100%) which was used without purification.

2-(4-(Hydroxymethyl)-1H-indol-1-yl)benzonitrile

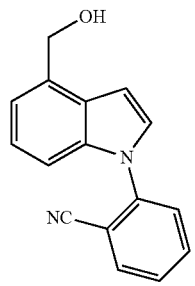 [SMILES: N#Cc1ccccc1-n1ccc2c(CO)cccc21]

Step 1: NaH (60% in mineral oil, 303 mg, 7.58 mmol, Eq: 1.1) was added to a solution of 1H-indole-4-carbaldehyde (1 g, 6.89 mmol, Eq: 1.00) in DMF (12 mL) at 0° C. After 10 min., the mixture was warmed to RT and treated with sonication for 2 min. 2-Fluorobenzonitrile (918 mg, 822 μl, 7.58 mmol, Eq: 1.1) was added and the mixture was treated with sonication for 3 min. After 3 h the mixture was diluted with sat. NH$_4$Cl, extracted with EtOAc, the combined extracts washed with H$_2$O and concentrated. The residue was triturated with Hexane/Et$_2$O to give 2-(4-formyl-1H-indol-1-yl)benzonitrile (1.2 g, 70.7%) as a grey solid.

Step 2: NaBH$_4$ (50 mg, 1.35 mmol Eq: 0.4) was added to a solution of 2-(4-formyl-1H-indol-1-yl)benzonitrile (810 mg, 3.29 mmol, Eq: 1.00) in EtOH (30 mL) and DCM (15 mL) at 0° C. and the mixture warmed to RT. After 3 h., the mixture was concentrated to remove the DCM. The resulting mixture was diluted with sat. NH$_4$Cl, extracted with DCM and the combined extracts concentrated. The residue was purified by silica gel chromatography to afford the title compound (810 mg, 99%) as a white solid.

(2-Chloro-1-(phenylsulfonyl)-1H-indol-3-yl)methanol

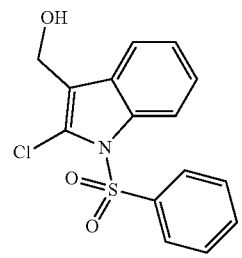 [SMILES: O=S(=O)(c1ccccc1)n1c(Cl)c(CO)c2ccccc21]

Step 1: Cs$_2$CO$_3$ (996 mg, 3.06 mmol) was added to a solution of 2-chloro-1H-indole-3-carbaldehyde (0.5 g, 2.78 mmol) and benzene sulfonyl chloride (0.39 mL, 3.06 mmol) in DMF (5 mL) and the mixture heated to 60° C. After 3 h the mixture was diluted with brine and extracted with EtOAc.

The combined extracts were dried over MgSO₄, filtered and concentrated. The residue was purified by silica gel chromatography to afford 2-chloro-1-(phenylsulfonyl)-1H-indole-3-carbaldehyde (33 mg, 5%) as a white solid.

Step 2: NaBH₄ (7.81 mg, 0.206 mmol) was added to a solution of 2-chloro-1-(phenylsulfonyl)-1H-indole-3-carbaldehyde (33 mg, 0.103 mmol) in DCM/MeOH 1:1 (10 mL). After 16 h the mixture was diluted with sat. NH₄Cl and EtOAc, the organic layer separated and washed with H₂O, dried over MgSO₄, filtered and the filtrate concentrated to give the title compound (33 mg, 99%) which was used without purification.

(2-(Methylsulfonyl)isoindolin-4-yl)methanol

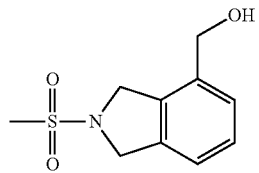

Step 1: DIEA (0.438 g, 3.39 mmol) was added to a solution of methyl isoindoline-4-carboxylate (0.5 g, 2.82 mmol) and mesyl chloride (0.36 g, 3.1 mmol) in DCM (10 mL). After 12 h the mixture was concentrated and the residue purified by silica gel chromatography to afford methyl 2-(methylsulfonyl)isoindoline-4-carboxylate (0.37 g 52%) as an off white solid.

Step 2: Lithium aluminum hydride (LAH, 1 M in THF, 2 mL, 2.0 mmol) was added to solution of methyl 2-(methylsulfonyl)isoindoline-4-carboxylate in THF (15 mL). After 10 h the mixture was diluted with 5% NaOH solution and extracted with EtOAc. The combined organic extracts were dried over MgSO₄ and concentrated. The residue was recrystallized from DCM to give the title compound (200 mg, 61%) as a grey solid.

4-(Bromomethyl)-6-fluoro-1-methyl quinolin-2(1H)-one

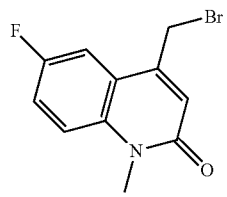

Step 1: MeI (130 mg, 0.914 mmol) was added into a suspension of 6-fluoro-4-methylquinolin-2(1H)-one (135 mg, 0.762 mmol) and Cs₂CO₃ (248 mg, 0.762 mmol) in DMF (10 mL). The reaction mixture was stirred overnight and partitioned between Na₂CO₃ solution and EtOAc. The organic layer was washed with brine, dried over MgSO₄ and concentrated. The resulting solid was washed with hexanes and dried to give 6-fluoro-1,4-dimethylquinolin-2(1H)-one (100 mg, 68%) as a white solid which was used without purification.

Step 2: 2,2'-Azobis(2-methylpropionitrile) (AIBN, 17.2 mg, 0.105 mmol) and N-bromosuccinimide (NBS, 97.7 mg, 0.549 mmol) were added to a suspension of 6-fluoro-1,4-dimethylquinolin-2(1H)-one (100 mg, 0.523 mmol) in CCl₄ (10 mL) at 70° C. After 1 h an additional 2 eq. of NBS and 0.4 eq. of AIBN were added and the mixture heated at 70° C. for 1 h. The mixture was concentrated and the residue purified by preparative TLC to give desired the title compound (55 mg, 31%) as white solid.

1-Benzyl-2-chloro-1H-indole-3-carbaldehyde

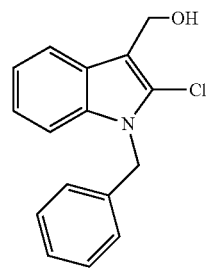 [SMILES: OCc1c(Cl)n(Cc2ccccc2)c2ccccc12]

NaBH4 (71.5 mg, 1.89 mmol) was added to a solution of 1-benzyl-2-chloro-1H-indole-3-carbaldehyde (0.51 g, 1.89 mmol) in MeOH (10 mL). After 12 h the mixture was diluted with sat. NH₄Cl and extracted with EtOAc. The combined extracts were washed with H₂O, dried over MgSO₄, filtered and concentrated to afford the title ompound (350 mg, 68%) as white solid which was used without purification.

(1-Ethyl-1H-indol-4-yl)methanol

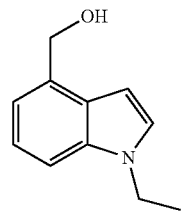

NaBH4 (49.8 mg, 1.32 mmol, Eq: 0.3) was added to a solution of 1-ethyl-1H-indole-4-carbaldehyde (800 mg, 4.39 mmol, Eq: 1.00) in EtOH (30 mL) and DCM (15 mL) at 0° C. and the mixture was warmed to RT and stirred overnight. The mixture concentrated to remove DCM and the resulting mixture diluted with NH₄Cl, extracted with DCM and concentrated. The residue was purified by silica gel chromatography to give the title compound (700 mg, 91%) as a yellow oil.

2-(3-(Bromomethyl)-1H-indazol-1-yl)benzonitrile

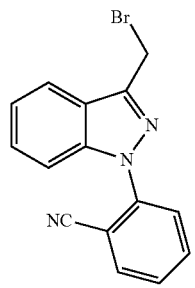 [SMILES: N#Cc1ccccc1-n1nc(CBr)c2ccccc21]

Step 1: Cs₂CO₃ (1.56 g, 4.8 mmol) was added to a solution of 3-methyl indazole (0.634 g, 4.8 mmol) and 2-fluorobenzonitrile (1 mL, 9.6 mmol) in DMF (20 mL) and the mixture stirred at RT for 12 h. The mixture was diluted with sat. NH₄Cl and a precipitate formed. The solid was filtered, washed with H₂O, hexane and dried under vacuum to give 2-(3-methyl-1H-indazol-1-yl)benzonitrile (1 g, 89%) which was used without purification.

Step 2: AIBN (141 mg, 0.857 mmol) and NBS (839 mg, 4.72 mmol) were added to a suspension of 2-(3-methyl-1H-indazol-1-yl)benzonitrile (1 g, 4.29 mmol) in CCl₄ (20 mL) and the mixture heated to reflux for 2 h. The mixture was concentrated and the residue was purified by silica gel chromatography to give the title compound (1.25 g, 93%) as an off white solid.

3-(Bromomethyl)-1-(2-cyanophenyl)-1H-indole-2-carbonitrile

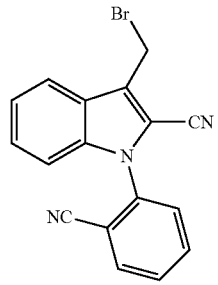 [SMILES: N#Cc1ccccc1-n1c(C#N)c(CBr)c2ccccc21]

Step 1: A mixture of 3-methyl-1H-indole-2-carbonitrile (500 mg, 3.2 mmol), 2-fluorobenzonitrile (388 mg, 3.2 mmol) and Cs₂CO₃ (1.05 g, 3.2 mmol) in DMF (10 mL) was heated at 60° C. overnight. The mixture was poured into H₂O and a precipitate formed. The solid was collected by filtration, washed with H₂O and hexane, and dried under vacuum to give 1-(2-cyanophenyl)-3-methyl-1H-indole-2-carbonitrile (780 mg, 94.6%) as an off white solid that was used without purification.

Step 2: In a similar manner to that described for the preparation of 3-(bromomethyl)-1-(2-cyanophenyl)-1H-indole-2-carbonitrile Step 2 except the mixture heated to reflux for 1.5 h, 1-(2-cyanophenyl)-3-methyl-1H-indole-2-carbonitrile was converted to the title compound (1.0 g, 98%) as an off white solid.

(S)-2-(Benzyloxycarbonyl-ethyl(d5)-amino)-propionic acid

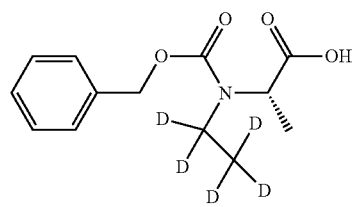 [SMILES: [2H]C([2H])([2H])C([2H])([2H])N(C(=O)OCc1ccccc1)[C@@H](C)C(=O)O]

NaH (60% in mineral oil, 480 mg, 12 mmol) was added to (S)-2-(benzyloxycarbonylamino)propanoic acid (0.892 g, 4 mmol) and d5-ethyl iodide (5.15 g, 2.64 mL, 32 mmol) in THF (20 mL) and the mixture heated to 60° C. overnight. The mixture was partitioned between EtOAc and H₂O and the organic layer was washed with H₂O. The combined aqueous mixture was acidified to pH of 4 with citric acid solution, extracted with EtOAc, the combined organic extracts dried over MgSO₄ filtered and the filtrate concentrated to afford the title compound 440 mg, 40%) as a colorless oil which was used without purification.

2-(3-(Bromomethyl)-6-fluoro-1H-indazol-1-yl)benzonitrile

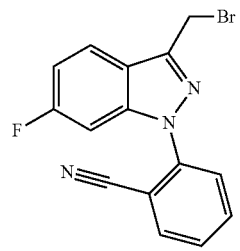 [SMILES: N#Cc1ccccc1-n1nc(CBr)c2ccc(F)cc21]

In a similar manner to that described for the preparation of 2-(3-(bromomethyl)-1H-indazol-1-yl)benzonitrile except in Step 1 the mixture was diluted with H₂O and in Step 2 the mixture was heated at reflux overnight, 6-fluoro-3-methyl-1H-indazole (2 g, 13.3 mmol) and 2-fluorobenzonitrile (1.73 mL, 16 mmol) were converted to the title compound (800 mg, 61%) as an off white solid.

2-(3-(Bromomethyl)-6-bromo-1H-indazol-1-yl)benzonitrile

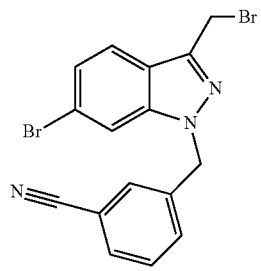 [SMILES: N#Cc1cccc(Cn2nc(CBr)c3ccc(Br)cc32)c1]

In a similar manner to that described for the preparation of 2-(3-(bromomethyl)-1H-indazol-1-yl)benzonitrile except in Step 1 the mixture was diluted with H₂O and in Step 2 the mixture was heated at reflux overnight, 6-bromo-3-methyl-1H-indazole (1 g, 4.74 mmol) and 2-fluorobenzonitrile (0.617 mL, 5.69 mmol) were converted to the title compound (800 mg, 64%) as an off white solid.

(R)-3-Amino-2,2-dimethyl-2,3-dihydrobenzo[b][1,4]thiazepin-4(5H)-one

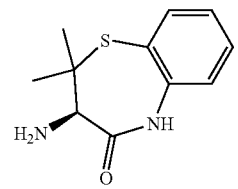

Step 1: NaHCO$_3$ (14.5 g, 172 mmol, Eq: 2.5) and H$_2$O (210 mL) were added to a slurry of (R)-2-(benzyloxycarbonylamino)-3-mercapto-3-methylbutanoic acid (19.5 g, 68.8 mmol, Eq: 1.00) in EtOH (70.0 mL). After 20 min. the mixture became homogeneous, 1-fluoro-2-nitrobenzene (9.71 g, 7.00 mL, 68.8 mmol, Eq: 1.00) was added and the mixture heated to reflux for 6 h. The mixture was cooled to RT, poured into H$_2$O (300 mL) and extracted with MTBE. The aqueous layer was acidified to pH 5 with 1 N HCl and extracted with Et$_2$O. The combined organic extracts were dried over Na$_2$SO$_4$ filtered and concentrated to give (R)-2-(benzyloxycarbonylamino)-3-methyl-3-(2-nitrophenylthio)butanoic acid (18.7 g, 67.2%) as a light yellow oil which was used without purification.

Step 2: A mixture of (R)-2-(benzyloxycarbonylamino)-3-methyl-3-(2-nitrophenylthio)butanoic acid (18.3 g, 45.2 mmol, Eq: 1.00), NH$_4$Cl (4.84 g, 90.5 mmol, Eq: 2) and Zn (45.9 g, 701 mmol, Eq: 15.5) in MeOH (500 mL) was heated at reflux for 6 h and the mixture was filtered through Celite. The filter cake was washed with hot MeOH. The filtrate was concentrated, the residue was triturrated with H$_2$O, 1:3 Et$_2$O/Hexane and azeotroped with toluene. The resulting material was dried under vacuum to give (R)-3-(2-aminophenylthio)-2-(benzyloxycarbonylamino)-3-methylbutanoic acid (16.9 g, 100%) which was used without purification.

Step 3: DIEA (4.14 g, 5.6 mL, 32.0 mmol, Eq: 2) and (benzotriazol-1-yloxy)tripyrrolidinophosphonium hexafluorophosphate (PyBOP, 12.5 g, 24.0 mmol, Eq: 1.5) were added to (R)-3-(2-aminophenylthio)-2-(benzyloxycarbonylamino)-3-methylbutanoic acid (6 g, 16.0 mmol, Eq: 1.00) in DMF (200 mL). The mixture was stirred at RT overnight then heated to 80° C. for 3 h. The mixture was poured onto sat. NH$_4$Cl and extracted with EtOAc. The combined extracts were washed with H$_2$O, concentrated and the residue was purified by silica gel chromatography to give (R)-benzyl 2,2-dimethyl-4-oxo-2,3,4,5-tetrahydrobenzo[b][1,4]thiazepin-3-ylcarbamate (3 g, 52%).

Step 4: (R-Benzyl 2,2-dimethyl-4-oxo-2,3,4,5-tetrahydrobenzo[b][1,4]thiazepin-3-ylcarbamate (0.67 g, 1.88 mmol, Eq: 1.00) was added to 33% HBr in AcOH (13.4 g, 9 mL, 54.7 mmol, Eq: 29.1). The mixture was stirred at RT for 75 min. and poured into 100 mL Et$_2$O resulting in a precipitate which was filtered and washed with Et$_2$O. The solid material was added to sat. NaHCO$_3$, the mixture extracted with DCM and the combined extracts concentrated to give the title compound (343 mg, 82.2%) as an oil which was used without purification.

Methyl 3-cyano-4-(3-(bromomethyl)-1H-indazol-1-yl)benzoate

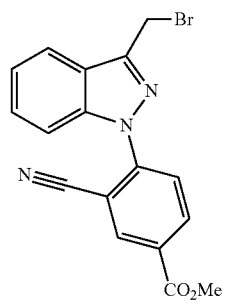 [SMILES: COC(=O)c1ccc(-n2nc(CBr)c3ccccc32)c(C#N)c1]

In a similar manner to that described for the preparation of 2-(3-(bromomethyl)-1H-indazol-1-yl)benzonitrile except in Step 1 the mixture was diluted with H$_2$O and the product recrystallized from MeOH and in Step 2 1,2-dichoroethane was used in place of CCl$_4$, 3-methyl-1H-indazole (1 g, 7.57 mmol)) and methyl 3-cyano-4-fluorobenzoate (1.36 g, 7.57 mmol) as a white solid.

(S)-tert-Butyl 4-oxo-9-(trifluoromethyl)-2,3,4,5-tetrahydrobenzo[b][1,4]oxazepin-3-ylcarbamate

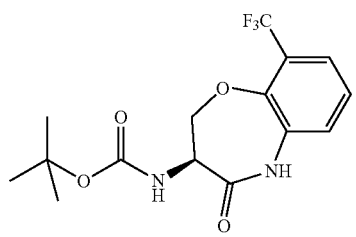 [SMILES: CC(C)(C)OC(=O)N[C@H]1COc2c(cccc2C(F)(F)F)NC1=O]

Step 1: A solution of BOC-Ser-OH (981 mg, 4.78 mmol) in DMF (5.00 mL) was added to a suspension of NaH (60% in mineral oil, 402 mg, 10.0 mmol) in DMF (5 mL). The mixture was stirred at 0° C. for 1 h and a solution of 2-fluoro-1-nitro-3-(trifluoromethyl)benzene (1 g, 4.78 mmol) in DMF (5 mL) was added. After 2 h the mixture was diluted with H$_2$O and acidified to pH 3 with 1 N HCl. The mixture was extracted with EtOAc, the combined extracts dried over MgSO$_4$, filtered and the filtrate concentrated to give a residue that was purified by silica gel chromatography to afford (S)-2-(tert-butoxycarbonylamino)-3-(2-nitro-6-(trifluoromethyl)phenoxy)propanoic acid (1.53 g, 81%) as a light yellow solid. MS m/z 417 (M+Na)'

Step 2: 10% Pd/C (150 mg) was added to a solution of (S)-2-(tert-butoxycarbonylamino)-3-(2-nitro-6-(trifluoromethyl)phenoxy)propanoic acid (1.5 g, 3.8 mmol) in MeOH and the mixture stirred under H$_2$. After 4 h the mixture was filtered through Celite, the filter cake washed with MeOH and the filtrate concentrated to afford (S)-3-(2-amino-6-(trifluoromethyl)phenoxy)-2-(tert-butoxycarbonylamino)propanoic acid (1.23 g, 89%) which was used without purification.

Step 3: A solution of (S)-3-(2-amino-6-(trifluoromethyl)phenoxy)-2-(tert-butoxycarbonylamino)propanoic acid (1.23 g, 3.38 mmol) and EDCI (803 mg, 4.19 mmol) in DMF (25 mL) was stirred at RT for 6 h, diluted with EtOAc and washed with H$_2$O. The combined aqueous washes were extracted with EtOAc and the combined organic solutions were dried over MgSO$_4$, filtered. The filtrate was concentrated to give a residue that was purified by silica gel chromatography to afford the title compound (1.04 g, 89%) as a light brown oil. MS m/z 369 (M+Na)$^+$ (2-(Difluoromethoxy)naphthalen-1-yl)methyl methanesulfonate

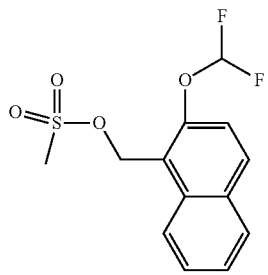 [SMILES: CS(=O)(=O)OCc1c(OC(F)F)ccc2ccccc12]

Step 1: NaBH₄ (255 mg, 6.73 mmol) was added to a suspension of 2-(difluoromethoxy)-1-naphthaldehyde (0.997 g, 4.49 mmol) in EtOH (29.9 mL). After 3 h the mixture was diluted with H₂O, extracted with EtOAc, the combined extracts were washed with brine (200 mL), dried over Na₂SO₄, filtered, and the filtrate concentrated to give a residue that was purified by silica gel chromatography to provide (2-(difluoromethoxy)naphthalen-1-yl)methanol (387 mg, 39%) as an orange solid.

Step 2: Methanesulfonyl chloride (160 µL, 2.07 mmol) was added to a mixture of (2-(difluoromethoxy)naphthalen-1-yl) methanol (387 mg, 1.73 mmol) in CH₂Cl₂ (8.63 mL) and TEA (505 µL, 3.62 mmol). After 20 h the mixture was diluted with CH₂Cl₂, washed with H₂O, brine, dried over Na₂SO₄, filtered and the filtrate was concentrated to provide (2-(difluoromethoxy)naphthalen-1-yl)methyl methanesulfonate (342 mg) as a brown oil that was used without further purification.

EXAMPLES

Example 1

(2S)-N-(5-((6-Bromo-2-methoxynaphthalen-1-yl) methyl)-(3S)-4-oxo-4,5-dihydro-3H-spiro[benzo[b] [1,4]oxazepine-2, 1'-cyclohexane]-3-yl)-2-(methylamino)propanamide hydrochloride

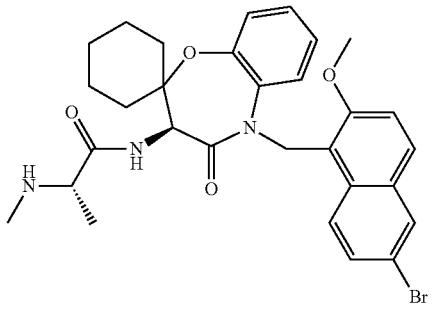 [SMILES: CN[C@@H](C)C(=O)N[C@@H]1C(=O)N(Cc2c(OC)ccc3cc(Br)ccc23)c2ccccc2OC12CCCCC2]

Step 1: A mixture of methyl-(tert-butyl)-(2S)-1-oxo-1-((3S)-(4-oxo-2',3',4,5,5',6'-hexahydro-3H-spiro[benzo[b][1,4]oxazepine-2,1'-cyclohexan]-3-ylamino))propan-2-yl carbamate (44.1 mg, 102 µmol, Eq: 1.00), 6-bromo-1-(chloromethyl)-2-methoxynaphthalene (43.8 mg, 153 µmol, Eq: 1.5) NaI (23.0 mg, 153 µmol, Eq: 1.5) and Cs₂CO₃ (49.9 mg, 153 µmol, Eq: 1.5) in DMF (2 mL) was heated to 65° C. After 18 h the mixture was diluted with EtOAc, washed with sat. NaCl, dried over Na₂SO₄ and concentrated. The residue was purified by flash chromatography to afford tert-butyl (2S)-1-(5-(((6-bromo-2-methoxynaphthalen-1-yl)methyl)-(3S)-4-oxo-4,5-dihydro-3H-spiro[benzo[b][1,4]oxazepine-2,1'-cyclohexane]-3-ylamino)-1-oxopropan-2-yl(methyl) carbamate (33.7 mg, 48%) as a white foam. MS m/z 682.0 (MH⁺)

Step 2: tert-Butyl (2S)-1-(5-(((6-bromo-2-methoxynaphthalen-1-yl)methyl)-(3S)-4-oxo-4,5-dihydro-3H-spiro [benzo[b][1,4]oxazepine-2,1'-cyclohexane]-3-ylamino)-1-oxopropan-2-yl(methyl)carbamate (33.7 mg, 49.5 µmol, Eq: 1.00) and 2 M HCl in Et₂O (2 mL, 4.00 mmol, Eq: 80.8) were combined with MeOH (0.5 mL) to give a colorless solution. After 90 min the mixture was concentrated, the residue dissolved in MeCN/H₂O, and lyophilized to afford the title compound (26.0 mg, white solid, 85%). MS m/z 582.0 (MH⁺).

Following analogous procedures described for the preparation of methyl-(tert-butyl)-(2S)-1-oxo-1-((3R)-(4-oxo-2',3',4,5,5',6'-hexahydro-3H-spiro[benzo[b][1,4]oxazepine-2,1'-cyclohexan]-3-ylamino))propan-2-ylcarbamate, methyl-(tert-butyl)-(2S)-1-oxo-1-((3S)-(4-oxo-2',3',4,5,5',6'-hexahydro-3H-spiro[benzo[b][1,4]oxazepine-2,1'-cyclohexan]-3-ylamino))propan-2-yl carbamate and in Example 1 for the preparation of (2S)-N-(5-((6-bromo-2-methoxynaphthalen-1-yl)methyl)-(3S)-4-oxo-4,5-dihydro-3H-spiro[benzo[b][1,4]oxazepine-2,1'-cyclohexane]-3-yl)-2-(methylamino)propanamide hydrochloride the compounds in Table 2 were prepared.

TABLE 2

| Ex | Starting Material | Amino Acid | Alkylating Agent | Product | MS |
|---|---|---|---|---|---|
| 1a | | | | | 541.9 |
| 1b | | | | | 583.0 |

TABLE 2-continued

| Ex | Starting Material | Amino Acid | Alkylating Agent | Product | MS |
|---|---|---|---|---|---|
| 1c | | | | | 568.0 |
| 1d | | | | | 660.9 |
| 1e | | | | | 660.9 |
| 1f | | | | | 584.0 |
| 1g | | | | | 584.0 |

TABLE 2-continued
| Ex | Starting Material | Amino Acid | Alkylating Agent | Product | MS |
|---|---|---|---|---|---|
| 1h | 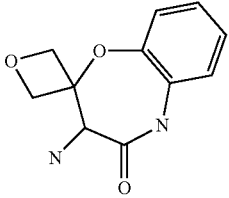 | 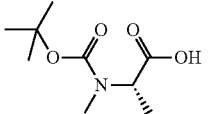 | 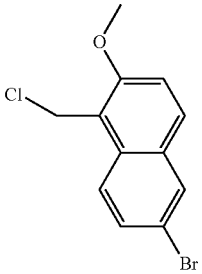 | 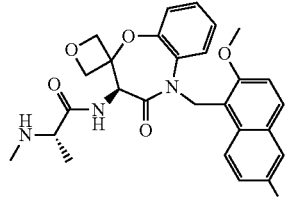 | 556.2 |
| 1i | 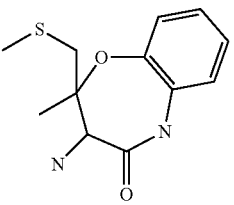 | 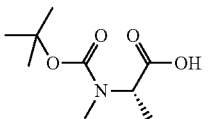 | 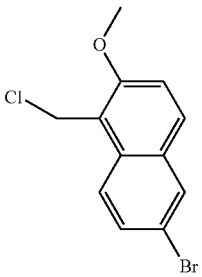 | 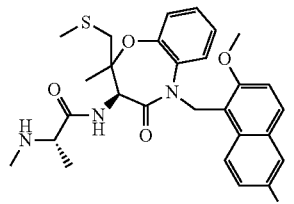 | 588.0 |
| 1j | 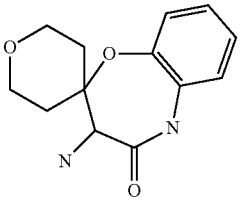 [SMILES: NC1C(=O)Nc2ccccc2OC12CCOCC2] | 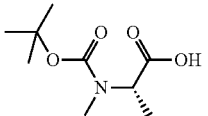 | 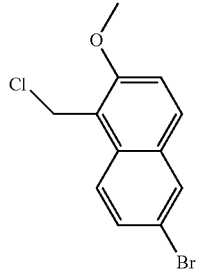 | 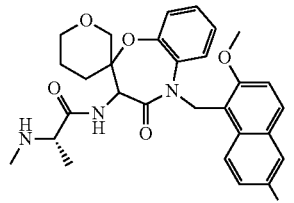 | 584.0 |
| 1k | 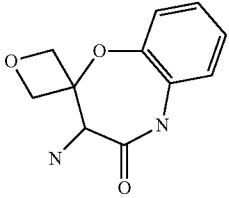 [SMILES: NC1C(=O)Nc2ccccc2OC12COC2] | 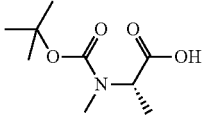 | 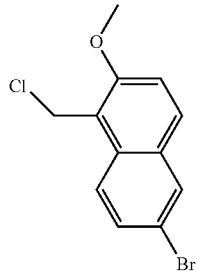 | 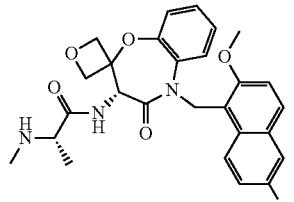 | 556.2 |
| 1L | 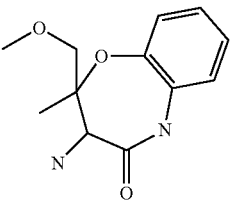 [SMILES: COCC1(C)Oc2ccccc2NC(=O)C1N] | 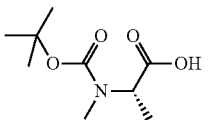 | 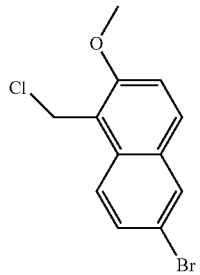 | 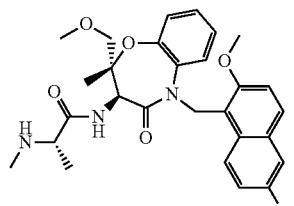 | 570.0 |

TABLE 2-continued

| Ex | Starting Material | Amino Acid | Alkylating Agent | Product | MS |
|---|---|---|---|---|---|
| 1m | | | | | 586.0 |
| 1n | | | | | 584.0 |
| 1o | | | | | 599.9 |
| 1p | | | | | 599.9 |
| 1q | | | | | 488.1 |
| 1r | | | | | 505.1 |

TABLE 2-continued
| Ex | Starting Material | Amino Acid | Alkylating Agent | Product | MS |
|---|---|---|---|---|---|
| 1s | 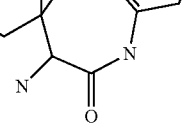 | 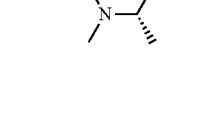 | 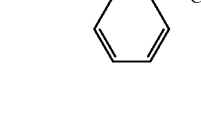 | 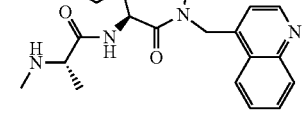 | 475.1 |
| 1t | 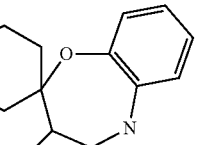 | 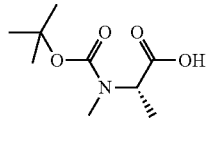 | 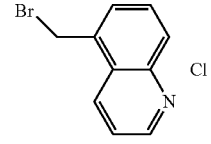 [SMILES: BrCc1cccc2ncccc12 ; Cl] | 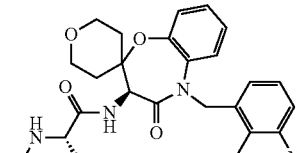 | 475.0 |
| 1u | 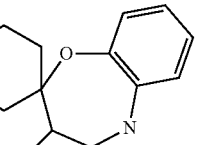 | 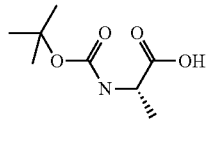 | 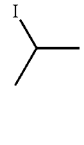 | 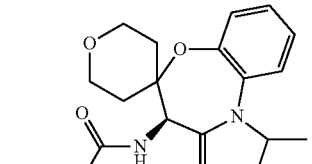 | 362.1 |
| 1v | 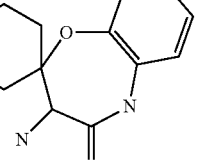 | 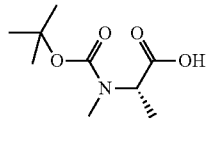 |  | 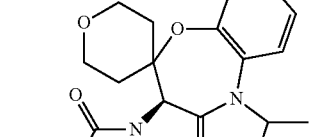 | 376.2 |
| 1w | 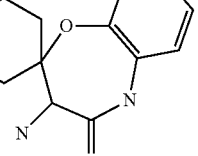 | 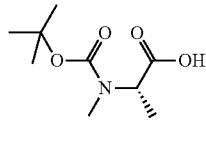 | 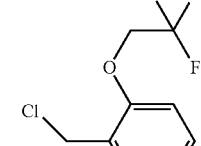 | 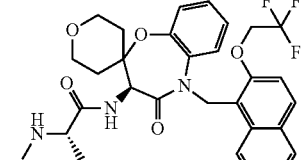 | 572.1 |
| 1x | 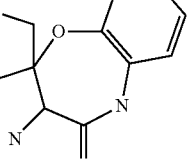 | 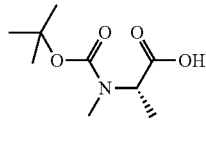 | 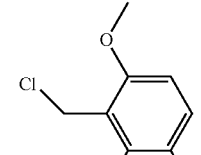 | 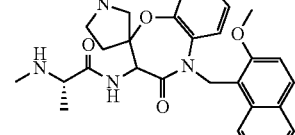<br>CIS diastereomer | 569.0 |

US 9,394,263 B2

TABLE 2-continued

| Ex | Starting Material | Amino Acid | Alkylating Agent | Product | MS |
|---|---|---|---|---|---|
| 1y | | | | | 569.9 |
| 1z | | | | | 569.9 |
| 1a' | | | | | 569.9 |
| 1b' | | | | | 569.9 |
| 1c' | | | | | 584.0 |
| 1d' | | | | | 526.0 |

Example 2

6-Methoxy-5-(((S)-3-((S)-2-(methylamino)propanamido)-4-oxo-2',3',5',6'-tetrahydro-3H-spiro[benzo[b][1,4]oxazepine-2,4'-pyran]-5(4H)-yl)methyl)-2-naphthoic acid trifluoroacetate

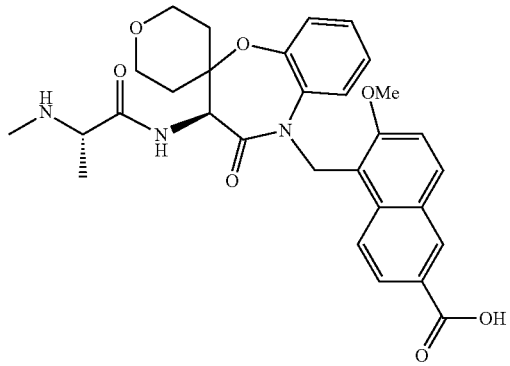 [SMILES: CN[C@@H](C)C(=O)N[C@@H]1C(=O)N(Cc2c(OC)ccc3cc(C(=O)O)ccc23)c2ccccc2OC12CCOCC2]

Step 1: tert-butyl (S)-1-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (0.17 g, 249 µmol, Eq: 1.00), Pd(OAc)₂ (2.24 mg, 9.96 µmol, Eq: 0.04) and 4,5-bis(diphenylphosphino)-9,9-dimethylxanthene (Xantphos) (11.5 mg, 19.9 µmol, Eq: 0.08) were combined in a 5 mL microwave tube, the vessel was evacuated and purged with N₂. MeOH (79.8 mg, 101 µl, 2.49 mmol, Eq: 10) and TEA (0.5 mL) were added, the vessel was purged with CO gas for approximately 30 sec and placed in an oil bath heated to 70° C. After 18 h, the mixture was cooled, diluted with EtOAc, washed with 1 N HCl, H₂O, and brine. The organic mixture was dried over Na₂SO₄, concentrated and the residue purified by flash chromatography to afford methyl 5-(((S)-3-((S)-2-(tert-butoxycarbonyl(methyl)amino)propanamido)-4-oxo-2',3',5',6'-tetrahydro-3H-spiro[benzo[b][1,4]oxazepine-2,4'-pyran]-5 (4H)-yl)methyl)-6-methoxy-2-naphthoate (110.5 mg, 67% as a light yellow foam.) MS m/z 662.3 (MH⁺)

Step 2: A solution of LiOH.H₂O (35.0 mg, 835 µmol, Eq: 5) in H₂O (4 mL) was added to a solution of methyl 5-(((S)-3-((S)-2-(tert-butoxycarbonyl(methyl)amino)propanamido)-4-oxo-2',3',5',6'-tetrahydro-3H-spiro[benzo[b][1,4]oxazepine-2,4'-pyran]-5 (4H)-yl)methyl)-6-methoxy-2-naphthoate (110.5 mg, 167 µmol, Eq: 1.00) in THF (3 mL). After 18 h, the mixture was poured into 1 M HCl (20 mL) and extracted with EtOAc. The combined organic extracts were washed with H₂O, brine, dried over Na₂SO₄ and concentrated. The residue was dissolved in MeCN/H₂O, and lyophilized to afford 5-((S)-3-((S)-2-(tert-butoxycarbonyl(methyl)amino)propanamido)-4-oxo-2',3',5',6'-tetrahydro-3H-spiro[benzo[b][1,4]oxazepine-2,4'-pyran]-5 (4H)-yl)methyl)-6-methoxy-2-naphthoic acid (95.2 mg, 88%) of white solid which was used without purification. MS m/z 648.2 (MH⁺)

Step 3: TFA (0.2 mL, 56.4 µmol, Eq: 1.00) was added to a solution of 5-(((S)-3-((S)-2-(tert-butoxycarbonyl(methyl)amino)propanamido)-4-oxo-2',3',5',6'-tetrahydro-3H-spiro[benzo[b][1,4]oxazepine-2,4'-pyran]-5 (4H)-yl)methyl)-6-methoxy-2-nap hthoic acid (36.5 mg, 56.4 µmol, Eq: 1.00) in DCM (1 mL). After 1 h, the mixture was concentrated, the residue dissolved in MeCN/H₂O, and lyophilized to afford the title compound (31.0 mg, 83%) as an off-white solid. MS m/z 548.4 (MH⁺)

Example 3

6-M ethoxy-5-(((S)-3-((S)-2-(methylamino)propanamido)-4-oxo-2',3',5',6'-tetrahydro-3H-spiro[benzo[b][1,4]oxazepine-2,4'-pyran]-5 (4H)-yl)methyl)-N-(methylsulfonyl)-2-naphthamide trifluoroacetate

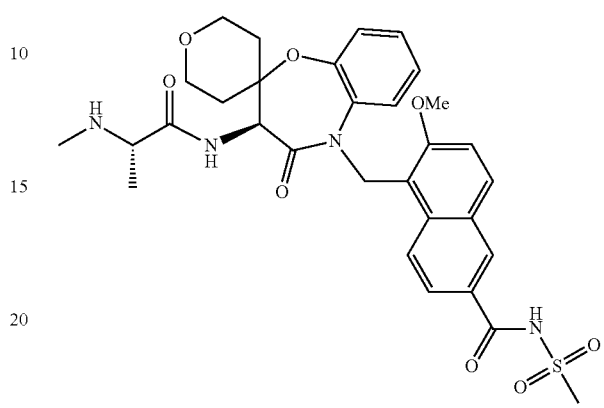

Methanesulfonamide (10.9 mg, 115 µmol, Eq: 1.25) was added to a mixture of 5-(((S)-3-((S)-2-(tert-butoxycarbonyl(methyl)amino)propanamido)-4-oxo-2',3',5',6'-tetrahydro-3H-spiro[benzo[b][1,4]oxazepine-2,4'-pyran]-5 (4H)-yl)methyl)-6-methoxy-2-nap hthoic acid (59.4 mg, 91.7 µmol, Eq: 1.00), EDCI (22.0 mg, 115 µmol, Eq: 1.25) and DMAP (14.0 mg, 115 µmol, Eq: 1.25) in DCM (5 mL). After 2 h, the mixture was diluted with DCM, washed with 1 M HCl, brine, dried over Na₂SO₄ and concentrated to afford 5-((S)-3-((S)-2-(tert-butoxycarbonyl(methyl)amino)propanamido)-4-oxo-2',3',5',6'-tetrahydro-3H-spiro[benzo[b][1,4]oxazepine-2,4'-pyran]-5 (4H)-yl)methyl)-6-methoxy-N-(methylsulfonyl)-2-naphthamide (65.4 mg) as a white foam which was used without purification.

Step 2: 5-(((S)-3-((S)-2-(tert-Butoxycarbonyl(methyl)amino)propanamido)-4-oxo-2',3',5',6'-tetrahydro-3H-spiro[benzo[b][1,4]oxazepine-2,4'-pyran]-5 (4H)-yl)methyl)-6-methoxy-N-(methylsulfonyl)-2-naphthamide dissolved in DCM (1 mL) and 0.25 mL TFA was added. After 90 min the mixture was concentrated, the residue was dissolved in MeCN/H₂O, and lyophilized to afford the title compound (45.4 mg, 67%) as a white solid. MS m/z 625.4 (MH⁺)

Example 4

(R)-N-[(S)-5-((6-Bromo-2-methoxy-naphthalen-1-ylmethyl)-2,2-dimethyl-4-oxo-2,3,4,5-tetrahydro-benzo[b][1,4]thiazepin-3-yl]-2-methylamino-propionamide hydrochloride

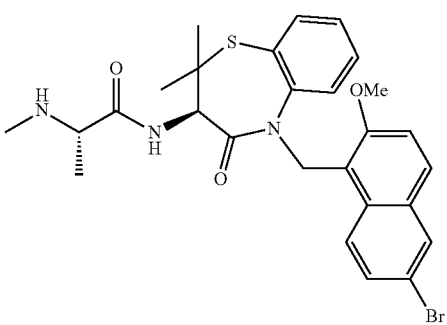 [SMILES: CN[C@@H](C)C(=O)N[C@@H]1C(=O)N(Cc2c(OC)ccc3cc(Br)ccc23)c2ccccc2SC1(C)C]

In a similar manner to that described for Example 1, except in step 1 the mixture was heated for 15 h and in step 2 the mixture was stirred for 2 h, tert-butyl (S)-1-((R)-2,2-dimethyl-4-oxo-2,3,4,5-tetrahydrobenzo[b][1,4]thiazepin-3-ylamino)-1-oxopropan-2-yl(methyl)carbamate (0.2067 g, 507 µmol, Eq: 1.00) and 6-bromo-1-(chloromethyl)-2-methoxynaphthalene (217 mg, 761 µmol, Eq: 1.5) were converted to the title compound (49.0 mg) as a yellow solid. MS m/z 557.7 (MH⁺)

Example 5

(S)-N-(5-Benzyl-4-oxo-2,3,4,5-tetrahydrobenzo[b][1,4]thiazepin-3-yl)-2-methylaminopropanamide hydrochloride

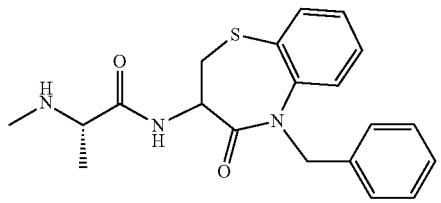 [SMILES: CN[C@@H](C)C(=O)NC1CSc2ccccc2N(Cc2ccccc2)C1=O]

Step 1: NaH (60% in mineral oil, 16 mg, 0.40 mmol, Eq: 1.50) was added to a solution of tert-butyl (S)-1-(4-oxo-2,3,4,5-tetrahydrobenzo[b][1,4]thiazepin-3-ylamino)-1-oxopropan-2-yl(methyl)carbamate (100 mg, 0.26 mmol, Eq: 1.00) in DMF at RT. After 5 min. benzyl bromide (35 µL, 0.29 mmol, Eq: 1.10) was added, the mixture was stirred for 35 min., diluted with 1 N HCl and extracted with EtOAc. The organic extracts were washed with sat. NaHCO₃, brine, dried over Na₂SO₄ and concentrated. The residue was purified by flash chromatography to afford tert-butyl (S)-1-(5-benzyl-4-oxo-2,3,4,5-tetrahydro-benzo[1)][1,4]thiazepin-3-ylamino)-1-oxopropan-2-yl(methyl)carbamate (96 mg, 77%).

Step 2: 1 M HCl in Et₂O (2 mL, 2.00 mmol, Eq: 26.7) was added to a solution of tert-butyl (S)-1-(5-benzyl-4-oxo-2,3,4,5-tetrahydro-benzo[b][1,4]thiazepin-3-ylamino)-1-oxopropan-2-yl(methyl)carbamate (35 mg, 75 µmol, Eq: 1.00) in MeOH (1 mL). After 2 h at RT, the mixture was stored in a freezer overnight, removed from the freezer and stirred an additional 2 h at RT. The mixture was concentrated, the residue dissolved in MeCN/H₂O, and lyophilized to afford the title compound (25 mg, 83%). MS m/z 370.0 (MH⁺)

Example 6

N-(5-Benzyl-1,1,4-trioxo-2,3,4,5-tetrahydrobenzo[b][1,4]thiazepin-3-yl)-2-(S)-(methylamino)propanamide hydrochloride

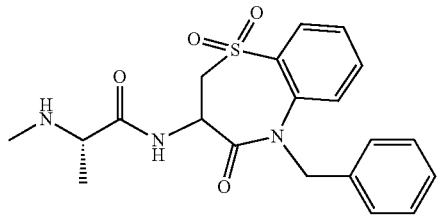 [SMILES: CN[C@@H](C)C(=O)NC1CS(=O)(=O)c2ccccc2N(Cc2ccccc2)C1=O]

Step 1: 77% 3-Chloroperoxybenzoic acid (mCPBA, 72 mg, 319 µmol, Eq: 2.50) was added to a solution of tert-butyl (S)-1-(5-benzyl-4-oxo-2,3,4,5-tetrahydro-benzo[1)][1,4]thiazepin-3-ylamino)-1-oxopropan-2-yl(methyl)carbamate (60 mg, 128 µmol, Eq: 1.00) in DCM (1.5 mL). After 45 min., the reaction was diluted with 1 N NaOH, extracted with EtOAc. The organic extracts were dried over Na₂SO₄ and concentrated to afford tert-butyl (S)-1-(5-benzyl-1,1,4-trioxo-2,3,4,5-tetrahydro-benzo[b][1,4]thiazepin-3-ylamino)-1-oxopropan-2-yl(methyl)carbamate (52 mg, 81% yield) as a colorless oil which solidified upon standing and was used without purification.

Step 2: 1 M HCl in Et₂O (4 mL, 4.00 mmol, Eq: 40) was added to a solution of tert-butyl (S)-1-(5-benzyl-1,1,4-trioxo-2,3,4,5-tetrahydro-benzo[b][1,4]thiazepin-3-ylamino)-1-oxopropan-2-yl(methyl)carbamate in MeOH (1.5 mL). After 3 h, the mixture was concentrated, the residue dissolved in MeCN/H₂O, and lyophilized to afford the title compound (45 mg, 100%). MS m/z 402.0 (MH⁺)

Example 7

N-(5-(4-Phenyl-butyl)-1,1,4-trioxo-2,3,4,5-tetrahydrobenzo[b][1,4]thiazepin-3-yl)-2-(S)-(methylamino)propanamide hydrochloride

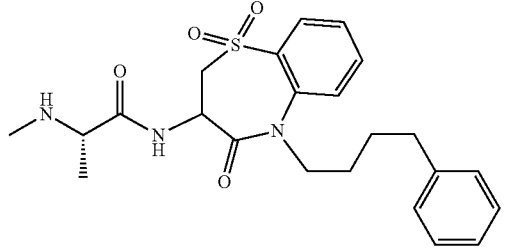 [SMILES: CN[C@@H](C)C(=O)NC1CS(=O)(=O)c2ccccc2N(CCCCc2ccccc2)C1=O]

Step 1: 77% mCPBA (62 mg, 274 µmol, Eq: 2.50) was added to a solution of tert-butyl (S)-1-(4-oxo-5-(4-phenyl-butyl)-2,3,4,5-tetrahydro-benzo[b][1,4]thiazepin-3-ylamino)-1-oxopropan-2-yl(methyl)carbamate (56 mg, 109 µmol, Eq: 1.00) in DCM (1.5 mL). and the mixture was stirred overnight. The mixture was diluted with 1 N NaOH and extracted with EtOAc. The combined extracts were washed with brine, dried over Na₂SO₄, filtered and concentrated to afford tert-butyl (S)-1-(5-(4-phenyl-butyl)-1,1,4-trioxo-2,3,4,5-tetrahydro-benzo[b][1,4]thiazepin-3-ylamino)-1-oxopropan-2-yl(methyl)carbamate (56 mg, 95%) which was used without purification.

Step 2: In a similar manner to that described for Example 1 Step 2, except the mixture was stirred for 2 h, tert-butyl (S)-1-(5-(4-phenyl-butyl)-1,1,4-trioxo-2,3,4,5-tetrahydro-benzo[b][1,4]thiazepin-3-ylamino)-1-oxopropan-2-yl(methyl)carbamate (56 mg, 103 µmol) was converted to the title compound (48 mg, 85%). MS m/z 440.0 (MH⁺)

Example 8

N-(5-Biphenyl-3-ylmethyl-4-oxo-2,3,4,5-tetrahydrobenzo[b][1,4]thiazepin-3-yl)-2-(S)-methylaminopropionamide hydrochloride

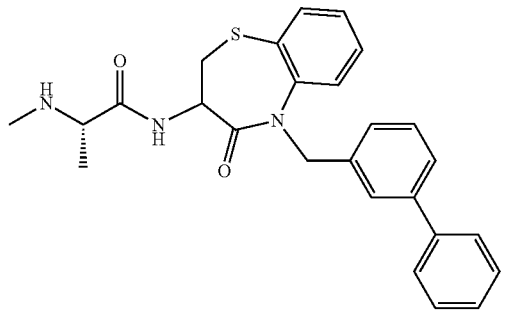 [SMILES: CN[C@@H](C)C(=O)NC1CSc2ccccc2N(Cc2cccc(-c3ccccc3)c2)C1=O]

Step 1: A mixture of tert-butyl (S)-1-(4-oxo-2,3,4,5-tetrahydrobenzo[b][1,4]thiazepin-3-ylamino)-1-oxopropan-2-yl(methyl)carbamate (200 mg, 527 μmol, Eq: 1.00), 3-bromomethyl-biphenyl (195 mg, 0.79 mmol, Eq: 1.5) and Cs₂CO₃ (49.9 mg, 153 μmol, Eq: 1.5) in DMF (6 mL) was heated to 60° C. After 1 h the mixture was diluted with 1 N HCl and extracted with EtOAc. The combined extracts were dried over Na₂SO₄, filtered and concentrated. The residue was purified by flash chromatography to afford tert-butyl (S)-1-((5-biphenyl-3-ylmethyl)-4-oxo-2,3,4,5-tetrahydrobenzo[b][1,4]thiazepin-3-ylamino)-1-oxopropan-2-yl(methyl)carbamate (264 mg, 92%).

Step 2: In a similar manner to that described for Example 1 Step 2, except the mixture was stirred for 3 h, tert-butyl (S)-1-((5-biphenyl-3-ylmethyl)-4-oxo-2,3,4,5-tetrahydrobenzo[b][1,4]thiazepin-3-ylamino)-1-oxopropan-2-yl(methyl)carbamate (44 mg, 80 μmol) was converted to the title compound (38 mg, 100%). MS m/z 445.9 (MH⁺)

Example 9

(2S)-N-(5-((6-Bromo-2-methoxynaphthalen-1-yl)methyl)-(3R)-8,9-difluoro-4-oxo-2',3',5',6'-tetrahydro-3H-spiro[benzo[b][1,4]oxazepine-2,4'-pyran]-3-yl)-2-(methylamino)propanamide hydrochloride

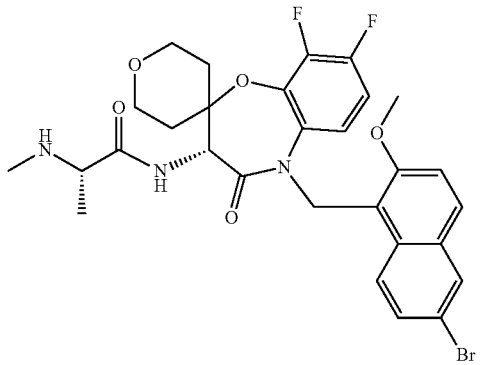 [SMILES: CN[C@@H](C)C(=O)N[C@H]1C(=O)N(Cc2c(OC)ccc3cc(Br)ccc23)c2ccc(F)c(F)c2OC12CCOCC2]

In a similar manner to that described for Example 1, except in Step 1 the mixture was heated at 60° C. and in Step 2 the mixture was stirred for 6 h, tert-butyl-(2S)-1-oxo-1-((3R)-(8,9-difluoro-4-oxo-2',3',4,5,5',6'-hexahydro-3H-spiro[benzo[b][1,4]oxazepine-2,4'-pyran]-3-ylamino))propan-2-yl carbamate (40 mg, 85.2 μmol) was converted to the title compound (40 mg). MS m/z 619.8 (MH⁺)

Example 10

(2S)-N-(5-((6-Bromo-2-methoxynaphthalen-1-yl)methyl)-(3S)-8,9-difluoro-4-oxo-2',3',5',6'-tetrahydro-3H-spiro[benzo[b][1,4]oxazepine-2,4'-pyran]-3-yl)-2-(methylamino)propanamide hydrochloride

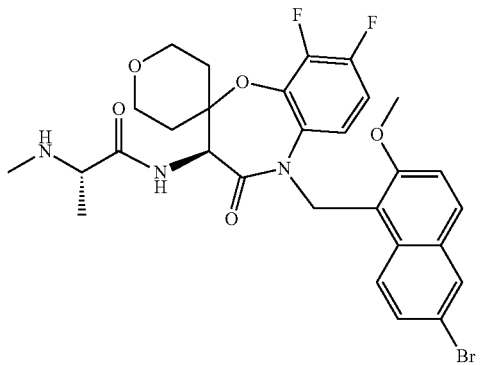 [SMILES: CN[C@@H](C)C(=O)N[C@@H]1C(=O)N(Cc2c(OC)ccc3cc(Br)ccc23)c2ccc(F)c(F)c2OC12CCOCC2]

In a similar manner to that described for Example 1, except in Step 1 the mixture was heated at 60° C. and in Step 2 the mixture was stirred for 6 h, tert-butyl-(2S)-1-oxo-1-((3S)-(8,9-difluoro-4-oxo-2',3',4,5,5',6'-hexahydro-3H-spiro[benzo[b][1,4]oxazepine-2,4'-pyran]-3-ylamino))propan-2-yl carbamate (42 mg, 89.5 μmol) was converted to the title compound (36 mg). MS m/z 619.8 (WO Example 11

(2S)-N-(5-((6-Bromo-2-methoxynaphthalen-1-yl)methyl)-(3R)-9-fluoro-4-oxo-2',3',5',6'-tetrahydro-3H-spiro[benzo[b][1,4]oxazepine-2,4'-pyran]-3-yl)-2-(methylamino)propanamide hydrochloride

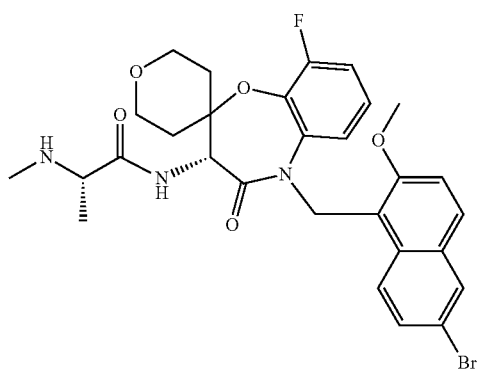 [SMILES: CN[C@@H](C)C(=O)N[C@H]1C(=O)N(Cc2c(OC)ccc3cc(Br)ccc23)c2cccc(F)c2OC12CCOCC2]

In a similar manner to that described for Example 1, except in Step 1 the mixture was stirred for 4.5 h and in Step 2 the mixture was stirred overnight, tert-butyl-(2S)-1-oxo-1-((3R)-(9-fluoro-4-oxo-2',3',4,5,5',6'-hexahydro-3H-spiro[benzo[b][1,4]oxazepine-2,4'-pyran]-3-ylamino))propan-2-yl carbamate (64 mg, 142 μmol) was converted to the title compound (63 mg). MS m/z 601.9 (MH⁺)

Example 12

(2S)-N-(5-((6-Bromo-2-methoxynaphthalen-1-yl)methyl)-(3S)-9-fluoro-4-oxo-2',3',5',6'-tetrahydro-3H-spiro[benzo[b][1,4]oxazepine-2,4'-pyran]-3-yl)-2-(methylamino)propanamide hydrochloride

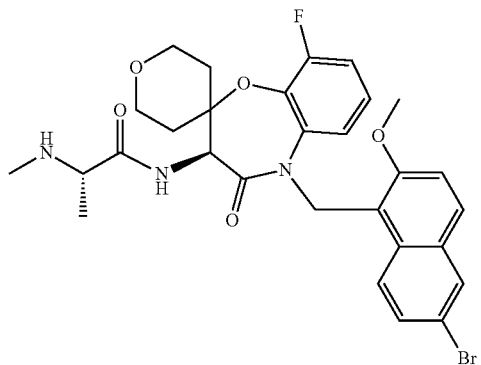 [SMILES: CN[C@@H](C)C(=O)N[C@@H]1C(=O)N(Cc2c(OC)ccc3cc(Br)ccc23)c2cccc(F)c2OC12CCOCC2]

In a similar manner to that described for Example 1, except in Step 1 the mixture was stirred for 4.5 h and in Step 2 the mixture was stirred overnight, tert-butyl-(2S)-1-oxo-1-((3S)-(9-difluoro-4-oxo-2',3',4,5,5',6'-hexahydro-3H-spiro[benzo[b][1,4]oxazepine-2,4'-pyran]-3-ylamino))propan-2-yl carbamate (49 mg, 109 μmol) was converted to the title compound (49 mg). MS m/z 601.9 (MH⁺)

Example 13

(2S)-N-(5-((6-Bromo-2-methoxynaphthalen-1-yl)methyl)-(3R)-9-fluoro-4-oxo-2',3',5',6'-tetrahydro-3H-spiro[benzo[b][1,4]oxazepine-2,4'-pyran]-3-yl)-2-(methylamino)butanamide hydrochloride

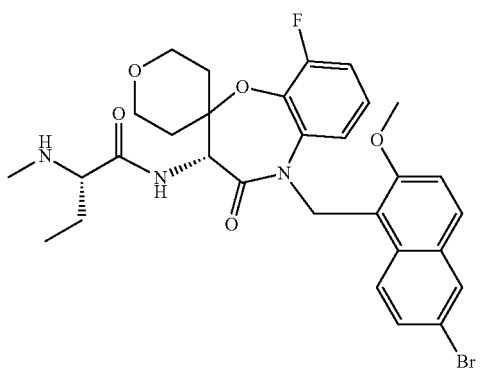 [SMILES: CC[C@H](NC)C(=O)N[C@H]1C(=O)N(Cc2c(OC)ccc3cc(Br)ccc23)c2cccc(F)c2OC12CCOCC2]

In a similar manner to that described for Example 1, except in Step 1 the mixture was stirred for 4 h and in Step 2 the mixture was stirred overnight, methyl-(tert-butyl)-(2S)-1-oxo-1-((3R)-(9-fluoro-4-oxo-2',3',4,5,5',6'-hexahydro-3H-spiro[benzo[b][1,4]oxazepine-2,4'-pyran]-3-ylamino))butan-2-yl carbamate (50 mg, 107 μmol) was converted to the title compound (57 mg). MS m/z 616.0 (MH$^+$)

Example 14

(2S)-N-(5-((6-Bromo-2-methoxynaphthalen-1-yl)methyl)-(3S)-9-fluoro-4-oxo-2',3',5',6'-tetrahydro-3H-spiro[benzo[b][1,4]oxazepine-2,4'-pyran]-3-yl)-2-(methylamino)butanamide hydrochloride

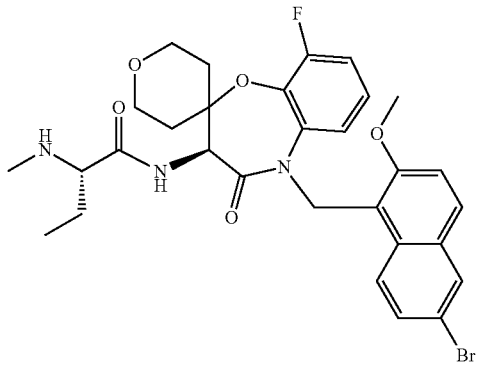 [SMILES: CC[C@H](NC)C(=O)N[C@@H]1C(=O)N(Cc2c(OC)ccc3cc(Br)ccc23)c2cccc(F)c2OC12CCOCC2]

In a similar manner to that described for Example 1, except in Step 1 the mixture was stirred for 4 h and in Step 2 the mixture was stirred overnight, methyl-(tert-butyl)-(2S)-1-oxo-1-((3S)-(9-fluoro-4-oxo-2',3',4,5,5',6'-hexahydro-3H-spiro[benzo[b][1,4]oxazepine-2,4'-pyran]-3-ylamino))butan-2-yl carbamate (51.5 mg, 180 μmol) was converted to the title compound (58 mg). MS m/z 615.9 (MH$^+$)

Example 15

(2S)-N-(5-((6-Bromo-2-methoxynaphthalen-1-yl)methyl)-(3S)-8-fluoro-4-oxo-2',3',5',6'-tetrahydro-3H-spiro[benzo[b][1,4]oxazepine-2,4'-pyran]-3-yl)-2-(methylamino)propanamide hydrochloride

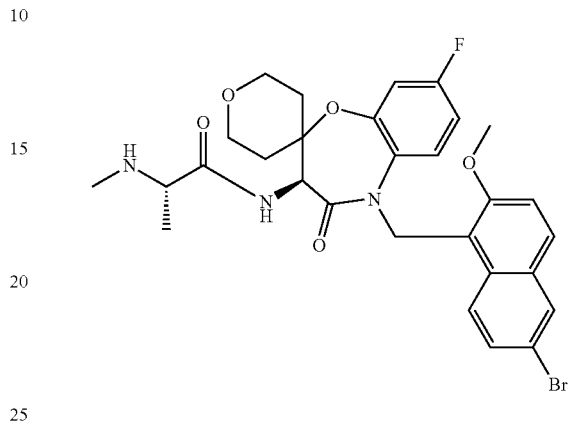

In a similar manner to that described for Example 1, except in Step 1 the mixture was stirred for 4 h and in Step 2 the mixture was stirred for 4 h, tert-butyl-(2S)-1-oxo-1-((3S)-(8-fluoro-4-oxo-2',3',4,5,5',6'-hexahydro-3H-spiro[benzo[b][1,4]oxazepine-2,4'-pyran]-3-ylamino))propan-2-yl carbamate (39.8 mg, 140 μmol) was converted to the title compound (30 mg). MS m/z 601.9 (MH$^+$)

Example 16

(2S)-N-(5-((6-Bromo-2-methoxynaphthalen-1-yl)methyl)-(3S)-8-fluoro-4-oxo-2',3',5',6'-tetrahydro-3H-spiro[benzo[b][1,4]oxazepine-2,4'-pyran]-3-yl)-2-(methylamino)butanamide hydrochloride

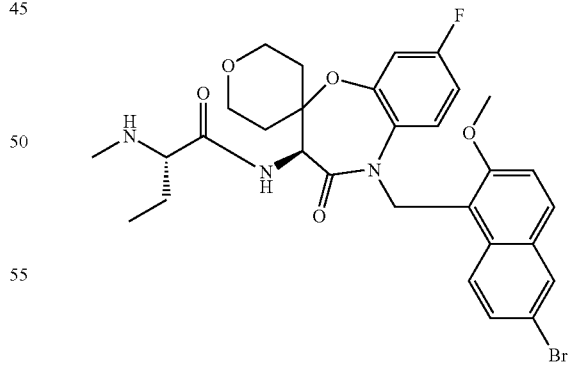

In a similar manner to that described for Example 1, except in Step 1 the mixture was stirred for 4 h and in Step 2 the mixture was stirred for 4 h, methyl-(tert-butyl)-(2S)-1-oxo-1-((3S)-(8-fluoro-4-oxo-2',3',4,5,5',6'-hexahydro-3H-spiro[benzo[b][1,4]oxazepine-2,4'-pyran]-3-ylamino))butan-2-yl carbamate (38.6 mg, 135 μmol) was converted to the title compound (29 mg). MS m/z 616.0 (WO

Example 17

(S)-N-((S)-5-((6-Bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-(2-hydroxyethyl amino)propanamide

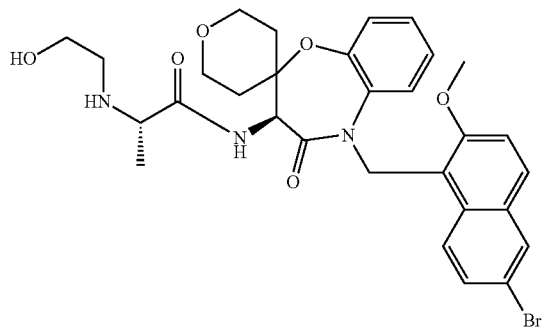 [SMILES: COc1ccc2cc(Br)ccc2c1CN1C(=O)[C@@H](NC(=O)[C@H](C)NCCO)C2(CCOCC2)Oc2ccccc21]

Sodium cyanoborohydride (5.14 mg, 81.8 µmol, Eq: 1.50) was added to a solution of (S)-N-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-amino-propanamide (31 mg, 54.5 µmol, Eq: 1.00), glycolaldehyde dimer (3.6 mg, 30.0 µmol, Eq: 0.55) and acetic acid (3.27 mg, 3.15 µl, 54.5 µmol, Eq: 1.00) in MeOH (1 mL) and the mixture was stirred at RT overnight. The mixture was diluted with 1 N HCl and H$_2$O/1 N NaOH was added to adjust the pH to ~8-9. The mixture was extracted with EtOAc, the combined extracts were washed with brine, dried over Na$_2$SO$_4$ and concentrated. The resulting material was purified by flash chromatography to afford the title compound (30 mg, 90% yield). MS m/z 613.8 (MH$^+$).

Example 18

(2S)-N-(5-((3-M ethoxyquinolin-N-oxide-4-yl)methyl)-(3S)-4-oxo-2',3',5',6'-tetrahydro-3H-spiro[benzo[b][1,4]oxazepine-2,4'-pyran]-3-yl)-2-(methyl amino)propanamide

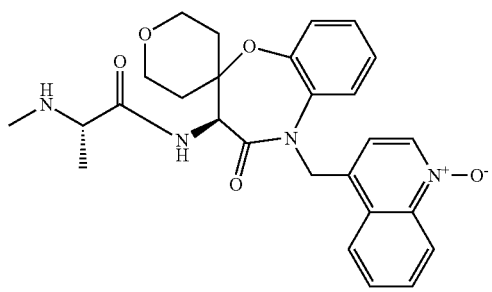 [SMILES: CN[C@@H](C)C(=O)N[C@@H]1C(=O)N(Cc2cc[n+]([O-])c3ccccc23)c2ccccc2OC12CCOCC2]

Step 1: 77% mCPBA (23.3 mg, 104 µmol, Eq: 2.1) was added to a solution of tert-butyl (S)-1-((S)-5-((3-methoxyquinolin-4-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (30 mg, 49.6 µmol, Eq: 1.00) in DCM (1 mL) and the mixture was stirred at RT overnight. The mixture was diluted with 0.1 N NaOH, extracted with EtOAc and the combined extracts washed with brine, dried over Na$_2$SO$_4$ and concentrated. The residue was purified by flash chromatography to afford tert-butyl (S)-1-((S)-5-((3-methoxyquinolin-N-oxide-4-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (22 mg, 71%). MS m/z 621.1 (MH$^+$)

Step 2: 2 M HCl in ether (403 µl, 806 µmol, Eq: 25) was added to a solution of tert-butyl (S)-1-((S)-5-((3-methoxyquinolin-N-oxide-4-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (20 mg, 32.2 µmol, Eq: 1.00) in MeOH (0.5 mL). After 2.5 h, the mixture was concentrated, the residue dissolved in MeCN/H$_2$O and the solution lyophilized. The resulting material was partitioned between EtOAc and 1 N HCl, the layers separated and the aqueous layer was made basic with 10 N NaOH and extracted with EtOAc. The combined organic layers were washed with brine, dried over Na$_2$SO$_4$ and concentrated under reduced pressure give a substance which was lyophilized from MeCN/H$_2$O to afford the title compound (14 mg, 84%). MS m/z 521.1 (MH$^+$)

Example 19

(2S)-N-(5-((6-Bromo-2-methoxynaphthalen-1-yl)methyl)-(3S)-4-oxo-2',3',5',6'-tetrahydro-3H-spiro[benzo[b][1,4]oxazepine-2,4'-pyran]-3-yl)-2-(methyl-d3-amino)propanamide hydrochloride

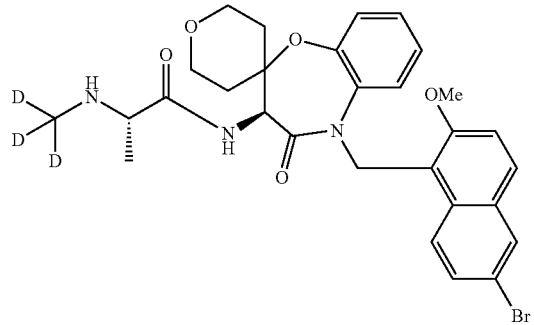 [SMILES: [2H]C([2H])([2H])N[C@@H](C)C(=O)N[C@@H]1C(=O)N(Cc2c(OC)ccc3cc(Br)ccc23)c2ccccc2OC12CCOCC2]

Step 1: Cs$_2$CO$_3$ (56.0 mg, 172 µmol, Eq: 1.5) and NaI (25.8 mg, 172 µmol, Eq: 1.5) were added to a solution of methyl-d3-(tert-butyl)-(2S)-1-oxo-1-((3S)-(4-oxo-2',3',4,5,5',6'-hexahydro-3H-spiro[benzo[b][1,4]oxazepine-2,4'-pyran]-3-ylamino))propan-2-yl carbamate (50 mg, 115 µmol, Eq: 1.00) and 6-bromo-1-(chloromethyl)-2-methoxynaphthalene (49.1 mg, 172 µmol, Eq: 1.5) and the mixture was stirred at 65° C. overnight. The mixture was diluted with H$_2$O and extracted with EtOAc, the combined extracts were washed with brine, dried over Na$_2$SO$_4$ and concentrated under reduced pressure. The resulting material was purified by flash chromatography to afford tert-butyl (S)-1-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl-d3)carbamate (57 mg, 73%). MS m/z 687.0 (MH$^+$)

Step 2: In a similar manner to that described for Example 1 Step 2 except the mixture was stirred 3 h, tert-butyl (S)-1-45)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl-d3)

carbamate (57 mg, 83.1 µmol) was converted to the title compound (42 mg, 81%). MS m/z 587.0 (MH⁺)

Example 20

(2S)-N-(5-((6-Bromo-2-(methoxy-d3)-naphthalen-1-yl)methyl)-(3S)-4-oxo-2',3',5',6'-tetrahydro-3H-spiro[benzo[b][1,4]oxazepine-2,4'-pyran]-3-yl)-2-(methyl-d3-amino)propanamide hydrochloride

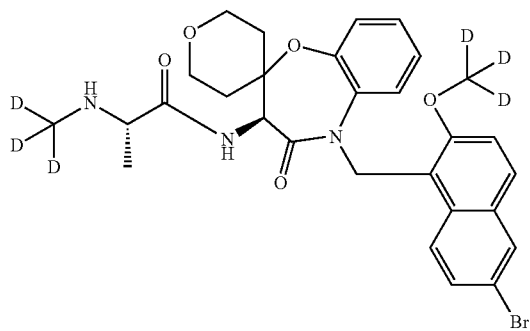 [SMILES: [2H]C([2H])([2H])N[C@@H](C)C(=O)N[C@@H]1C(=O)N(Cc2c(OC([2H])([2H])[2H])ccc3cc(Br)ccc23)c2ccccc2OC12CCOCC2]

In a similar manner to that described for Example 19 except in Step 1 the NaI was omitted and in Step 2 the mixture was stirred for 2 h, methyl-d3-(tert-butyl)-(2S)-1-oxo-1-((3S)-(4-oxo-2',3',4,5,5',6'-hexahydro-3H-spiro[benzo[b][1,4]oxazepine-2,4'-pyran]-3-ylamino))propan-2-yl carbamate (65 mg, 149 µmol, Eq: 1.00) and 6-bromo-1-chloromethyl-2-(methoxy-d3)-naphthalene (64.5 mg, 223 µmol, Eq: 1.5) were converted to the title compound (35 mg). MS m/z 589.8 (MH⁺)

Example 21

(R)-N-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-aminopropanamide and (S-N-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-aminopropanamide

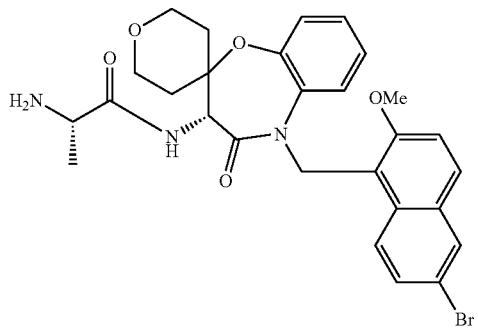

-continued

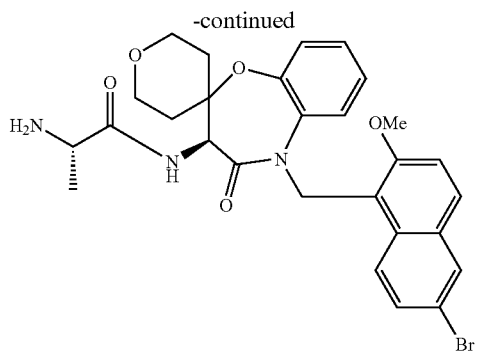

Step 1: A solution of HBTU (550 mg, 1.45 mmol, Eq: 1.2) and HOBT.H₂O (222 mg, 1.45 mmol, Eq: 1.2) in DMF (8 mL) were added to a solution of 3-amino-2',3',5',6'-tetrahydro-3H-spiro[benzo[b][1,4]oxazepine-2,4'-pyran]-4(5H)-one (0.3 g, 1.21 mmol, Eq: 1.00), BOC-Ala-OH (229 mg, 1.21 mmol, Eq: 1.00) and TEA (367 mg, 505 µl, 3.62 mmol, Eq: 3) in DMF (8 mL). After 2 d, the mixture was poured into EtOAc, washed with 1:1 sat NaHCO₃/sat NaCl, brine, dried over Na₂SO₄ and concentrated. The residue was purified by flash chromatography to afford tert-butyl (2S)-1-oxo-1-(4-oxo-2',3',4,5,5',6'-hexahydro-3H-spiro[benzo[b][1,4]oxazepine-2,4'-pyran]-3-ylamino)propan-2-ylcarbamate (0.46 g, 91%) as a white foam. MS m/z 420.0 (MH⁺)

Step 2: In a similar manner to that described for Example 1 Step 1 except the mixture was heated at 60° C. for 6 h, tert-butyl (2S)-1-oxo-1-(4-oxo-2',3',4,5,5',6'-hexahydro-3H-spiro[benzo[b][1,4]oxazepine-2,4'-pyran]-3-ylamino)propan-2-ylcarbamate (0.46 g, 1.1 mmol, Eq: 1.00) and 6-bromo-1-(chloromethyl)-2-methoxynaphthalene (470 mg, 1.64 mmol, Eq: 1.5) were converted to tert-butyl (2S)-1-(5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-ylamino)-1-oxopropan-2-ylcarbamate (0.5222 g, 71.2%) as a white foam. MS m/z 669.9 (MH⁺)

Step 3: 2.0 M HCl in Et₂O (25 mL, 50.0 mmol, Eq: 64.0) was added to a solution of tert-butyl (2S)-1-(5-(6-bromo-2-methoxynaphthalen-1-yl)methyl)-4-oxo-2',3',4,5,5',6'-hexahydro-3H-spiro[benzo[b][1,4]oxazepine-2,4'-pyran]-3-ylamino)-1-oxopropan-2-ylcarbamate (0.5222 g, 781 µmol, Eq: 1.00) in MeOH (5 mL). After 90 min. the reaction was concentrated to remove the Et₂O, the resulting solution poured into 1 M NaOH and the mixture extracted with DCM. The combined organic extracts were washed with H₂O, brine, dried over Na₂SO₄ and concentrated to afford a diastereomeric mixture of compounds (0.4186 g) as a white solid. The diastereomers were separated by chiral SFC to afford (R-N-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-aminopropanamide (47.5 mg) which eluted first (MS m/z 569.9 (MH⁺)) and (S)-N-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-aminopropanamide (42.7 mg) which eluted second. MS m/z 569.9 (MH⁺)

Example 22

(S)-N-{(R)-9-[2-(2-Methoxy-ethoxy)-acetylamino]-5-naphthalen-1-ylmethyl-4-oxo-2,3,4,5-tetrahydro-benzo[b][1,4]thiazepin-3-yl}-2-methylamino-propionamide hydrochloride

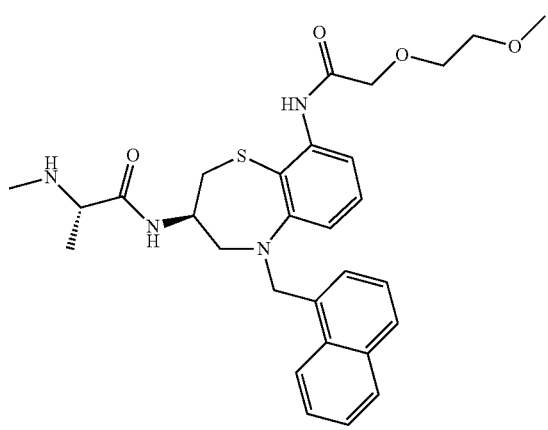

Step 1: (2-Methoxy-ethoxy)-acetyl chloride (29.8 µL, 224 µmol) was added to a solution of [(S)-1-((R)-9-amino-5-naphthalen-1-ylmethyl-4-oxo-2,3,4,5-tetrahydro-benzo[b][1,4]thiazepin-3-ylcarbamoyl)-ethyl]-methyl-carbamic acid tert-butyl ester (100 mg, 187 µmol), DMAP (1.1 mg, 9.4 µmol) and TEA (104 µL, 748 µmol) in pyridine (2 mL). After 6 h the mixture was poured into 0.5 M HCl (5 mL) and extracted with EtOAc. The combined extracts were washed with H₂O, brine, dried over Na₂SO₄, filtered and concentrated. The residue was purified by silica gel chromatography ((S)-1-{(R)-9-[2-(2-methoxy-ethoxy)-acetylamino]-5-naphthalen-1-ylmethyl-4-oxo-2,3,4,5-tetrahydro-benzo[b][1,4]thiazepin-3-ylcarbamoyl}-ethyl)-methyl-carbamic acid tert-butyl ester (80 mg, 66%)

Step 2: Hydrogen chloride gas was bubbled into a solution of ((S)-1-{(R)-9-[2-(2-methoxy-ethoxy)-acetylamino]-5-naphthalen-1-ylmethyl-4-oxo-2,3,4,5-tetrahydro-benzo[b][1,4]thiazepin-3-ylcarbamoyl}-ethyl)-methyl-carbamic acid tert-butyl ester (70 mg, 108 µmol) in dioxane (5 mL) at 0° C. for 1 min, the mixture was warmed to RT and stirred for 1 h. The mixture was concentrated, the residue was triturated with Et₂O and the resulting solid was filtered, washed with Et₂O and dried to give the title compound (25 mg, 40%). HR-MS: calcd for $C_{29}H_{34}N_4O_5S$ (MH⁺) 551.2326. found 551.2323.

Following the procedures described for the preparation of Example 22 the compounds in Table 3 were prepared.

TABLE 3

| Ex | Structure | HRMS (MH⁺) Calcd. | Found |
|---|---|---|---|
| 22a | 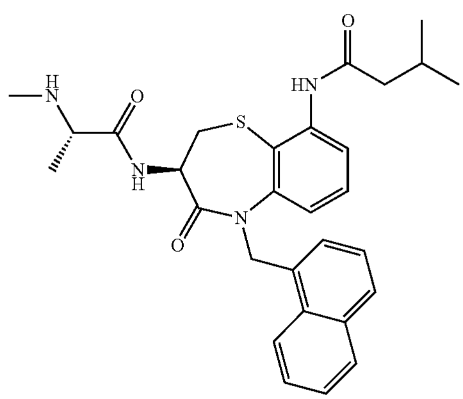 [SMILES: CN[C@@H](C)C(=O)N[C@H]1CSc2c(NC(=O)CC(C)C)cccc2N(Cc2cccc3ccccc23)C1=O] | 519.2425 | 519.2425 |
| 22b | 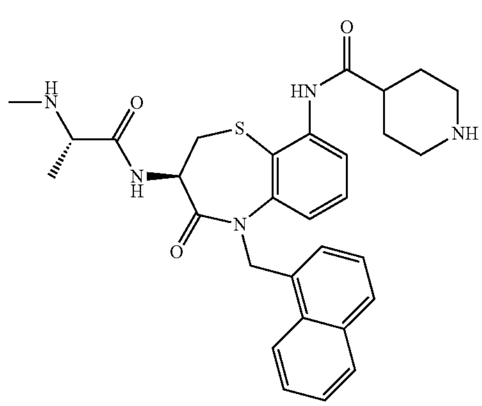 [SMILES: CN[C@@H](C)C(=O)N[C@H]1CSc2c(NC(=O)C3CCNCC3)cccc2N(Cc2cccc3ccccc23)C1=O] | 546.2534 | 546.2534 |

TABLE 3-continued
| Ex | Structure | HRMS (MH+) Calcd. | Found |
|---|---|---|---|
| 22c | 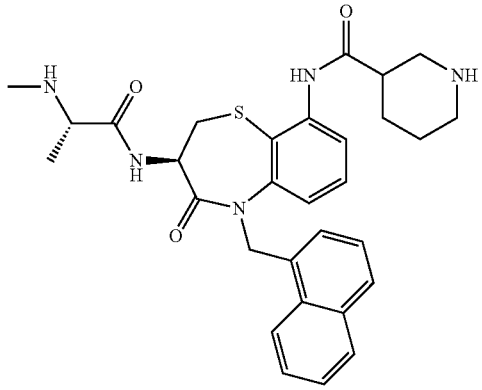 [SMILES: CN[C@@H](C)C(=O)N[C@H]1CSc2c(NC(=O)C3CCCNC3)cccc2N(Cc2cccc3ccccc23)C1=O] | 560.2690 | 560.2690 |
| 22d | 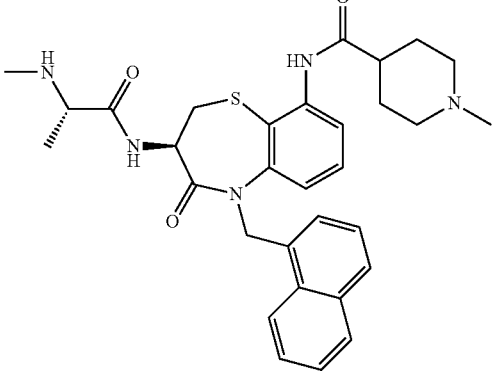 | 560.2690 | 560.2690 |
| 22e | 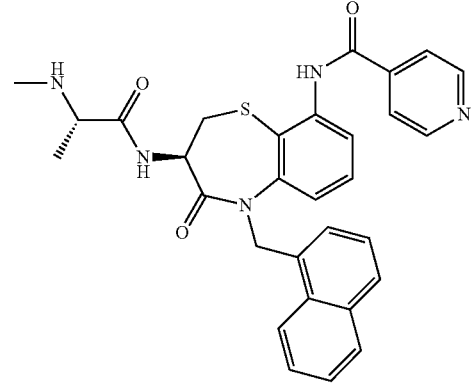 [SMILES: CN[C@@H](C)C(=O)N[C@H]1CSc2c(NC(=O)c3ccncc3)cccc2N(Cc2cccc3ccccc23)C1=O] | 540.2064 | 540.2061 |
| 22f | 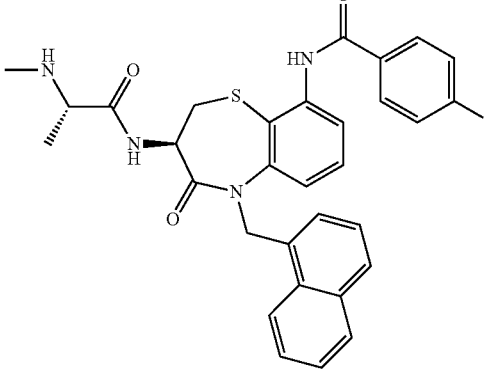 | 569.2217 | 569.2217 |

TABLE 3-continued

| Ex | Structure | HRMS (MH+) Calcd. | Found |
|---|---|---|---|
| 22g | 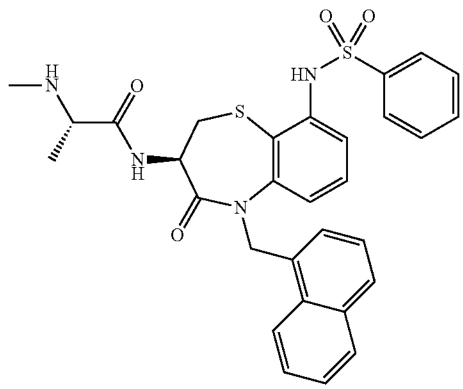 [SMILES: CN[C@@H](C)C(=O)N[C@H]1CSc2c(NS(=O)(=O)c3ccccc3)cccc2N(Cc2cccc3ccccc23)C1=O] | 575.1781 | 575.1780 |
| 22h | 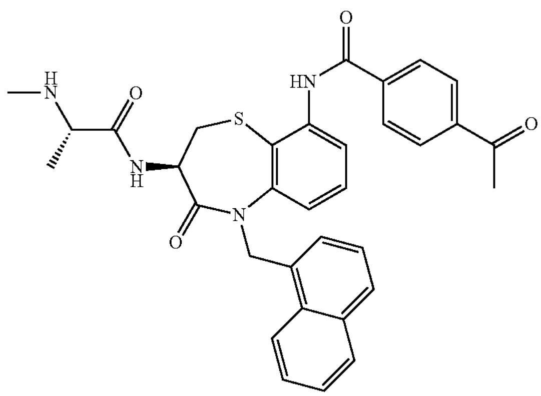 [SMILES: CN[C@@H](C)C(=O)N[C@H]1CSc2c(NC(=O)c3ccc(C(C)=O)cc3)cccc2N(Cc2cccc3ccccc23)C1=O] | 581.2217 | 581.2217 |

Example 23

1-Acetyl-piperidine-4-carboxylic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide

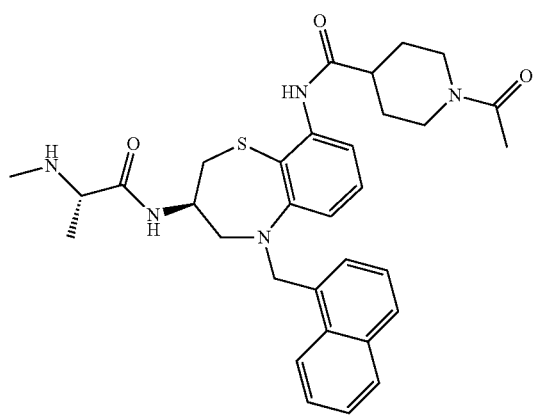 [SMILES: CN[C@@H](C)C(=O)N[C@H]1CSc2c(NC(=O)C3CCN(C(C)=O)CC3)cccc2N(Cc2cccc3ccccc23)C1]

In a similar manner to that described for Example 22, [(S)-1-((R)-9-amino-5-naphthalen-1-ylmethyl-4-oxo-2,3,4,5-tetrahydro-benzo[b][1,4]thiazepin-3-ylcarbamoyl)-ethyl]-methyl-carbamic acid tert-butyl ester and 1-acetyl-piperidine-4-carbonyl chloride were converted to 1-acetyl-piperidine-4-carboxylic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide hydrochloride. The material obtained after trituration was purified by reverse phase HPLC to give 1-acetyl-piperidine-4-carboxylic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide trifluoroacetate and this material was partitioned between EtOAc (10 mL) and a saturated solution of NaHCO$_3$ (5 mL). The organic layer was washed with H$_2$O, brine, dried over Na$_2$SO$_4$, filtered and concentrated to give the title compound. HRMS: calcd. for C$_{32}$H$_{37}$N$_5$O$_4$S (MH$^+$) 588.2639. found 588.2639.

Example 24

5-Oxo-hexanoic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide hydrochloride

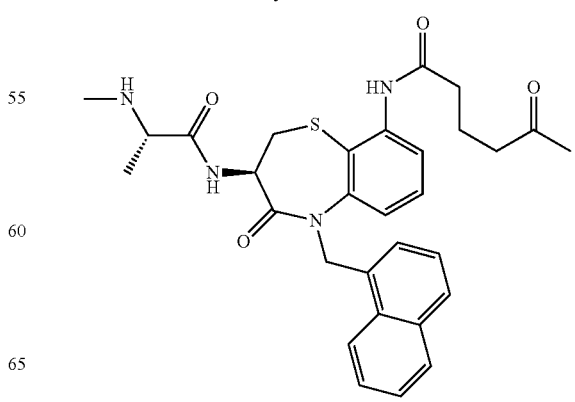

Phosphorus oxychloride (34.4 mg, 0.22 mmol) was added to a solution of [(S)-1-((R)-9-amino-5-naphthalen-1-ylmethyl-4-oxo-2,3,4,5-tetrahydro-benzo[b][1,4]thiazepin-3-ylcarbamoyl)-ethyl]-methyl-carbamic acid tert-butyl ester (80 mg, 0.15 mmol) and 5-oxo-hexanoic acid (29.2 mg, 0.22 mmol) in pyridine (1.0 mL). After 2 h, the mixture was poured into 0.5 M HCl (5 mL) and extracted with EtOAc, the combined extracts were washed with water, brine, dried over $Na_2SO_4$, filtered and concentrated. The residue was purified by silica gel chromatography to afford the title compound. HR-MS: calcd. for $C_{30}H_{34}N_4O_4S$ (MH$^+$) 547.2374. found 547.2374.

Example 25

3,4,5-Trimethoxy-N-[(R)-3-((S)-2-methylamino-propionylamino)-5-naphthalen-1-ylmethyl-4-oxo-2,3,4,5-tetrahydro-benzo[b][1,4]thiazepin-9-yl]-benzamide hydrochloride

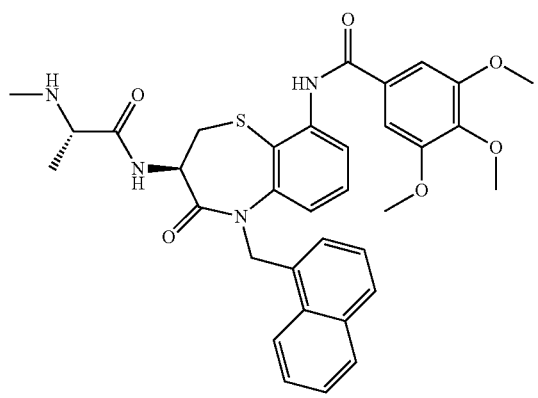

In a similar manner to that described for Example 24, [(S)-1-((R)-9-amino-5-naphthalen-1-ylmethyl-4-oxo-2,3,4,5-tetrahydro-benzo[b][1,4]thiazepin-3-ylcarbamoyl)-ethyl]-methyl-carbamic acid tert-butyl ester and 3,4,5-trimethoxy-benzoic acid were converted to the title compound. HR-MS: calcd. for $C_{34}H_{36}N_4O_6S$ (MH$^+$) 629.2429. found 629.2428.

Example 26

6-Oxo-heptanoic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide hydrochloride

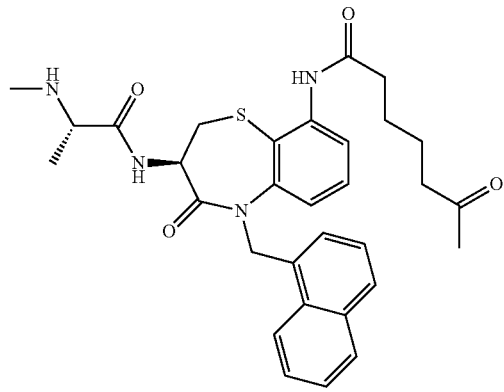 [SMILES: CN[C@@H](C)C(=O)N[C@H]1CSc2c(NC(=O)CCCCC(C)=O)cccc2N(Cc2cccc3ccccc23)C1=O]

In a similar manner to that described for Example 24, [(S)-1-((R)-9-amino-5-naphthalen-1-ylmethyl-4-oxo-2,3,4,5-tetrahydro-benzo[b][1,4]thiazepin-3-ylcarbamoyl)-ethyl]-methyl-carbamic acid tert-butyl ester and 6-oxo-heptanoic acid were converted to the title compound. HR-MS: calcd. for $C_{31}H_{36}N_4O_4S$ (MH$^+$) 561.2530. found 561.2530.

Example 27

(S)-N-((R)-9-Amino-5-naphthalen-1-ylmethyl-4-oxo-2,3,4,5-tetrahydro-benzo[b][1,4]thiazepin-3-yl)-2-methylamino-propionamide hydrochloride

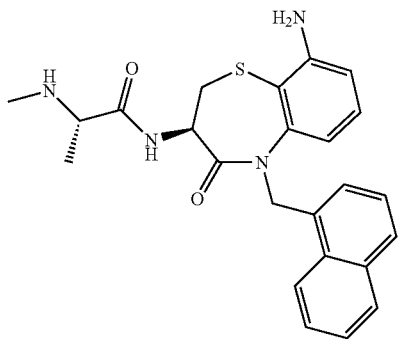 [SMILES: CN[C@@H](C)C(=O)N[C@H]1CSc2c(N)cccc2N(Cc2cccc3ccccc23)C1=O]

In a similar manner to that described for Example 22 Step 2, [(S)-1-((R)-9-amino-5-naphthalen-1-ylmethyl-4-oxo-2,3,4,5-tetrahydro-benzo[b][1,4]thiazepin-3-ylcarbamoyl)-ethyl]-methyl-carbamic acid tert-butyl ester was converted to the title compound. HR-MS: calcd. for $C_{24}H_{26}N_4O_2S$ (MH$^+$) 435.1849. found 435.1850.

Example 28

N-[(R)-3-((S)-2-Methylamino-propionylamino)-5-naphthalen-1-ylmethyl-4-oxo-2,3,4,5-tetrahydro-benzo[b][1,4]thiazepin-9-yl]-benzamide hydrochloride

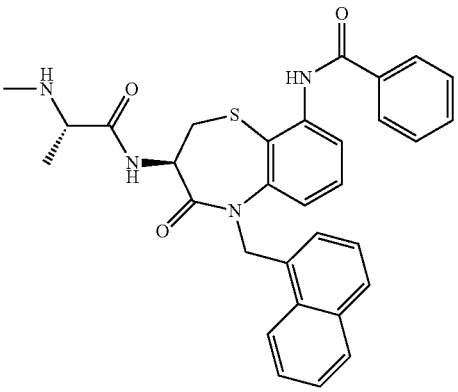 [SMILES: CN[C@@H](C)C(=O)N[C@H]1CSc2c(NC(=O)c3ccccc3)cccc2N(Cc2cccc3ccccc23)C1=O]

In a similar manner to that described for Example 22, [(S)-1-((R)-9-amino-5-naphthalen-1-ylmethyl-4-oxo-2,3,4,5-tetrahydro-benzo[b][1,4]thiazepin-3-ylcarbamoyl)-ethyl]-methyl-carbamic acid tert-butyl ester and benzoyl chloride were converted to the title compound. MS m/z 539 (MH+)

Example 29

(S)-N-[(S)-9-(6-Bromo-2-methoxy-naphthalen-1-ylmethyl)-8-oxo-6,7,8,9-tetrahydro-5-oxa-9-aza-benzocyclohepten-7-yl]-2-methylamino-propionamide trifluoroacetate

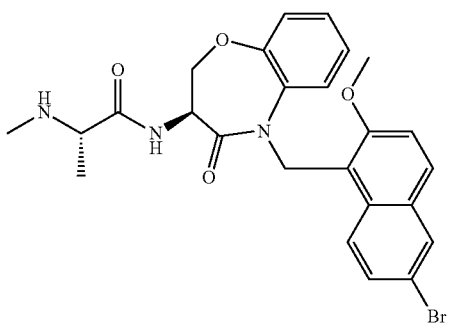 [SMILES: CN[C@@H](C)C(=O)N[C@H]1COc2ccccc2N(Cc2c(OC)ccc3cc(Br)ccc23)C1=O]

Step 1: A mixture of tert-butyl methyl((S)-1-oxo-1-((S)-4-oxo-2,3,4,5-tetrahydrobenzo[b][1,4]oxazepin-3-ylamino)propan-2-yl)carbamate (1.1 g, 3.03 mmol, Eq: 1.00) (Example 1), 6-bromo-1-(chloromethyl)-2-methoxynaphthalene (951 mg, 3.33 mmol, Eq: 1.10), Cs$_2$CO$_3$ (1.08 g, 3.33 mmol, Eq: 1.10), and NaI (499 mg, 3.33 mmol, Eq: 1.1) in DMF (20 mL) was stirred for 3.5 at RT then heated at 50° C. for 1 h then at 60° C. for 30 min. The mixture was cooled, diluted with EtOAc, washed with water and brine. The organic solution was dried over Na$_2$SO$_4$ and concentrated. The residue was purified by silica gel chromatography to afford tert-butyl (S)-1-((S)-5-((6-bromo-2-methoxynaphthalen-1-yl)methyl)-4-oxo-2,3,4,5-tetrahydrobenzo[b][1,4]oxazepin-3-ylamino)-1-oxopropan-2-yl(methyl)carbamate (1.00 g, 1.63 mmol, 53.9%) as a light yellow foam.

Step 2: TFA (1.48 g, 1 mL, 13.0 mmol, Eq: 153) was added to a solution of tert-butyl (S)-1-((S)-5-((6-bromo-2-methoxynaphthalen-1-yl)methyl)-4-oxo-2,3,4,5-tetrahydrobenzo[b][1,4]oxazepin-3-ylamino)-1-oxopropan-2-yl(methyl)carbamate (52 mg, 84.9 µmol, Eq: 1.00) in DCM and at 0° C. After 1 h the mixture was concentrated and the residue was triturated with Et$_2$O to afford the title compound (30 mg, 58.5 µmol, 69.0%) as a light brown solid. MS m/z (MH+) 363.0

In a similar manner to that described for Example 29, the conditions can be varied so that the temperature can range from 50° C. 70° C. and the reaction time can range from 2 24 h and 1.3 eq. of NaI can be optionally added tert-butyl methyl ((S)-1-oxo-1-((S)-4-oxo-2,3,4,5-tetrahydrobenzo[b][1,4]oxazepin-3-ylamino)propan-2-yl)carbamate can be converted the compounds shown in Table 4.

TABLE 4

| Entry | Final Product | m/z (MH+) |
|---|---|---|
| 29a | | 484.0 |
| 29b | | 434.2 |
| 29c | | 384.4 |

Example 30

(S)-N-[(S)-9-(6-Cyclopropyl-2-methoxy-naphthalen-1-ylmethyl)-8-oxo-6,7,8,9-tetrahydro-5-oxa-9-aza-benzocyclohepten-7-yl]-2-methylamino-propionamide trifluoroacetate

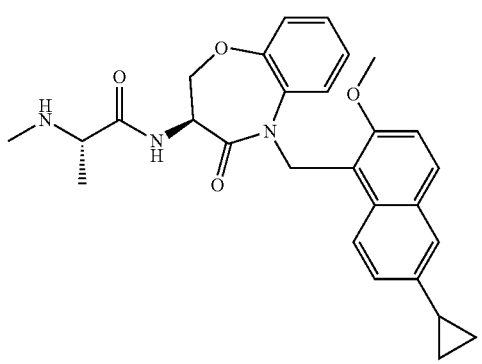 [SMILES: CN[C@@H](C)C(=O)N[C@H]1COc2ccccc2N(Cc2c(OC)ccc3cc(C4CC4)ccc23)C1=O]

Step 1: For a duration of 5 min., N$_2$ was bubbled through a mixture of tert-butyl (S)-1-((S)-5-((6-bromo-2-methoxynaphthalen-1-yl)methyl)-4-oxo-2,3,4,5-tetrahydrobenzo

[b][1,4]oxazepin-3-ylamino)-1-oxopropan-2-yl(methyl)carbamate (200 mg, 327 μmol, Eq: 1.00), cyclopropylboronic acid (33.7 mg, 392 μmol, Eq: 1.20), Na₂CO₃ (408 μl, 816 μmol, Eq: 2.50) in 1,4-dioxane (2 mL) then Pd(Ph₃P)₄ (18.9 mg, 16.3 μmol, Eq: 0.05) was added. The mixture was heated to reflux overnight, cooled and diluted with EtOAc. The mixture was washed with water, brine, dried over Na₂SO₄ and concentrated to give tert-butyl (S)-1-((S)-5-((6-cyclopropyl-2-methoxynaphthalen-1-yl)methyl)-4-oxo-2,3,4,5-tetrahydrobenzo[b][1,4]oxazepin-3-ylamino)-1-oxopropan-2-yl (methyl)carbamate (24 mg, 41.8 μmol, 12.8%) which was used without purification.

Step 2: In a similar manner to that described for Example 29 Step 2 except the mixture was stirred at 0° C. for 1 h and at RT for 1 h, tert-butyl (S)-1-((S)-5-((6-cyclopropyl-2-methoxynaphthalen-1-yOmethyl)-4-oxo-2,3,4,5-tetrahydrobenzo[b][1,4]oxazepin-3-ylamino)-1-oxopropan-2-yl(methyl)carbamate (24 mg, 41.8 μmol) was converted to the title compound (23 mg, 96%). MS m/z (MH⁺) 474.1

Example 31

Methyl 6-methoxy-5-(((S)-3-((S)-2-(methylamino)propanamido)-4-oxo-3,4-dihydrobenzo[b][1,4]oxazepin-5(2H)-yl)methyl)-2-naphthoate trifluoroacetate

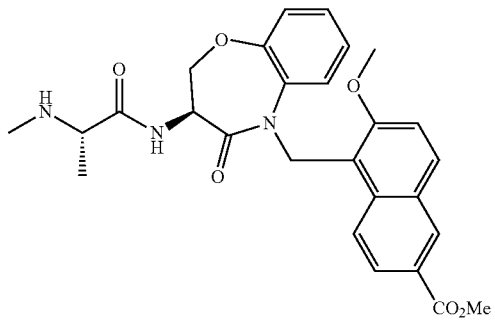 [SMILES: CN[C@@H](C)C(=O)N[C@H]1COc2ccccc2N(Cc2c(OC)ccc3cc(C(=O)OC)ccc23)C1=O]

Step 1: A mixture of tert-butyl (S)-1-((S)-5-((6-bromo-2-methoxynaphthalen-1-yl)methyl)-4-oxo-2,3,4,5-tetrahydrobenzo[b][1,4]oxazepin-3-ylamino)-1-oxopropan-2-yl (methyl)carbamate (1.8 g, 2.94 mmol, Eq: 1.00), Pd(OAc)₂ (33.0 mg, 147 μmol, Eq: 0.05) and 4,5-bis(diphenylphosphino)-9,9-dimethylxanthene (Xantphos) (170 mg, 294 μmol, Eq: 0.10) in a microwave tube was evacuated and purged with N₂. MeOH (1.43 g, 1.8 mL, 44.5 mmol, Eq: 15.1) and TEA were added, the vessel was purged with CO and heated at 70° C. under CO overnight. The mixture was concentrated and the residue was purified by silica gel chromatography to afford methyl 5-(((S)-3-((S)-2-(tert-butoxycarbonyl (methyl)amino)propanamido)-4-oxo-3,4-dihydrobenzo[b][1,4]oxazepin-5(2H)-yl)methyl)-6-methoxy-2-naphthoate (1.24 g, 2.1 mmol, 71.3%).

Step 2: In a similar manner to that described for Example 29 Step 2, methyl 5-(((S)-3-((S)-2-(tert-butoxycarbonyl(methyl)amino)propanamido)-4-oxo-3,4-dihydrobenzo[b][1,4]oxazepin-5(2H)-yl)methyl)-6-methoxy-2-naphthoate (100 mg, 169 iumol) was converted to the title compound (75 mg, 124 μmol, 73.3%). MS m/z (MH⁺) 492.2

Example 32

6-Methoxy-5-(((S)-3-((S)-2-(methylamino)propanamido)-4-oxo-3,4-dihydrobenzo[b][1,4]oxazepin-5 (2H)-yl)methyl)-2-naphthoic acid trifluoroacetate

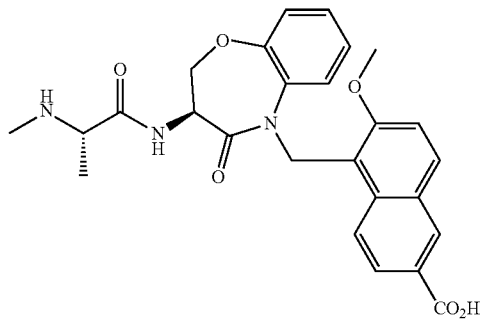 [SMILES: CN[C@@H](C)C(=O)N[C@H]1COc2ccccc2N(Cc2c(OC)ccc3cc(C(=O)O)ccc23)C1=O]

Step 1: LiOH.H₂O (24.0 mg, 573 μmol, Eq: 3) was dissolved in water and the solution was added to a solution of methyl 5-(((S)-3-((S)-2-(tert-butoxycarbonyl(methyl) amino)propanamido)-4-oxo-3,4-dihydrobenzo[b][1,4]oxazepin-5(2H)-yl)methyl)-6-methoxy-2-naphthoate (113 mg, 191 μmol, Eq: 1.00) in MeOH (3 mL) and the mixture was heated to 50° C. for 1 h and then to 60° C. for 1 h. The mixture was cooled, KHSO₄ solution was added and the mixture extracted with EtOAc. The combined extracts were concentrated and the residue purified by silica gel chromatography to afford 5-(((S)-3-((S)-2-(tert-butoxycarbonyl(methyl)amino) propanamido)-4-oxo-3,4-dihydrobenzo[b][1,4]oxazepin-5 (2H)-yl)methyl)-6-methoxy-2-naphthoic acid (103 mg, 93%) as a white powder.

Step 2: In a similar manner to that described for Example 29 Step 2, 5-(((S)-3-((S)-2-(tert-butoxycarbonyl(methyl) amino)propanamido)-4-oxo-3,4-dihydrobenzo[b][1,4]oxazepin-5(2H)-yl)methyl)-6-methoxy-2-naphthoic acid (102 mg, 177 μmol) was converted to the title compound (73 mg, 58%). MS m/z (MH⁺) 478.2

Example 33

6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carboxylic acid (2-hydroxy-ethyl)-methyl-amide

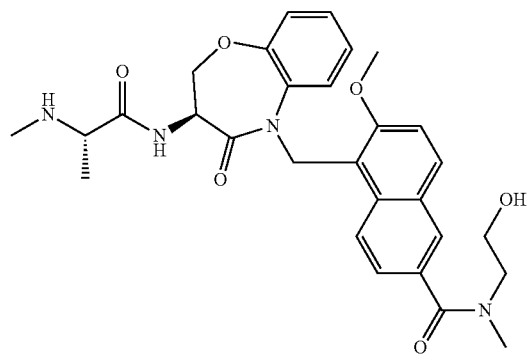 [SMILES: CN[C@@H](C)C(=O)N[C@H]1COc2ccccc2N(Cc2c(OC)ccc3cc(C(=O)N(C)CCO)ccc23)C1=O]

Step 1: A mixture of 5-(((S)-3-((S)-2-(tert-butoxycarbonyl (methyl)amino)propanamido)-4-oxo-3,4-dihydrobenzo[b] [1,4]oxazepin-5(2H)-yl)methyl)-6-methoxy-2-naphthoic acid (100 mg, 173 μmol, Eq: 1.00), 2-(methylamino)ethanol (26.0 mg, 27.8 μl, 346 μmol, Eq: 2.00), HOBT.H₂O (31.8 mg, 208 μmol, Eq: 1.20), HBTU (78.8 mg, 208 μmol, Eq: 1.2), DIEA (67.1 mg, 90.5 μl, 519 μmol, Eq: 3.00) in DMF was stirred at 0° C. for 2 h. The mixture was diluted with EtOAc, washed with water, brine, dried over Na₂SO₄ and concentrated. The residue was purified by silica gel chromatography to afford tert-butyl (S)-1-((S)-5-((6-((2-hydroxyethyl)(methyl)carbamoyl)-2-methoxynaphthalen-1-yl)methyl)-4-oxo-2,3,4,5-tetrahydrobenzo[b][1,4]oxazepin-3-ylamino)-1-oxopropan-2-yl(methyl)carbamate (94 mg, 85% yield) as an oil.

Step 2: TFA (1.48 g, lmL, 13.0 mmol, Eq: 88.6) was added to a solution of tert-butyl (S)-1-((S)-5-((6-((2-hydroxyethyl)(methyl)carbamoyl)-2-methoxynaphthalen-1-yl)methyl)-4-oxo-2,3,4,5-tetrahydrobenzo[b][1,4]oxazepin-3-ylamino)-1-oxopropan-2-yl(methyl)carbamate (93 mg, 147 μmol, Eq: 1.00) in DCM at 0° C. After 1 h, the mixture was concentrated and the residue triturated with Et₂O. The resulting material was dissolved in DCM, washed with sat. NaHCO₃ solution and the organic layer concentrated. The residue was purified by silica gel chromatography to afford the title compound as a white powder. MS m/z (MH⁺) 535.2

Example 34

4-({6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carbonyl}-amino)-butyric acid trifluoroacetate

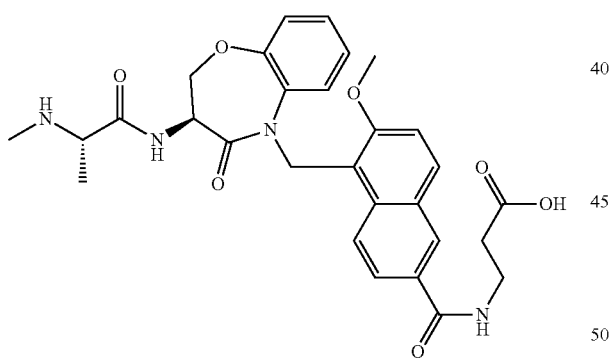

Step 1: A mixture of 5-((S)-3-((S)-2-(tert-butoxycarbonyl (methyl)amino)propanamido)-4-oxo-3,4-dihydrobenzo[b] [1,4]oxazepin-5(2H)-yl)methyl)-6-methoxy-2-naphthoic acid (100 mg, 173 μmol, Eq: 1.00), DIEA (90.5 μl, 519 μmol, Eq: 3.00), HOBT.H₂O (31.8 mg, 208 μmol, Eq: 1.20), HBTU (78.8 mg, 208 μmol, Eq: 1.2), tert-butyl 3-aminopropanoate hydrochloride (31.6 mg, 173 μmol, Eq: 1.00) in DMF was stirred at 0° C. for 2 h. The mixture was diluted with EtOAc, washed with water and brine. The organic solution was dried over Na₂SO₄, filtered, concentrated and the residue purified by silica gel chromatography to afford 3-[(5-{(S)-7-[(S)-2-(tert-butoxycarbonyl-methyl-amino)-propionyl amino]-8-oxo-7,8-dihydro-6H-5-oxa-9-aza-benzocyclohepten-9-ylmethyl}-6-methoxy-naphthalene-2-carbonyl)-amino]-propionic acid tert-butyl ester (93 mg, 76%).

Step 2: In a similar manner to that described for Example 29 Step 2, 3-[(5-{(S)-7-[(S)-2-(tert-butoxycarbonyl-methyl-amino)-propionylamino]-8-oxo-7,8-dihydro-6H-5-oxa-9-aza-benzocyclohepten-9-ylmethyl}-6-methoxy-naphthalene-2-carbonyl)-amino]-propionic acid tert-butyl ester (91 mg, 129 μmol) was converted to the title compound. MS m/z (MH⁺) 549.5

Example 35

6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carboxylic acid dimethylamide trifluoroacetate

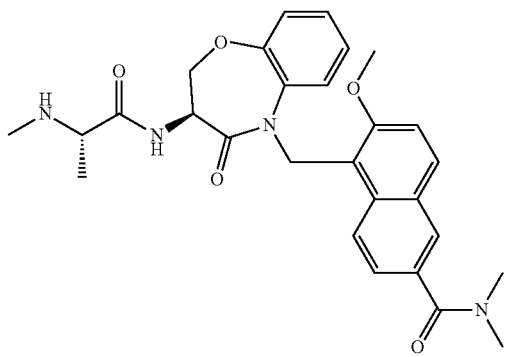

In a similar manner to that described for Example 33 except in Step 1 DIEA was omitted, THF was used in place of DMF and the material was not purified, 5-(((S)-3-((S)-2-(tert-butoxycarbonyl(methyl)amino)propanamido)-4-oxo-3,4-dihydrobenzo[b][1,4]oxazepin-5(2H)-yl)methyl)-6-methoxy-2-naphthoic acid (96 mg, 166 μmol, Eq: 1.00) and dimethylamine (249 μl, 499 μmol, Eq: 3.00) was converted to the title compound (99 mg). MS m/z (MH⁺) 505.2

Example 36

(S)-N-[(S)-9-(7-Bromo-3-methoxy-naphthalen-2-ylmethyl)-3-methyl-8-oxo-6,7,8,9-tetrahydro-5-oxa-9-aza-benzocyclohepten-7-yl]-2-methylamino-propionamide trifluoroacetate

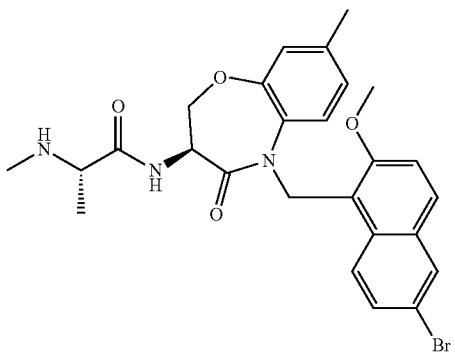 [SMILES: CN[C@@H](C)C(=O)N[C@H]1COc2cc(C)ccc2N(Cc2c(OC)ccc3cc(Br)ccc23)C1=O]

Step 1: A mixture of (S)-3-amino-8-methyl-2,3-dihydrobenzo[b][1,4]oxazepin-4(5H)-one trifluoroacetate (1.60 g, 5.23 mmol, Eq: 1.00), (S)-2-(tert-butoxycarbonyl(methyl)

amino)propanoic acid (1.06 g, 5.23 mmol, Eq: 1.00), HOBT (801 mg, 5.23 mmol, Eq: 1.00), HBTU (1.98 g, 5.23 mmol, Eq: 1.00) at 0° C. and DIEA (2.03 g, 2.73 mL, 15.7 mmol, Eq: 3.00) in DMF (50 mL) was stirred at 0° C. for 1 h, diluted with EtOAc, washed with water, brine, dried over Na₂SO₄, filtered and concentrated. The residue was purified by silica gel chromatography to afford methyl-[(S)-1-((S)-3-methyl-8-oxo-6,7,8,9-tetrahydro-5-oxa-9-aza-benzocyclohepten-7-ylcarbamoyl)-ethyl]-carbamic acid tert-butyl ester (2.04 g) which was used without purification.

Step 2: A mixture of methyl-[(S)-1-((S)-3-methyl-8-oxo-6,7,8,9-tetrahydro-5-oxa-9-aza-benzocyclohepten-7-ylcarbamoyl)-ethyl]-carbamic acid tert-butyl ester (241 mg, 639 µmol, Eq: 1.00), NaI (95.7 mg, 639 µmol, Eq: 1.00), Cs₂CO₃ (312 mg, 958 µmol, Eq: 1.50), 6-bromo-1-(chloromethyl)-2-methoxynaphthalene (219 mg, 766 µmol, Eq: 1.20) in DMF (3 mL) was stirred at RT for 1 h and at 50° C. for 1 h. The mixture was diluted with EtOAc, washed with water, brine, dried over Na₂SO₄, filtered and concentrated. The resulting material was purified by silica gel chromatography to afford {(S)-1-[(S)-9-(6-bromo-2-methoxy-naphthalen-1-ylmethyl)-3-methyl-8-oxo-6,7,8,9-tetrahydro-5-oxa-9-aza-benzocyclohepten-7-ylcarbamoyl]-ethyl}-methyl-carbamic acid tert-butyl ester (63 mg, 16%) as an oil.

Step 3: In a similar manner to that described for Example 29 Step 2, {(S)-1-[(S)-9-(6-bromo-2-methoxy-naphthalen-1-ylmethyl)-3-methyl-8-oxo-6,7,8,9-tetrahydro-5-oxa-9-aza-benzocyclohepten-7-ylcarbamoyl]-ethyl}-methyl-carbamic acid tert-butyl ester (60 mg, 95.8 1=01) was converted to the title compound (37 mg). MS m/z MH⁺ 527.8

Example 37

(2S,3R)-2-Amino-N-[(S)-9-(7-bromo-3-methoxy-naphthalen-2-ylmethyl)-3-methyl-8-oxo-6,7,8,9-tetrahydro-5-oxa-9-aza-benzocyclohepten-7-yl]-3-hydroxy-butyramide trifluoracetate

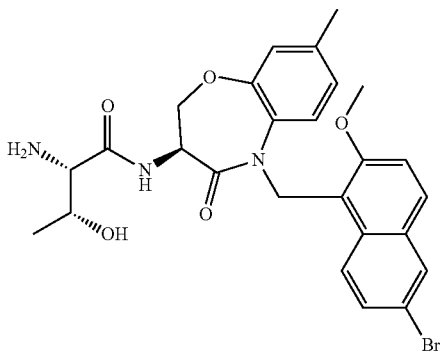 [SMILES: COc1ccc2cc(Br)ccc2c1CN1C(=O)[C@@H](NC(=O)[C@@H](N)[C@@H](C)O)COc2cc(C)ccc21]

Step 1: In a similar manner to that described for Example 36 Step 1 except 4 equivalents of DIEA were used and the mixture was stirred at 0° C. for 2 h, (S)-3-amino-8-methyl-2,3-dihydrobenzo[b][1,4]oxazepin-4(5H)-one trifluoroacetate (0.50 g, 1.63 mmol) and (2S,3R)-2-(tert-butoxycarbonylamino)-3-hydroxybutanoic acid (358 mg, 1.63 mmol) were converted to tert-butyl (2S,3R)-3-hydroxy-1-((S)-8-methyl-4-oxo-2,3,4,5-tetrahydrobenzo[b][1,4]oxazepin-3-ylamino)-1-oxobutan-2-ylcarbamate (500 mg, 78%) as a light yellow foam.

Step 2: In a similar manner to that described for Example 36 Step 2 except the mixture was heated at 50° C. for 2 h, tert-butyl (2S,3R)-3-hydroxy-1-((S)-8-methyl-4-oxo-2,3,4,5-tetrahydrobenzo[b][1,4]oxazepin-3-ylamino)-1-oxobutan-2-ylcarbamate (160 mg, 407 µmol, Eq: 1.00) and 6-bromo-1-(chloromethyl)-2-methoxynaphthalene (174 mg, 610 1=01, Eq: 1.50) were converted to tert-butyl (2S,3R)-1-((S)-5-((6-bromo-2-methoxynaphthalen-1-yl)methyl)-8-methyl-4-oxo-2,3,4,5-tetrahydrobenzo[b][1,4]oxazepin-3-ylamino)-3-hydroxy-1-oxobutan-2-ylcarbamate (128 mg, 49%) as white powder.

Step 3: In a similar manner to that described for Example 29 Step 2, tert-butyl (2S,3R)-1-((S)-5-((6-bromo-2-methoxynaphthalen-1-yl)methyl)-8-methyl-4-oxo-2,3,4,5-tetrahydrobenzo[b][1,4]oxazepin-3-ylamino)-3-hydroxy-1-oxobutan-2-ylcarbamate (80 mg, 125 µmol) was converted to the title compound (54 mg, 66%). MS m/z MH⁺ 543.9

Example 38

(2S,3S)-2-Amino-N-[(S)-9-(7-bromo-3-methoxy-naphthalen-2-ylmethyl)-3-methyl-8-oxo-6,7,8,9-tetrahydro-5-oxa-9-azabenzocyclohepten-7-yl]-3-hydroxy-butyramide trifluoroacetate

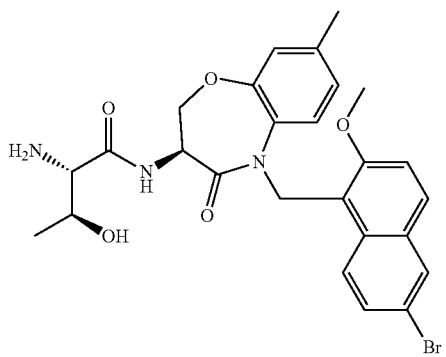 [SMILES: COc1ccc2cc(Br)ccc2c1CN1C(=O)[C@@H](NC(=O)[C@@H](N)[C@H](C)O)COc2cc(C)ccc21]

Step 1: In a similar manner to that described for Example 36 Step 1 except 4 equivalents of DIEA were used and the mixture was stirred at 0° C. for 2 h, (S)-3-amino-8-methyl-2,3-dihydrobenzo[b][1,4]oxazepin-4(5H)-one trifluoroacetate (0.3 g, 980 µmol) and (2S,3S)-2-(tert-butoxycarbonylamino)-3-hydroxybutanoic acid dicyclohexylamine salt (0.39 mg, 980 µmol, Eq: 1.00) were converted to [(1S,2S)-2-hydroxy-1-((S)-3-methyl-8-oxo-6,7,8,9-tetrahydro-5-oxa-9-aza-benzocyclohepten-7-ylcarbamoyl)-propyl]-carbamic acid tert-butyl ester (0.37 g, 99%).

Step 2: In a similar manner to that described for Example 36 Step 2 the mixture was heated at 50° C. for 2 h, [(1S,2S)-2-hydroxy-1-((S)-3-methyl-8-oxo-6,7,8,9-tetrahydro-5-oxa-9-aza-benzocyclohepten-7-ylcarbamoyl)-propyl]-carbamic acid tert-butyl ester (280 mg, 712 µmol) and 6-bromo-1-(chloromethyl)-2-methoxynaphthalene (244 mg, 854 µmol) were converted to {(1S,2S)-1-[(S)-9-(6-bromo-2-methoxy-naphthalen-1-ylmethyl)-3-methyl-8-oxo-6,7,8,9-tetrahydro-5-oxa-9-aza-benzocyclohepten-7-ylcarbamoyl]-2-hydroxy-propyl}-carbamic acid tert-butyl ester (190 mg, 42%).

Step 3: In a similar manner to that described for Example 29 Step 2, {(1S,2S)-1-[(S)-9-(6-bromo-2-methoxy-naphthalen-1-ylmethyl)-3-methyl-8-oxo-6,7,8,9-tetrahydro-5-oxa-9-aza-benzocyclohepten-7-ylcarbamoyl]-2-hydroxy-propyl}-carbamic acid tert-butyl ester (185 mg, 288 µmol) was converted to the title compound (180 mg, 274 µmol). MS m/z MH⁺ 544.1

Example 39

(S)-N-((2S,3S)-5-((6-Bromo-2-methoxynaphthalen-1-yl)methyl)-2,8-dimethyl-4-oxo-2,3,4,5-tetrahydrobenzo[b][1,4]oxazepin-3-yl)-2-(methylamino)propanamide trifluoroacetate

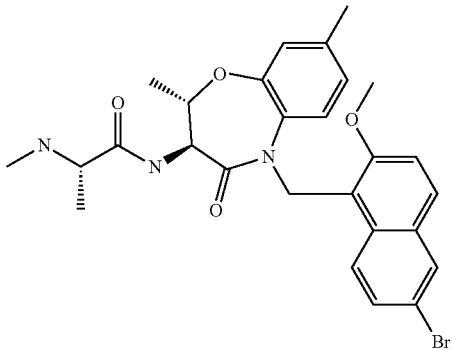 [SMILES: CN[C@@H](C)C(=O)N[C@@H]1C(=O)N(Cc2c(OC)ccc3cc(Br)ccc23)c2ccc(C)cc2O[C@H]1C]

Step 1: In a similar manner to that described for Example 36 Step 1 except 4 equivalents of DIEA were used, (2S,3S)-3-amino-2,8-dimethyl-2,3-dihydrobenzo[b][1,4]oxazepin-4(5H)-one trifluoroacetate (100 mg, 278 μmol) and (S)-2-(tert-butoxycarbonyl(methyl)amino)propanoic acid (56.5 mg, 278 μmol) were converted to tert-butyl (S)-1-((2S,3S)-2,8-dimethyl-4-oxo-2,3,4,5-tetrahydrobenzo[b][1,4]oxazepin-3-ylamino)-1-oxopropan-2-yl(methyl)carbamate (95 mg, 87%).

Step 2: In a similar manner to that described for Example 36 Step 2 the mixture was heated at 60° C. for 1 h and NaI was omitted, tert-butyl (S)-1-((2S,3S)-2,8-dimethyl-4-oxo-2,3,4,5-tetrahydrobenzo[b][1,4]oxazepin-3-ylamino)-1-oxopropan-2-yl(methyl)carbamate (92 mg, 235 μmol) and 6-bromo-1-(chloromethyl)-2-methoxynaphthalene (101 mg, 352 μmol) were converted to tert-butyl (S)-1-((2S,3S)-5-((6-bromo-2-methoxynaphthalen-1-yl)methyl)-2,8-dimethyl-4-oxo-2,3,4,5-tetrahydrobenzo[b][1,4]oxazepin-3-ylamino)-1-oxopropan-2-yl(methyl)carbamate (89 mg, 59%).

Step 3: In a similar manner to that described for Example 29 Step 2 except the product was not triturated, tert-butyl (S)-1-((2S,3S)-5-((6-bromo-2-methoxynaphthalen-1-yl)methyl)-2,8-dimethyl-4-oxo-2,3,4,5-tetrahydrobenzo[b][1,4]oxazepin-3-ylamino)-1-oxopropan-2-yl(methyl)carbamate (15 mg, 23.4 μmol) was converted to the title compound (12.4 mg, 81%) MS m/z MH+ 542.2

Example 40

Methyl 5-(((2S,3S)-2,8-dimethyl-3-((S)-2-(methylamino)propanamido)-4-oxo-3,4-dihydrobenzo[b][1,4]oxazepin-5(2H)-yl)methyl)-6-methoxy-2-naphthoate trifluoroacetate

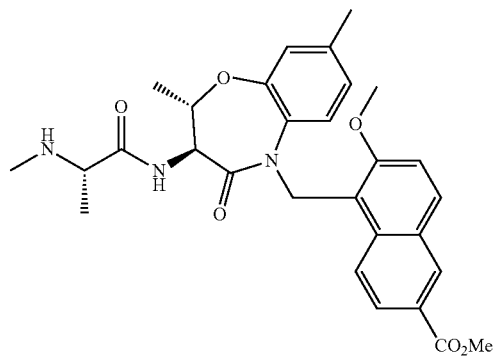 [SMILES: CN[C@@H](C)C(=O)N[C@@H]1C(=O)N(Cc2c(OC)ccc3cc(C(=O)OC)ccc23)c2ccc(C)cc2O[C@H]1C]

Step 1: A mixture of tert-butyl (S)-1-((2S,3S)-5-((6-bromo-2-methoxynaphthalen-1-yl)methyl)-2,8-dimethyl-4-oxo-2,3,4,5-tetrahydrobenzo[b][1,4]oxazepin-3-ylamino)-1-oxopropan-2-yl(methyl)carbamate (70 mg, 109 μmol, Eq: 1.00), Pd(OAc)$_2$ (2.45 mg, 10.9 μmol, Eq: 0.1), Xantphos (12.6 mg, 21.9 μmol, Eq: 0.2), MeOH (35.0 mg, 44.2 μl, 1.09 mmol, Eq: 10), and TEA in a microwave tube was purged with CO and heated at 70° C. under CO overnight. The mixture was diluted with EtOAc, water, brine, dried over Na$_2$SO$_4$ and concentrated. The residue was purified by silica gel chromatography to afford methyl 5-(((2S,3S)-3-((S)-2-(tert-butoxycarbonyl(methyl)amino)propanamido)-2,8-dimethyl-4-oxo-3,4-dihydrobenzo[b][1,4]oxazepin-5(2H)-yl)methyl)-6-methoxy-2-naphthoate (43 mg, 63%)

Step 2: In a similar manner to that described for Example 29 Step 2, methyl 5-(((2S,3S)-3-((S)-2-(tert-butoxycarbonyl(methyl)amino)propanamido)-2,8-dimethyl-4-oxo-3,4-dihydrobenzo[b][1,4]oxazepin-5(2H)-yl)methyl)-6-methoxy-2-naphthoate (41 mg, 66.2 gmol) was converted to the title compound (35 mg, 83%). MS m/z MH+ 520.2

Example 41

(2S,3S)-2-Amino-N-[(6S,7S)-9-(6-bromo-2-methoxy-naphthalen-1-ylmethyl)-3,6-dimethyl-8-oxo-6,7,8,9-tetrahydro-5-oxa-9-aza-benzocyclohepten-7-yl]-3-hydroxy-butyramide trifluoroacetate

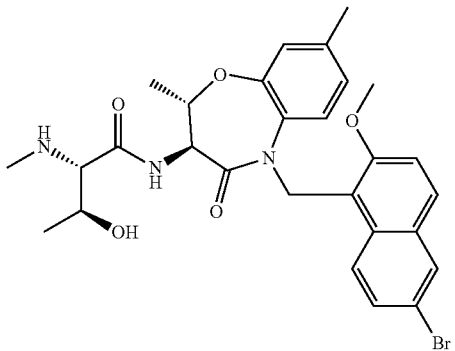 [SMILES: CN[C@H](C(=O)N[C@@H]1C(=O)N(Cc2c(OC)ccc3cc(Br)ccc23)c2ccc(C)cc2O[C@H]1C)[C@H](C)O]

Step 1: In a similar manner to that described for Example 36 Step 1 except 4 equivalents of DIEA were used and the mixture was stirred at 0° C. for 2 h, (2S,3S)-3-amino-2,8-dimethyl-2,3-dihydrobenzo[b][1,4]oxazepin-4(5H)-one trifluoroacetate (75 mg, 208 μmol) and (2S,3S)-2-(tert-butoxycarbonylamino)-3-hydroxybutanoic acid dicyclohexylamine salt (83.4 mg, 208 μmol, Eq: 1.00) were converted to tert-butyl (2S,3S)-1-((2S,3S)-2,8-dimethyl-4-oxo-2,3,4,5-tetrahydrobenzo[b][1,4]oxazepin-3-ylamino)-3-hydroxy-1-oxobutan-2-ylcarbamate (72 mg, 85%).

Step 2: In a similar manner to that described for Example 36 Step 2 except the mixture was heated at 60° C. for 2 h and NaI was omitted, tert-butyl (2S,3S)-1-((2S,3S)-2,8-dimethyl-4-oxo-2,3,4,5-tetrahydrobenzo[b][1,4]oxazepin-3-ylamino)-3-hydroxy-1-oxobutan-2-ylcarbamate (70 mg, 172 μmol, Eq: 1.00) and 6-bromo-1-(chloromethyl)-2-methoxynaphthalene (73.6 mg, 258 μmol, Eq: 1.50) were converted to tert-butyl (2S,3S)-1-((2S,3S)-5-((6-bromo-2-methoxynaphthalen-1-yl)methyl)-2,8-dimethyl-4-oxo-2,3,4,5-tetrahydrobenzo[b][1,4]oxazepin-3-ylamino)-3-hydroxy-1-oxobutan-2-ylcarbamate (3.5 mg, 3%).

Step 3: In a similar manner to that described for Example 29 Step 2 except the product was not triturated, tert-butyl (2S,3S)-1-((2S,3S)-5-((6-bromo-2-methoxynaphthalen-1-yl)methyl)-2,8-dimethyl-4-oxo-2,3,4,5-tetrahydrobenzo[b][1,4]oxazepin-3-ylamino)-3-hydroxy-1-oxobutan-2-ylcarbamate (3.5 mg, 5.33 μmol) was converted to the title compound (3.1 mg, 86%). MS m/z MH+ 558.1

Example 42

(S)-N-((S)-5-((6-Bromo-2-methoxynaphthalen-1-yl)methyl)-4-oxo-7-(trifluoromethyl)-2,3,4,5-tetrahydrobenzo[b][1,4]oxazepin-3-yl)-2-(methylamino)propanamide trifluoroacetate

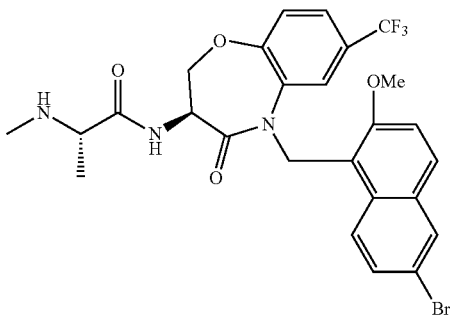 [SMILES: CN[C@@H](C)C(=O)N[C@H]1COc2ccc(C(F)(F)F)cc2N(Cc2c(OC)ccc3cc(Br)ccc23)C1=O]

Step 1: In a similar manner to that described for Example 36 Step 1 except 6 equivalents of DIEA were used, the mixture was stirred at 0° C. for 30 min. and the product was used without purification, (S)-3-amino-8-trifluormethyl-2,3-dihydrobenzo[b][1,4]oxazepin-4(5H)-one trifluoroacetate (0.70 g, 1.97 mmol, Eq: 1.00) and (S)-2-(tert-butoxycarbonyl(methyl)amino)propanoic acid (0.40 g, 1.97 mmol, Eq: 1.00) was converted to tert-butyl methyl((S)-1-oxo-1-((S)-4-oxo-7-(trifluoromethyl)-2,3,4,5-tetrahydrobenzo[b][1,4]oxazepin-3-ylamino)propan-2-yl)carbamate (0.90 g).

Step 2: In a similar manner to that described for Example 36 Step 2 except 1 equivalent of Cs$_2$CO$_3$ was used, tert-butyl methyl ((S)-1-oxo-1-((S)-4-oxo-7-(trifluoromethyl)-2,3,4,5-tetrahydrobenzo[b][1,4]oxazepin-3-ylamino)propan-2-yl)carbamate (863 mg, 2 mmol) and 6-bromo-1-(chloromethyl)-2-methoxynaphthalene (571 mg, 2.00 mmol) were converted to tert-butyl (S)-1-((S)-5-((6-bromo-2-methoxynaphthalen-1-yl)methyl)-4-oxo-7-(trifluoromethyl)-2,3,4,5-tetrahydrobenzo[b][1,4]oxazepin-3-ylamino)-1-oxopropan-2-yl(methyl)carbamate (0.51 g, 38%) as a yellow foam.

Step 3: In a similar manner to that described for Example 29 Step 2, tert-butyl (S)-1-((S)-5-((6-bromo-2-methoxynaphthalen-1-yl)methyl)-4-oxo-7-(trifluoromethyl)-2,3,4,5-tetrahydrobenzo[b][1,4]oxazepin-3-ylamino)-1-oxopropan-2-yl(methyl)carbamate (0.50 g, 735 μmol) was converted to the title compound (245 mg, 48%). MS m/z MH$^+$ 582.0

Example 43

(S)-N-[(6S,7S)-9-(6-Bromo-2-methoxy-naphthalen-1-ylmethyl)-6-methyl-8-oxo-2-trifluoromethyl-6,7,8,9-tetrahydro-5-oxa-9-aza-benzocyclohepten-7-yl]-2-methylamino-propionamide trifluoroacetate

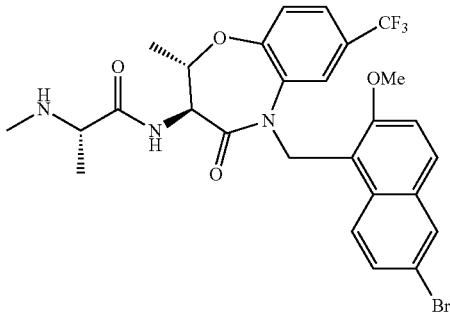 [SMILES: CN[C@@H](C)C(=O)N[C@@H]1C(=O)N(Cc2c(OC)ccc3cc(Br)ccc23)c2cc(C(F)(F)F)ccc2O[C@H]1C]

Step 1: In a similar manner to that described for Example 36 Step 1 except 4 equivalents of DIEA were used, (2S,3S)-3-amino-2-methyl-7-(trifluoromethyl)-2,3-dihydrobenzo[b][1,4]oxazepin-4(5H)-one trifluoroacetate (58 mg, 0.155 mmol) and (S)-2-(tert-butoxycarbonyl(methyl)amino)propanoic acid (31.5 mg, 155 μmol) were converted to a material which was purified by silica gel chromatography to afford methyl-[(S)-1-(((6S,7S)-6-methyl-8-oxo-2-trifluoromethyl-6,7,8,9-tetrahydro-5-oxa-9-aza-benzocyclohepten-7-ylcarbamoyl)-ethyl]-carbamic acid tert-butyl ester (52 mg, 75%)

Step 2: In a similar manner to that described for Example 36 Step 2 except 2 equivalents of Cs$_2$CO$_3$ was used and the mixture was heated at 50° C. for 2 h, methyl-[(S)-1-((6S,7S)-6-methyl-8-oxo-2-trifluoromethyl-6,7,8,9-tetrahydro-5-oxa-9-aza-benzocyclohepten-7-ylcarbamoyl)-ethyl]-carbamic acid tert-butyl ester (52 mg, 0.117 mmol) and 6-bromo-1-(chloromethyl)-2-methoxynaphthalene (66.7 mg, 0.233 mmol) were converted to tert-butyl (S)-1-((2S,3S)-5-((6-bromo-2-methoxynaphthalen-1-yl)methyl)-2-methyl-4-oxo-7-(trifluoromethyl)-2,3,4,5-tetrahydrobenzo[b][1,4]oxazepin-3-ylamino)-1-oxopropan-2-yl(methyl)carbamate (72 mg, 88%).

Step 3: In a similar manner to that described for Example 29 Step 2, tert-butyl (S)-1-((2S,3S)-5-((6-bromo-2-methoxynaphthalen-1-yl)methyl)-2-methyl-4-oxo-7-(trifluoromethyl)-2,3,4,5-tetrahydrobenzo[b][1,4]oxazepin-3-ylamino)-1-oxopropan-2-yl(methyl)carbamate (70 mg, 101 μmol) was converted to the title compound (55 mg, 77%). MS m/z MH$^+$ 596.2

Example 44

(S)-2-Methylamino-N-[(S)-9-((2-methyl-naphthalen-1-ylmethyl)-8-oxo-6,7,8,9-tetrahydro-5-oxa-9-aza-benzocyclohepten-7-yl]-propionamide

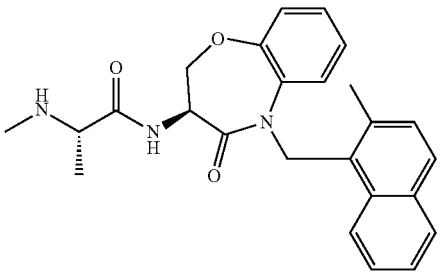 [SMILES: CN[C@@H](C)C(=O)N[C@H]1COc2ccccc2N(Cc2c(C)ccc3ccccc23)C1=O]

Step 1: 1 M lithium bis(trimethylsilyl) amide in THF (3.07 mL, 1 eq) was added to a solution of ((S)-8-oxo-6,7,8,9-tetrahydro-5-oxa-9-aza-benzocyclohepten-7-yl)-carbamic acid-t-butyl ester (855 mg, 3.07 mmol, 1.0 eq) in THF (10 mL) at −78° C. After 30 min. 1-(chloromethyl)-2-methyl-naphthalene (586 mg, 3.07 mmol, 1 eq) and NaI (461 mg, 3.07 mmol, 1 eq) were added and the mixture warmed to RT over 2 h. The solvent was removed and the residue was suspened in EtOAc and washed with H$_2$O. The aqueous extracts were extracted with EtOAc and the combined organic layers were dried over Na$_2$SO$_4$, filtered and concentrated. The residue was purified by silica chromatography to afford (S)-tert-butyl 5-((2-methylnaphthalen-1-yl)methyl)-4-oxo-2,3,4,5-tetrahydrobenzo[b][1,4]oxazepin-3-ylcarbamate (1.01 g, 75%) as a yellow foam.

Step 2: TFA (7.68 g, 67.3 mmol, Eq: 28.8) was added to a solution of (S)-tert-butyl 5-((2-methylnaphthalen-1-yl)methyl)-4-oxo-2,3,4,5-tetrahydrobenzo[b][1,4]oxazepin-3-ylcarbamate (1.01 g, 2.34 mmol, Eq: 1.00) and the mixture was stirred 2 h and the solvent removed. The residue was treated with sat. $NaHCO_3$ and the aqueous mixture extracted with EtOAc. The combined organic extracts were dried over $Na_2SO_4$, filtered and concentrated. The residue was purified by silica gel chromatography to afford (S)-3-amino-5-((2-methylnaphthalen-1-yl)methyl)-2,3-dihydrobenzo[b][1,4]oxazepin-4(5H)-one (606 mg, 76%) as a white foam.

Step 3: DIEA (146 mg, 1.13 mmol, Eq: 2.50) was added to a mixture of (S)-3-amino-5-((2-methylnaphthalen-1-yl)methyl)-2,3-dihydrobenzo[b][1,4]oxazepin-4 (5H)-one (150 mg, 451 µmol, Eq: 1.00), (S)-2-(methylamino)propanoic acid (46.5 mg, 451 µmol, Eq: 1.00), HBTU (180 mg, 474 µmol, Eq: 1.05) and $HOBT.H_2O$ (64.0 mg, 474 µmol, Eq: 1.05) in DMF. After 2 h at RT the mixture was diluted with EtOAc and washed with $H_2O$, 2% $KHSO_4$, 5% $NaHCO_3$ and 5% brine. The organic mixture was dried over $Na_2SO_4$, filtered and concentrated to give a residue which was combined with a second batch of material prepared following the same procedure. This material was purified by silica gel chromatography to give a substance that was triturated in $Et_2O$/pentane to afford the title compound (51 mg). HRMS: calcd. for $C_{25}H_{27}N_3O_3$ ($MH^+$) 418.2124. found 418.2125.

Example 45

(S)-N-((S)-5-((2-Chlorobenzyl)-4-oxo-2,3,4,5-tetrahydrobenzo[b][1,4]oxazepin-3-yl)-2-(methylamino)propanamide

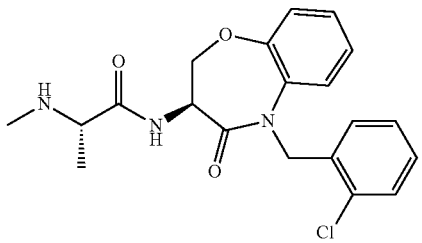 [SMILES: CN[C@@H](C)C(=O)N[C@H]1COc2ccccc2N(Cc2ccccc2Cl)C1=O]

Step 1: $Cs_2CO_3$ (229 mg, 702 µmol, Eq: 1.50) was added to a solution of tert-butyl methyl((S)-1-oxo-1-((S)-4-oxo-2,3,4,5-tetrahydrobenzo[b][1,4]oxazepin-3-ylamino)propan-2-yl)carbamate (170 mg, 468 µmol, Eq: 1.00) and 1-(bromomethyl)-2-chlorobenzene (144 mg, 702 µmol, Eq: 1.50) in DMF and the mixture stirred at RT overnight. The mixture was poured into $H_2O$ and extracted with EtOAc. The combined extracts were dried over $Na_2SO_4$, filtered and concentrated. The residue was purified by silica chromatography to afford tert-butyl (S)-1-((S)-5-((2-chlorobenzyl)-4-oxo-2,3,4,5-tetrahydrobenzo[b][1,4]oxazepin-3-ylamino)-1-oxopropan-2-yl(methyl)carbamate (170 mg, 75%) as a yellow foam.

Step 2: TFA (794 mg, 6.97 mmol, Eq: 20.00) was added to a solution of tert-butyl (S)-1-((S)-5-((2-chlorobenzyl)-4-oxo-2,3,4,5-tetrahydrobenzo[b][1,4]oxazepin-3-ylamino)-1-oxopropan-2-yl(methyl)carbamate (170 mg, 348 µmol, Eq: 1.00) in DCM (1.42 mL) at 0° C. After 30 min. the solvent was removed, the residue slurried in 1/1 mix DCM/5% $NaHCO_3$ and the layers separated. The aqueous layer was extracted with DCM, the combined extracts were dried over $Na_2SO_4$, filtered and concentrated. The residue was purified by silica gel chromatography to give a material which was triturated with $Et_2O$/pentane to afford the title compound (118 mg, 87%) as a pale yellow foam. $^1H$ NMR (DMSO-$d_6$) δ: 8.21 (d, J=7.8 Hz, 1H), 7.47-7.56 (m, 1H), 7.38-7.45 (m, 1H), 7.17-7.36 (m, 6H), 5.30 (d, J=16.8 Hz, 1H), 5.00 (d, J=16.8 Hz, 1H), 4.83 (dt, J=11.1, 8.2 Hz, 1H), 4.33-4.50 (m, 2H), 2.93 (q, J=6.9 Hz, 1H), 2.18 (s, 3H), 2.06 (br. s., 1H), 1.08 (d, J=6.9 Hz, 3H)

Example 46

(S)-N-((S)-5-(3-Chlorobenzyl)-4-oxo-2,3,4,5-tetrahydrobenzo[13,][1,4]oxazepin-3-yl)-2-(methylamino)propanamide

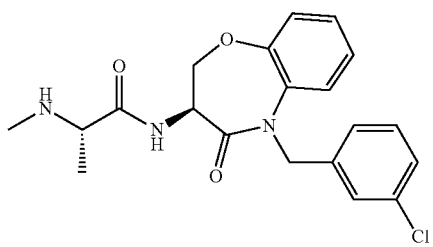 [SMILES: CN[C@@H](C)C(=O)N[C@H]1COc2ccccc2N(Cc2cccc(Cl)c2)C1=O]

In a similar manner to that described for Example 45 except in Step 1 the mixture was stirred at RT for 2 h, tert-butyl methyl((S)-1-oxo-1-((S)-4-oxo-2,3,4,5-tetrahydrobenzo[b][1,4]oxazepin-3-ylamino)propan-2-yl)carbamate (175 mg, 482 µmol) and 1-(bromomethyl)-3-chlorobenzene (104 mg, 506 µmol) were converted to the title compound (125 mg) as an off-white foam. HRMS: calcd. for $C_{20}H_{22}N_3O_3Cl$: ($MH^+$) 388.1421. found 388.1423.

Example 47

(S)-N-((S)-5-(4-Chlorobenzyl)-4-oxo-2,3,4,5-tetrahydrobenzo[b][1,4]oxazepin-3-yl)-2-(methylamino)propanamide

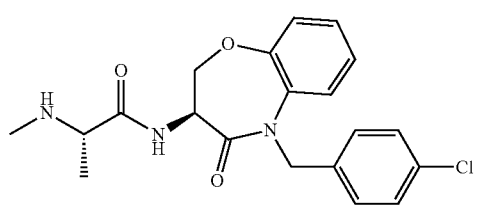 [SMILES: CN[C@@H](C)C(=O)N[C@H]1COc2ccccc2N(Cc2ccc(Cl)cc2)C1=O]

In a similar manner to that described for Example 45 except in Step 2 the material obtained after chromatography was not triturated, tert-butyl methyl((S)-1-oxo-1-((S)-4-oxo-2,3,4,5-tetrahydrobenzo[b][1,4]oxazepin-3-ylamino)propan-2-yl) carbamate (173 mg, 476 iumol) and 1-(bromomethyl)-4-chlorobenzene (103 mg, 500 µmol) were converted to the title compound (113 mg) as an off-white foam. HRMS: calcd. for $C_{20}H_{22}N_3O_3Cl$: ($MH^+$) 388.1422. found 388.1423.

Example 48

(S)-5-((6-bromo-2-methoxynaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate

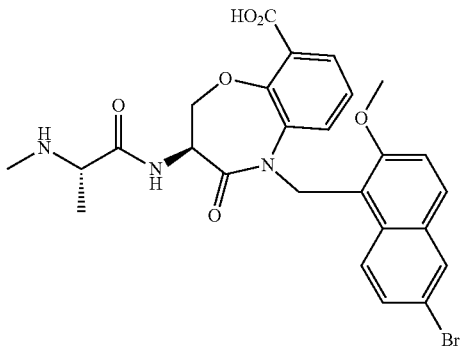 [SMILES: CN[C@@H](C)C(=O)N[C@H]1COc2c(C(=O)O)cccc2N(Cc2c(OC)ccc3cc(Br)ccc23)C1=O]

In a similar manner to that described for Example 45 Step 2, (S)-5-((6-bromo-2-methoxynaphthalen-1-yl)methyl)-3-((S)-2-(tert-butoxycarbonyl(methyl)amino)propanamido)-4-oxo-2,3,4,5-tetrahydrobenzo[b][1,4]oxazepine-9-carboxylic acid (68 mg, 104 μmol) was converted to the title compound (51 mg, 73%) as an off white solid. $^1$H NMR (300 MHz, DMSO-$d_6$) δ ppm 13.09 (br. s., 1 H) 9.08 (d, J=7.8 Hz, 1 H) 8.77 (br.s., 2 H) 8.02-8.09 (m, 2 H) 7.82 (d, J=9.4 Hz, 1 H) 7.77 (d, J=8.2 Hz, 1 H) 7.52 (dd, J=9.1, 2.1 Hz, 1 H) 7.45 (dd, J=7.8, 1.5 Hz, 1 H) 7.36 (d, J=9.1 Hz, 1 H) 7.25 (t, J=8.0 Hz, 1 H) 5.91 (d, J=14.8 Hz, 1 H) 5.26 (d, J=14.8 Hz, 1 H) 4.69-4.86 (m, 1 H) 4.46 (dd, J=9.8, 7.4 Hz, 1 H) 4.20 (dd, J=11.6, 9.8 Hz, 1 H) 3.81-3.95 (m, 1 H) 3.80 (s, 3 H) 2.51 2.53 (m, 3 H) 1.42 (d, J=6.9 Hz, 3 H)

Example 49

(S)-5-((2-Methoxynaphthalen-1-yl)methyl)-34S)-2-(methylamino)propanamido)-4-oxo-2,3,4,5-tetrahydrobenzo[b][1,4]oxazepine-9-carboxylic acid trifluoroacetate

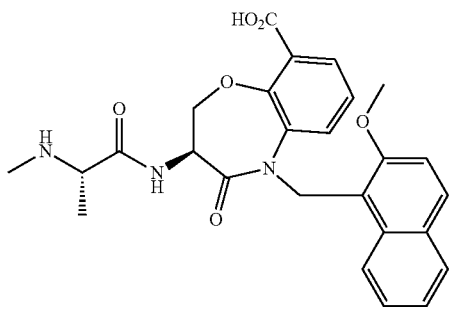 [SMILES: CN[C@@H](C)C(=O)N[C@H]1COc2c(C(=O)O)cccc2N(Cc2c(OC)ccc3ccccc23)C1=O]

Step 1: A mixture of (S)-methyl 5-((6-bromo-2-methoxynaphthalen-1-yl)methyl)-3-((S)-2-(tert-butoxycarbonyl(methyl)amino)propanamido)-4-oxo-2,3,4,5-tetrahydrobenzo[b][1,4]oxazepine-9-carboxylate (100 mg, 149 μmol, Eq: 1.00) and 10% Pd/C (5.22 mg, 4.92 μmol, Eq: 0.033) in MeOH (5 mL) was hydrogenated at RT overnight. The mixture was filtered through Celite and the filtrate concentrated to afford (S)-methyl 3-((S)-2-(tert-butoxycarbonyl(methyl)amino)propanamido)-5-((2-methoxynaphthalen-1-yl)methyl)-4-oxo-2,3,4,5-tetrahydrobenzo[b][1,4]oxazepine-9-carboxylate (95 mg, 97%) as a tan foam.

Step 2: LiOH.H$_2$O (9.1 mg, 217 μmol, Eq: 1.5) and H$_2$O (1 mL) were added to a solution of (S)-methyl 3-((S)-2-(tert-butoxycarbonyl(methyl)amino)propanamido)-5-((2-methoxynaphthalen-1-yl)methyl)-4-oxo-2,3,4,5-tetrahydrobenzo[b][1,4]oxazepine-9-carboxylate (95 mg, 145 μmol, Eq: 1.00) in MeOH (4 mL). The mixture was heated to 50° C. After 2 h, LiOH.H$_2$O (18 mg, 429 μmol, Eq: 2.95) was added and the temperature was increased to 60° C. After 4 h, the mixture was concentrated to a volume of approximately 1.5 mL. This mixture was acidified to pH 2 with 1 N HCl and extracted with EtOAc. The combined extracts were washed with brine, dried over Na$_2$SO$_4$ filtered and concentrated to give a material that was purified by silica gel chromatography to afford (S)-3-((S)-2-(tert-butoxycarbonyl(methyl)amino)propanamido)-5-((2-methoxynaphthalen-1-yl)methyl)-4-oxo-2,3,4,5-tetrahydrobenzo[b][1,4]oxazepine-9-carboxylic acid (31 mg, 37%) as an off-white foam.

Step 3: TFA (1.22 g, 797 μL, 10.7 mmol, Eq: 200.00) was added to a solution of (S)-3-((S)-2-(tert-butoxycarbonyl(methyl)amino)propanamido)-5-((2-methoxynaphthalen-1-yl)methyl)-4-oxo-2,3,4,5-tetrahydrobenzo[b][1,4]oxazepine-9-carboxylic acid (31 mg, 53.7 μmol, Eq: 1.00) in DCM (806 μL) at 0° C. After 45 min. the mixture was concentrated. The residue was dissolved in a minimum of DCM and Et$_2$O was added which resulted in the formation of a white solid. Pentane was added, the supernatant was decanted and the resulting material was dried in vacuo to afford the title compound (29 mg, 91%). $^1$H NMR (300 MHz, DMSO-$d_6$) δ ppm 13.06 (br. s., 1 H) 9.09 (d, J=8.8 Hz, 1 H) 8.75 (br. s., 2 H) 8.10 (d, J=8.8 Hz, 1 H) 7.79 (t, J=8.0 Hz, 3 H) 7.40-7.47 (m, 2 H) 7.16-7.37 (m, 3H) 5.94 (d, J=14.5 Hz, 1 H) 5.28 (d, J=14.5 Hz, 1 H) 4.75 (br. s., 1 H) 4.45 (t, J=8.6 Hz, 1 H) 4.13-4.26 (m, 1 H) 3.82-3.90 (m, 1 H) 3.80 (s, 3 H) 2.51-2.52 (m, 3 H) 1.42 (d, J=6.9 Hz, 3 H)

Example 50

3-{[(S)-9-(6-Bromo-2-methoxy-naphthalen-1-ylmethyl)-74S)-2-methylamino-propionylamino)-8-oxo-6,7,8,9-tetrahydro-5-oxa-9-aza-benzocycloheptene-4-carbonyl]-amino}-propionic acid trifluoroacetate

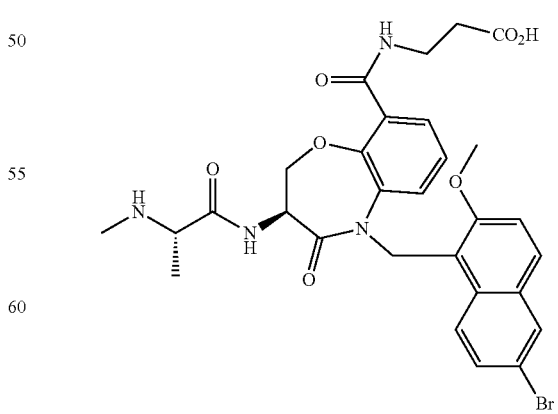

Step 1: DIEA (177 mg, 242 μl, 1.37 mmol, Eq: 5.00) was added to a mixture of (S)-5-((6-bromo-2-methoxynaphthalen-1-yl)methyl)-3-((S)-2-(tert-butoxycarbonyl(methyl)amino)propanamido)-4-oxo-2,3,4,5-tetrahydrobenzo[b][1,4]oxazepine-9-carboxylic acid (180 mg, 274 µmol, Eq: 1.00), tert-butyl 3-aminopropanoate hydrochloride (49.8 mg, 274 µmol, Eq: 1.00), HBTU (104 mg, 274 µmol, Eq: 1.0) and HOBT.H$_2$O (37.0 mg, 274 µmol, Eq: 1.0) in DMF (3.41 mL) at 0° C. and the mixture was warmed to RT. After 45 min. the mixture was diluted with EtOAc, washed with H$_2$O, brine, dried over Na$_2$SO$_4$, filtered and concentrated. The residue was purified by silica gel chromatography to afford 3-({(S)-9-(6-bromo-2-methoxy-naphthalen-1-ylmethyl)-7-[(S)-2-(tert-butoxycarbonyl-methyl-amino)-propionylamino]-8-oxo-6,7,8,9-tetrahydro-5-oxa-9-aza-benzocycloheptene-4-carbonyl}-amino)-propionic acid tert-butyl ester (150 mg, 69%) as an off-white foam.

Step 2: In a similar manner to that described Example 49 step 3, ({(S)-9-(6-bromo-2-methoxy-naphthalen-1-ylmethyl)-7-[(S)-2-(tert-butoxycarbonyl-methyl-amino)-propionylamino]-8-oxo-6,7,8,9-tetrahydro-5-oxa-9-aza-benzocycloheptene-4-carbonyl}-amino)-propionic acid tert-butyl ester (60 mg, 76.6 µmol) was converted to the title compound (54 mg, 95%) as an off white solid. $^1$H NMR (300 MHz, DMSO-d$_6$) δ ppm 12.23 (br. s., 1 H) 9.06 (d, J=6.9 Hz, 1 H) 8.77 (br. s., 2 H) 8.31 (br. s., 1 H) 8.02-8.12 (m, 2 H) 7.82 (d, J=9.4 Hz, 1 H) 7.68 (d, J=7.5 Hz, 1 H) 7.52 (d, J=9.4 Hz, 1 H) 7.37 (d, J=9.1 Hz, 1 H) 7.16-7.32 (m, 2 H) 5.89 (d, J=14.8 Hz, 1 H) 5.26 (d, J=14.8 Hz, 1 H) 4.77 (br. s., 1 H) 4.37-4.50 (m, 1 H) 4.14-4.28 (m, 1 H) 3.83 (br. s., 1 H) 3.79 (s, 3 H) 3.23-3.36 (m, 2 H) 2.41 (t, J=6.8 Hz, 2 H) 1.44 (d, J=6.6 Hz, 3 H)

Example 51

4-({[(S)-9-(6-Bromo-2-methoxy-naphthalen-1-ylmethyl)-7-((S)-2-methylamino-propionylamino)-8-oxo-6,7,8,9-tetrahydro-5-oxa-9-aza-benzocycloheptene-4-carbonyl]-amino}-methyl)-benzoic acid methyl ester

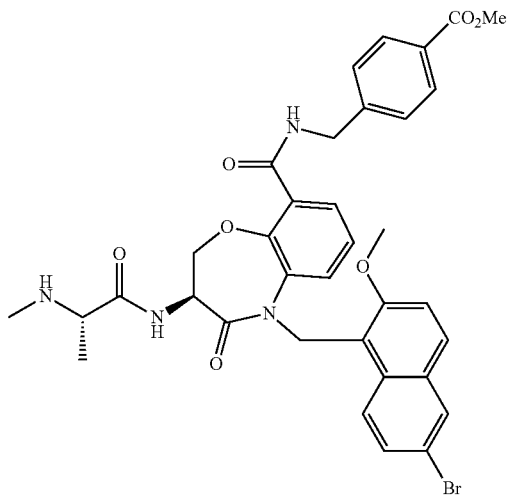 [SMILES: CN[C@@H](C)C(=O)N[C@H]1COc2c(C(=O)NCc3ccc(C(=O)OC)cc3)cccc2N(Cc2c(OC)ccc3cc(Br)ccc23)C1=O]

Step 1: In a similar manner to that described for Example 50 Step 1 except the reaction mixture was stirred 1 h 15 min., (S)-5-(((6-bromo-2-methoxynaphthalen-1-yl)methyl)-3-4S)-2-(tert-butoxycarbonyl(methyl)amino)propanamido)-4-oxo-2,3,4,5-tetrahydrobenzo[b][1,4]oxazepine-9-carboxylic acid (80 mg, 122 µmol) and methyl 4-(aminomethyl)benzoate hydrochloride (25 mg, 122 µmol) were converted to 4-[({(S)-9-(6-bromo-2-methoxy-naphthalen-1-ylmethyl)-7-[(S)-2-(tert-butoxycarbonyl-methyl-amino)-propionylamino]-8-oxo-6,7,8,9-tetrahydro-5-oxa-9-aza-benzocycloheptene-4-carbonyl}-amino)-methyl]-benzoic acid methyl ester (67 mg, 68%) as an off white foam.

Step 2: TFA (340 mg, 222 µl, 2.99 mmol, Eq: 200.00) was added to a solution of 4-[({(S)-9-(6-bromo-2-methoxy-naphthalen-1-ylmethyl)-7-[(S)-2-(tert-butoxycarbonyl-methyl-amino)-propionyl amino]-8-oxo-6,7,8,9-tetrahydro-5-oxa-9-aza-benzocycloheptene-4-carbonyl}-amino)-methyl]-benzoic acid methyl ester (12 mg, 14.9 µmol, Eq: 1.00) in DCM (300 µl) at 0° C. After 1 h the mixture was concentrated and the residue dissolved in DCM. The solution was washed with sat. NaHCO$_3$ and the NaHCO$_3$ solution back extracted with DCM. The combined organic extracts were dried over Na$_2$SO$_4$, filtered and concentrated. The residue was dissolved in a minimum of DCM. Et$_2$O was added followed by pentane which resulted in a precipitate. The supernatant was decanted, the residue was washed with pentane and dried in vacuo to afford the title compound (10 mg, 95%) as a white solid. $^1$H NMR (DMSO-d$_6$) δ: 8.81 (br. s., 1H), 8.22 (d, J=8.2 Hz, 1H), 8.03-8.12 (m, 2H), 7.87 (d, J=8.5 Hz, 2H), 7.79 (d, J=9.1 Hz, 1H), 7.65 (d, J=7.8 Hz, 1H), 7.53 (dd, J=9.2, 2.0 Hz, 1H), 7.32-7.40 (m, 3H), 7.25-7.31 (m, 1H), 7.16-7.25 (m, 1H), 5.87 (d, J=14.8 Hz, 1H), 5.24 (d, J=14.8 Hz, 1H), 4.66-4.82 (m, 1H), 4.13-4.52 (m, 4H), 3.78 (s, 3H), 2.94 (d, J=6.9 Hz, 1H), 2.20 (s, 3H), 1.08 (d, J=6.9 Hz, 3H)

Example 52

(S)-5-((6-Carboxy-2-methoxynaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate

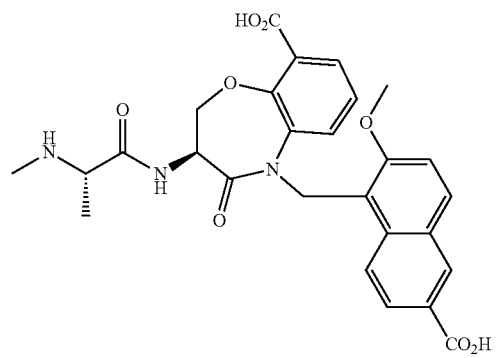 [SMILES: CN[C@@H](C)C(=O)N[C@H]1COc2c(C(=O)O)cccc2N(Cc2c(OC)ccc3cc(C(=O)O)ccc23)C1=O]

Step 1: N$_2$ was bubbled through a mixture of (S)-methyl 5-((6-bromo-2-methoxynaphthalen-1-yl)methyl)-3-(tert-butoxycarbonylamino)-4-oxo-2,3,4,5-tetrahydrobenzo[b][1,4]oxazepine-9-carboxylate (100 mg, 171 µmol, Eq: 1.00), Pd(OAc)$_2$ (1.53 mg, 6.83 µmol, Eq: 0.04), and 4,5-bis(diphenylphosphino)-9,9-dimethylxanthene (7.91 mg, 13.7 µmol, Eq: 0.08), TEA (0.7 mL) and MeOH (82.1 mg, 104 µl, 2.56 mmol, Eq: 15.00) in a microwave tube for 5 min. CO was then bubbled through the mixture for 5 min. and the mixture was heated at 70° C. overnight. The mixture was diluted with EtOAc, then washed with 0.5 N HCl, H₂O and brine. The organic mixture was dried over Na₂SO₄ filtered and concentrated to give a residue that was purified by silica gel chromatography to afford (S)-methyl 3-(tert-butoxycarbonylamino)-5-((2-methoxy-6-(methoxycarbonyl)naphthalen-1-yl)methyl)-4-oxo-2,3,4,5-tetrahydrobenzo[b][1,4]oxazepine-9-carboxylate (90 mg, 90%).

Step 2: In a similar manner to that described Example 49 step 3, (S)-methyl 3-(tert-butoxycarbonylamino)-5-((2-methoxy-6-(methoxycarbonyl)naphthalen-1-yl)methyl)-4-oxo-2,3,4,5-tetrahydrobenzo[b][1,4]oxazepine-9-carboxylate (169 mg, 299 μmol) was converted to (S)-methyl 3-amino-5-((2-methoxy-6-(methoxycarbonyl)naphthalen-1-yl)methyl)-4-oxo-2,3,4,5-tetrahydrobenzo[b][1,4]oxazepine-9-carboxylate trifluoroacetate (173 mg, 99%) which was used without purification.

Step 3: DIEA (193 mg, 264 μl, 1.5 mmol, Eq: 5.00) was added to a mixture of (S)-methyl 3-amino-5-((2-methoxy-6-(methoxyc arbonyl)naphthalen-1-yl)methyl)-4-oxo-2,3,4,5-tetrahydrobenzo[b][1,4]oxazepine-9-carboxylate trifluoroacetate (173 mg, 299 μmol, Eq: 1.00), (S)-2-(tert-butoxycarbonyl(methyl)amino)propanoic acid (60.8 mg, 299 μmol, Eq: 1.0), HBTU (113 mg, 299 μmol, Eq: 1.0) and HOBT.H₂O (40.4 mg, 299 μmol, Eq: 1.0) in, DMF (4 mL) at 0° C. The mixture was warmed to RT, stirred for 1.5 h and diluted with EtOAc. The resulting mixture was washed with H₂O and brine, then dried over Na₂SO₄. The mixture was filtered and concentrated to give a residue that was purified by silica gel chromatography to afford (S)-methyl 3-((S)-2-(tert-butoxycarbonyl(methyl)amino)propanamido)-5-((2-methoxy-6-(methoxycarbonyl)naphthalen-1-yl)methyl)-4-oxo-2,3,4,5-tetrahydrobenzo[b][1,4]oxazepine-9-carboxylate (169 mg, 87%) as a white foam.

Step 4: LiOH.H₂O (22.0 mg, 523 μmol, Eq: 2.00) and H₂O (0.5 mL) was added to a solution of (S)-methyl 3-((S)-2-(tert-butoxycarbonyl(methyl)amino)propanamido)-5-((2-methoxy-6-(methoxycarbonyl)naphthalen-1-yl)methyl)-4-oxo-2,3,4,5-tetrahydrobenzo[b][1,4]oxazepine-9-carboxylate (170 mg, 262 μmol, Eq: 1.00) in MeOH (5 mL). The mixture was heated to 50° C. After 3.5 h, LiOH.H₂O (44 mg, 1.04 mmol) was added and temperature increased to 60° C. After 1.5 h, the MeOH was removed under vacuum, the aqueous mixture diluted with water and extracted with Et₂O. The aqueous mixture was acidified to pH 2.0 with 1 N HCl and extracted with EtOAc. The combined organic extracts were washed brine and concentrated to give a residue that was triturated with Et₂O to afford (S)-3-((S)-2-(tert-butoxycarbonyl(methyl)amino)propanamido)-5-((6-carboxy-2-methoxynaphthalen-1-yl)methyl)-4-oxo-2,3,4,5-tetrahydrobenzo[b][1,4]oxazepine-9-carboxylic acid (47 mg) as a white solid.

Step 5: In a similar manner to that described for Example 49 step 3, (S)-3-((S)-2-(tert-butoxycarbonyl(methyl)amino)propanamido)-5-((6-carboxy-2-methoxynaphthalen-1-yl)methyl)-4-oxo-2,3,4,5-tetrahydrobenzo[b][1,4]oxazepine-9-carboxylic acid (47 mg, 75.6 gmol) was converted to the title compound (48 mg, 99%) as an off white solid. MS m/z 522.4 (MH⁺)

Example 53

5-(((S)-9-((2-Hydroxyethyl)(methyl)carbamoyl)-3-((S)-2-(methylamino)propanamido)-4-oxo-3,4-dihydrobenzo[b][1,4]oxazepin-5(2H)-yl)methyl)-6-methoxy-2-naphthoic acid trifluoroacetate

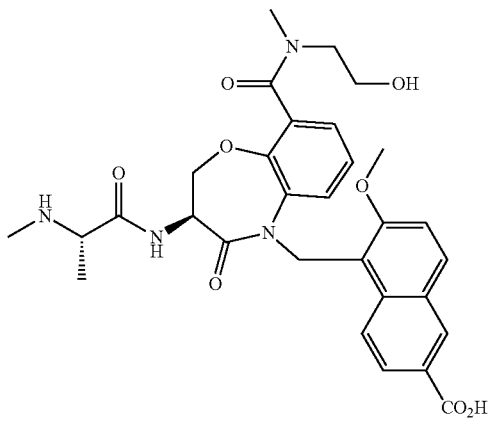 [SMILES: CN[C@@H](C)C(=O)N[C@H]1COc2c(C(=O)N(C)CCO)cccc2N(Cc2c(OC)ccc3cc(C(=O)O)ccc23)C1=O]

Step 1: A 0.1 M aqueous solution of LiOH.H₂O (5.98 mL, 598 μmol, Eq: 1.00) was added to a solution of (S)-methyl 5-((6-bromo-2-methoxynaphthalen-1-yl)methyl)-3-(tert-butoxycarbonylamino)-4-oxo-2,3,4,5-tetrahydrobenzo[b][1,4]oxazepine-9-carboxylate (0.35 g, 598 μmol, Eq: 1.00) in MeOH (20 mL) and the mixture was warmed to 45-50° C. After 7 h, the MeOH was removed in vacuo and the mixture diluted with sat. NaHCO₃ then extracted with EtOAc. The aqueous mixture was cooled to 0° C., acidifed to pH 3.0 with 3 N HCl and extracted with EtOAc. The combined organic extracts were washed with brine and concentrated a to give a material that was purified by silica gel chromatography to afford (S)-5-((6-bromo-2-methoxynaphthalen-1-yl)methyl)-3-(tert-butoxycarbonylamino)-4-oxo-2,3,4,5-tetrahydrobenzo[b][1,4]oxazepine-9-carboxylic acid (310 mg, 90%) as a white foam.

Step 2: In a similar manner to that described for Example 50 Step 1, (S)-5-((6-bromo-2-methoxynaphthalen-1-yl)methyl)-3-(tert-butoxycarbonylamino)-4-oxo-2,3,4,5-tetrahydrobenzo[b][1,4]oxazepine-9-carboxylic acid (150 mg, 263 μmol, Eq: 1.00) and 2-(methylamino)ethanol (21.7 mg, 289 μmol, Eq: 1.1) were converted to (S)-tert-butyl 5-((6-bromo-2-methoxynaphthalen-1-yl)methyl)-9-((2-hydroxyethyl)(methyl)carbamoyl)-4-oxo-2,3,4,5-tetrahydrobenzo[b][1,4]oxazepin-3-ylcarbamate (128 mg) as a white foam.

Step 3: In a similar manner to that described for Example 52 Step 1, (S)-tert-butyl 5-((6-bromo-2-methoxynaphthalen-1-yl)methyl)-9-((2-hydroxyethyl)(methyl)carbamoyl)-4-oxo-2,3,4,5-tetrahydrobenzo[b][1,4]oxazepin-3-ylcarbamate (123 mg, 196 μmol, Eq: 1.00), Pd(OAc)₂ (2.42 mg, 10.8 μmol, Eq: 0.055), and 4,5-bis(diphenylphosphino)-9,9-dimethylxanthene (9.06 mg, 15.7 μmol, Eq: 0.08), TEA (896 μl) and MeOH (94.1 mg, 119 μl, 2.94 mmol, Eq: 15.00) were reacted to give a material that was purified by silica gel chromatography to afford (S)-methyl 5-((3-(tert-butoxycarbonyl amino)-9-((2-hydroxyethyl)(methyl)carbamoyl)-4-oxo-3,4-dihydrobenzo[b][1,4]oxazepin-5(2H)-yl)methyl)-6-methoxy-2-naphthoate (103 mg, 87%) as an off white foam.

Step 4: In a similar manner to that described for Example 49 step 3, (S)-methyl 5-((3-(tert-butoxycarbonylamino)-9-((2-hydroxyethyl)(methyl)carbamoyl)-4-oxo-3,4-dihydrobenzo[b][1,4]oxazepin-5(2H)-yl)methyl)-6-methoxy-2-naphthoate (103 mg, 170 iumol) was converted to (S)-methyl 5-((3-amino-9-((2-hydroxyethyl)(methyl)carbamoyl)-4-oxo-3,4-dihydrobenzo[b][1,4]oxazepin-5(2H)-yl)methyl)-6-methoxy-2-naphthoate trifluoroacetate (104 mg, 98%) as an off white solid.

Step 5: In a similar manner to that described for the preparation of (S)-methyl 5-(((6-bromo-2-methoxynaphthalen-1-yl)methyl)-3-((S)-2-(tert-butoxycarbonyl(methyl)amino)propanamido)-4-oxo-2,3,4,5-tetrahydrobenzo[b][1,4]oxazepine-9-carboxylate Step 1, (S)-methyl 5-((3-amino-9-((2-hydroxyethyl)(methyl)carbamoyl)-4-oxo-3,4-dihydrobenzo[b][1,4]oxazepin-5(2H)-yl)methyl)-6-methoxy-2-naphthoate trifluoroacetate (104 mg, 167 µmol, Eq: 1.00) and (S)-2-(tert-butoxycarbonyl(methyl)amino)propanoic acid (34.0 mg, 167 µmol, Eq: 1.0) were converted to methyl 5-(((S)-3-((S)-2-(tert-butoxycarbonyl(methyl)amino)propanamido)-9-((2-hydroxyethyl)(methyl)carbamoyl)-4-oxo-3,4-dihydrobenzo[b][1,4]oxazepin-5(2H)-yl)methyl)-6-methoxy-2-naphthoate (59 mg, 50%)

Step 6: LiOH.H$_2$O (7.15 mg, 170 µmol, Eq: 2.00) and H$_2$O (200 µl) were added to a solution of methyl 5-(((S)-3-((S)-2-(tert-butoxycarbonyl(methyl)amino)propanamido)-9-((2-hydroxyethyl)(methyl)carbamoyl)-4-oxo-3,4-dihydrobenzo[b][1,4]oxazepin-5(2H)-yl)methyl)-6-methoxy-2-naphthoate (59 mg, 85.2 µmol, Eq: 1.00) in MeOH (2 mL) and the mixture heated to 50° C. After 4 h an additional portion of LiOH.H$_2$O (2 mg, 48 µmol, Eq. 0.65) was added. After 1 h the mixture was diluted with sat. NaHCO$_3$ and extracted with Et$_2$O. The aqueous mixture was acidified to pH 2.0 with 1 N HCl, extracted with EtOAc and the combined organic extracts were washed with brine, dried over Na$_2$SO$_4$ and concentrated to afford 5-(((S)-3-((S)-2-(tert-butoxycarbonyl(methyl)amino)propanamido)-9-((2-hydroxyethyl)(methyl)carbamoyl)-4-oxo-3,4-dihydrobenzo[b][1,4]oxazepin-5(2H)-yl)methyl)-6-methoxy-2-naphthoic acid (43 mg, 74%) which was used without purification.

Step 7: In a similar manner to that described for Example 49 step 3, 5-(((S)-3-((S)-2-(tert-butoxycarbonyl(methyl)amino)propanamido)-9-((2-hydroxyethyl)(methyl)carbamoyl)-4-oxo-3,4-dihydrobenzo[b][1,4]oxazepin-5(2H)-yl)methyl)-6-methoxy-2-naphthoic acid (43 mg, 63.4 µmol) was converted to the title compound (40 mg, 91%) as a white solid. $^1$H NMR (MeOH-d$_4$) δ: 8.41 (d, J=8.5 Hz, 1H), 8.01-8.11 (m, 2H), 7.91-8.00 (m, 1H), 7.79-7.90 (m, 1H), 7.53 (d, J=7.5 Hz, 2H), 7.30 (d, J=9.1 Hz, 1H), 7.11 (d, J=7.2 Hz, 1H), 6.96 (d, J=7.2 Hz, 1H), 6.02 (d, J=14.2 Hz, 1H), 5.39 (d, J=14.8 Hz, 1H), 4.28 (d, J=11.2 Hz, 2H), 3.95 (s, 5H), 2.95 (s, 2H), 2.64 (s, 3H), 1.61 (d, J=6.3 Hz, 3H)

Example 54

(S)-5-((4-Bromonaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate

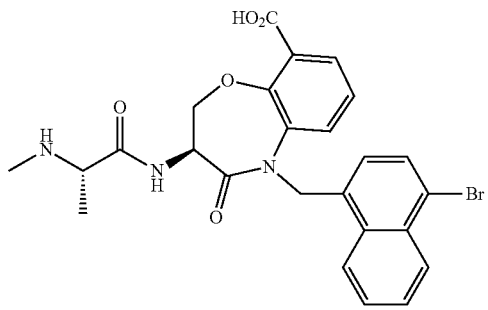 [SMILES: CN[C@@H](C)C(=O)N[C@H]1COc2c(C(=O)O)cccc2N(Cc2ccc(Br)c3ccccc23)C1=O]

In a similar manner to that described for Example 49 step 3, (S)-5-((4-bromonaphthalen-1-yl)methyl)-3-((S)-2-(tert-bu-toxycarbonyl(methyl)amino)propanamido)-4-oxo-2,3,4,5-tetrahydrobenzo[b][1,4]oxazepine-9-carboxylic acid (25 mg, 39.9 µmol) was converted to the title compound (21 mg, 82%). MS m/z 527.4 (MH$^+$)

Example 55

(S)-N-((S)-5-((4-Bromonaphthalen-1-yl)methyl)-9-(4-(2-hydroxyethyl)piperazine-1-carbonyl)-4-oxo-2,3,4,5-tetrahydrobenzo[b][1,4]oxazepin-3-yl)-2-(methylamino)propanamide

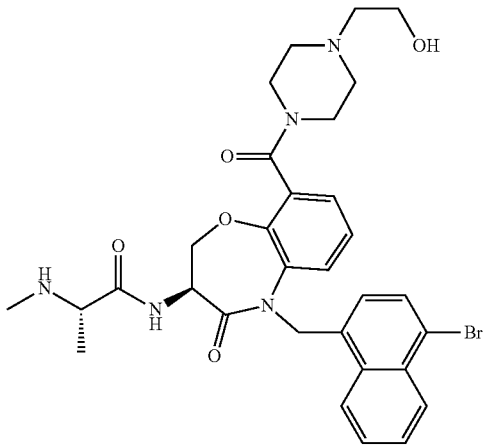 [SMILES: CN[C@@H](C)C(=O)N[C@H]1COc2c(C(=O)N3CCN(CCO)CC3)cccc2N(Cc2ccc(Br)c3ccccc23)C1=O]

Step 1: In a similar manner to that described for Example 50 Step 1 except the material was not purified, (S)-5-((4-bromonaphthalen-1-yl)methyl)-3-((S)-2-(tert-butoxycarbonyl(methyl)amino)propanamido)-4-oxo-2,3,4,5-tetrahydrobenzo[b][1,4]oxazepine-9-carboxylic acid (130 mg, 208 µmol, Eq: 1.00) and 2-(piperazin-1-yl)ethanol (27 mg, 208 µmol, Eq: 1 were converted to tert-butyl (S)-1-((S)-5-((4-bromonaphthalen-1-yl)methyl)-9-(4-(2-hydroxyethyl)piperazine-1-carbonyl)-4-oxo-2,3,4,5-tetrahydrobenzo[b][1,4]oxazepin-3-ylamino)-1-oxopropan-2-yl(methyl)carbamate (130 mg, 86%) obtained as a white foam.

Step 2: In a similar manner to that described for Example 51 Step 2, tert-butyl (S)-1-((S)-5-((4-bromonaphthalen-1-yl)methyl)-9-(4-(2-hydroxyethyl)piperazine-1-carbonyl)-4-oxo-2,3,4,5-tetrahydrobenzo[b][1,4]oxazepin-3-ylamino)-1-oxopropan-2-yl(methyl)carbamate (130 mg, 176 µmol) was converted to the title compound (83 mg, 74%) obtained as a white solid. MS m/z 639 (WI)

Example 56

(S)-N-((S)-5-((4-Bromonaphthalen-1-yl)methyl)-9-(4-(3-hydroxypropyl)piperazine-1-carbonyl)-4-oxo-2,3,4,5-tetrahydrobenzo[b][1,4]oxazepin-3-yl)-2-(methylamino)propanamide

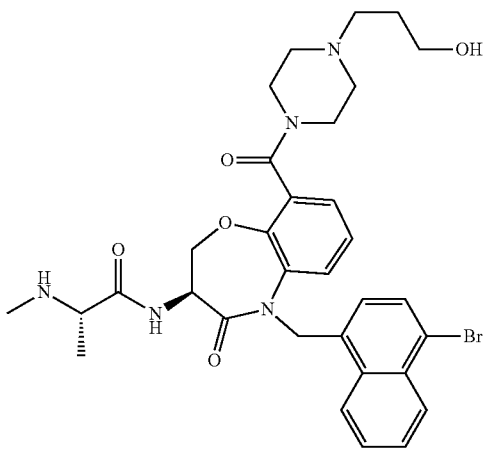 [SMILES: CN[C@@H](C)C(=O)N[C@H]1COc2c(C(=O)N3CCN(CCCO)CC3)cccc2N(Cc2ccc(Br)c3ccccc23)C1=O]

Step 1: In a similar manner to that described for Example 50 Step 1 except the material was not purified, (S)-5-((4-bromonaphthalen-1-yl)methyl)-3-((S)-2-(tert-butoxycarbonyl(methyl)amino)propanamido)-4-oxo-2,3,4,5-tetrahydrobenzo[b][1,4]oxazepine-9-carboxylic acid (70 mg, 112 µmol, Eq: 1.00) and 3-(piperazin-1-yl)propan-1-ol (16.1 mg, 112 µmol, Eq: 1.00) were converted to tert-butyl (S)-1-((S)-5-((4-bromonaphthalen-1-yl)methyl)-9-(4-(3-hydroxypropyl)piperazine-1-carbonyl)-4-oxo-2,3,4,5-tetrahydrobenzo[b][1,4]oxazepin-3-ylamino)-1-oxopropan-2-yl(methyl)carbamate (79 mg, 94%) obtained as a white foam.

Step 2: In a similar manner to that described for Example 51 step 2, tert-butyl (S)-1-((S)-5-((4-bromonaphthalen-1-yl)methyl)-9-(4-(3-hydroxypropyl)piperazine-1-carbonyl)-4-oxo-2,3,4,5-tetrahydrobenzo[b][1,4]oxazepin-3-ylamino)-1-oxopropan-2-yl(methyl)carbamate (79 mg, 105 µmol) was converted to the title compound (50 mg, 73%) obtained as a white solid. MS m/z 653 (MH$^+$)

Example 57

(S)-N-((S)-5-((2-Chloro-1-(2-cyanophenyl)-1H-indol-3-yl)methyl)-4-oxo-2,3,4,5-tetrahydrobenzo[b][1,4]oxazepin-3-yl)-2-(methylamino)propanamide

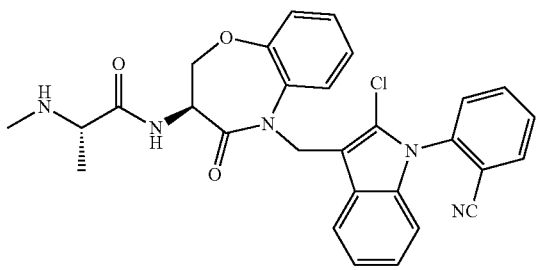 [SMILES: CN[C@@H](C)C(=O)N[C@H]1COc2ccccc2N(Cc2c(Cl)n(-c3ccccc3C#N)c3ccccc23)C1=O]

Step 1: Diethyl azodicarboxylate solution 40 wt. % in toluene (DEAD 40% w/w, 360 mg, 377 µl, 828 µmol, Eq: 2) was added to a solution of tert-butyl methyl((S)-1-oxo-1-((S)-4-oxo-2,3,4,5-tetrahydrobenzo[b][1,4]oxazepin-3-ylamino)propan-2-yl)carbamate (226 mg, 621 µmol, Eq: 1.5), 2-(2-chloro-3-(hydroxymethyl)-1H-indol-1-yl)benzonitrile (117 mg, 414 1=01, Eq: 1.00) and Ph$_3$P (217 mg, 828 µmol, Eq: 2) in THF (5 mL) and the mixture was stirred at RT for 2.5 d. The mixture was diluted with MeOH (10 mL), concentrated and the residue purified by preparative TLC to give tert-butyl (S)-1-((S)-5-((2-chloro-1-(2-cyanophenyl)-1H-indol-3-yl)methyl)-4-oxo-2,3,4,5-tetrahydrobenzo[b][1,4]oxazepin-3-ylamino)-1-oxopropan-2-yl(methyl)carbamate (130 mg, 50%) as a yellow solid.

Step 2: TFA (5 mL) was added to a solution of tert-butyl (S)-1-((S)-5-((2-chloro-1-(2-cyanophenyl)-1H-indol-3-yl)methyl)-4-oxo-2,3,4,5-tetrahydrobenzo[b][1,4]oxazepin-3-ylamino)-1-oxopropan-2-yl(methyl)carbamate (130 mg, 207 µmol, Eq: 1.00) in DCM (5 mL). The mixture was stirred at RT for 16 h, then concentrated. Sat. NaHCO$_3$ was added to the residue and the mixture was extracted with DCM. The combined organic extracts were concentrated and the residue purified by preparative TLC to give the title compound (50 mg, 43%) as a white solid. MS m/z 529 (MH$^+$)

Example 58

(S)-N-((S)-5-((1-(2-Cyanophenyl)-1H-indol-4-yl)methyl)-4-oxo-2,3,4,5-tetrahydrobenzo[b][1,4]oxazepin-3-yl)-2-(methylamino)propanamide

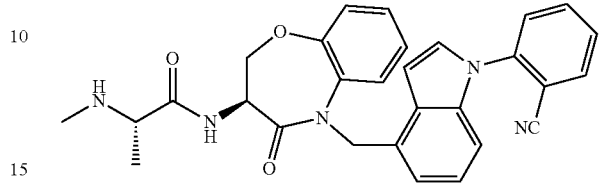

In a similar manner to that described for Example 57 except in Step 1 the mixture was heated at 60° C. for 2.5 d and in Step 2 the material was purified by silica gel chromatography, tert-butyl methyl((S)-1-oxo-1-((S)-4-oxo-2,3,4,5-tetrahydrobenzo[b][1,4]oxazepin-3-ylamino) propan-2-yl)carbamate (250 mg, 688 µmol, Eq: 1.00), 2-(4-(hydroxymethyl)-1H-indol-1-yl)benzonitrile (440 mg, 1.77 mmol, Eq: 2.58) was converted to the title compound (35 mg) as a white solid. MS m/z 494 (MH$^+$)

Example 59

(S)-N-((S)-5-((2-Chloro-1-(phenylsulfonyl)-1H-indol-3-yl)methyl)-4-oxo-2,3,4,5-tetrahydrobenzo[b][1,4]oxazepin-3-yl)-2-(methylamino)propanamide

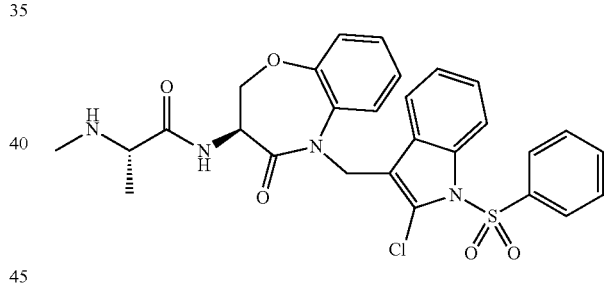

Step 1: DEAD 40% w/w (119 mg, 124 µl, 273 µmol, Eq: 2) was added to a solution of (2-chloro-1-(phenylsulfonyl)-1H-indol-3-yl)methanol (44 mg, 137 µmol, Eq: 1.00), tert-butyl methyl ((S)-1-oxo-1-((S)-4-oxo-2,3,4,5-tetrahydrobenzo[b][1,4]oxazepin-3-ylamino)propan-2-yl)carbamate (99.4 mg, 273 µmol, Eq: 2) and Ph$_3$P (71.7 mg, 273 µmol, Eq: 2) in THF (10.0 mL). After stirring at RT for 12 h, the mixture was diluted with brine and extracted with EtOAc. The combined extracts were dried over MgSO$_4$, filtered and the filtrate was concentrated. The residue was purified by preparative TLC to afford tert-butyl (S)-1-((S)-5-((2-chloro-1-(phenylsulfonyl)-1H-indol-3-yl)methyl)-4-oxo-2,3,4,5-tetrahydrobenzo[b][1,4]oxazepin-3-ylamino)-1-oxopropan-2-yl(methyl)carbamate (36 mg, 36%) as a white solid.

Step 2: In a similar manner to that described for Example 57 Step 2, tert-butyl (S)-1-((S)-5-((2-chloro-1-(phenylsulfonyl)-1H-indol-3-yl)methyl)-4-oxo-2,3,4,5-tetrahydrobenzo[b][1,4]oxazepin-3-ylamino)-1-oxopropan-2-yl(methyl)carbamate (42 mg, 63.0 µmol) was converted to the title compound (32 mg, 89.6%) as a waxy solid. MS m/z 568 (MH$^+$)

Example 60

(S)-N-[(S)-9-(1-Benzenesulfonyl-2-chloro-1H-indol-3-ylmethyl)-8-oxo-6,7,8,9-tetrahydro-5-oxa-9-azabenzocyclohepten-7-yl]-2-methylamino-propionamide hydrochloride

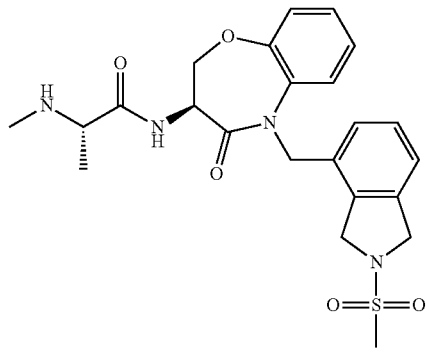 [SMILES: CN[C@@H](C)C(=O)N[C@H]1COc2ccccc2N(Cc2cccc3c2CN(S(C)(=O)=O)C3)C1=O]

Step 1: In a similar manner to that described for Example 57 Step 1 except the mixture was stirred for 16 h, tert-butyl methyl((S)-1-oxo-1-((S)-4-oxo-2,3,4,5-tetrahydrobenzo[b][1,4]oxazepin-3-ylamino)propan-2-yl)carbamate (150 mg, 413 µmol, Eq: 1.00), (2-(methylsulfonyl)isoindolin-4-yl)methanol (250 mg, 1.1 mmol, Eq: 2.66) was converted to t-butyl methyl((S)-1-((S)-5-((2-(methylsulfonyl)isoindolin-4-yl)methyl)-4-oxo-2,3,4,5-tetrahydrobenzo[b][1,4]oxazepin-3-ylamino)-1-oxopropan-2-yl)carbamate (170 mg, 72%).

Step 2: 4 M HCl in dioxane (8.4 g, 7 mL, 28.0 mmol, Eq: 94.3) and t-butyl methyl((S)-1-((S)-5-((2-(methylsulfonyl)isoindolin-4-yl)methyl)-4-oxo-2,3,4,5-tetrahydrobenzo[b][1,4]oxazepin-3-ylamino)-1-oxopropan-2-yl)carbamate (170 mg, 297 µmol, Eq: 1.00) were combined and the mixture stirred at RT. After 16 h the mixture was concentrated and the residue triturated with Et$_2$O to give the title compound (120 mg, 79%). MS m/z 473 (MH$^+$)

Example 61

(S)-N-((S)-5-((6-Fluoro-1-methyl-2-oxo-1,2-dihydroquinolin-4-yl)methyl)-4-oxo-2,3,4,5-tetrahydrobenzo[b][1,4]oxazepin-3-yl)-2-(methylamino)propanamide

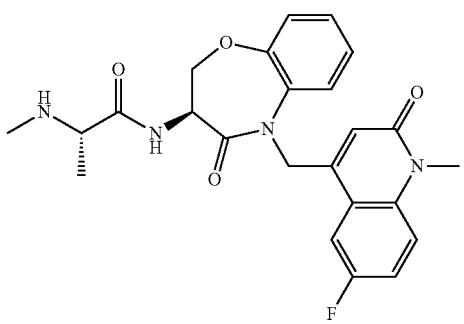

Step 1: In a similar manner to that described for Example 1 Step 1 except the NaI was omitted and the product was purified by preparative TLC, tert-butyl methyl((S)-1-oxo-1-((S)-4-oxo-2,3,4,5-tetrahydrobenzo[b][1,4]oxazepin-3-ylamino)propan-2-yl)carbamate (87.5 mg, 0.241 mmol) and 4-(bromomethyl)-6-fluoro-1-methylquinolin-2(1H)-one (50 mg, 0.185 mmol) were converted to tert-butyl (S)-1-((S)-5-((6-fluoro-1-methyl-2-oxo-1,2-dihydroquinolin-4-yl)methyl)-4-oxo-2,3,4,5-tetrahydrobenzo[b][1,4]oxazepin-3-ylamino)-1-oxopropan-2-yl(methyl)carbamate (40 mg, 40%).

Step 2: A mixture of 3 M HCl in dioxane (36.0 g, 30 mL, 120 mmol, Eq: 1660) and tert-butyl (S)-1-((S)-5-((6-fluoro-1-methyl-2-oxo-1,2-dihydroquinolin-4-yl)methyl)-4-oxo-2,3,4,5-tetrahydrobenzo[b][1,4]oxazepin-3-ylamino)-1-oxopropan-2-yl(methyl)carbamate (40 mg, 72.4 µmol, Eq: 1.00) were stirred at RT overnight. The mixture was diluted with sat. NaHCO$_3$ and extracted with DCM The combined extracts were washed with H$_2$O and concentrated. The residue was purified was purified by preparative TLC to give the title compound (26 mg, 95%) as a white solid. MS m/z 453 (MH$^+$)

Example 62

(S)-N-[(S)-9-(1-Benzyl-2-chloro-1H-indol-3-ylmethyl)-8-oxo-6,7,8,9-tetrahydro-5-oxa-9-aza-benzocyclohepten-7-yl]-2-methyl amino-propionamide

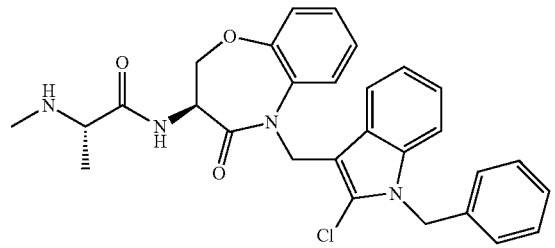 [SMILES: CN[C@@H](C)C(=O)N[C@H]1COc2ccccc2N(Cc2c(Cl)n(Cc3ccccc3)c3ccccc23)C1=O]

In a similar manner to that described for Example 59 Step 1 except 3 eq. each of Ph$_3$P and DEAD were used, (1-benzyl-2-chloro-1H-indol-3-yl)methanol (310 mg, 1.14 mmol, Eq: 3.03) and tert-butyl methyl((S)-1-oxo-1-((S)-4-oxo-2,3,4,5-tetrahydrobenzo[b][1,4]oxazepin-3-ylamino)propan-2-yl)carbamate (137 mg, 377 µmol, Eq: 1.00) were converted to tert-butyl (S)-1-((S)-5-((1-benzyl-2-chloro-1H-indol-3-yl)methyl)-4-oxo-2,3,4,5-tetrahydrobenzo[b][1,4]oxazepin-3-ylamino)-1-oxopropan-2-yl(methyl)carbamate (90 mg, 39%) as a viscous oil.

Step 2: 1 M HCl in Et$_2$O (24.0 g, 20 mL, 20.0 mmol, Eq: 137) was added to tert-butyl (S)-1-((S)-5-((l-benzyl-2-chloro-1H-indol-3-yl)methyl)-4-oxo-2,3,4,5-tetrahydrobenzo[b][1,4]oxazepin-3-ylamino)-1-oxopropan-2-yl(methyl)carbamate (90 mg, 146 µmol, Eq: 1.00) and the mixture was stirred overnight at RT. The precipitate that formed was filtered, washed with ether and dried under vacuum to afford the title compound (8 mg, 12%). MS m/z 517 (MH$^+$)

Example 63

(S)-N-((S)-5-((1-Ethyl-2-oxoindolin-4-yl)methyl)-4-oxo-2,3,4,5-tetrahydrobenzo[b][1,4]oxazepin-3-yl)-2-(methylamino)propanamide

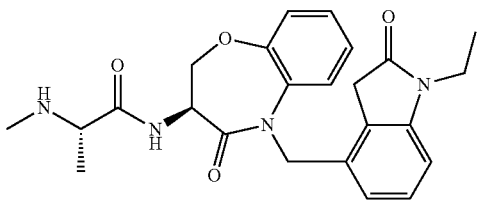 [SMILES: CCN1C(=O)Cc2c(CN3C(=O)[C@@H](NC(=O)[C@H](C)NC)COc4ccccc43)cccc21]

Step 1: DEAD 40% w/w (359 mg, 376 μl, 826 μmol, Eq: 3) was added to a mixture of tert-butyl methyl((S)-1-oxo-1-((S)-4-oxo-2,3,4,5-tetrahydrobenzo[b][1,4]oxazepin-3-ylamino)propan-2-yl)carbamate (100 mg, 275 μmol, Eq: 1.00), (1-ethyl-1H-indol-4-yl)methanol (48.2 mg, 275 μmol, Eq: 1.00) and polymer-bound Ph₃P (500 mg, 275 μmol, Eq: 1.00) in THF (10 mL). After 2.5 d., additional portions of (1-ethyl-1H-indol-4-yl)methanol (48.2 mg, 275 μmol, Eq: 1.00), polymer-bound Ph₃P (1 eq) and DEAD (1 eq), were added. After 1 d, the mixture was filtered and the filter cake washed with MeOH and THF. The filtrate was concentrated and the residue was purified by preparative TLC to afford tert-butyl (S)-1-((S)-5-((1-ethyl-1H-indol-4-yl)methyl)-4-oxo-2,3,4,5-tetrahydrobenzo[b][1,4]oxazepin-3-ylamino)-1-oxopropan-2-yl(methyl)carbamate (73 mg, 51%).

Step 2: A solution of N-chlorosuccinimide (NCS, 17.2 mg, 129 μmol, Eq: 1.00) in DMF (2 mL) was added dropwise to a solution of tert-butyl (S)-1-((S)-5-((1-ethyl-1H-indol-4-yl)methyl)-4-oxo-2,3,4,5-tetrahydrobenzo[b][1,4]oxazepin-3-ylamino)-1-oxopropan-2-yl(methyl)carbamate (67 mg, 129 μmol, Eq: 1.00) in DMF (12 mL) at 0° C. After 2 h at 0° C. the mixture was diluted with sat. NaHCO₃ and extracted with EtOAc. The combined extracts were washed with H₂O, concentrated and the residue was purified by preparative TLC to give tert-butyl (S)-1-((S)-5-((3-chloro-1-ethyl-1H-indol-4-yl)methyl)-4-oxo-2,3,4,5-tetrahydrobenzo[b][1,4]oxazepin-3-ylamino)-1-oxopropan-2-yl(methyl)carbamate (65 mg, 91%).

Step 3: Phosphoric acid (13.2 mg, 2 mL, 108 μmol, Eq: 1.00) was added to tert-butyl (S)-1-((S)-5-((3-chloro-1-ethyl-1H-indol-4-yl)methyl)-4-oxo-2,3,4,5-tetrahydrobenzo[b][1,4]oxazepin-3-ylamino)-1-oxopropan-2-yl(methyl)carbamate (60 mg, 108 μmol, Eq: 1.00) and the mixture stirred at RT for 2 h. The mixture was diluted with sat. NaHCO₃ and extracted with DCM. The combined extracts were concentrated and the residue was purified by preparative TLC to give the title compound (7 mg, 14%) as a solid. MS m/z 437 (MH⁺)

Example 64

(S)-2-Amino-N-((S)-5-((1-(2-cyanophenyl)-1H-indazol-3-yl)methyl)-4-oxo-2,3,4,5-tetrahydrobenzo[b][1,4]oxazepin-3-yl)propanamide

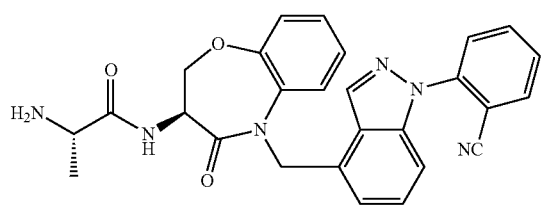 [SMILES: C[C@H](N)C(=O)N[C@H]1COc2ccccc2N(Cc2cccc3c2cnn3-c2ccccc2C#N)C1=O]

Step 1: In a similar manner to that described for Example 1 Step 1 except the NaI was omitted and the product was purified by preparative TLC, (S)-tert-butyl 4-oxo-2,3,4,5-tetrahydrobenzo[b][1,4]oxazepin-3-ylcarbamate (589 mg, 1.8 mmol) and 2-(3-(bromomethyl)-1H-indazol-1-yl)benzonitrile (673 mg, 2.16 mmol) were converted to (S)-tert-butyl 5-((1-(2-cyanophenyl)-1H-indazol-3-yl)methyl)-4-oxo-2,3,4,5-tetrahydrobenzo[b][1,4]oxazepin-3-ylcarbamate (915 mg, 100%)

Step 2: In a similar manner to that described for Example 57 Step 2 except the mixture was stirred at 0° C. for 1 h and the product was purified by silica gel chromatography, (S)-tert-butyl 5-((1-(2-cyanophenyl)-1H-indazol-3-yl)methyl)-4-oxo-2,3,4,5-tetrahydrobenzo[b][1,4]oxazepin-3-ylcarbamate (915 mg, 1.8 mmol) was converted to (S)-2-(3-((3-amino-4-oxo-3,4-dihydrobenzo[b][1,4]oxazepin-5(2H)-yl)methyl)-1H-indazol-1-yl)benzonitrile (650 mg, 88%).

Step 3: (Benzotriazol-1-yloxy)tris(dimethylamino)phosphonium hexafluorophosphate (BOP, 486 mg, 1.1 mmol, Eq: 1.5) was added to a mixture of (S)-2-(3-((3-amino-4-oxo-3,4-dihydrobenzo[b][1,4]oxazepin-5(2H)-yl)methyl)-1H-indazol-1-yl)benzonitrile (300 mg, 733 μmol, Eq: 1.00), (S)-2-(tert-butoxycarbonylamino)propanoic acid (208 mg, 1.1 mmol, Eq: 1.5) and DIEA (284 mg, 383 μl, 2.2 mmol, Eq: 3) in THF (10.0 mL) and the mixture was stirred at RT overnight. The mixture was diluted with brine and extracted with EtOAc, then the combined extracts were dried over Na₂SO₄. The mixture was filtered, concentrated and the residue was purified by silica gel chromatographyto give tert-butyl (S)-1-((S)-5-((1-(2-cyanophenyl)-1H-indazol-3-yl)methyl)-4-oxo-2,3,4,5-tetrahydrobenzo[b][1,4]oxazepin-3-yl amino)-1-oxopropan-2-ylcarbamate (380 mg, 89%).

Step 4: In a similar manner to that described for Example 57 Step 2, tert-butyl (S)-1-((S)-5-((1-(2-cyanophenyl)-1H-indazol-3-yl)methyl)-4-oxo-2,3,4,5-tetrahydrobenzo[b][1,4]oxazepin-3-ylamino)-1-oxopropan-2-ylcarbamate (30 mg, 51.7 μmol) was converted to the title compound (18 mg, 72.5%). MS m/z 481 (MH⁺)

Example 65

(S)-N-((S)-5-((2-Cyano-1-(2-cyanophenyl)-1H-indol-3-yl)methyl)-4-oxo-2,3,4,5-tetrahydrobenzo[b][1,4]oxazepin-3-yl)-2-(methylamino)propanamide trifluoroacetate

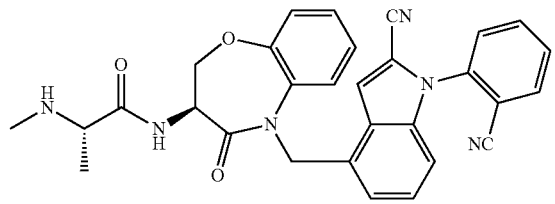 [SMILES: CN[C@@H](C)C(=O)N[C@H]1COc2ccccc2N(Cc2cccc3c2cc(C#N)n3-c2ccccc2C#N)C1=O]

Step 1: In a similar manner to that described for Example 1 Step 1 except the NaI was omitted, the mixture was stirred at RT for 16 h and the product was purified by preparative TLC, tert-butyl methyl ((S)-1-oxo-1-((S)-4-oxo-2,3,4,5-tetrahydrobenzo[b][1,4]oxazepin-3-ylamino)propan-2-yl)carbamate (30 mg, 82.6 μmol, Eq: 1.00) and 3-(bromomethyl)-1-(2-cyanophenyl)-1H-indole-2-carbonitrile (40 mg, 119 μmol, Eq: 1.44) were converted to tert-butyl (S)-1-((S)-5-((2-cyano-1-(2-cyanophenyl)-1H-indol-3-yl)methyl)-4-oxo-2,3,4,5-tetrahydrobenzo[b][1,4]oxazepin-3-ylamino)-1-oxopropan-2-yl(methyl)carbamate (45 mg, 88%).

Step 2: TFA (1.48 g, 1 mL, 13.0 mmol, Eq: 178) was added to a solution of tert-butyl (S)-1-((S)-5-((2-cyano-1-(2-cyanophenyl)-1H-indol-3-yl)methyl)-4-oxo-2,3,4,5-tetrahydrobenzo[b][1,4]oxazepin-3-ylamino)-1-oxopropan-2-yl (methyl)carbamate (45 mg, 72.7 µmol, Eq: 1.00) in DCM (1.7 mL) at 0° C. After 1 h, the mixture was concentrated and the residue triturated with Et₂O/Hexanes to give a solid which was lyophilized from MeCN/H₂O to give the title compound (43 mg, 93.5%) as a solid. MS m/z 519 (MH⁺)

Example 66

(S)-N-((S)-5-((1-(2-Cyanophenyl)-1H-indazol-3-yl)methyl)-4-oxo-2,3,4,5-tetrahydrobenzo[b,][1,4]oxazepin-3-yl)-2-(oxetan-3-ylamino)propanamide

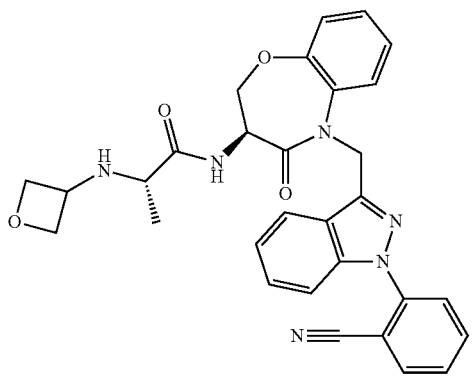 [SMILES: C[C@H](NC1COC1)C(=O)N[C@H]1COc2ccccc2N(Cc2nn(-c3ccccc3C#N)c3ccccc23)C1=O]

NaBH₃CN (10 mg, 159 µmmol) and AcOH (1 mL) were added to a mixture of (S)-2-amino-N-((S)-5-((1-(2-cyanophenyl)-1H-indazol-3-yl)methyl)-4-oxo-2,3,4,5-tetrahydrobenzo[b][1,4]oxazepin-3-yl)propanamide (40 mg, 83.2 µmol) and oxetan-3-one (19 mg, 264 µmmol) in MeOH (5 mL). After 16 h the mixture was concentrated, the residue treated with sat. NaHCO₃ and the resulting mixture extracted with DCM. The combined extracts were washed with H₂O, concentrated and the residue was purified by preparative TLC to give the title compound (10 mg, 22.4%). MS m/z 537 (MH⁺)

Example 67

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(2-hydroxy-2-methylpropylamino)propanamide

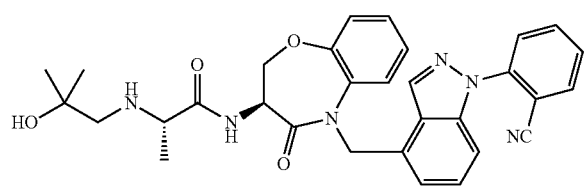 [SMILES: C[C@H](NCC(C)(C)O)C(=O)N[C@H]1COc2ccccc2N(Cc2cccc3c2cnn3-c2ccccc2C#N)C1=O]

(S)-2-Amino-N-((S)-5-((1-(2-cyanophenyl)-1H-indazol-3-yl)methyl)-4-oxo-2,3,4,5-tetrahydrobenzo[b][1,4]oxazepin-3-yl)propanamide (50 mg, 104 µmol, Eq: 1.00), LiClO₄ (11.1 mg, 4.56 µl, 104 µmol, Eq: 1.00) and 2,2-dimethyloxirane (1 mL) were mixed with EtOH (7 mL) in a microwave reaction vial, the vial was sealed and heated in the microwave at 100° C. After 2 h, 20 eq of 2,2-dimethyloxirane were added and heating was continued under microwave at 100° C. for 3 h. The mixture was concentrated and the residue was purified by preparative TLC to give the title compound (34 mg, 59.1%) as a solid. MS m/z 553 (MH⁺)

Example 68

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(2-hydroxyethylamino)propanamide

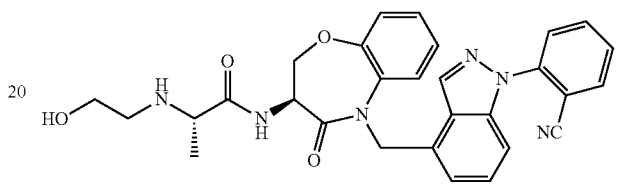

Na(OAc)₃BH (14.2 mg, 67.0 µmol, Eq: 1.4) was added to a solution of (S)-2-amino-N-((S)-5-((1-(2-cyanophenyl)-1H-indazol-3-yl)methyl)-4-oxo-2,3,4,5-tetrahydrobenzo[b][1,4]oxazepin-3-yl)propanamide (23 mg, 47.9 µmol, Eq: 1.00) and glycolaldehyde dimer (3.16 mg, 26.3 µmol, Eq: 0.55) in DCM (1.5 mL). After 72 h. at RT, the mixture was diluted with NaHCO₃ and extracted with DCMThecombined extracts were concentrated. The residue was purified by preparative TLC to give the title compound (16 mg, 95%) as a solid. MS m/z 525 (MH⁺)

Example 69

(S)-N-((S)-5-((1-(2-Cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide

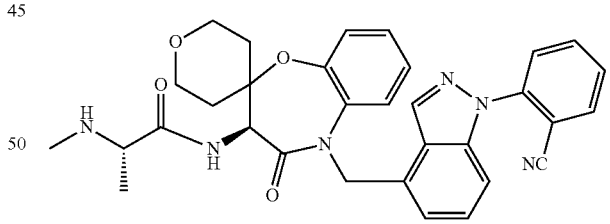

Step 1: In a similar manner to that described for Example 1 Step 1 except the NaI was omitted and the product was purified by preparative TLC, tert-butyl methyl((S)-1-oxo-1-((S)-4-oxo-2',3',4,5,5',6'-hexahydro-3H-spiro[benzo[b][1,4]oxazepine-2,4'-pyran]-3-ylamino)propan-2-yl)carbamate (55 mg, 127 µmol, Eq: 1.00) and 2-(3-(bromomethyl)-1H-indazol-1-yl)benzonitrile (78 mg, 250 µmol, Eq: 1.97) were converted to (S)-2-amino-N-((S)-5-((1-(2-cyanophenyl)-1H-indazol-3-yl)methyl)-4-oxo-2,3,4,5-tetrahydrobenzo[b][1,4]oxazepin-3-yl)propanamide (60 mg, 71.1%).

Step 2: In a similar manner to that described for Example 57 Step 2 except the mixture was stirred at 0° C. for 1 h, tert-butyl (S)-1-((S)-5-((1-(2-cyanophenyl)-1H-indazol-3- yl)methyl)-4-oxo-2',3',4,5,5',6'-hexahydro-3H-spiro[benzo[b][1,4]oxazepine-2,4'-pyran]-3-ylamino)-1-oxopropan-2-yl (methyl)carbamate (60 mg, 90.3 µmol) was converted to the title compound (48 mg, 94.2%). MS m/z 565 (MH+)

Example 70

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(ethyl-d5-amino)propanamide

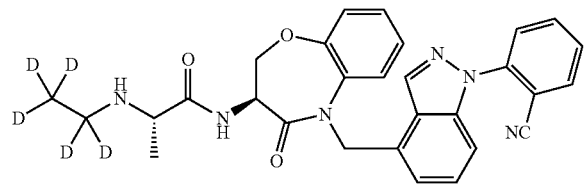 [SMILES: [2H]C([2H])([2H])C([2H])([2H])N[C@@H](C)C(=O)N[C@H]1COc2ccccc2N(Cc2cccc3c2cnn3-c2ccccc2C#N)C1=O]

Step 1: PyBOP (215 mg, 414 µmol, Eq: 1.5) was added to a mixture of (S)-2-(benzyloxycarbonyl-ethyl(d5)-amino)-propionic acid (106 mg, 414 µmol, Eq: 1.5), (S)-2-(3-((3-amino-4-oxo-3,4-dihydrobenzo[b][1,4]oxazepin-5(2H)-yl)methyl)-1H-indazol-1-yl)benzonitrile (113 mg, 276 µmol, Eq: 1.00) and DIEA (71.3 mg, 96.4 µl, 552 µmol, Eq: 2) in THF (2.00 mL). After 2 h, the mixture was diluted with EtOAc, washed with sat. NaHCO3 and NH4Cl. The organic mixture was concentrated and the residue was purified by preparative TLC to give ((S)-1-{(S)-9-[1-(2-cyano-phenyl)-1H-indazol-3-ylmethyl]-8-oxo-6,7,8,9-tetrahydro-5-oxa-9-aza-benzocyclohepten-7-ylcarbamoyl}-ethyl)-ethyl-d5-carbamic acid benzyl ester (77 mg, 43.1%).

Step 2: 5% Pd/C (35 mg) was added to a solution of ((S)-1-{(S)-9-[1-(2-cyano-phenyl)-1H-indazol-3-ylmethyl]-8-oxo-6,7,8,9-tetrahydro-5-oxa-9-aza-benzocyclohepten-7-ylcarbamoyl}-ethyl)-ethyl-d5-carbamic acid benzyl ester (77 mg, 119 µmol, Eq: 1.00) in MeOH (70 mL) and the mixture was stirred under H2. After 4 h, the mixture was filtered through Celite and the filter cake washed with MeOH. The filtrate was concentrated and the residue was purified by preparative TLC to give the title compound (40 mg, 65%). MS m/z 514 (MH+)

Example 71

(S)-N-((S)-5-((1-(2-Cyanophenyl)-6-fluoro-1H-indazol-3-yl)methyl)-4-oxo-2,3,4,5-tetrahydrobenzo[b][1,4]oxazepin-3-yl)-2-(ethylamino)propanamide

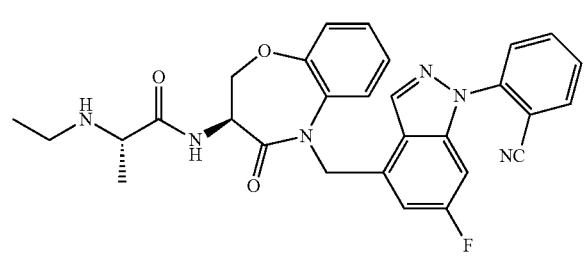 [SMILES: CCN[C@@H](C)C(=O)N[C@H]1COc2ccccc2N(Cc2cc(F)cc3c2cnn3-c2ccccc2C#N)C1=O]

Step 1: In a similar manner to that described for Example 1 Step 1 except the NaI was omitted and the product was used without purification, (S)-tert-butyl 4-oxo-2,3,4,5-tetrahydrobenzo[b][1,4]oxazepin-3-ylcarbamate (0.125 g, 449 µmol) and 2-(3-(bromomethyl)-6-fluoro-1H-indazol-1-yl)benzonitrile (162 mg, 494 µmol) were converted to (S)-tert-butyl 5-((1-(2-cyanophenyl)-6-fluoro-1H-indazol-3-yl)methyl)-4-oxo-2,3,4,5-tetrahydrobenzo[b][1,4]oxazepin-3-yl carbamate (237 mg, 100%).

Step 2: In a similar manner to that described for Example 57 Step 2 except the mixture was stirred at 0° C. for 1.5 h and the product was used without purification, (S)-tert-butyl 5-((1-(2-cyanophenyl)-6-fluoro-1H-indazol-3-yl)methyl)-4-oxo-2,3,4,5-tetrahydrobenzo[b][1,4]oxazepin-3-ylcarbamate (150 mg, 284 µmol) was converted to (S)-2-(3-((3-amino-4-oxo-3,4-dihydrobenzo[b][1,4]oxazepin-5(2H)-yl)methyl)-6-fluoro-1H-indazol-1-yl)benzonitrile (121 mg, 100%).

Step 3: PyBOP (223 mg, 428 µmol, Eq: 1.5) was added to a mixture of (S)-2-(3-((3-amino-4-oxo-3,4-dihydrobenzo[b][1,4]oxazepin-5(2H)-yl)methyl)-6-fluoro-1H-indazol-1-yl)benzonitrile (122 mg, 285 µmol, Eq: 1.00) and (S)-2-((benzyloxycarbonyl)(ethyl)amino)propanoic acid (Tetrahedron: Asymmetry 2008, 19, 970-975, 108 mg, 428 µmol, Eq: 1.5) and DIEA (111 mg, 150 µl, 856 µmol, Eq: 3) in THF (2 mL). After 3 h the mixture was diluted with NH4Cl and extracted with EtOAc. The combined extracts were washed with sat. NaHCO3 and concentrated. The residue was purified by preparative TLC to give (S)-1-((S)-5-((1-(2-cyanophenyl)-6-fluoro-1H-indazol-3-yl)methyl)-4-oxo-2,3,4,5-tetrahydrobenzo[b][1,4]oxazepin-3-ylamino)-1-oxopropan-2-yl (ethyl)carbamate (150 mg, 79.5%)

Step 4: In a similar manner to that described for Example 70 except the mixture was stirred under H2 for 4 h, (S)-1-((S)-5-((1-(2-cyanophenyl)-6-fluoro-1H-indazol-3-yl)methyl)-4-oxo-2,3,4,5-tetrahydrobenzo[b][1,4]oxazepin-3-ylamino)-1-oxopropan-2-yl(ethyl)carbamate (150 mg, 227 µmol) was converted to the title compound (30 mg, 23%). MS m/z 527 (MH+)

Example 72

(S)-N-((S)-5-((6-Bromo-1-(2-cyanophenyl)-1H-indazol-3-yl)methyl)-4-oxo-2,3,4,5-tetrahydrobenzo[b][1,4]oxazepin-3-yl)-2-(methylamino)propanamide trifluoroacetate

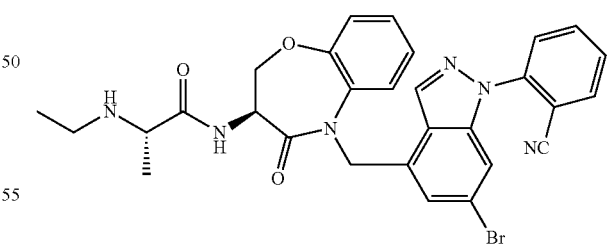

Step 1: Cs2CO3 (163 mg, 494 µmol) was added to a mixture of (S)-tert-butyl 4-oxo-2,3,4,5-tetrahydrobenzo[b][1,4]oxazepin-3-ylcarbamate (0.125 g, 449 µmol) and, 2-(3-(bromomethyl)-6-bromo-1H-indazol-1-yl)benzonitrile (193 mg, 494 µmol) in DMF (5 mL) and the mixture heated at 70° C. overnight. The mixture was cooled and poured into sat. NH4Cl resulting in a precipitate. The solid was filtered, washed with H2O, hexane and dried under vacuum to give (S)-tert-butyl 5-((6-bromo-1-(2-cyanophenyl)-1H-indazol- 3-yl)methyl)-4-oxo-2,3,4,5-tetrahydrobenzo[b][1,4]ox-azepin-3-yl carbamate (237 mg, 100%) which was used without purification.

Step 2: In a similar manner to that described for Example 57 Step 2 except the mixture was stirred at 0° C. for 1.5 h and the product was used without purification, (S)-tert-butyl 5-((6-bromo-1-(2-cyanophenyl)-1H-indazol-3-yl)methyl)-4-oxo-2,3,4,5-tetrahydrobenzo[b][1,4]oxazepin-3-ylcarbamate (95 mg, 161 µmol) was converted to (S)-2-(3-((3-amino-4-oxo-3,4-dihydrobenzo[b][1,4]oxazepin-5(2H)-yl)methyl)-6-bromo-1H-indazol-1-yl)benzonitrile (79 mg, 100%).

Step 3: In a similar manner to that described for Example 71 Step 3, (S)-2-(3-((3-amino-4-oxo-3,4-dihydrobenzo[b][1,4]oxazepin-5(2H)-yl)methyl)-6-bromo-1H-indazol-1-yl)benzonitrile (78 mg, 160 µmol, Eq: 1.00) and (S)-2-(tert-butoxycarbonyl(methyl)amino)propanoic acid (65 mg, 320 µmol, Eq: 2.00) were converted to tert-butyl (S)-1-((S)-5-((6-bromo-1-(2-cyanophenyl)-1H-indazol-3-yl)methyl)-4-oxo-2,3,4,5-tetrahydrobenzo[b][1,4]oxazepin-3-ylamino)-1-oxopropan-2-yl(methyl)carbamate (75 mg, 70%) as a white solid.

Step 4: In a similar manner to that described for Example 65, tert-butyl (S)-1-((S)-5-((6-bromo-1-(2-cyanophenyl)-1H-indazol-3-yl)methyl)-4-oxo-2,3,4,5-tetrahydrobenzo[b][1,4]oxazepin-3-ylamino)-1-oxopropan-2-yl(methyl)carbamate (75 mg, 111 µmol) was converted to the title compound (65 mg, 85%) as a white powder. MS m/z 575 (MH+)

Example 73

(S)-N-((S)-5-((2-Cyano-1-(2-cyanophenyl)-1H-indol-3-yl)methyl)-4-oxo-2',3',4,5,5',6'-hexahydro-3H-spiro[benzo[b][1,4]oxazepine-2,4'-pyran]-3-yl)-2-(methylamino)propanamide

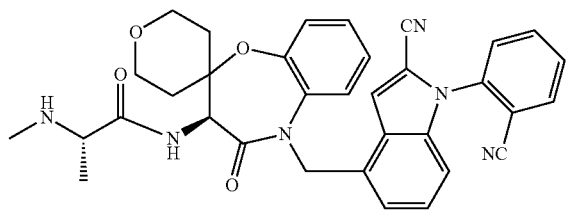 [SMILES: CN[C@@H](C)C(=O)N[C@@H]1C(=O)N(Cc2cccc3c2cc(C#N)n3-c2ccccc2C#N)c2ccccc2OC12CCOCC2]

Step 1: Cs₂CO₃ (9.58 g, 29.4 mmol, Eq: 1.5) was added to a mixture of 3-(bromomethyl)-1-(2-cyanophenyl)-1H-indole-2-carbonitrile (9.89 g, 29.4 mmol, Eq: 1.5) and tert-butyl methyl((S)-1-oxo-1-((S)-4-oxo-2',3',4,5,5',6'-hexahydro-3H-spiro[benzo[b][1,4]oxazepine-2,4'-pyran]-3-ylamino)propan-2-yl)carbamate (8.5 g, 19.6 mmol, Eq: 1.00) in DMF (20 mL) and the mixture heated to 70° C. for 1 h. The mixture was cooled, diluted with sat. NH₄Cl and extracted with EtOAc. The combined extracts were washed with H₂O, dried over Na₂SO₄ and concentrated to give a material that was purified by silica gel chromatography to afford tert-butyl (S)-1-((S)-5-((2-cyano-1-(2-cyanophenyl)-1H-indol-3-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (13 g, 96.3%) as a light yellow solid.

Step 2: TFA (37.0 g, 25 mL, 324 mmol, Eq: 55.9) was added dropwise over 2 h to a solution of tert-butyl (S)-1-((S)-5-((2-cyano-1-(2-cyanophenyl)-1H-indol-3-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (4 g, 5.81 mmol) in DCM (50 mL) at 0° C. After 30 min. the mixture was added to sat. NaHCO₃/H₂O 1:1, the organic phase was separated, dried over Na₂SO₄, filtered and concentration to give the title compound (3.4 g, 97%) as a light yellow solid. MS m/z 589 (MH+)

Example 74

(2S)-N-((2S,3S)-5-((1-(2-Cyanophenyl)-1H-indazol-3-yl)methyl)-2-methyl-4-oxo-2,3,4,5-tetrahydrobenzo[b][1,4]oxazepin-3-yl)-2-(ethylamino)propanamide trifluoroacetate

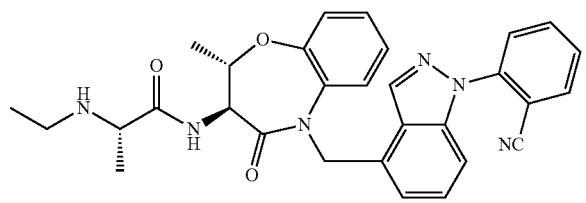 [SMILES: CCN[C@@H](C)C(=O)N[C@@H]1C(=O)N(Cc2cccc3c2cnn3-c2ccccc2C#N)c2ccccc2O[C@H]1C]

Step 1: In a similar manner to that described for Example 71 Step 3 except 1.3 eq. each of DIEA and PyBOP were used and the sat. NaHCO₃ wash was omitted, (2S,3S)-3-amino-2-methyl-2,3-dihydrobenzo[b][1,4]oxazepin-4(5H)-one (113 mg, 588 µmol, Eq: 1.00) and (S)-2-(tert-butoxycarbonyl(ethyl)amino)propanoic acid (Peptides: Struct. Funct., Proc. Am. Pept. Symp. 1983, 8, 143-6, 166 mg, 764 µmol, Eq: 1.3) was converted to tert-butyl ethyl((S)-1-((2S,3S)-2-methyl-4-oxo-2,3,4,5-tetrahydrobenzo[b][1,4]oxazepin-3-ylamino)-1-oxopropan-2-yl)carbamate (35 mg, 82%).

Step 2: In a similar manner to that described for Example 65 except the product was not lyophilized, tert-butyl (2S)-1-((2S,3S)-5-((1-(2-cyanophenyl)-1H-indazol-3-yl)methyl)-2-methyl-4-oxo-2,3,4,5-tetrahydrobenzo[b][1,4]oxazepin-3-ylamino)-1-oxopropan-2-yl(ethyl)carbamate (35 mg, 56.2 µmol) was converted to the title compound (30 mg, 80%) as an off white solid. MS m/z 523 (MH+)

Example 75

(S)-N-((R)-5-((2-Cyano-1-(2-cyanophenyl)-1H-indol-3-yl)methyl)-2,2-dimethyl-4-oxo-2,3,4,5-tetrahydrobenzo[b][1,4]thiazepin-3-yl)-2-(ethylamino)propanamide

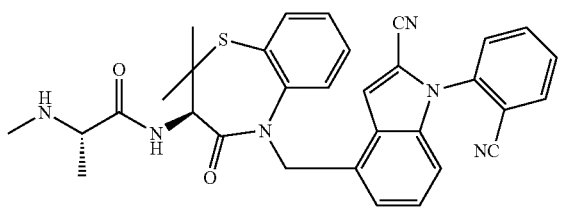 [SMILES: CN[C@@H](C)C(=O)N[C@@H]1C(=O)N(Cc2cccc3c2cc(C#N)n3-c2ccccc2C#N)c2ccccc2SC1(C)C]

Step 1: In a similar manner to that described for Example 71 Step 3 except the reaction was stirred at RT for 16 h, (R)-3-amino-2,2-dimethyl-2,3-dihydrobenzo[b][1,4]thiazepin-4(5H)-one (343 mg, 1.54 mmol, Eq: 1.00) and (S)-2-(tert-butoxycarbonyl(ethyl)amino)propanoic acid (436 mg, 2.01 mmol, Eq: 1.3) were converted to tert-butyl ethyl((S)-1-((2S,3S)-2-methyl-4-oxo-2,3,4,5-tetrahydrobenzo[b][1,4]oxazepin-3-yl amino)-1-oxopropan-2-yl)carbamate (500 mg, 77%).

Step 2: In a similar manner to that described for Example 1 Step 1 except the NaI was omitted and the product was purified by preparative TLC, tert-butyl ethyl((S)-1-((2S,3S)-2-methyl-4-oxo-2,3,4,5-tetrahydrobenzo[b][1,4]oxazepin-3-ylamino)-1-oxopropan-2-yl)carbamate (27 mg, 69.0 µmol, Eq: 1.00) and 2-(3-(bromomethyl)-1H-indazol-1-yl)benzonitrile (32.3 mg, 103 µmol, Eq: 1.5) were converted to tert-butyl (S)-1-((R)-5-((2-cyano-1-(2-cyanophenyl)-1H-indol-3-yl)methyl)-2,2-dimethyl-4-oxo-2,3,4,5-tetrahydrobenzo[b][1,4]thiazepin-3-ylamino)-1-oxopropan-2-yl(ethyl)carbamate (35 mg, 81.5%).

Step 3: In a similar manner to that described for Example 57 Step 2 except the mixture was stirred at 0° C. for 1 h, (S)-1-((R)-5-((2-cyano-1-(2-cyanophenyl)-1H-indol-3-yl)methyl)-2,2-dimethyl-4-oxo-2,3,4,5-tetrahydrobenzo[b][1,4]thiazepin-3-ylamino)-1-oxopropan-2-yl(ethyl)carbamate (200 mg, 295 µmol) was converted to the title compound (82 mg yield 45.7%). MS m/z 577 (MH⁺)

Example 76

(S)-N-((2S,3S)-5-((2-Cyano-1-(2-cyanophenyl)-1H-indol-3-yl)methyl)-2-methyl-4-oxo-2,3,4,5-tetrahydrobenzo[b][1,4]oxazepin-3-yl)-2-(methylamino)propanamide

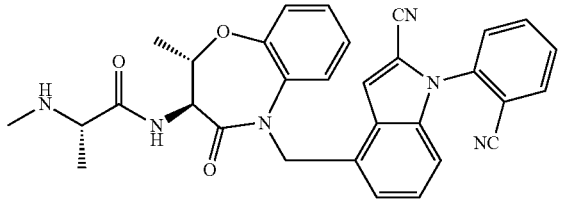 [SMILES: CN[C@@H](C)C(=O)N[C@@H]1C(=O)N(Cc2cccc3c2cc(C#N)n3-c2ccccc2C#N)c2ccccc2O[C@H]1C]

Step 1: In a similar manner to that described for Example 1 Step 1 except the NaI was omitted, the reaction mixture was heated at 65° C. for 1.5 h and the product was purified by preparative TLC, tert-butyl (2S,3S)-2-methyl-4-oxo-2,3,4,5-tetrahydrobenzo[b][1,4]oxazepin-3-ylcarbamate (Bioorg. Med. Chem. Lett. 1994, 4, 1789-94, 400 mg, 1.37 mmol, Eq: 1.00) and 3-(bromomethyl)-1-(2-cyanophenyl)-1H-indole-2-carbonitrile (598 mg, 1.78 mmol, Eq: 1.3) were converted to tert-butyl (2S,3S)-5-((2-cyano-1-(2-cyanophenyl)-1H-indol-3-yl)methyl)-2-methyl-4-oxo-2,3,4,5-tetrahydrobenzo[b][1,4]oxazepin-3-ylcarbamate (320 mg, 43%).

Step 2: In a similar manner to that described for Example 57 Step 2 except the mixture was stirred at 0° C. for 1 h and the product was not purified, tert-butyl (2S,3S)-5-((2-cyano-1-(2-cyanophenyl)-1H-indol-3-yl)methyl)-2-methyl-4-oxo-2,3,4,5-tetrahydrobenzo[b][1,4]oxazepin-3-ylcarbamate (320 mg, 584 µmol) was converted to 3-(((2S,3S)-3-amino-2-methyl-4-oxo-3,4-dihydrobenzo[b][1,4]oxazepin-5(2H)-yl)methyl)-1-(2-cyanophenyl)-1H-indole-2-carbonitrile (261 mg, 99%) which was used without purification.

Step 3: In a similar manner to that described for Example 71 Step 3 except the reaction was stirred at RT for 16 h and 1.5 eq. each of DIEA and PyBOP were used, 3-(((2S,3S)-3-amino-2-methyl-4-oxo-3,4-dihydrobenzo[b][1,4]oxazepin-5(2H)-yl)methyl)-1-(2-cyanophenyl)-1H-indole-2-carbonitrile (95 mg, 212 µmol, Eq: 1.00) and (S)-2-(tert-butoxycarbonyl(methyl)amino)propanoic acid (64.7 mg, 318 µmol, Eq: 1.5) were converted to (S)-1-((2S,3S)-5-((2-cyano-1-(2-cyanophenyl)-1H-indol-3-yl)methyl)-2-methyl-4-oxo-2,3,4,5-tetrahydrobenzo[b][1,4]oxazepin-3-ylamino)-1-oxopropan-2-yl(methyl)carbamate (102 mg, 76%).

Step 4: In a similar manner to that described for Example 57 Step 2 except the mixture was stirred at 0° C. for 1 h, tert-butyl (S)-1-((2S,3S)-5-((2-cyano-1-(2-cyanophenyl)-1H-indol-3-yl)methyl)-2-methyl-4-oxo-2,3,4,5-tetrahydrobenzo[b][1,4]oxazepin-3-ylamino)-1-oxopropan-2-yl(methyl)carbamate (102 mg, 161 µmol) was converted to the title compound (78 mg, 95%). MS m/z 533 (MH⁺)

Example 77

(S)-N-((2S,3S)-5-((2-Cyano-1-(2-cyanophenyl)-1H-indol-3-yl)methyl)-2-methyl-4-oxo-2,3,4,5-tetrahydrobenzo[b][1,4]oxazepin-3-yl)-2-(ethylamino)propanamide

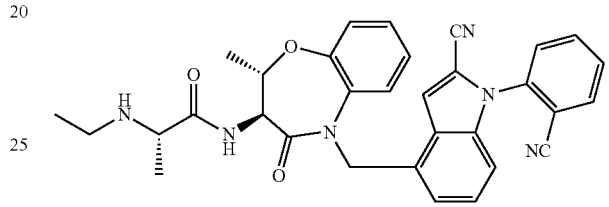

Step 1: In a similar manner to that described for Example 71 Step 3 except the reaction was stirred at RT for 16 h and 1.5 eq. each of DIEA and PyBOP were used, 3-(((2S,3S)-3-amino-2-methyl-4-oxo-3,4-dihydrobenzo[b][1,4]oxazepin-5(2H)-yl)methyl)-1-(2-cyanophenyl)-1H-indole-2-carbonitrile (95 mg, 212 µmol, Eq: 1.00) and (S)-2-(tert-butoxycarbonyl(ethyl)amino)propanoic acid (69.2 mg, 318 µmol, Eq: 1.5) were converted to tert-butyl (S)-1-((2S,3S)-5-((2-cyano-1-(2-cyanophenyl)-1H-indol-3-yl)methyl)-2-methyl-4-oxo-2,3,4,5-tetrahydrobenzo[b][1,4]oxazepin-3-ylamino)-1-oxopropan-2-yl(ethyl)carbamate (120 mg, 87%).

Step 2: In a similar manner to that described for Example 57 Step 2 except the mixture was stirred at 0° C. for 1 h, tert-butyl (S)-1-((2S,3S)-5-((2-cyano-1-(2-cyanophenyl)-1H-indol-3-yl)methyl)-2-methyl-4-oxo-2,3,4,5-tetrahydrobenzo[b][1,4]oxazepin-3-ylamino)-1-oxopropan-2-yl(ethyl)carbamate (120 mg, 186 µmol) was converted to the title compound (69 mg, 68%). MS m/z 547 (MH⁺)

Example 78

(S)-N-((S)-8-Bromo-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide trifluoroacetate

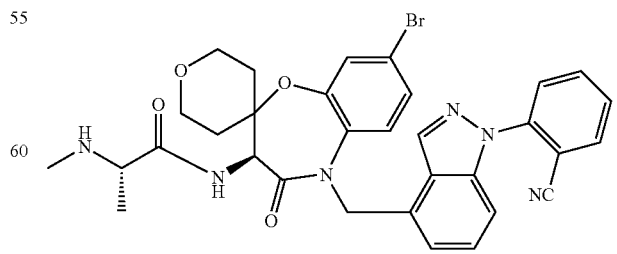

Step 1: Cs₂CO₃ (331 mg, 1.01 mmol, Eq: 2.2) was added was added to a solution of tert-butyl methyl((S)-1-oxo-1-((S)-4-oxo-2',3',4,5,5',6'-hexahydro-3H-spiro[benzo[b][1,4]

oxazepine-2,4'-pyran]-3-ylamino)propan-2-yl)carbamate (200 mg, 461 µmol, Eq: 1.00) and DMF (10 mL) and the mixture was cooled to 0° C. and a solution of NBS (82.1 mg, 461 µmol, Eq: 1.00) in 2 mL DMF was added dropwise over 5 min. and the mixture warmed to RT. After 10 h the mixture was diluted with sat. NH₄Cl and extracted with EtOAc. The combined extracts were washed with H₂O, concentrated and the residue was purified by preparative TLC to give tert-butyl (S)-1-((S)-8-bromo-4-oxo-2',3',4,5,5',6'-hexahydro-3H-spiro[benzo[b][1,4]oxazepine-2,4'-pyran]-3-ylamino)-1-oxopropan-2-yl(methyl)carbamate (300 mg, 98%).

Step 2: In a similar manner to that described for Example 1 Step 1 except the NaI was omitted and the product was purified by preparative TLC, tert-butyl (S)-1-((S)-8-bromo-4-oxo-2',3',4,5,5',6'-hexahydro-3H-spiro[benzo[b][1,4]oxazepine-2,4'-pyran]-3-ylamino)-1-oxopropan-2-yl(methyl) carbamate (300 mg, 585 µmol, Eq: 1.00) and 2-(3-(bromomethyl)-1H-indazol-1-yl)benzonitrile (274 mg, 878 µmol, Eq: 1.5) were converted to tert-butyl (S)-1-((S)-8-bromo-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl) carbamate (300 mg, 69%).

Step 3: In a similar manner to that described for Example 65 Step 2, tert-butyl (S)-1-((S)-8-bromo-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (33.5 mg, 45.0 µmol) was converted to the title compound (30 mg, 88%) as an off white solid. MS m/z 644.8 (MH⁺)

Example 79

(S)-N-((S)-8-Cyano-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide 2,2,2-trifluoroacetate

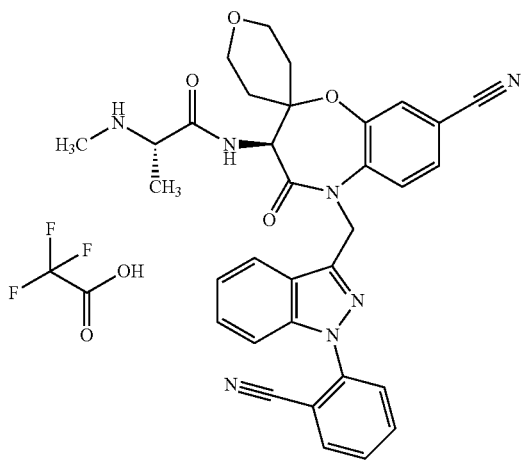 [SMILES: O=C(O)C(F)(F)F ; CN[C@@H](C)C(=O)N[C@@H]1C(=O)N(Cc2nn(-c3ccccc3C#N)c3ccccc23)c2ccc(C#N)cc2OC12CCOCC2]

Step 1: A solution of tert-butyl (S)-1-((S)-8-bromo-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (50 mg, 67.2 µmol, Eq: 1.00) in DMF (1.5 mL) was degassed with argon and Zn(CN)₂ (15.8 mg, 134 µmol, Eq: 2) and Pd(Ph₃P)₄ (23.3 mg, 20.2 µmol, Eq: 0.3) were added. The mixture was heated in microwave at 110° C. for 30 min., cooled, diluted with sat. NH₄Cl and extracted with EtOAc. The combined extracts were washed with H₂O, then concentrated and the residue was purified by preparative TLC to give tert-butyl (S)-1-((S)-8-cyano-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (43.5 mg, 94%)

Step 2: In a similar manner to that described for Example 65 Step 2, tert-butyl (S)-1-((S)-8-cyano-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (43.5 mg, 63.1 µmol) was converted to the title compound (40 mg, 86%). MS m/z 590 (MH⁺)

Example 80

3-Cyano-4-(3-(((2S,3S)-2-methyl-3-((S)-2-(methylamino)propanamido)-4-oxo-3,4-dihydrobenzo[b][1,4]oxazepin-5(2H)-yl)methyl)-1H-indazol-1-yl)benzoic acid trifluoroacetate

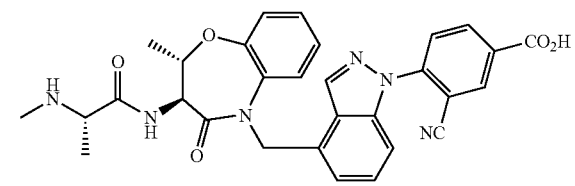 [SMILES: CN[C@@H](C)C(=O)N[C@@H]1C(=O)N(Cc2cccc3c2cnn3-c2ccc(C(=O)O)cc2C#N)c2ccccc2O[C@H]1C]

Step 1: In a similar manner to that described for Example 72 Step 1 except the mixture was heated at 70° C. for 1 h, (2S,3S)-2-methyl-4-oxo-2,3,4,5-tetrahydrobenzo[b][1,4]oxazepin-3-ylcarbamate (200 mg, 0.684 mmol) and methyl 4-(3-(bromomethyl)-1H-indazol-1-yl)-3-cyanobenzoate were converted to methyl 4-(3-(((2S,3S)-3-(tert-butoxycarbonylamino)-2-methyl-4-oxo-3,4-dihydrobenzo[b][1,4]oxazepin-5(2H)-yl)methyl)-1H-indazol-1-yl)-3-cyanobenzoate (395 mg, 97%) obtained as a white solid.

Step 2: In a similar manner to that described for Example 57 Step 2 except the reaction mixture was stirred at 0° C. for 1 h, methyl 4-(3-(((2S,3S)-3-(tert-butoxycarbonylamino)-2-methyl-4-oxo-3,4-dihydrobenzo[b][1,4]oxazepin-5(2H)-yl)methyl)-1H-indazol-1-yl)-3-cyanobenzoate (254 mg, 437 µmol) was converted to methyl 4-(3-(((2S,3S)-3-amino-2-methyl-4-oxo-3,4-dihydrobenzo[b][1,4]oxazepin-5(2H)-yl)methyl)-1H-indazol-1-yl)-3-cyanobenzoate (210 mg, 99%) obtained as a brown oil.

Step 3: PyBop (295 mg, 567 µmol, Eq: 1.3) was added to a mixture of methyl 4-(3-(((2S,3S)-3-amino-2-methyl-4-oxo-3,4-dihydrobenzo[b][1,4]oxazepin-5(2H)-yl)methyl)-1H-indazol-1-yl)-3-cyanobenzoate (210 mg, 436 µmol, Eq: 1.00), (S)-2-(tert-butoxycarbonyl(methyl)amino)propanoic acid (115 mg, 567 µmol, Eq: 1.3) and DIEA (73.3 mg, 99.0 µl, 567 µmol, Eq: 1.3) in THF (7 mL). After 16 h, the mixture was diluted with sat. NH₄Cl and H₂O, extracted with EtOAc. The combined extracts were washed with H₂O, concentrated and the residue purified by preparative TLC to afford 4-(3-(42S, 3S)-3-((S)-2-(tert-butoxycarbonyl(methyl)amino)propanamido)-2-methyl-4-oxo-3,4-dihydrobenzo[b][1,4]oxazepin-5(2H)-yl)methyl)-1H-indazol-1-yl)-3-cyanobenzoate (230 mg, 79.1%).

Step 4: LiOH (1 N, 448 μl, 448 μmol, Eq: 1.3) was added to a solution of 4-(3-(((2S,3S)-3-((S)-2-(tert-butoxycarbonyl(methyl)amino)propanamido)-2-methyl-4-oxo-3,4-dihydrobenzo[b][1,4]oxazepin-5(2H)-yl)methyl)-1H-indazol-1-yl)-3-cyanobenzoate (230 mg, 345 μmol, Eq: 1.00) in THF (7 mL) at 0° C. and H₂O (3 mL) was added. After 7 h the mixture was acidified with citric acid to pH 4-5 and was extracted with EtOAc. The combined extracts were washed with H₂O, dried over Na₂SO₄ and concentrated to give 4-(3-(((2S,3S)-3-((S)-2-(tert-butoxycarbonyl(methyl)amino)propanamido)-2-methyl-4-oxo-3,4-dihydrobenzo[b][1,4]oxazepin-5(2H)-yl)methyl)-1H-indazol-1-yl)-3-cyanobenzoic acid (220 mg, 97.7%) which was used without purification.

Step 5: In a similar manner to that described for Example 65 Step 2, 4-(3-((2S,3S)-3-((S)-2-(tert-butoxycarbonyl(methyl)amino)propanamido)-2-methyl-4-oxo-3,4-dihydrobenzo[b][1,4]oxazepin-5(2H)-yl)methyl)-1H-indazol-1-yl)-3-cyanobenzoic acid (28.5 mg, 43.7 μmol) was converted to the title compound (26 mg, 85%). MS m/z 553 (MH⁺)

Example 81

3-Cyano-N-ethyl-4-(3-(((2S,3S)-2-methyl-3-((S)-2-(methyl amino)propanamido)-4-oxo-3,4-dihydrobenzo[b][1,4]oxazepin-5(2H)-yl)methyl)-1H-indazol-1-yl)benzamide trifluoroacetate

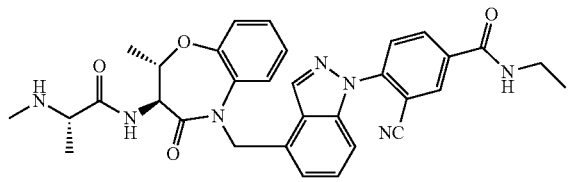 [SMILES: CCNC(=O)c1ccc(-n2ncc3c(CN4C(=O)[C@@H](NC(=O)[C@H](C)NC)[C@H](C)Oc5ccccc54)cccc32)c(C#N)c1]

Step 1: Ethylamine (100 μl, 200 μmol, Eq: 3.11) was added to a mixture of 4-(3-(((2S,3S)-3-((S)-2-(tert-butoxycarbonyl(methyl)amino)propanamido)-2-methyl-4-oxo-3,4-dihydrobenzo[b][1,4]oxazepin-5(2H)-yl)methyl)-1H-indazol-1-yl)-3-cyanobenzoic acid (42 mg, 64.3 μmol, Eq: 1.00), DIEA (37.0 mg, 50 μl, 286 μmol, Eq: 4.45) and PyBOP (43.5 mg, 83.7 μmol, Eq: 1.3). After 16 h the mixture was diluted with sat. NH₄Cl and extracted with EtOAc. The combined extracts were washed with sat. NaHCO₃, NH₄Cl, and H₂O, then dried over Na₂SO₄ and concentrated to give a residue that was purified by preparative TLC to afford tert-butyl (S)-1-((2S,3S)-5-((1-(2-cyano-4-(ethylcarbamoyl)phenyl)-1H-indazol-3-yl)methyl)-2-methyl-4-oxo-2,3,4,5-tetrahydrobenzo[b][1,4]oxazepin-3-ylamino)-1-oxopropan-2-yl(methyl)carbamate (40 mg, 92%).

Step 2: In a similar manner to that described for Example 65 Step 2, tert-butyl (S)-1-((2S,3S)-5-((1-(2-cyano-4-(ethylcarbamoyl)phenyl)-1H-indazol-3-yl)methyl)-2-methyl-4-oxo-2,3,4,5-tetrahydrobenzo[b][1,4]oxazepin-3-ylamino)-1-oxopropan-2-yl(methyl)carbamate (40 mg, 58.8 μmol) was converted to the title compound (30 mg, 75%). MS m/z 580 (MH⁺)

Example 82

(S)-N-((S)-5-((6-Bromo-2-methoxynaphthalen-1-yl)methyl)-4-oxo-2,3,4,5-tetrahydro benzo[b][1,4]oxazepin-3-yl)-2-(methylamino)butanamide hydrochloride

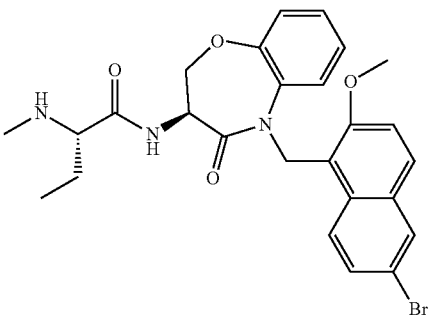 [SMILES: CC[C@H](NC)C(=O)N[C@H]1COc2ccccc2N(Cc2c(OC)ccc3cc(Br)ccc23)C1=O]

Step 1: A mixture of (S)-tert-butyl 4-oxo-2,3,4,5-tetrahydrobenzo[b][1,4]oxazepin-3-ylcarbamate (1.412 g, 5.07 mmol), 6-bromo-1-(chloromethyl)-2-methoxynaphthalene (1.59 g, 5.58 mmol), Cs₂CO₃ (1.98 g, 6.09 mmol), and NaI (913 mg, 6.09 mmol) in DMF (16.9 mL) was stirred at RT for 22 h, diluted with H₂O and extracted with EtOAc. The combined extracts were washed with brine, dried over Na₂SO₄ and. The filtrate was concentrated to give a residue that was purified by silica gel chromatography to give (S)-tert-butyl 5-((6-bromo-2-methoxynaphthalen-1-yl)methyl)-4-oxo-2,3,4,5-tetrahydrobenzo[b][1,4]oxazepin-3-ylcarbamate (1.804 g, 67%) as an off-white solid. MS m/z 549/551 (MNa)⁺

Step 2: A solution of (S)-tert-butyl 5-((6-bromo-2-methoxynaphthalen-1-yl)methyl)-4-oxo-2,3,4,5-tetrahydrobenzo[b][1,4]oxazepin-3-ylcarbamate (1.803 g, 3.42 mmol) in 4 M HCl in dioxane (17.1 mL) was stirred at RT for 2 h. The mixture was concentrated and the residue triturated with Et₂O to provide (S)-3-amino-5-((6-bromo-2-methoxynaphthalen-1-yl)methyl)-2,3-dihydrobenzo[b][1,4]oxazepin-4(5H)-one hydrochloride (1.415 g, 89%) as an off-white solid. MS m/z 427/429 MH Step 3: A mixture of (S)-3-amino-5-((6-bromo-2-methoxynaphthalen-1-yl)methyl)-2,3-dihydrobenzo[b][1,4]oxazepin-4(5H)-one hydrochloride (54 mg, 116 μmol), (S)-2-(tert-butoxycarbonyl(methyl)amino)butanoic acid (27.8 mg, 128 μmol), DIEA (80.6 μl, 466 iumol), and HBTU (48.6 mg, 128 μmol) in DMF (388 μL) was stirred at RT for 30 min. The mixture was diluted with EtOAc, washed with sat. NaHCO₃, H₂O and brine, then dried over Na₂SO₄, and filtered. The filtrate was concentrated to give a residue that was purified by silica gel chromatography to provide tert-butyl (S)-1-((S)-5-((6-bromo-2-methoxynaphthalen-1-yl)methyl)-4-oxo-2,3,4,5-tetrahydrobenzo[b][1,4]oxazepin-3-ylamino)-1-oxobutan-2-yl(methyl)carbamate (67.5 mg, 93%) as a white solid. MS m/z 648/650 (MNa)⁺

Step 4: 2 M HCl in Et₂O (419 μL) was added to a solution of tert-butyl (S)-1-((S)-5-((6-bromo-2-methoxynaphthalen-1-yl)methyl)-4-oxo-2,3,4,5-tetrahydrobenzo[b][1,4]oxazepin-3-ylamino)-1-oxobutan-2-yl(methyl)carbamate (65.7 mg, 105 μmol) in MeOH (105 μL). After 4 h the mixture was concentrated and the residue was dissolved in MeCN/H₂O and the solution lyophilized to provide the title compound (55.9 mg, 95%) as a white solid. MS m/z 526/528 (MH)'

Example 83

(S)-N-((S)-5-((6-Bromo-2-methoxynaphthalen-1-yl)methyl)-4-oxo-2,3,4,5-tetrahydrobenzo[b][1,4]oxazepin-3-yl)-2-(2-hydroxyethylamino)butanamide trifluoroacetate

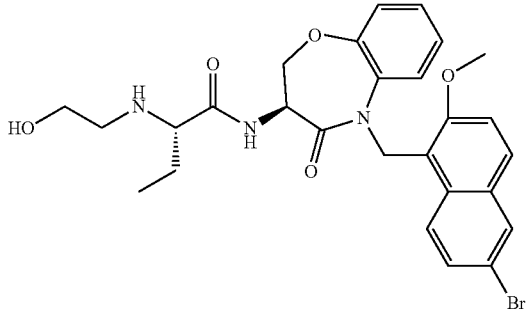 [SMILES: CC[C@H](NCCO)C(=O)N[C@H]1COc2ccccc2N(Cc2c(OC)ccc3cc(Br)ccc23)C1=O]

Step 1: A mixture of (S)-3-amino-5-((6-bromo-2-methoxynaphthalen-1-yl)methyl)-2,3-dihydrobenzo[b][1,4]oxazepin-4(5H)-one hydrochloride (348 mg, 750 µmol), (S)-2-(tert-butoxycarbonylamino)butanoic acid (168 mg, 825 µmol), DIEA (519 µL, 3.00 mmol), and HBTU (313 mg, 825 µmol) in DMF (2.5 mL) was stirred at RT for 30 min. The mixture was diluted with EtOAc, washed with sat. NaHCO$_3$, H$_2$O, and brine brine, then dried over Na$_2$SO$_4$, and filtered. The filtrate was concentrated to give a residue that was purified by silica gel chromatography to provide tert-butyl (S)-1-((S)-5-((6-bromo-2-methoxynaphthalen-1-yl)methyl)-4-oxo-2,3,4,5-tetrahydrobenzo[b][1,4]oxazepin-3-ylamino)-1-oxobutan-2-ylcarbamate (431 mg, 94%) as a white solid. MS m/z 634/636 (MNa)$^+$ Step 2: A solution of tert-butyl (S)-1-((S)-5-((6-bromo-2-methoxynaphthalen-1-yl)methyl)-4-oxo-2,3,4,5-tetrahydrobenzo[b][1,4]oxazepin-3-ylamino)-1-oxobutan-2-ylcarbamate (430 mg, 702 µmol) in 4 M HCl in dioxane (3.51 mL) was stirred at RT for 1 h, and concentrated. the residue was triturated with Et$_2$O to provide (S)-2-amino-N-((S)-5-((6-bromo-2-methoxynaphthalen-1-yl)methyl)-4-oxo-2,3,4,5-tetrahydrobenzo[b][1,4]oxazepin-3-yl)butanamide hydrochloride (357 mg, 93%) as a white solid.

Step 3: A solution of (S)-2-amino-N-((S)-5-((6-bromo-2-methoxynaphthalen-1-yl)methyl)-4-oxo-2,3,4,5-tetrahydrobenzo[b][1,4]oxazepin-3-yl)butanamide hydrochloride (283 mg) in 25% MeOH/CH$_2$Cl$_2$ was treated with silica-supported carbonate (SiliCycle, 3 eq) for 1 h, filtered, and the filtrate concentrated to provide (S)-2-amino-N-((S)-5-((6-bromo-2-methoxynaphthalen-1-yl)methyl)-4-oxo-2,3,4,5-tetrahydrobenzo[b][1,4]oxazepin-3-yl)butanamide (264 mg) as a white foam. MS m/z 512/514 (MH)$^+$ Step 4: Na(OAc)$_3$BH (45.1 mg, 213 µmol) was added to a solution of (S)-2-amino-N-((S)-5-((6-bromo-2-methoxynaphthalen-1-yl)methyl)-4-oxo-2,3,4,5-tetrahydrobenzo[b][1,4]oxazepin-3-yl)butanamide (77.8 mg, 152 µmol) and glycolaldehyde dimer (9.57 mg, 79.7 µmol) in dichloroethane (1.52 mL). After 30 min. the mixture was diluted with sat. NaHCO$_3$ and extracted with EtOAc. The combined extracts were washed with brine, dried over Na$_2$SO$_4$, filtered, the filtrate was concentrated to give a residue that was purified by preparative reverse phase HPLC to provide, after lyophilization, the title compound (36.9 mg, 36%) as a white solid. MS m/z 556/558 (MH)$^+$

Example 84

(S)-N-((S)-5-(Benzo[d]isoxazol-3-ylmethyl)-4-oxo-2',3',4,5,5',6'-hexahydro-3H-spiro[benzo[b][1,4]oxazepine-2,4'-pyran]-3-yl)-2-(methylamino)propanamide hydrochloride

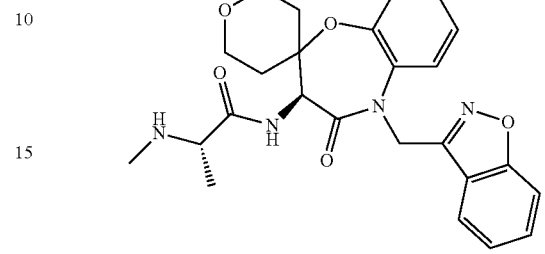

Step 1: A mixture of tert-butyl methyl((2S)-1-oxo-1-(4-oxo-2',3',4,5,5',6'-hexahydro-3H-spiro[benzo[b][1,4]oxazepine-2,4'-pyran]-3-ylamino)propan-2-yl)carbamate (156 mg, 360 µmol), 3-(bromomethyl)benzo[d]isoxazole (83.9 mg, 396 µmol), Cs$_2$CO$_3$ (141 mg, 432 µmol) and NaI (64.7 mg, 432 µmol) in DMF (900 µL) was stirred at RT for 18 h, diluted with EtOAc, washed with H$_2$O, brine, dried over Na$_2$SO$_4$, filtered, and the filtrate concentrated to give a residue that was purified by silica gel chromatography. The resulting material was purified by supercritical fluid chromatography (SFC) to provide tert-butyl (S)-1-((S)-5-(benzo[d]isoxazol-3-ylmethyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (54.5 mg, 27%) as a white foam.

Step 2: In a similar manner to that described for Example 82 Step 4, tert-butyl (S)-1-((S)-5-(benzo[d]isoxazol-3-ylmethyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (51.6 mg, 91.4 µmol) was converted to the title compound (42.2 mg, 92%) as a white solid. MS m/z 465 (MH)$^+$

Example 85

(S)-N-((S)-5-((2-(Difluoromethoxy)naphthalen-1-yl)methyl)-4-oxo-2',3',4,5,5',6'-hexahydro-3H-spiro[benzo[b][1,4]oxazepine-2,4'-pyran]-3-yl)-2-(methylamino)propanamide hydrochloride

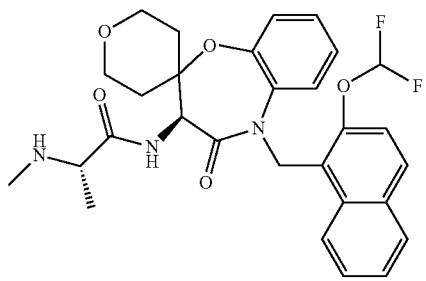 [SMILES: CN[C@@H](C)C(=O)N[C@@H]1C(=O)N(Cc2c(OC(F)F)ccc3ccccc23)c2ccccc2OC12CCOCC2]

Step 1: A mixture of tert-butyl methyl((2S)-1-oxo-1-(4-oxo-2',3',4,5,5',6'-hexahydro-3H-spiro[benzo[b][1,4]oxazepine-2,4'-pyran]-3-ylamino)propan-2-yl)carbamate (118 mg, 272 µmol), (2-(difluoromethoxy)naphthalen-1-yl)methyl methanesulfonate (98.7 mg, 327 µmol) and Cs$_2$CO$_3$ (115 mg, 354 µmol) in DMF (681 µL) was stirred at RT for 20 h.

The mixture was diluted with EtOAc, washed with H₂O and brine, then dried over Na₂SO₄, and filtered. The filtrate was concentrated to give a residue that was purified by silica gel chromatography. The resulting material was purified by SFC to provide tert-butyl (S)-1-((S)-5-((2-(difluoromethoxy)naphthalen-1-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (52.6 mg, 30%) as a white foam (MS m/z 662 (MNa)') and tert-butyl (S)-1-((R)-5-((2-(difluoromethoxy)naphthalen-1-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (72.8 mg, 42%) as a white foam (MS m/z 662 (MNa)⁺).

Step 2: In a similar manner to that described for Example 82 Step 4, tert-butyl (S)-1-((S)-5-((2-(difluoromethoxy)naphthalen-1-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (52.6 mg, 82.2 µmol) was converted to the title compound (46.3 mg, 98%) as a white solid. MS m/z 540 (MH)⁺

Example 86

(S)-N-((R)-5-((2-(Difluoromethoxy)naphthalen-1-yl)methyl)-4-oxo-2',3',4,5,5',6'-hexahydro-3H-spiro[benzo[b][1,4]oxazepine-2,4'-pyran]-3-yl)-2-(methylamino)propanamide hydrochloride

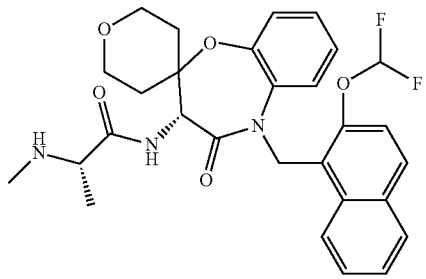 [SMILES: CN[C@@H](C)C(=O)N[C@H]1C(=O)N(Cc2c(OC(F)F)ccc3ccccc23)c2ccccc2OC12CCOCC2]

In a similar manner to that described for Example 82 Step 4, (S)-1-((R)-5-((2-(difluoromethoxy)naphthalen-1-yl)methyl)-4-oxo-2',3',4,5,5',6'-hexahydro-3H-spiro[benzo[b][1,4]oxazepine-2,4'-pyran]-3-ylamino)-1-oxopropan-2-yl(methyl)carbamate (72.8 mg, 114 µmol) was converted to the title compound (61.7 mg, 94%) as a white solid. MS m/z 540 (MH)⁺

Example 87

(S)-N-((S)-5-((6-Bromo-2-methoxynaphthalen-1-yl)methyl)-9-fluoro-4-oxo-2,3,4,5-tetrahydrobenzo[b][1,4]oxazepin-3-yl)-2-(methylamino)propanamide hydrochloride

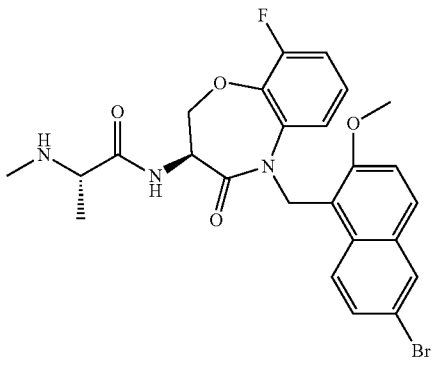 [SMILES: CN[C@@H](C)C(=O)N[C@H]1COc2c(F)cccc2N(Cc2c(OC)ccc3cc(Br)ccc23)C1=O]

Step 1: A solution of BOC-Ser-OH (2.58 g, 12.6 mmol) in DMF (10.00 mL) was added to a suspension of NaH (60% in mineral oil, 1.06 g, 26.4 mmol) in DMF (10 mL) at 0° C. over 10 min. After 1 h at 0° C. a solution of 1,2-difluoro-3-nitrobenzene (2 g, 12.6 mmol) in DMF (10 mL) was added and the mixture stirred at 0° C. for 2 h. The mixture was diluted with H₂O and acidified to pH 3 with 1 N HCl, then extracted with EtOAc. The combined extracts were dried over MgSO₄ and the filtrate was concentrated to give a residue that was purified by silica gel chromatography to afford (S)-2-(tert-butoxycarbonylamino)-3-(2-fluoro-6-nitrophenoxy)propanoic acid (2.94 g, 68%) as a yellow foam.

Step 2: A mixture of (S)-2-(tert-butoxycarbonylamino)-3-(2-fluoro-6-nitrophenoxy)propanoic acid (2.94 g, 8.54 mmol) and 10% Pd/C (150 mg) in MeOH was stirred under H₂ for 4 h. The mixture was filtered through Celite and the cake was washed with MeOH. The filtrate was concentrated to afford (S)-3-(2-amino-6-fluorophenoxy)-2-(tert-butoxycarbonylamino)propanoic acid (2.6 g, 97%) which was used without purification.

Step 3: A solution of (S)-3-(2-amino-6-fluorophenoxy)-2-(tert-butoxycarbonylamino)propanoic acid (2.6 g, 8.27 mmol) and EDCI (1.97 mg, 10.3 mmol) in DMF (40 mL) was stirred at RT for 6 h. The mixture was diluted with EtOAc and washed with H₂O. The combined aqueous layers were extracted with EtOAc. The combined organic extracts were dried over MgSO₄, filtered and the filtrate was concentrated to give a residue that was purified by silica gel chromatography to afford (S)-tert-butyl 9-fluoro-4-oxo-2,3,4,5-tetrahydrobenzo[b][1,4]oxazepin-3-ylcarbamate (1.03 g, 42%) as an orange solid. MS m/z 319 (M+Na)⁺

Step 4: In a similar manner to that described for Example 82 Step 1, (S)-tert-butyl 9-fluoro-4-oxo-2,3,4,5-tetrahydrobenzo[b][1,4]oxazepin-3-ylcarbamate (0.503 g, 1.7 mmol) and 6-bromo-1-(chloromethyl)-2-methoxynaphthalene (582 mg, 2.04 mmol were converted to (S)-tert-butyl 5-((6-bromo-2-methoxynaphthalen-1-yl)methyl)-9-fluoro-4-oxo-2,3,4,5-tetrahydrobenzo[b][1,4]oxazepin-3-ylcarbamate (634 mg, 69%) as an orange solid. MS m/z 567/569 (MNa)⁺

Step 5: In a similar manner to that described for Example 82 Step 2, (S)-tert-butyl 5-((6-bromo-2-methoxynaphthalen-1-yl)methyl)-9-fluoro-4-oxo-2,3,4,5-tetrahydrobenzo[b][1,4]oxazepin-3-ylcarbamate (634 mg, 1.16 mmol) was converted to (S)-3-amino-5-((6-bromo-2-methoxynaphthalen-1-yl)methyl)-9-fluoro-2,3-dihydrobenzo[b][1,4]oxazepin-4(5H)-one hydrochloride (545 mg, 97%) as a light yellow solid. MS m/z 445/447 (MH)⁺

Step 6: In a similar manner to that described for Example 82 Step 3, (S)-3-amino-5-((6-bromo-2-methoxynaphthalen-1-yl)methyl)-9-fluoro-2,3-dihydrobenzo[b][1,4]oxazepin-4(5H)-one hydrochloride (86.8 mg, 180 µmol) and Boc-N-methyl-L-alanine (40.3 mg, 198 µmol) were converted to tert-butyl (S)-1-((S)-5-((6-bromo-2-methoxynaphthalen-1-yl)methyl)-9-fluoro-4-oxo-2,3,4,5-tetrahydrobenzo[b][1,4]oxazepin-3-ylamino)-1-oxopropan-2-yl(methyl)carbamate (103.2 mg, 91%) obtained as a light yellow solid. MS m/z 652/654 (MNa)'

Step 7: In a similar manner to that described for Example 82 Step 4, tert-butyl (S)-1-((S)-5-((6-bromo-2-methoxynaphthalen-1-yl)methyl)-9-fluoro-4-oxo-2,3,4,5-tetrahydrobenzo[b][1,4]oxazepin-3-ylamino)-1-oxopropan-2-yl(methyl)carbamate was converted to the title compound (85.9 mg, 94%) obtained as an off-white solid. MS m/z 530/532 (MH)⁺

Example 88

(S)-N-((S)-5-((6-Bromo-2-methoxynaphthalen-1-yl)methyl)-4-oxo-9-(trifluoromethyl)-2,3,4,5-tetrahydrobenzo[b][1,4]oxazepin-3-yl)-2-(methylamino)propanamide hydrochloride

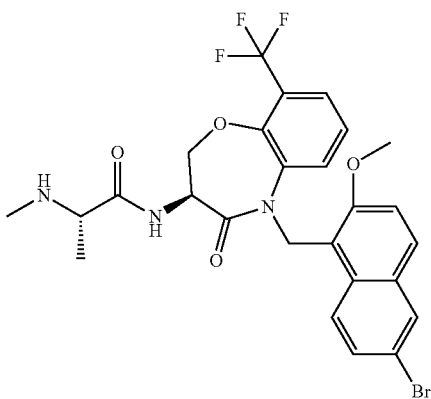 [SMILES: CN[C@@H](C)C(=O)N[C@H]1COc2c(cccc2C(F)(F)F)N(Cc2c(OC)ccc3cc(Br)ccc23)C1=O]

Step 1: A mixture of (S)-tert-butyl 4-oxo-9-(trifluoromethyl)-2,3,4,5-tetrahydrobenzo[b][1,4]oxazepin-3-ylcarbamate (389 mg, 1.12 mmol), 6-bromo-1-(chloromethyl)-2-methoxynaphthalene (481 mg, 1.68 mmol), NaI (253 mg, 1.68 mmol) and $Cs_2CO_3$ (549 mg, 1.68 mmol) in DMF (15.6 mL) was stirred at RT for 6 h and diluted with EtOAc. The mixture was washed with brine, dried over $Na_2SO_4$, filtered and the filtrate concentrated to give a residue that was purified by silica gel chromatography to afford (S)-tert-butyl 5-((6-bromo-2-methoxynaphthalen-1-yl)methyl)-4-oxo-9-(trifluoromethyl)-2,3,4,5-tetrahydrobenzo[b][1,4]oxazepin-3-ylcarbamate (321 mg, 48%) as a colorless waxy solid. MS m/z 617/619 (MNa)$^+$ Step 2: In a similar manner to that described for Example 82 Step 2, (S)-tert-butyl 5-((6-bromo-2-methoxynaphthalen-1-yl)methyl)-4-oxo-9-(trifluoromethyl)-2,3,4,5-tetrahydrobenzo[b][1,4]oxazepin-3-ylcarbamate (320 mg, 537 μmol) was converted to (S)-3-amino-5-((6-bromo-2-methoxynaphthalen-1-yl)methyl)-9-(trifluoromethyl)-2,3-dihydrobenzo[b][1,4]oxazepin-4(5H)-one hydrochloride (252 mg, 88%) obtained as a light yellow solid. MS m/z 495/497 (MH)$^+$ Step 3: In a similar manner to that described for Example 82 Step 3, (S)-3-amino-5-((6-bromo-2-methoxynaphthalen-1-yl)methyl)-9-(trifluoromethyl)-2,3-dihydrobenzo[b][1,4]oxazepin-4(5H)-one hydrochloride (77.9 mg, 146 μmol) and Boc-N-methyl-L-alanine (32.8 mg, 161 μmol) were converted to tert-butyl (S)-1-((S)-5-((6-bromo-2-methoxynaphthalen-1-yl)methyl)-4-oxo-9-(trifluoromethyl)-2,3,4,5-tetrahydrobenzo[b][1,4]oxazepin-3-ylamino)-1-oxopropan-2-yl(methyl)carbamate (78.7 mg, 79%) obtained as a white solid. MS m/z 702/704 (MNa)$^+$ Step 4: In a similar manner to that described for Example 82 Step 4, tert-butyl (S)-1-((S)-5 #6-bromo-2-methoxynaphthalen-1-yl)methyl)-4-oxo-9-(trifluoromethyl)-2,3,4,5-tetrahydrobenzo[b][1,4]oxazepin-3-ylamino)-1-oxopropan-2-yl(methyl)carbamate was converted to the title compound (64.1 mg, 92%) obtained as a white solid. MS m/z 580/582 (MH)$^+$

Example 89

(S)-2-(Methylamino)-N-((S)-5-((2-methylnaphthalen-1-yl)methyl)-4-oxo-9-(trifluoromethyl)-2,3,4,5-tetrahydrobenzo[b][1,4]oxazepin-3-yl)propanamide hydrochloride

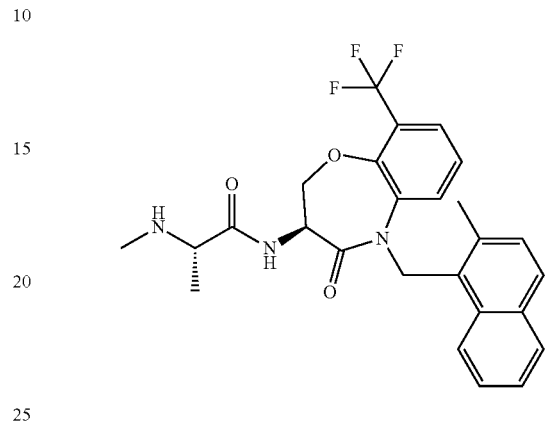

Step 1: In a similar manner to that described for Example 88 Step 1, (S)-tert-butyl 4-oxo-9-(trifluoromethyl)-2,3,4,5-tetrahydrobenzo[b][1,4]oxazepin-3-yl carbamate (200 mg, 578 μmol) and 1-(chloromethyl)-2-methylnaphthalene (165 mg, 866 μmol) were converted to (S)-tert-butyl 5-((2-methylnaphthalen-1-yl)methyl)-4-oxo-9-(trifluoromethyl)-2,3,4,5-tetrahydrobenzo[b][1,4]oxazepin-3-ylcarbamate (184 mg, 64%) obtained as a colorless oil. MS m/z 523 (MNa)$^+$ Step 2: TFA (533 μl) was added to a solution of (S)-tert-butyl 5-((2-methylnaphthalen-1-yl)methyl)-4-oxo-9-(trifluoromethyl)-2,3,4,5-tetrahydrobenzo[b][1,4]oxazepin-3-ylcarbamate (71 mg, 142 μmol) in DCM (2 mL) at 0° C. After 2.5 h the mixture was concentrated and the residue azeotroped with MeCN to afford (S)-3-amino-5-((2-methylnaphthalen-1-yl)methyl)-9-(trifluoromethyl)-2,3-dihydrobenzo[b][1,4]oxazepin-4(5H)-one trifluoroacetate (73 mg, 100%) which was used without purification.

Step 3: In a similar manner to that described for Example 82 Step 3, (S)-3-amino-5-((2-methylnaphthalen-1-yl)methyl)-9-(trifluoromethyl)-2,3-dihydrobenzo[b][1,4]oxazepin-4(5H)-one trifluoroacetate (73 mg, 142 μmol) and (S)-2-(tert-butoxycarbonyl(methyl)amino)propanoic acid (32 mg, 156 μmol) were converted to tert-butyl methyl((S)-1-((S)-5-((2-methylnaphthalen-1-yl)methyl)-4-oxo-9-(trifluoromethyl)-2,3,4,5-tetrahydrobenzo[b][1,4]oxazepin-3-ylamino)-1-oxopropan-2-yl)carbamate (66 mg, 79%) obtained as a colorless oil. MS m/z 608 (MNa)$^+$ Step 4: 2 M solution of HCl in $Et_2O$ (1.26 mL) was added to a solution of tert-butyl methyl((S)-1-((S)-5-((2-methylnaphthalen-1-yl)methyl)-4-oxo-9-(trifluoromethyl)-2,3,4,5-tetrahydrobenzo[b][1,4]oxazepin-3-ylamino)-1-oxopropan-2-yl)carbamate (66 mg, 113 μmol) in MeOH (400 μL) After 2.5 h the mixture was concentrated, MeCN was added to the residue and the mixture concentrated. The residue was lyophilized from MeCN/$H_2O$ to afford the title compound (48 mg, 82%) as a white powder. MS m/z 486 (MH)$^+$

Example 90

(S)-N-((S)-5-(Benzo[d]isoxazol-3-ylmethyl)-4-oxo-9-(trifluoromethyl)-2,3,4,5-tetrahydrobenzo[b][1,4]oxazepin-3-yl)-2-(methylamino)propanamide hydrochloride

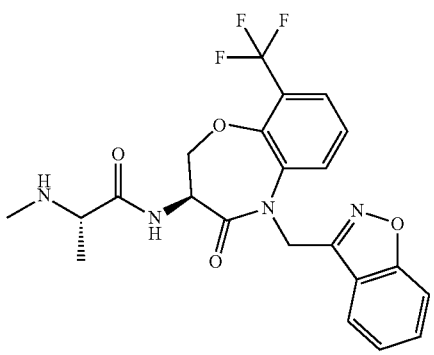 [SMILES: CN[C@@H](C)C(=O)N[C@H]1COc2c(cccc2C(F)(F)F)N(Cc2noc3ccccc23)C1=O]

Step 1: In a similar manner to that described for Example 88 Step 1, (S)-tert-butyl 4-oxo-9-(trifluoromethyl)-2,3,4,5-tetrahydrobenzo[b][1,4]oxazepin-3-yl carbamate (200 mg, 578 µmol) and 3-(bromomethyl)benzo[d]isoxazole (184 mg, 866 µmol) was converted to (S)-tert-butyl 5-(benzo[d]isoxazol-3-ylmethyl)-4-oxo-9-(trifluoromethyl)-2,3,4,5-tetrahydrobenzo[b][1,4]oxazepin-3-ylcarbamate (168 mg, 61%) obtained as a white foam. MS m/z 500 (MNa)+

Step 2: In a similar manner to that described for Example 89 Step 2, (S)-tert-butyl 5-(benzo[d]isoxazol-3-ylmethyl)-4-oxo-9-(trifluoromethyl)-2,3,4,5-tetrahydrobenzo[b][1,4]oxazepin-3-ylcarbamate (73 mg, 153 µmol) was converted to (S)-3-amino-5-(benzo[d]isoxazol-3-ylmethyl)-9-(trifluoromethyl)-2,3-dihydrobenzo[b][1,4]oxazepin-4(5H)-one trifluoroacetate (75 mg, 100%) which was used without purification.

Step 3: In a similar manner to that described for Example 89 Step 3, (S)-3-amino-5-(benzo[d]isoxazol-3-ylmethyl)-9-(trifluoromethyl)-2,3-dihydrobenzo[b][1,4]oxazepin-4(5H)-one trifluoroacetate (75 mg, 153 µmol) and (S)-2-(tert-butoxycarbonyl(methyl)amino)propanoic acid (34 mg, 168 µmol) was converted to tert-butyl (S)-1-((S)-5-(benzo[d]isoxazol-3-ylmethyl)-4-oxo-9-(trifluoromethyl)-2,3,4,5-tetrahydrobenzo[b][1,4]oxazepin-3-ylamino)-1-oxopropan-2-yl(methyl)carbamate (76 mg, 89%) obtained as a colorless oil. MS m/z 585 (MNa)'

Step 4: In a similar manner to that described for Example 89 Step 4, tert-butyl (S)-1-((S)-5-(benzo[d]isoxazol-3-ylmethyl)-4-oxo-9-(trifluoromethyl)-2,3,4,5-tetrahydrobenzo[b][1,4]oxazepin-3-ylamino)-1-oxopropan-2-yl(methyl)carbamate (76 mg, 135 µmol) was converted to the title compound (55 mg, 82%) obtained as a white powder. MS m/z 463 (MH)+

Example 91

(S)-N-((S)-9-Bromo-5-((2-methylnaphthalen-1-yl)methyl)-4-oxo-2,3,4,5-tetrahydrobenzo[b][1,4]oxazepin-3-yl)-2-(methylamino)propanamide hydrochloride

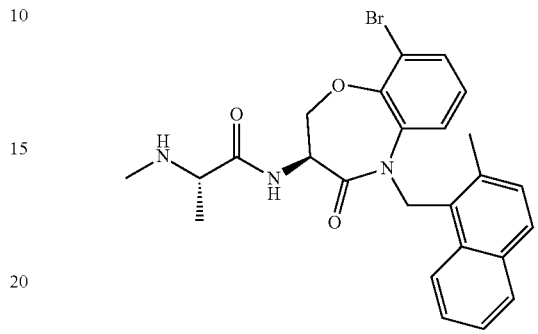

Step 1: In a similar manner to that described for Example 87 Step 1, BOC-Ser-OH (1.87 g, 9.09 mmol) and 3-bromo-2-fluoronitrobenzene (2 g, 9.09 mmol) were converted to (S)-3-(2-bromo-6-nitrophenoxy)-2-(tert-butoxycarbonylamino)propanoic acid (2.45 g, 67%) obtained as a yellow gum.

Step 2: A mixture of (S)-3-(2-bromo-6-nitrophenoxy)-2-(tert-butoxycarbonylamino)propanoic acid (2.1 g, 5.18 mmol), zinc dust (3.39 g, 51.8 mmol) and NH₄Cl (2.77 g, 51.8 mmol) in MeOH/THF 1:1 (40 mL) was stirred at RT until TLC indicated the reaction was complete. The mixture was then filtered and the filtrate concentrated. The residue was mixed with H₂O/EtOAc (50 mL/50 mL) and extracted with EtOAc. The combined organic extracts were dried over MgSO₄, filtered and the filtrate concentrated to afford (S)-3-(2-amino-6-bromophenoxy)-2-(tert-butoxycarbonylamino) propanoic acid (1.88 g, 97%) as an off-white foam which was used without purification.

Step 3: In a similar manner to that described for Example 87 Step 3 except the reaction mixture was stirred overnight, (S)-3-(2-amino-6-bromophenoxy)-2-(tert-butoxycarbonylamino)propanoic acid (1.88 g, 5.02 mmol) and EDCI (1.19 g, 6.22 mmol) was converted to (S)-tert-butyl 9-bromo-4-oxo-2,3,4,5-tetrahydrobenzo[b][1,4]oxazepin-3-ylcarbamate (452 mg, 25%) obtained as a brown oil.

Step 4: In a similar manner to that described for Example 88 Step 1, (S)-tert-butyl 9-bromo-4-oxo-2,3,4,5-tetrahydrobenzo[b][1,4]oxazepin-3-ylcarbamate (200 mg, 560 µmol) and 1-(chloromethyl)-2-methylnaphthalene (160 mg, 840 µmol) were converted to (S)-tert-butyl 9-bromo-5-((2-methylnaphthalen-1-yl)methyl)-4-oxo-2,3,4,5-tetrahydrobenzo[b][1,4]oxazepin-3-ylcarbamate (95 mg, 33%) obtained as an orange foam. MS m/z 533/535 (MNa)+

Step 5: In a similar manner to that described for Example 89 Step 2 except the reaction was stirred 45 min., (S)-tert-butyl 9-bromo-5-((2-methylnaphthalen-1-yl)methyl)-4-oxo-2,3,4,5-tetrahydrobenzo[b][1,4]oxazepin-3-ylcarbamate (40 mg, 78.2 µmol) in DCM (2 mL) was cooled to 0° C. and treated with TFA (300 µl). After 45 min, the mixture was concentrated to dryness and the residue azeotroped with MeCN to afford (S)-3-amino-9-bromo-5-((2-methylnaphthalen-1-yl)methyl)-2,3-dihydrobenzo[b][1,4]oxazepin-4 (5H)-one trifluoroacetate (41 mg), which was used without purification.

Step 6: In a similar manner to that described for Example 82 Step 3 except 1.5 eq. HBTU and 6.4 eq. DIEA were used and the mixture was stirred for 1 h, (S)-3-amino-9-bromo-5-((2-methylnaphthalen-1-yl)methyl)-2,3-dihydrobenzo[b][1,4]oxazepin-4(5H)-one trifluoroacetate (41 mg, 76 µmol) and (S)-2-(tert-butoxycarbonyl(methyl)amino)propanoic acid (22 mg, 107 µmol) were converted to tert-butyl (S)-1-((S)-9-bromo-5-((2-methylnaphthalen-1-yl)methyl)-4-oxo-2,3,4,5-tetrahydrobenzo[b][1,4]oxazepin-3-ylamino)-1-oxopropan-2-yl(methyl)carbamate (37 mg, 64%) obtained as a colorless oil. MS m/z 618/620 (MNa)$^+$ Step 7: In a similar manner to that described for Example 89 Step 4, tert-butyl (S)-1-((S)-9-bromo-5-((2-methylnaphthalen-1-yl)methyl)-4-oxo-2,3,4,5-tetrahydrobenzo[b][1,4]oxazepin-3-ylamino)-1-oxopropan-2-yl(methyl)carbamate (35 mg, 58.7 µmol) was converted to the title compound (29 mg, 93%) obtained as a white powder. MS m/z 496/498 (MH)$^+$ Example 92

(S)-N-((S)-5-((6-Bromo-2-methoxynaphthalen-1-yl)methyl)-9-methyl-4-oxo-2,3,4,5-tetrahydrobenzo[b][1,4]oxazepin-3-yl)-2-(methylamino)propanamide hydrochloride

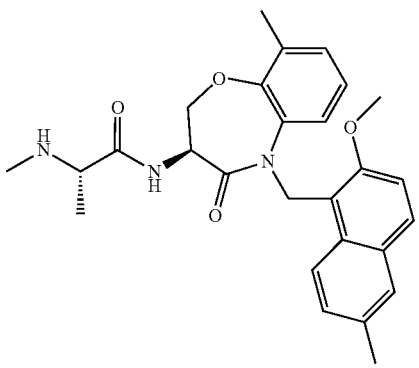 [SMILES: CN[C@@H](C)C(=O)N[C@H]1COc2c(C)cccc2N(Cc2c(OC)ccc3cc(C)ccc23)C1=O]

Step 1: In a similar manner to that described for Example 87 Step 1, BOC-Ser-OH (1.98 g, 9.67 mmol) and 2-fluoro-1-methyl-3-nitrobenzene (1.5 g, 9.67 mmol) was converted to (S)-2-(tert-butoxycarbonylamino)-3-(2-methyl-6-nitrophenoxy)propanoic acid (2.93 g, 89%) obtained as a yellow oil.

Step 2: In a similar manner to that described for Example 87 Step 2, (S)-2-(tert-butoxycarbonylamino)-3-(2-methyl-6-nitrophenoxy)propanoic acid (2.93 g, 8.61 mmol) was converted to (S)-3-(2-amino-6-methylphenoxy)-2-(tert-butoxycarbonylamino)propanoic acid (2.60 g, 97%) obtained as a brown oil.

Step 3: In a similar manner to that described for Example 87 Step 3, (S)-3-(2-amino-6-methylphenoxy)-2-(tert-butoxycarbonylamino)propanoic acid (2.60 g, 8.38 mmol) was converted to (S)-tert-butyl 9-methyl-4-oxo-2,3,4,5-tetrahydrobenzo[b][1,4]oxazepin-3-ylcarbamate (846 mg, 35%) obtained as a white solid. MS m/z 315 (MNa)$^+$ Step 4: In a similar manner to that described for Example 88 Step 1, (S)-tert-butyl 9-methyl-4-oxo-2,3,4,5-tetrahydrobenzo[b][1,4]oxazepin-3-ylcarbamate (150 mg, 513 µmol) and 6-bromo-1-(chloromethyl)-2-methoxynaphthalene (220 mg, 770 µmol) was converted to (S)-tert-butyl 5-((6-bromo-2-methoxynaphthalen-1-yl)methyl)-9-methyl-4-oxo-2,3,4,5-tetrahydrobenzo[b][1,4]oxazepin-3-ylcarbamate (122 mg, 44%) obtained as a colorless oil. MS m/z 563/565 (MNa)$^+$ Step 5: A solution of (S)-tert-butyl 5-((6-bromo-2-methoxynaphthalen-1-yl)methyl)-9-methyl-4-oxo-2,3,4,5-tetrahydrobenzo[b][1,4]oxazepin-3-yl carbamate (122 mg, 225 µmol) in DCM (5 mL) was cooled to 0° C. and treated with TFA (750 µl). After 2.5 h, the mixture was concentrated to dryness and the residue azeotroped with MeCN to afford (S)-3-amino-5-((6-bromo-2-methoxynaphthalen-1-yl)methyl)-9-methyl-2,3-dihydrobenzo[b][1,4]oxazepin-4(5H)-one trifluoroacetate (125 mg), which was used without purification.

Step 6: In a similar manner to that described for Example 82 Step 3 except the mixture was stirred for 5 h, (S)-3-amino-5-((6-bromo-2-methoxynaphthalen-1-yl)methyl)-9-methyl-2,3-dihydrobenzo[b][1,4]oxazepin-4(5H)-one trifluoroacetate (125 mg, 225 µmol) and (S)-2-(tert-butoxycarbonyl(methyl)amino)propanoic acid (50 mg, 248 µmol) were converted to tert-butyl (S)-1-((S)-5-((6-bromo-2-methoxynaphthalen-1-yl)methyl)-9-methyl-4-oxo-2,3,4,5-tetrahydrobenzo[b][1,4]oxazepin-3-ylamino)-1-oxopropan-2-yl(methyl)carbamate (117 mg, 83%) obtained as a colorless waxy solid. MS m/z 648/650 (MNa)$^+$ Step 7: In a similar manner to that described for Example 89 Step 4, tert-butyl (S)-1-((S)-5-((6-bromo-2-methoxynaphthalen-1-yl)methyl)-9-methyl-4-oxo-2,3,4,5-tetrahydrobenzo[b][1,4]oxazepin-3-ylamino)-1-oxopropan-2-yl(methyl)carbamate (114 mg, 182 µmol) was converted to the title compound (95 mg, 93%) obtained as a light yellow powder. MS m/z 526/528 (MH)$^+$ Example 93

Biochemical Assays
TR-FRET Assay for BIR2 and BIR3
The ability of a test compound to inhibit the binding of BIR2 and/or BIR3 domains of the XIAP protein to Peptide A (a SMAC-derived peptide described below) evidences that the test compound acts as a SMAC-mimetic resulting in reactivation of a cell's apoptotic pathway.

The peptide AVPIAQKSEK-(8-biotin)-OH 1:2 TFA ("Peptide A") was identified as a substrate for the TR-FRET assay by screening the 6x Histidine-tagged BIR2 domain and BIR3 domain of XIAP against a set of 29 peptides synthesized based on sequences reported by Sweeny et al. (Biochemistry, 2006, 45, 14740 14748). The peptides were labeled with the fluorescent tags FITC or TAMRA and Kd values were determined by fluorescence polarization assay. The sequence:

(SEQ ID NO: 1)
AVPIAQKSEK was identified as optimal for using in an assay. The peptide sequence was derivatized with biotin to provide AVPIAQK-SEK-(8-biotin)-OH 1:2 TFA as the substrate for the TR-FRET assay.

The XIAP protein sequence was obtained from the SWISS-PROT protein sequence database and the BIR2 and BIR3 domains were derived from that. The sequence of the BIR2 domain used for the TR-FRET assay is:

(SEQ ID NO: 2)
MRHHHHHHRDHFALDRPSETHADYLLRTGQVVDISDTIYPRNPAMYSEEA

RLKSFQNWPDYAHLTPRELASAGLYYTGIGDQVQCFACGGKLKNWEPGDR

AWSEHRRHFPNCFFVLGRNLNIRSE

The sequence of the BIR3 domain used for the TR-FRET assay is:

(SEQ ID NO: 3)
MRHHHHHHRSDAVSSDRNFPNSTNLPRNPSMADYEARIFTFGTWIYSVNK
EQLARAGFYALGEGDKVKCFHCGGGLTDWKPSEDPWEQHAKWYPGCKYLL
EQKGQEYINNIHLTHSLEECLVRTT

Ten nanomolar of 6x Histidine-tagged BIR2 domain, corresponding to amino acids 124-240 of XIAP, or BIR3 domain, corresponding to amino acids 241-356 of XIAP, was mixed with 20 nM of the peptide AVPIAQKSEK-(8-biotin)-OH 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 min. incubation at 37° C., Europium-Streptavidin and Allophycocyanin conjugated anti-Histidine antibody were added to a final concentration of 1.5 nM and 15 nM, respectively. Time-resolved fluorescence resonance energy transfer (TR-FRET) signals were measured 1 hour later at room temperature. Test compound potency was assessed at 10 serially diluted concentrations. Percentage of inhibition at each concentration was determined to generate an $IC_{50}$ value for each test compound.

| Ex No | BIR2 $IC_{50}$ (μM) | BIR3 $IC_{50}$ (μM) |
| --- | --- | --- |
| 1 | 0.88 | 54.8 |
| 1a | 0.152 | 37.035 |
| 1b | 0.929 | 41.545 |
| 1c | 0.193 | 54.8 |
| 1d | 0.301 | 28.835 |
| 1e | 6.051 | 54.8 |
| 1f | 4.362 | 54.8 |
| 1g | 0.065 | 23.465 |
| 1h | 0.057 | 36.19 |
| 1i | 0.054 | 37.32 |
| 1j | 0.056 | 33.03 |
| 1k | 2.039 | 54.8 |
| 1L | 0.042 | 25.525 |
| 1m | 0.345 | 54.8 |
| 1n | 0.070 | 46.07 |
| 1o | 0.054 | 54.8 |
| 1p | 0.932 | 54.8 |
| 1q | 0.634 | 48.49 |
| 1r | 0.141 | 22.76 |
| 1s | 0.965 | 35.06 |
| 1t | 0.665 | 36.69 |
| 1u | 3.362 | 54.8 |
| 1v | 8.615 | 54.8 |
| 1w | 0.241 | 54.8 |
| 1x | 0.367 | 38.38 |
| 1y | 12.200 | 54.8 |
| 1z | 20.630 | 54.8 |
| 1a' | 0.024 | 40.15 |
| 1b' | 0.267 | 36.56 |
| 1c' | 0.086 | 19.11 |
| 1d' | 0.029 | 31.92 |
| 2 |  | 22.64 |
| 3 |  | 30.28 |
| 4 |  | >54.8 |
| 5 |  | >54.2 |
| 6 |  | >54.2 |
| 7 |  | >54.2 |
| 8 |  | 14.885 |
| 9 |  | >54.8 |
| 10 |  | 12.52 |
| 11 |  | >54.8 |
| 12 |  | 11.44 |
| 13 |  | >54.8 |
| 14 |  | 22.3 |
| 15 |  | 8.455 |
| 16 |  | >50.0 |
| 17 |  | >54.8 |
| 18 |  | 48.62 |
| 19 |  | 22.9 |
| 20 |  | 26.23 |
| 21 |  | >54.8 |
| 21 |  | 17.7 |
| 22 |  | >54.8 |
| 22a |  | >54.8 |
| 22b |  | 14.19 |
| 22c |  | 37.14 |
| 22d |  | >54.8 |
| 22e |  | >54.8 |
| 22f |  | >54.8 |
| 22g |  | 17.565 |
| 22h |  | >54.8 |
| 23 | 0.373 | >54.8 |
| 24 | 0.373 | >54.8 |
| 25 | 0.402 | >54.8 |
| 26 | 0.245 | >54.8 |
| 27 | 1.403 | >54.8 |
| 28 | 1.424 | >54.8 |
| 29 | 0.101 |  |
| 29a | 0.6755 | >54.8 |
| 29b | 0.198 | >54.8 |
| 29c | 5.121 | >54.8 |
| 30 | 0.382 | 43.19 |
| 31 | 0.189 | >54.8 |
| 32 | 0.055 | >54.8 |
| 33 | 2.168 | >54.8 |
| 34 | 0.316 | >54.8 |
| 35 | 2.290 | >54.8 |
| 36 | 0.080 | 41.8 |
| 37 | 7.080 | >54.8 |
| 38 | 0.077 | >54.8 |
| 39 | 0.054 | >54.8 |
| 40 | 0.080 | 37.65 |
| 41 | 0.082 | 27.17 |
| 42 | 0.057 | >54.8 |
| 43 | 0.092 | >54.8 |
| 44 | 0.845 | >54.8 |
| 45 | 5.608 | >54.8 |
| 46 | 3.105 | >54.8 |
| 47 | 6.031 | >54.8 |
| 48 | 0.089 | >54.8 |
| 49 | 0.164 | >54.8 |
| 50 | 0.134 | >54.8 |
| 51 | 0.410 | >54.8 |
| 52 | 0.059 | >54.8 |
| 53 | 0.090 | >54.8 |
| 54 | 0.649 | >54.8 |
| 55 | 0.957 | >54.8 |
| 56 | 1.601 | >54.8 |
| 57 | 0.015 | 37.16 |
| 58 | 1.159 | >54.8 |
| 59 | 0.045 | 17.19 |
| 60 | 1.737 | 53.21 |
| 61 | 0.686 | >54.8 |
| 62 | 0.167 | 12.98 |
| 63 | 1.121 | >54.8 |
| 64 | 0.069 | >54.8 |
| 65 | 0.021 | 13.63 |
| 66 | 7.389 | >54.8 |
| 67 | 1.017 | >54.8 |
| 68 | 0.116 | >54.8 |
| 69 | 0.183 | >53.1 |
| 70 | 0.183 | >54.8 |
| 71 | 0.227 | >54.8 |
| 72 | 0.281 | >54.8 |
| 73 | 0.032 | 2.863 |
| 74 | 0.146 | >54.8 |
| 75 | 0.249 | 43.56 |
| 76 | 0.031 | 13.81 |
| 77 | 0.107 | >54.8 |
| 78 | 0.067 | 13.1 |
| 79 | 0.151 | 15.2 |
| 80 | 0.118 | >54.8 |
| 81 | 0.132 | >54.8 |
| 82 | 0.014 | 16.53 |

| BIR2 Ex No | IC$_{50}$ (μM) | BIR3 IC$_{50}$ (μM) |
| --- | --- | --- |
| 83 | 0.044 | >54.8 |
| 84 | 0.569 | >54.8 |
| 85 | 0.410 | 36.2 |
| 86 | 6.406 | >54.8 |
| 87 | 0.042 | 32.35 |
| 88 | 0.050 | 23.44 |
| 89 | 0.142 | 35.99 |
| 90 | 0.490 | >54.8 |
| 91 | 0.124 | 32.41 |
| 92 | 0.027 | 16.81 |

We claim:

1. A compound of the formula 1

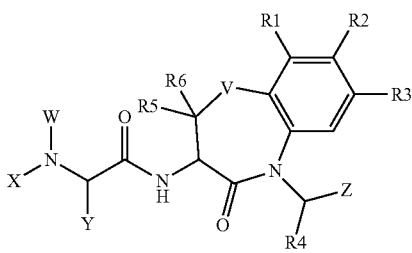

wherein:

W and X are the same or different and are independently selected from H, $C_{1-6}$-alkyl, hydoxy-$C_{1-6}$-alkyl, aryl-$C_{1-6}$-alkyl, $C_{3-7}$-cycloalkyl-$C_{1-6}$alkyl, $C_{2-6}$-alkenyl-$C_{1-6}$-alkyl, $C_{2-6}$-alkynyl-$C_{1-6}$alkyl and heterocycle; or X and W together with the nitrogen to which they are bound can form a $C_{2-9}$-heterocycle, or W together with the nitrogen to which it is bound and Y together with the carbon to which it is bound can form a $C_{3-9}$heterocycle;

Y is $C_{1-6}$-alkyl, hydoxy-$C_{1-6}$-alkyl or $C_{3-7}$-cycloalkyl-$C_{1-6}$-alkyl;

R1 is selected from H, halo, $C_{1-6}$-alkyl, halo-$C_{1-6}$-alkyl, aryl-$C_{1-6}$-alkyl, $C_{3-7}$-cycloalkyl-$C_{1-6}$-alkyl, COOH, C(O)NR8'R9', acyl, OR7, SR7, NR8R9, cyano and $SO_2R10$;

R2 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, cyano and $SO_2R10$;

R3 is selected from H, halo, $C_{1-6}$alkyl, halo-$C_{1-6}$-alkyl, aryl-$C_{1-6}$-alkyl, $C_{3-7}$-cycloalkyl-$C_{1-6}$-alkyl, acyl, OR7, SR7, NR8R9, cyano and $SO_2R10$;

R4 is H or $C_{1-6}$-alkyl;

R5 and R6 are the same or different and are independently selected from H, $C_{1-6}$-alkyl, $C_{1-6}$-alkyl-S—$C_{1-6}$-alkyl, $C_{1-6}$-alkyl-O—$C_{1-6}$-alkyl, aryl and $C_{3-7}$cycloalkyl, or R5 and R6 together with the carbon to which they are bound can form a $C_{4-7}$-carbocycle or heterocycle, which is optionally substituted by $C_{1-6}$-alkyl-$SO_2$;

V is S, O or SO2

Z is selected from $C_{1-6}$alkyl, aryl, optionally substituted by $C_{3-7}$cycloalkyl, $C_{1-6}$-alkyl, $C_{1-6}$-alkoxy, halo, halo-$C_{1-6}$-alkoxy, C(O)N($C_{1-6}$-alkyl, $C_{1-6}$-alkyl), C(O)NHSO_2—$C_{1-6}$-alkyl, C(O)N($C_{1-6}$-alkyl, hydroxy-$C_{1-6}$-alkyl), C(O)N($C_{1-6}$-alkyl, COOH—$C_{1-6}$-alkyl), phenyl optionally substituted by cyano, COO—$C_{1-6}$-alkyl or COOH; aryl-$C_{1-6}$-alkyl, heteroaryl, optionally substituted by cyano, $C_{1-6}$-alkoxy or phenyl optionally substituted by C(O)N(H,$C_{1-6}$-alkyl), cyano or COOH, polycyclic aromatics, polycyclic heteroaromatics, optionally substituted by halo, $SO_2$-phenyl, $C_{1-6}$alkyl-phenyl or phenyl optionally substituted by cyano;

mixed aryl and non-aryl polycycles and mixed aryl and non-aryl polyheterocycles; optionally substituted by $SO_2$—$C_{1-6}$-alkyl, oxo, halo or $C_{1-6}$-alkyl;

R7 is $C_{1-6}$-alkyl, aryl, or heteroaryl;

R8 and R9 are the same or different and independently selected from H, $C_{1-6}$-alkyl, aryl, aryl-$C_{1-6}$-alkyl, whereby the alkyl portion is optionally substituted by oxo; and heteroaryl-$C_{1-6}$-alkyl, R8' is selected from H and $C_{1-6}$-alkyl R9' is selected from HOOC—$C_{1-6}$-alkyl, hydroxy-$C_{1-6}$-alkyl and aryl-$C_{1-6}$-alkyl, wherein the aryl portion is substituted by COOH, or R8' and R9' form together with the nitrogen to which they are attached a heterocyclyl, substituted by hydroxy-$C_{1-6}$-alkyl; and R10 is $C_{1-6}$-alkyl, aryl, heterocyclyl, or aryl-$C_{1-6}$-alkyl, or a pharmaceutically acceptable salt thereof; and wherein acyl is —C(O)R11 where R11 is selected from H, alkyl, aryl, arylalkyl, and heterocyclyl;

heterocycle is selected from pyrrolidin-2-yl, pyrrolidin-3-yl, piperidinyl, and morpholin-4-yl; and heteroaryl is selected from thienyl, furyl, indolyl, pyrrolyl, pyridinyl, pyrazinyl, oxazolyl, thiaxolyl, quinolinyl, pyrimidinyl, imidazole, triazolyl and tetrazolyl.

2. The compound of claim 1, wherein W is H.

3. The compound of claim 1, wherein X is $C_{1-6}$-alkyl.

4. The compound of claim 1, wherein Y is $C_{1-6}$-alkyl.

5. The compound of claim 1, wherein R1, R2, R3 and R4 are H.

6. The compound of claim 1, wherein R5 and R6 are individually selected from H, $C_{1-6}$-alkyl and $C_{4-7}$-carbocycle.

7. The compound of claim 1, wherein Z is naphthyl, optionally substituted with one or two substituents selected from halo, $C_{1-6}$-alkyl and $C_{1-6}$-alkoxy.

8. The compound of claim 1 of the formula

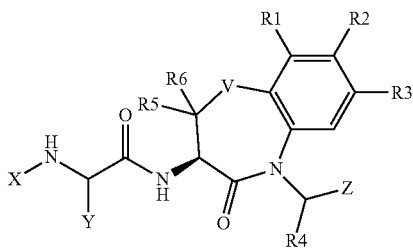

wherein:
X is selected from $C_{1-6}$-alkyl, aryl-$C_{1-6}$-alkyl, $C_{3-7}$-cycloalkyl-$C_{1-6}$-alkyl, $C_{2-6}$-alkenyl-$C_{1-6}$-alkyl or $C_{2-6}$-alkynyl-$C_{1-6}$alkyl;
Y is selected from $C_{1-6}$-alkyl or $C_{3-7}$-cycloalkyl-$C_{1-6}$-alkyl;
R1 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, cyano or $SO_2R10$;
R2 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, cyano or $SO_2R10$;
R3 is selected from H, halo, $C_{1-6}$-alkyl, aryl-$C_{1-6}$-alkyl, $C_{3-7}$-cycloalkyl-$C_{1-6}$-alkyl, acyl, OR7, SR7, NR8R9, cyano or $SO_2R10$;
R4 is selected from H or $C_{1-6}$-alkyl;
R5 and R6 are the same or different and independently selected from H, $C_{1-6}$-alkyl, aryl or $C_{3-7}$-cycloalkyl-$C_{1-6}$-alkyl, or R5 and R6 together with the carbon to which they are bound can form a $C_{3-7}$-carbocycle or heterocycle with the proviso that R5 and R6 are not both hydrogen;
V is selected from S or O;
Z is selected from aryl, heteroaryl, polycyclic aromatics, polycyclic heteroaromatics, mixed aryl and non-aryl polycycles or mixed aryl and non-aryl polyheterocycles;
R7 is $C_{1-6}$-alkyl, aryl, or heteroaryl;
R8 and R9 are the same or different and independently selected from H, $C_{1-6}$-alkyl, aryl, aryl-$C_{1-6}$-alkyl or heteroaryl-$C_{1-6}$-alkyl;
R10 is selected from $C_{1-6}$-alkyl, aryl, heterocyclyl or aryl-$C_{1-6}$-alkyl;
or a pharmaceutically acceptable salt thereof.

9. The compound of claim 1 of the formula

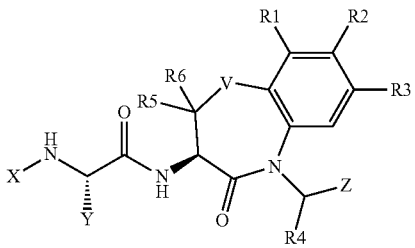

wherein:
X is selected from $C_{1-6}$-alkyl, aryl-$C_{1-6}$-alkyl or $C_{3-7}$-cycloalkyl-$C_{1-6}$-alkyl;
Y is selected from $C_{1-6}$-alkyl or $C_{3-7}$-cycloalkyl-$C_{1-6}$-alkyl;
R1 is selected from H, halo, $C_{1-6}$-alkyl, acyl, OR7, cyano or $SO_2R10$;
R2 is selected from H, halo, $C_{1-6}$-alkyl, acyl, OR7, cyano or $SO_2R10$;
R3 is selected from H, halo, $C_{1-6}$-alkyl, acyl, OR7, cyano or $SO_2R10$;
R4 is selected from H or $C_{1-6}$-alkyl;
R5 and R6 are the same or different and independently selected from H or $C_{1-6}$-alkyl but are not both hydrogen, or R5 and R6 together with the carbon to which they are bound can form a $C_{3-6}$carbocycle or heterocycle;
V is selected from S or O;
Z is selected from aryl, heteroaryl, polycyclic aromatics or polycyclic heteroaromatics;
R7 is $C_{1-6}$-alkyl, aryl, or heteroaryl;
R10 is selected from $C_{1-6}$-alkyl, aryl, heterocyclyl or aryl-$C_{1-6}$-alkyl;
or a pharmaceutically acceptable salt thereof.

10. The compound of claim 1 wherein
X is selected from methyl, ethyl, methyl-d3, ethyl-d5, n-propyl; i-propyl, 2-hydroxyethyl, 3-hydroxypropyl, cyclopropyl, cyclobutyl, cyclopentyl or oxetan-3-yl;
Y is selected from methyl, ethyl, cyclopropyl, methylcycloproplyl, hydroxymethyl, (S)-1-hydroxyethyl or (R)-1-hydroxyethyl;
R1 is selected from H, halo, $C_{1-6}$-alkyl, acyl, OR7, or cyano;
R2 is selected from H, halo, $C_{1-6}$-alkyl, acyl, OR7, or cyano;
R3 is selected from H, halo, $C_{1-6}$-alkyl, acyl, OR7, or cyano;
R4 is selected from H or $C_{1-6}$-alkyl;
R5 and R6 are the same or different and independently selected from H or $C_{1-6}$-alkyl but are not both hydrogen, or R5 and R6 together with the carbon to which they are bound can form a $C_{3-6}$carbocycle or heterocycle;
V is selected from S or O;
Z is selected from aryl, heteroaryl, polycyclic aromatics or polycyclic heteroaromatics;
R7 is $C_{1-6}$-alkyl, aryl, or heteroaryl;
or a pharmaceutically acceptable salt thereof.

11. The compound of claim 1 wherein
X is selected from methyl, ethyl, methyl-d3, ethyl-d5 or 2-hydroxyethyl;
Y is selected from methyl, ethyl, cyclopropyl, hydroxymethyl or (S)-1-hydroxyethyl;
R1 is selected from H, halo, $C_{1-6}$-alkyl, acyl, cyano;
R2 is selected from H, halo, $C_{1-6}$-alkyl, acyl, cyano;
R3 is selected from H, halo, $C_{1-6}$-alkyl, acyl, or cyano;
R4 is selected from H, methyl or ethyl;
R5 and R6 are the same or different and independently selected from H or $C_{1-6}$-alkyl but are not both hydrogen, or R5 and R6 together with the carbon to which they are bound can form a $C_{3-6}$-carbocycle or heterocycle;
V is selected from S or O;
Z is selected from aryl, heteroaryl, polycyclic aromatics or polycyclic heteroaromatics;
or a pharmaceutically acceptable salt thereof.

12. The compound of claim 1 wherein
X is selected from methyl, ethyl, methyl-d3, ethyl-d5 or 2-hydroxyethyl;
Y is selected from methyl, ethyl, hydroxymethyl or (S)-1-hydroxyethyl;
R1 is selected from H, F, Cl, Br, carboxyamide, or cyano;
R2 is selected from H, F, Cl, Br, carboxyamide, or cyano;
R3 is selected from H, F, Cl, Br, carboxyamide, or cyano;
R4 is H;

R5 and R6 are the same or different and independently selected from H or $C_{1-6}$-alkyl but are not both hydrogen, or R5 and R6 together with the carbon to which they are bound can form a $C_{3-6}$-carbocycle or heterocycle;

V is selected from S or O;

Z is selected from aryl, heteroaryl, polycyclic aromatics or polycyclic heteroaromatics;

or a pharmaceutically acceptable salt thereof.

13. The compound of claim 1 wherein
X is selected from methyl, ethyl, methyl-d3 or ethyl-d5;
Y is selected from methyl, ethyl, hydroxymethyl or (S)-1-hydroxyethyl;
R1 is selected from H, F, Cl, Br, carboxyamide, or cyano;
R2 is selected from H, F, Cl, Br, carboxyamide, or cyano;
R3 is selected from H, F, Cl, Br or cyano;
R4 is H;
R5 and R6 are the same or different and independently selected from H or $C_{1-6}$-alkyl but are not both hydrogen, or R5 and R6 together with the carbon to which they are bound can form a $C_{3-6}$carbocycle or heterocycle;
V is O;
Z is selected from 2,5-disubstituted phenyl, 2-substituted-naphthalen-1-yl, 2,5-disubstituted-naphthalen-1-yl, 2,6-disubstituted-naphthalen-1-yl, 2,7-disubstituted-naphthalen-1-yl, 5-substituted-naphthalen-1-yl, 1-substituted-1H-indazol 3-yl, benzo[d]isoxazole-3-yl, 4quinolinyl, 5-quinolinyl, 3-substituted-quinolin-4-yl, 1,2-disubstituted-indol3-yl, 1,6-disubstituted-1H-indazol-3-yl, 1-substituted-1,3-dihydro-indol-2-one-4-yl, 1,6-1H-quinolin-2-one-4-yl, 2-substituted-2,3-dihydro-1H-isoindol-4-yl, 2-(4-methyl-indol-1-yl)-benzonitrile or 1-substituted-indol-4-yl;
or a pharmaceutically acceptable salt thereof.

14. The compound of claim 1 wherein
X is selected from methyl, ethyl, methyl-d3 or ethyl-d5;
Y is selected from methyl, ethyl, hydroxymethyl or (S)-1-hydroxyethyl;
R1 is selected from H, F, Cl, Br, carboxyamide, or cyano;
R2 is selected from H, F, Cl, Br, carboxyamide, or cyano;
R3 is selected from H, F, Cl, Br or cyano;
R4 is H;
R5 and R6 are methyl or H but are not both hydrogen;
V is O;
Z is selected from 5-bromo-2-methoxynaphthalen-1-yl, 6-bromo-2-(d3-methoxy)-naphthalen-1-yl, 6-bromo-2-methoxy-naphthalen-1-yl, 3-methoxy-quinolin-4-yl, quinolin-4-yl, 2-(2,2,2-trifluoroethoxy)naphthalen-1-yl, 2-difluoromethoxy-naphthalen-1-yl,

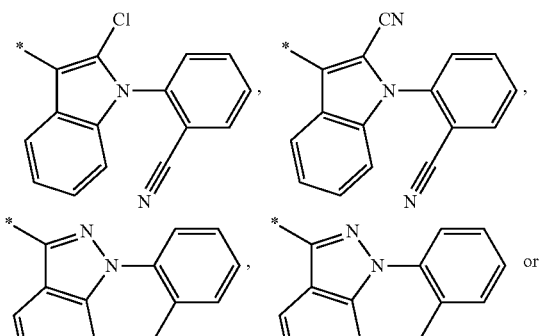

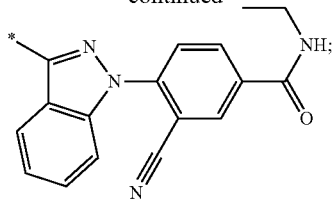

or a pharmaceutically acceptable salt thereof.

15. The compound of claim 1 wherein
X is selected from methyl, ethyl, methyl-d3 or ethyl-d5;
Y is selected from methyl, ethyl, hydroxymethyl or (S)-1-hydroxyethyl;
R1 is selected from H, F, Cl, Br, carboxyamide, or cyano;
R2 is selected from H, F, Cl, Br, carboxyamide, or cyano;
R3 is selected from H, F, Cl, Br or cyano;
R4 is H;
R5 and R6 together form a ring selected from

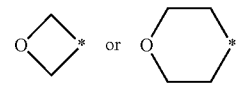

V is O;
Z is selected from 5-bromo-2-methoxynaphthalen-1-yl, 6-bromo-2-(d3-methoxy)-naphthalen-1-yl, 6-bromo-2-methoxy-naphthalen-1-yl, 3-methoxy-quinolin-4-yl, quinolin-4-yl, 2-(2,2,2-trifluoroethoxy)naphthalen-1-yl, 2-difluoromethoxy-naphthalen-1-yl,

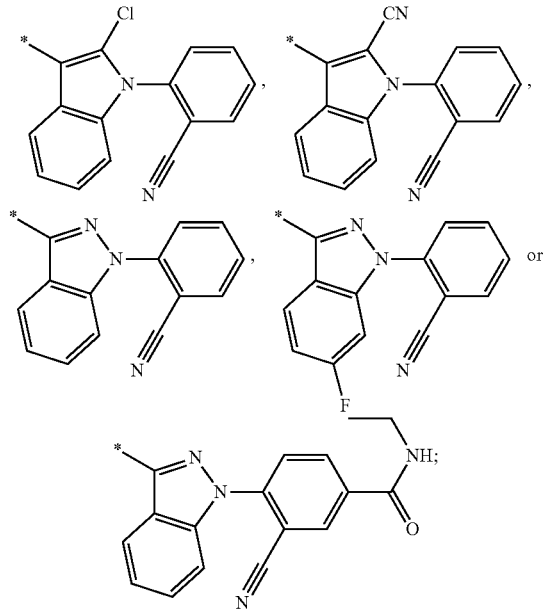

or a pharmaceutically acceptable salt thereof.

16. The compound of claim 1 wherein
X is selected from methyl, ethyl, methyl-d3 or ethyl-d5;
Y is selected from methyl, ethyl, hydroxymethyl or (S)-1-hydroxyethyl;
R1 is selected from H, F, Cl, Br, carboxyamide, or cyano;
R2 is selected from H, F, Cl, Br, carboxyamide, or cyano;
R3 is selected from H, F, Cl, Br or cyano;
R4 is H;

R5 is

R6 is

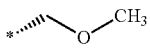

V is O;
Z is selected from 5-bromo-2-methoxynaphthalen-1-yl, 6-bromo-2-(d3-methoxy)-naphthalen-1-yl, 6-bromo-2-methoxy-naphthalen-1-yl, 3-methoxy-quinolin-4yl, quinolin-4-yl, 2-(2,2,2-trifluoroethoxy)naphthalen-1-yl, 2-difluoromethoxy-naphthalen-1-yl,

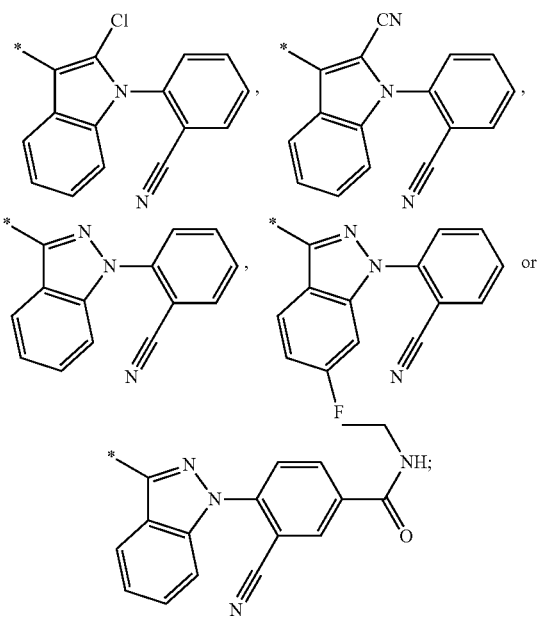

or a pharmaceutically acceptable salt thereof.

17. The compound of claim 1 wherein
X is selected from methyl, ethyl, methyl-d3 or ethyl-d5;
Y is selected from methyl, ethyl, hydroxymethyl or (S)-1-hydroxyethyl;
R1 is selected from H, F, Cl, Br, carboxyamide, or cyano;
R2 is selected from H, F, Cl, Br, carboxyamide, or cyano;
R3 is selected from H, F, Cl, Br or cyano;
R4 is H;
R5 is

R6 is

V is O;
Z is selected from 5-bromo-2-methoxynaphthalen-1-yl, 6-bromo-2-(d3-methoxy)-naphthalen-1-yl, 6-bromo-2-methoxy-naphthalen-1-yl, 3-methoxy-quinolin-4-yl, quinolin-4-yl, 2-(2,2,2-trifluoroethoxy)naphthalen-1-yl, 2-difluoromethoxy-naphthalen-1-yl,

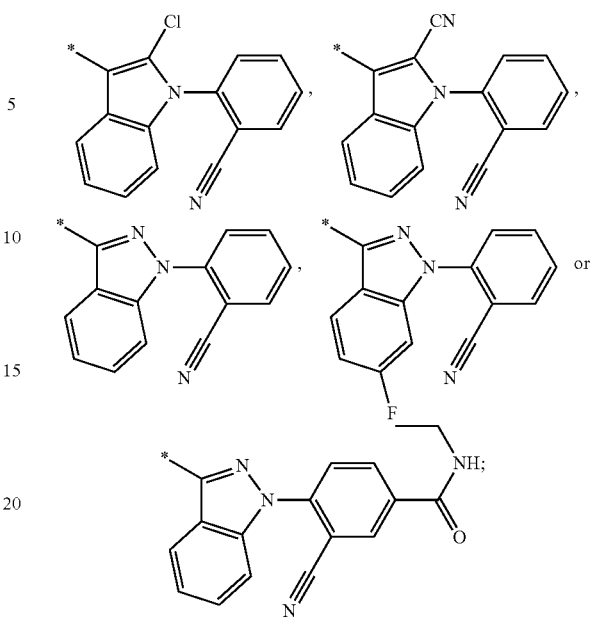

or a pharmaceutically acceptable salt thereof.

18. A compound of claim 1 selected from the group consisting of
(2S)-N-(5-((6-Bromo-2-methoxynaphthalen-1-yl)methyl)-(3S)-4-oxo-4,5-dihydro-3H-spiro[benzo[b][1,4]oxazepine-2,1'-cyclohexane]-3-yl)-2-(methylamino)propanamide hydrochloride;
6-Methoxy-5-(((S)-3-((S)-2-(methylamino)propanamido)-4-oxo-2',3',5',6'-tetrahydro-3H-spiro[benzo[b][1,4]oxazepine-2,4'-pyran]-5(4H)-yl)methyl)-2-naphthoic acid trifluoroacetate;
6-Methoxy-5-(((S)-3-((S)-2-(methylamino)propanamido)-4-oxo-2',3',5',6'-tetrahydro-3H-spiro[benzo[b][1,4]oxazepine-2,4'-pyran]-5(4H)-yl)methyl)-N-(methylsulfonyl)-2-naphthamide trifluoroacetate;
(R)-N-[(S)-5-(6-Bromo-2-methoxy-naphthalen-1-ylmethyl)-2,2-dimethyl-4-oxo-2,3,4,5-tetrahydro-benzo[b][1,4]thiazepin-3-yl]-2-methylamino-propionamide hydrochloride
(S)-N-(5-Benzyl-4-oxo-2,3,4,5-tetrahydrobenzo[b][1,4]thiazepin-3-yl)-2-methylaminopropanamide hydrochloride;
N-(5-Benzyl-1,1,4-trioxo-2,3,4,5-tetrahydrobenzo[b][1,4]thiazepin-3-yl)-2-(S)-(methylamino)propanamide hydrochloride;
N-(5-(4-Phenyl-butyl)-1,1,4-trioxo-2,3,4,5-tetrahydrobenzo[b][1,4]thiazepin-3-yl)-2-(S)-(methylamino)propanamide hydrochloride;
N-(5-Biphenyl-3-ylmethyl-4-oxo-2,3,4,5-tetrahydrobenzo[b][1,4]thiazepin-3-yl)-2-(S)-methylamino-propionamide hydrochloride;
(2S)-N-(5-((6-Bromo-2-methoxynaphthalen-1-yl)methyl)-(3R)-8,9-difluoro-4-oxo-2',3',5',6'-tetrahydro-3H-spiro[benzo[b][1,4]oxazepine-2,4'-pyran]-3-yl)-2-(methylamino)propanamide hydrochloride;
(2S)-N-(5-((6-Bromo-2-methoxynaphthalen-1-yl)methyl)-(3S)-8,9-difluoro-4-oxo-2',3',5',6'-tetrahydro-3H-spiro[benzo[b][1,4]oxazepine-2,4'-pyran]-3-yl)-2-(methylamino)propanamide hydrochloride;
(2S)-N-(5-((6-Bromo-2-methoxynaphthalen-1-yl)methyl)-(3R)-9-fluoro-4-oxo-2',3',5',6'-tetrahydro-3H- spiro[benzo[b][1,4]oxazepine-2,4'pyran]-3-yl)-2-(methylamino)propanamide hydrochloride;

(2S)-N-(5-(((6-Bromo-2-methoxynaphthalen-1-yl)methyl)-(3S)-9-fluoro-4-oxo-2',3',5',6'-tetrahydro-3H-spiro[benzo[b][1,4]oxazepine-2,4'-pyran]-3-yl)-2-(methylamino)propanamide hydrochloride and (2S)-N-(5-(((6-Bromo-2-methoxynaphthalen-1-yl)methyl)-(3R)-9-fluoro-4-oxo-2',3',5',6'-tetrahydro-3H-spiro[benzo[b][1,4]oxazepine-2,4'-pyran]-3-yl)-2-(methylamino)butanamide hydrochloride;

(2S)-N-(5-(((6-Bromo-2-methoxynaphthalen-1-yl)methyl)-(3S)-9-fluoro-4-oxo-2',3',5',6'-tetrahydro-3H-spiro[benzo[b][1,4]oxazepine-2,4'-pyran]-3-yl)-2-(methylamino)butanamide hydrochloride;

(2S)-N-(5-(((6-Bromo-2-methoxynaphthalen-1-yl)methyl)-(3S)-8-fluoro-4-oxo-2',3',5',6'-tetrahydro-3H-spiro[benzo[b][1,4]oxazepine-2,4'-pyran]-3-yl)-2-(methylamino)propanamide hydrochloride;

(2S)-N-(5-(((6-Bromo-2-methoxynaphthalen-1-yl)methyl)-(3S)-8-fluoro-4-oxo-2',3',5',6'-tetrahydro-3H-spiro[benzo[b][1,4]oxazepine-2,4'-pyran]-3-yl)-2-(methylamino)butanamide hydrochloride;

(S)-N-((S)-5-((6-Bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-(2-hydroxyethylamino)propanamide;

(2S)-N-(5-((3-Methoxyquinolin-N-oxide-4-yl)methyl)-(3S)-4-oxo-2',3',5',6'-tetrahydro-3H-spiro[benzo[b][1,4]oxazepine-2,4'-pyran]-3-yl)-2-(methylamino)propanamide;

(2S)-N-(5-(((6-Bromo-2-methoxynaphthalen-1-yl)methyl)-(3S)-4-oxo-2',3',5',6'-tetrahydro-3H-spiro[benzo[b][1,4]oxazepine-2,4'-pyran]-3-yl)-2-(methyl-d3-amino)propanamide hydrochloride;

(2S)-N-(5-(((6-Bromo-2-(methoxy-d3)-naphthalen-1-yl)methyl)-(3S)-4-oxo-2',3',5',6'-tetrahydro-3H-spiro[benzo[b][1,4]oxazepine-2,4'-pyran]-3-yl)-2-(methyl-d3-amino)propanamide hydrochloride;

(R)-N-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-aminopropanamide;

(S)-N-((S)-5-((6-bromo-2-methoxynaphthalen-1-yl)methyl)-4-oxo-2',3',4,5,5',6'-hexahydro-3H-spiro[benzo[b][1,4]oxazepine-2,4'-pyran]-3-yl)-2-aminopropanamide;

(S)-N-{(R)-9-[2-(2-Methoxy-ethoxy)-acetylamino]-5-naphthalen-1-ylmethyl-4-oxo-2,3,4,5-tetrahydro-benzo[b][1,4]thiazepin-3-yl}-2-methylamino-propionamide hydrochloride;

1-Acetyl-piperidine-4-carboxylic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide and 5-Oxo-hexanoic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide hydrochloride;

3,4,5-Trimethoxy-N-[(R)-3-((S)-2-methylamino-propionylamino)-5-naphthalen-1-ylmethyl-4-oxo-2,3,4,5-tetrahydro-benzo[b][1,4]thiazepin-9-yl]-benzamide hydrochloride;

6-Oxo-heptanoic acid [(R)-3-((S)-2-methylamino-propionylamino)-5-naphthalen-1-ylmethyl-4-oxo-2,3,4,5-tetrahydro-benzo[b][1,4]thiazepin-9-yl]-amide hydrochloride;

(S)-N-((R)-9-Amino-5-naphthalen-1-ylmethyl-4-oxo-2,3,4,5-tetrahydro-benzo[b][1,4]thiazepin-3-yl)-2-methylamino-propionamide hydrochloride;

N-[(R)-3-((S)-2-Methylamino-propionylamino)-5-naphthalen-1-ylmethyl-4-oxo-2,3,4,5-tetrahydro-benzo[b][1,4]thiazepin-9-yl]-benzamide hydrochloride;

(S)-N-[(S)-9-(6-Bromo-2-methoxy-naphthalen-1-ylmethyl)-8-oxo-6,7,8,9-tetrahydro-5-oxa-9-aza-benzocyclohepten-7-yl]-2-methylamino-propionamide trifluoroacetate;

(S)-N-[(S)-9-(6-Cyclopropyl-2-methoxy-naphthal en-1-ylmethyl)-8-oxo-6,7,8,9-tetrahydro-5-oxa-9-aza-benzocyclohepten-7-yl]-2-methyla mino-propionamide trifluoroacetate;

Methyl 6-methoxy-5-(((S)-3-((S)-2-(methylamino)propanamido)-4-oxo-3,4-dihydrobenzo[b][1,4]oxazepin-5(2H)-yl)methyl)-2-naphthoate trifluoroacetate;

6-Methoxy-5-(((S)-3-((S)-2-(methylamino)propanamido)-4-oxo-3,4-dihydrobenzo[b][1,4]oxazepin-5(2H)-yl)methyl)-2-naphthoic acid trifluoroacetate;

6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carboxylic acid (2-hydroxy-ethyl)-methyl-amide;

4-({6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carbonyl}-amino)-butyric acid trifluoroacetate ;

6-Methoxy-7-[(S)-7-((S)-2-methylamino-propionylamino)-8-oxo-7,8-dihydro-6H-5-oxa-9-aza-benzocyclohepten-9-ylmethyl]-naphthalene-2-carboxylic acid dimethylamide trifluoroacetate and (S)-N-[(S)-9-(7-Bromo-3-methoxy-naphthalen-2-ylmethyl)-3-methyl-8-oxo-6,7,8,9-tetrahydro-5-oxa-9-aza-benzocyclohepten-7-yl]-2-methylamino-propionamide trifluoroacetate;

(2S,3R)-2-Amino-N-[(S)-9-(7-bromo-3-methoxy-naphthalen-2-ylmethyl)-3-methyl-8-oxo-6,7,8,9-tetrahydro-5-oxa-9-aza-benzocyclohepten-7-yl]-3-hydroxy-butyramide trifluoracetate;

(2S,3S)-2-Amino-N-[(S)-9-(7-bromo-3-methoxy-naphthalen-2-ylmethyl)-3-methyl-8-oxo-6,7,8,9-tetrahydro-5-oxa-9-azabenzocyclohepten-7-yl]-3-hydroxy-butyramide trifluoroacetate;

(S)-N-((2S,3S)-5-((6-Bromo-2-methoxynaphthalen-1-yl)methyl)-2,8-dimethyl-4-oxo-2,3,4,5-tetrahydrobenzo[b][1,4]oxazepin-3-yl)-2-(methylamino)propanamide trifluoroacetate;

Methyl 5-(((2S,3S)-2,8-dimethyl-3-((S)-2-(methylamino)propanamido)-4-oxo-3,4-dihydrobenzo[b][1,4]oxazepin-5(2H)-yl)methyl)-6-methoxy-2-naphthoate trifluoroacetate;

(2S,3S)-2-Amino-N-[(6S,7S)-9-(6-bromo-2-methoxy-naphthalen-1-ylmethyl)-3,6-dimethyl-8-oxo-6,7,8,9-tetrahydro-5-oxa-9-aza-benzocyclohepten-7-yl]-3-hydroxy-butyramide trifluoroacetate;

(S)-N-((S)-5-((6-Bromo-2-methoxynaphthalen-1-yl)methyl)-4-oxo-7-(trifluoromethyl)-2,3,4,5-tetrahydrobenzo[b][1,4]oxazepin-3-yl)-2-(methylamino)propanamide trifluoroacetate;

(S)-N-[(6S,7S)-9-(6-Bromo-2-methoxy-naphthalen-1-ylmethyl)-6-methyl-8-oxo-2-trifluoromethyl-6,7,8,9-tetrahydro-5-oxa-9-aza-benzocyclohepten-7-yl]-2-methylamino-propionamide trifluoroacetate;

(S)-2-Methylamino-N-[(S)-9-(2-methyl-naphthalen-1-ylmethyl)-8-oxo-6,7,8,9-tetrahydro-5-oxa-9-aza-benzocyclohepten-7-yl]-propionamide;

(S)-N-((S)-5-(2-Chlorobenzyl)-4-oxo-2,3,4,5-tetrahydrobenzo[b][1,4]oxazepin-3-yl)-2-(methylamino)propanamide;

(S)-N-((S)-5-(3-Chlorobenzyl)-4-oxo-2,3,4,5-tetrahydrobenzo[b][1,4]oxazepin-3-yl)-2-(methylamino)propanamide;

(S)-N-((S)-5-(4-Chlorobenzyl)-4-oxo-2,3,4,5-tetrahydrobenzo[b][1,4]oxazepin-3-yl)-2-(methylamino)propanamide;

(S)-5-((6-bromo-2-methoxynaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate and 3-{[(S)-9-(6-Bromo-2-methoxy-naphthalen-1-ylmethyl)-7-((S)-2-methylamino-propionylamino)-8-oxo-6,7,8,9-tetrahydro-5-oxa-9-aza-benzocycloheptene-4-carbonyl]-amino}-propionic acid trifluoroacetate;

4-({[(S)-9-(6-Bromo-2-methoxy-naphthalen-1-ylmethyl)-7-((S)-2-methylamino-propionylamino)-8-oxo-6,7,8,9-tetrahydro-5-oxa-9-aza-benzocycloheptene-4-carbonyl]-amino}-methyl)-benzoic acid methyl ester;

(S)-5-((6-Carboxy-2-methoxynaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate;

5-(((S)-2-Hydroxyethyl)(methyl)carbamoyl)-3-((S)-2-methylamino)propanamido)-4-oxo-3,4-dihydrobenzo[b][1,4]oxazepin-5(2H)-yl)methyl)-6-methoxy-2-naphthoic acid trifluoroacetate;

S)-5-((4-Bromonaphthalen-1-yl)methyl)-3-((S)-2methylamino)propanamido)-4-oxo-2,3,4,5-tetrahydrobenzo[b][1,4]oxazepine-9-carboxylic acid trifluoroacetate;

(S)-N-((S)-5-((4-Bromonaphthalen-1-yl)methyl)-9-(4-(2-hydroxyethyl)piperazine-1-carbonyl)-4-oxo-2,3,4,5-tetrahydrobenzo[b][1,4]oxazepin-3-yl)-2-(methylamino)propanamide;

(S)-N-((S)-5-((4-Bromonaphthalen-1-yl)methyl)-9-(4-(3-hydroxypropyl)piperazine-1-carbonyl)-4-oxo-2,3,4,5-tetrahydrobenzo[b][1,4]oxazepin-3-yl)-2-(methylamino)propanamide;

(S)-N-((S)-5((2-Chloro-1-(2-cyanophenyl)-1H-indol-3-yl)methyl)-4-oxo-2,3,4,5-tetrahydrobenzo[b][1,4]oxazepin-3-yl)-2-(methylamino)propanamide;

(S)-N-((S)-5((1-(2-Cyanophenyl)-1H-indol-4-yl)methyl)-4-oxo-2,3,4,5-tetrahydrobenzo[b][1,4]oxazepin-3-yl)-2-(methylamino)propanamide;

(S)-N-((S)-5((2-Chloro-1-(phenylsulfonyl)-1H-indol-3-yl)methyl)-4-oxo-2,3,4,5-tetrahydrobenzo[b][1,4]oxazepin-3-yl)-2-(methylamino)propanamide;

(S)-N-[(S)-9-(1-Benzenesulfonyl-2-chloro-1H-indol3-ylmethyl)-8-oxo-6,7,8,9-tetrahydro-5-oxa-9-aza-benzocyclohepten-7-yl]-2-methylamino-propionamide hydrochloride;

(S)-N-((S)-5-((6-Fluoro-1-methyl-2-oxo-1,2-dihydroquinolin-4-yl)methyl)-4-oxo-2,3,4,5-tetrahydrobenzo[b][1,4]oxazepin-3-yl)-2-(methylamino)propanamide;

(S)-N-[(S)-9-(1-Benzyl-2-chloro-1H-indol-3-ylmethyl)-8-oxo-6,7,8,9-tetrahydro-5-oxa-9-aza-benzocyclohepten-7-yl]-2-methylamino-propionamide and (S)-N-((S)-5-((1-Ethyl-2-oxoindolin-4-yl)methyl)-4-oxo-2,3,4,5-tetrahydrobenzo[b][1,4]oxazepin-3-yl)-2-(methylamino)propanamide;

(S)-2-Amino-N-((S)-5-((1-(2-cyanophenyl)-1H-indazol-3-yl)methyl)-4-oxo-2,3,4,5-tetrahydrobenzo[b][1,4]oxazepin-3-yl)propanamide;

(S)-N-((S)-5-((2-Cyano-1-(2-cyanophenyl)-1H-indol-3-yl)methyl)-4-oxo-2,3,4,5-tetrahydrobenzo[b][1,4]oxazepin-3-yl)-2-(methylamino)propanamide trifluoroacetate;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(oxetan-3-ylamino)propanamide;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(2-hydroxy-2-methylpropylamino)propanamide;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(2-hydroxyethylamino)propanamide;

(S)-N-((S)-5-((1-(2-Cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide;

(S)-N-((S)-5-((1-(2-Cyanophenyl)-1H-indazol-3-yl)methyl)-4-oxo-2,3,4,5-tetrahydrobenzo[b][1,4]oxazepin-3-yl)-2-(ethyl-d5-amino)propanamide;

(S)-N-((S)-5-((1-(2-Cyanophenyl)-6-fluoro-1H-indazol-3-yl)methyl)-4-oxo-2,3,4,5-tetrahydrobenzo[b][1,4]oxazepin-3-yl)-2-(ethylamino)propanamide;

S)-N-((S)-5-((6-Bromo-1-(2-cyanophenyl)-1H-indazol-3-yl)methyl)-4-oxo-2,3,4,5-tetrahydrobenzo[b][1,4]oxazepin-3-yl)-2-(methylamino)propanamide trifluoroacetate;

(S)-N-((S)-5-((2-Cyano-1-(2-cyanophenyl)-1H-indol-3-yl)methyl)-4-oxo-2',3',4,5,5',6'-hexahydro-3H-spiro[benzo[b][1,4]oxazepine-2,4'-pyran]-3-yl)-2-(methylamino)propanamide;

(2S)-N-((2S,3S)-5-((1-(2-Cyanophenyl)-1H-indazol-3-yl)methyl)-2-methyl-4-oxo-2,3,4,5-tetrahydrobenzo[b][1,4]oxazepin-3-yl)-2-(ethylamino)propanamide trifluoroacetate;

(S)-N-((R)-5-((2-Cyano-1-(2-cyanophenyl)-1H-indol-3-yl)methyl)-2,2-dimethyl-4-oxo-2,3,4,5-tetrahydrobenzo[b][1,4]thiazepin-3-yl)-2(ethylamino)propanamide and (S)-N-((2S,3S)-5-((2-Cyano-1-(2-cyanophenyl)-1H-indol-3-yl)methyl)-2-methyl-4-oxo-2,3,4,5-tetrahydrobenzo[b][1,4]oxazepin-3-yl)-2-(methylamino)propanamide;

(S)-N-((2S,3S)-5-((2-Cyano-1-(2-cyanophenyl)-1H-indol-3-yl)methyl)-2-methyl-4-oxo-2,3,4,5-tetrahydrobenzo[b][1,4]oxazepin-3-yl)-2-(ethylamino)propanamide;

(S)-N-((S)-8-Bromo-5-((1-(2-cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide trifluoroacetate;

(S)-N-((S)-8-Cyano-5-((2-cyanophenyl)-1H-indazol-3-yl)methyl)-4-oxo-2',3',4,5,5',6'-hexahydro-3H-spiro[benzo[b][1,4]oxazepine-2,4'-pyran]-3-yl)-2-(methylamino)propanamide 2,2,2-trifluoroacetate;

3-Cyano-4-(3-(((2S,3S)-2-methyl-3-((S)-2-(methylamino)propanamido)-4-oxo-3,4-dihydrobenzo[b][1,4]oxazepin-5(2H)-yl)methyl)-1H-indazol-1-yl)benzoic acid trifluoroacetate;

3-Cyano-N-ethyl-4-(3-(((2S,3S)-2-methyl-3-((S)-2-(methylamino)propanamido)-4-oxo-3,4-dihydrobenzo[b][1,4]oxazepin-5(2H)-yl)methyl)-1H-indazol-1-yl)benzamide trifluoroacetate;

(S)-N-((S)-5-((6-Bromo-2-methoxynaphthalen-1-yl)methyl)-4-oxo-2,3,4,5-tetrahydrobenzo[b][1,4]oxazepin-3-yl)-2-(methylamino)butanamide hydrochloride;

(S)-N-((S)-5-((6-Bromo-2-methoxynaphthalen-1-yl)methyl)-4-oxo-2,3,4,5-tetrahydrobenzo[b][1,4]oxazepin-3-yl)-2-(2-hydroxyethylamino)butanamide trifluoroacetate;

(S)-N-((S)-5-(Benzo[d]isoxazol-3-ylmethyl)-4-oxo-2',3',4,5,5',6'-hexahydro-3H-spiro[benzo[b][1,4]oxazepine-2,4'-pyran]-3-yl)-2-(methylamino)propanamide hydrochloride;

(S)-N-((S)-5-((2-(Difluoromethoxy)naphthalen-1-yl)methyl)-4-oxo-2',3',4,5,5',6'-hexahydro-3H-spiro[benzo[b][1,4]oxazepine-2,4'-pyran]-3-yl)-2-(methylamino)propanamide hydrochloride;

(S)-N-((R)-5-((2-(Difluoromethoxy)naphthalen-1-yl)methyl)-4-oxo-2',3',4,5,5',6'-hexahydro-3H-spiro[benzo[b][1,4]oxazepine-2,4'-pyran]-3-yl)-2-(methylamino)propanamide hydrochloride;

(S)-N-((S)-5-((6-Bromo-2-methoxynaphthalen-1-yl)methyl)-9-fluoro-4-oxo-2,3,4,5-tetrahydrobenzo[b][1,4]oxazepin-3-yl)-2-(methylamino)propanamide hydrochloride and (S)-N-((S)-5-((6-Bromo-2-methoxynaphthalen-1-yl)methyl)-4-oxo-9-(trifluoromethyl)-2,3,4,5-tetrahydrobenzo[b][1,4]oxazepin-3-yl)-2-(methylamino)propanamide hydrochloride;

(S)-2-(Methylamino)-N-((S)-5-((2-methylnaphthalen-1-yl)methyl)-4-oxo-9-(trifluoromethyl)-2,3,4,5-tetrahydrobenzo[b][1,4]oxazepin-3-yl)propanamide hydrochloride;

(S)-N-((S)-5-(Benzo[d]isoxazol-3-ylmethyl)-4-oxo-9-(trifluoromethyl)-2,3,4,5-tetrahydrobenzo[b][1,4]oxazepin-3-yl)-2-(methylamino)propanamide hydrochloride;

(S)-N-((S)-9-Bromo-5-((2-methylnaphthalen-1-yl)methyl)-4-oxo-2,3,4,5-tetrahydrobenzo[b][1,4]oxazepin-3-yl)-2-(methylamino)propanamide hydrochloride;

(S)-5-((2-Methoxynaphthalen-1-yl)methyl)-3-((S)-2-(methylamino)propanamido)-4-oxo-2,3,4,5-tetrahydrobenzo[b][1,4]oxazepine-9-carboxylic acid trifluoroacetate and (S)-N-((S)-5-((6-Bromo-2-methoxynaphthalen-1-yl)methyl)-9-methyl-4-oxo-2,3,4,5-tetrahydrobenzo[b][1,4]oxazepin-3-yl)-2-(methylamino)propanamide hydrochloride.

19. A pharmaceutical composition comprising a compound of claim 1 and a therapeutically inert carrier.

\* \* \* \* \*